US007312358B2

(12) United States Patent
Quattropani et al.

(10) Patent No.: US 7,312,358 B2
(45) Date of Patent: Dec. 25, 2007

(54) PHARMACEUTICALLY ACTIVE SULFANILIDE DERIVATIVES

(75) Inventors: Anna Quattropani, Geneve (CH); Matthias Schwarz, Thonex (CH); Catherine Joran-Lebrun, Contamine-Sarzin (FR); Dennis Church, Commugny (CH); Alexander Scheer, Versoix (CH)

(73) Assignee: Laboratoires Serono SA, Vaud (CH)

( * ) Notice: Subject to any disclaimer, the term of this patent is extended or adjusted under 35 U.S.C. 154(b) by 682 days.

(21) Appl. No.: 10/399,040

(22) PCT Filed: Oct. 15, 2001

(86) PCT No.: PCT/EP01/11865

§ 371 (c)(1),
(2), (4) Date: Sep. 25, 2003

(87) PCT Pub. No.: WO02/32864

PCT Pub. Date: Apr. 25, 2002

(65) Prior Publication Data

US 2004/0072816 A1 Apr. 15, 2004

(30) Foreign Application Priority Data

Oct. 17, 2000 (EP) ................... 00122588

(51) Int. Cl.
*C07C 303/00* (2006.01)
(52) U.S. Cl. ...................................... 564/80
(58) Field of Classification Search .......... 514/210.17, 514/227.5, 237.5, 255.01, 317, 365, 374, 514/400, 423, 602
See application file for complete search history.

(56) References Cited

U.S. PATENT DOCUMENTS

| 5,338,755 | A | * | 8/1994 | Wagnon et al. ............ 514/414 |
| 5,756,497 | A |  | 5/1998 | Bell et al. |
| 2004/0072816 | A1 |  | 4/2004 | Quattropani et al. |

FOREIGN PATENT DOCUMENTS

| EP | 0 469 984 | 2/1992 |
| EP | 0 526 348 | 2/1993 |
| GB | 1 414 887 | 11/1975 |
| WO | 96/22775 | 8/1996 |
| WO | 00 06340 | 2/1999 |
| WO | 99/67221 | 12/1999 |
| WO | 00/50391 | 8/2000 |
| WO | 00 51975 | 9/2000 |

OTHER PUBLICATIONS

Bartoli. Pathophysiology of Na and water retention in liver cirrhosis and its correction with vasoconstrictors and aquaretics. Expert Opin, Ther.Patents (2006) 16 (1) 59-68.*

Chemical Abstracts, vol. 55, No. 14, XP002162400, Jul. 10, 1961.
Chemical Abstracts, vol. 58, No. 6, XP002162458, Mar. 18, 1963, abstract only.
Chemical Abstracts, vol. 59, No. 9, XP002162459, Oct. 28, 1963, abstract only.
Chemical Abstracts, vol. 60, No. 9, XP002162460, Apr. 27, 1964, abstract only.
Chemical Abstracts, vol. 61, No. 13, XP002162461, Oct. 26, 1964, abstract only.
Chemical Abstracts, vol. 62, No. 13, XP002162462, Jun. 21, 1965, abstract only.
Chemical Abstracts, vol. 64, No. 1, XP002162463, Jan. 3, 1966, abstract only.
W. Baker, et al.: "Cyclic meso-ionic compounds. Part III. Further properties of the sydnones and the mechanism of their formation" Journal of the Chemical Society, pp. 1542-1551, 1950.
W. Patterson et al.: "Azobenzocycloheptenones. Part IV. An azodibenzotropone" Journal of the Chemical Society, No. 9, pp. 3468-3472, Sep. 1962.
A. Acero-Alarcon et al.: "Unusual ring closure reaction of amides with pyrimidines: novel stereoselective synthesis of hexahydroimidazo'1,2-c]pyrimidines", SYNTHESIS, No. 12, pp. 2124-2130, Dec. 1999.
M.-R. Chang et al.: "Synthesis of 7-substituted indolo'3,2,-b]quinoline derivatives", HETEROCYCLES, vol. 33, No. 1, pp. 147-152, 1992.
K. Goerlitzer et al.: Anellierte chinoline, 6. Mitt. 10H-indolo'3,2-Archiv Der Pharmazie., vol. 318, pp. 852-861, 1981.
Mario Maggi et al.: "Human myometrium during pregnancy contains and responds to V1 vasopressin receptors as well as oxytocin receptors" Journal of Clinical Endocrinology and Metabolism, vol. 70, No. 4, pp. 1142-1154, 1990.
Ben E. Evans et al.: "Orally active, nonpeptide oxytocin antagonists" J. Med. Che., vol. 35, pp. 3919-3927, 1992.

(Continued)

*Primary Examiner*—Yvonne Eyler
*Assistant Examiner*—M Louisa Lao
(74) *Attorney, Agent, or Firm*—Oblon, Spivak. McClelland, Maier & Neustadt, P.C.

(57) ABSTRACT

The present invention relates to sulfanilide derivatives of formula (I), in which $R^1$ and $R^2$ are optionally substituted aryl and heteroaryl groups and the other variables are as defined in the claims, for use as pharmaceutically active compounds, as well as pharmaceutical formulations containing such sulfanilide derivatives. Said derivatives are useful in the treatment and/or prevention of preterm labor, premature birth, dysmenorrhea, inappropriate secretion of vasopressin, congestive heart failure, arterial hypertension, liver cirrhosis, nephrotic syndrome and ocular hypertension. In particular, the present invention is related to sulfanilide derivatives displaying a substantial modulatory, in particular antagonistic activity, of the oxytocin and/or vasopressin receptor. More preferably, said compounds are useful in the treatment and/or prevention of disease states mediated by oxytocin and/or vasopressin, including preterm labor, premature birth, dysmenorrhea, inappropriate secretion of vasopressin, congestive heart failure, arterial hypertension, liver cirrhosis, nephrotic syndrome and ocular hypertension. The present invention is furthermore related to novel sulfanilide derivatives as well as to methods of their preparation.

43 Claims, No Drawings

OTHER PUBLICATIONS

M. Thibonnier et al.: "The basic and clinical pharmacology of nonpeptide vasopressin receptor antagonists" Adv. Rev. Pharmacol. Toxicol.., vol. 41, pp. 175-202, 2001.

Marc Thibonnier et al.: "Molecular pharmacology of human vasopressin receptors" Adv. Exp. Med. Biolog., vol. 449, pp. 251-276, 1998.

Christian Rivalle et al.: "Ethyl (4-N-acytaminopyridin-3-yl)glyoxylate and 5-azaisatin as new synthons for a route to various new polyheterocycles" Heterocyclic Chem., vol. 34, pp. 441-444, 1997.

Leslie W. Deady et al.: "Synthesis and antitumor properties of N-[2-(dimethylamino)ethyl]carboxamide derivatives of fused tetracyclic quinolines and quinoxalines: a new class of putative topoisomerase inhibitors", J. Med. Chem., vol. 40, pp. 2040-2046, 1997.

Robert Ramage et al.: "An acid labile arginine derivative for peptide synthesis: NG-2,2,5,7,8-pentamethylchroman-6-sulphonyl-L-arginine", TETRAHEDRON, vol. 47, pp. 6353-6370, 1991.

John P. Wolfe et al.: "Simple, efficient catalyst system for the palladium catalyzed amination of aryl chlorides, bromides, and triflates", J. Org. Chem., vol. 65, pp. 1158-1174, 2000.

Andrew J. Souers et al.: "Preparation of enantioenriched a-bromo acids incorporating diverse functionality", SYNTHESIS, pp. 583-585, 1999.

Andrew P. Combs et al.: "N-arylation of sulfonamides on solid supports", J. Comb. Chem., vol. 2, pp. 29-32, 2000.

U.S. Appl. No. 11/449,802, filed Jun. 9, 2006, Schwarz, et al.

K. Goerlitzer et al., "Anellierte chinoline, 6. Mitt. 10H-indolo'3,2-b]chinoline," Archiv Der Pharmazie., vol. 318, pp. 852-861, 1981.

* cited by examiner

PHARMACEUTICALLY ACTIVE SULFANILIDE DERIVATIVES

FIELD OF THE INVENTION

The present invention is related to sulfanilide derivatives, in particular for use as medicaments, as well as pharmaceutical Formulations containing such sulfanilide derivatives. Said sulfanilide derivatives are useful in the treatment and/or prevention of preterm labor, premature birth, dysmenorrhea, inappropriate secretion of vasopressin, congestive heart failure, arterial hypertension, liver cirrhosis, nephrotic syndrome and ocular hypertension. Preferably, the sulfanilide derivatives display a modulatory, notably an antagonist activity of the oxytocin and/or vasopressin receptor. More preferably, said compounds are useful in the treatment and/or prevention of disease states mediated by oxytocin and/or vasopressin, including preterm labor, premature birth, inappropriate secretion of vasopressin, congestive heart failure, arterial hypertension, liver cirrhosis, nephrotic syndrome, hypertension and dysmenorrhea.

BACKGROUND OF THE INVENTION

Arginine vasopressin (AVP) and oxytocin (OT) are cyclic nonapeptides whose actions are mediated by activation of specific G protein-coupled receptors currently classifid into $V_1$-vascular ($V_1R$), $V_2$-renal ($V_2R$) and $V_3$-pituitary ($V_3R$) AVP receptors, as well as OT receptors (OT-R).

Oxytocin (OT) is a peptide hormone that causes the contraction of the uterus of mammals during labor. The corresponding oxytocin receptor belongs to the family of G-protein-coupled receptors and is similar to $V_1$ and $V_2$ vasopressin receptors. OT receptors increase dramatically during the course of pregnancy. The concentration of OT receptors has been shown to correlate with spontaneous uterine activity (M. Maggi et al. *J. Clin. Endocrinol Metabol;* 70; 1142, 1990). Premature labor, though, and premature birth is undesired as it represents a major cause of perinatal morbidity and mortality. Hence, the management of preterm labor represents a significant problem in the field of obstetrics.

Vasopressin is a cyclic nonapeptide hormone that exhibits a series of physiological effects including free water reabsorption, vasoconstriction, cellular proliferation and adrenocorticotrophic hormone (ACTH) secretion. In a healthy organism, vasopressin plays an important role in the homeostasis of fluid osmolality and volume status. However, in several diseases or conditions such as the syndrome of inappropriate secretion of vasopressin, congestive heart failure, arterial hypertension, liver cirrhosis, nephrotic syndrome, dysmenorrhea and ocular hypertension, vasopressin is assumed to play an important role (Thibonnier et al. *Adv. Rev. Pharmacol. Toxicol.,* 2001; 41: 175-202; Thibonnier et al. *Adv. Exp. Med. Biolog.;* 1998; 449: 251-203).

In recent years, strong evidence has accumulated indicating that the hormone oxytocin plays a major role in iniating labor in mammals, in particular in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process. This "up-regulation" of oxytocin receptors and increased uterine sensitivity seems to be due to trophic effects of rising plasma levels of estrogen towards term. By down-regulating oxytocin, it is expected that both the direct (contractile) and indirect (increased prostaglandin synthesis) effects of oxytocin on the uterine could be blocked. An oxytocin modulator, e.g. blocker or antagonists would likely be more efficacious for treating preterm labor than current regimens. Moreover, as oxytocin at term has only an effect on the uterus, such an oxytocin modulator would have only few or no side effects.

A further condition being related to oxytocin is dysmenorrhea, which is characterised by cyclic pain associated with menses during ovulatory cycles. Said pain is believed to result from uterine contractions and ischemia, probably mediated by the effect of prostaglandins produced in the secretory endometrium. By blocking both the indirect and direct effects of oxytocin on the uterus, an oxytocin antagonist is belived more efficacious for treating dysmenorrhea than current regimens.

Some agents counteracting the action of oxytocin are currently used in clinical studies. Such tocolytic agents (i.e. uterine-relaxing agents) include beta-2-adrenergic agonists, magnesium sulfate and ethanol. The leading beta-2-adrenergic agonists is Ritodrine, which causes a number of cardiovascular and metabolic side effects, including tachycardia, increased renin secretion, hyperglycemia and reactive hypoglycemia in the infant. Further beta-2-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

The principal drawback to the use of peptide antagonists including also atosiban is the problem of low oral bioavailability resulting from intestinal degradation. Hence, they must be administered parenterally.

The development of non-peptide ligands for peptide hormone receptors are expected to overcome this problem. Small molecule selective oxytocin antagonists have been reported by Merck. In addition to cyclic hexapeptides, Merck suggested indanylpiperidines and tolyl-piperazines as orally deliverable OT antagonists (Evans et al. *J. Med. Chem.,* 35, 3919 (1992). In WO 96/22775 and U.S. Pat. No. 5,756,497 Merck reported benzoxazinylpiperidines or benzoxazinones as OT receptor antagonists.

Specific sulfonamides have been reported to antagonize ocytocin at the ocytocin receptor. Elf Sanofi's EP-A-0469984 and EP-A-0526348 report N-sulfonyl indolines acting as antagonists of the vasopressin and the oxytocin receptors.

It is an object of the present invention to provide substances which down-regulate—up to antagonizing—the function of OT and/or V1a in disease states in animals, preferably mammals, especially in humans. It is another object of this invention to provide a method of antagonizing the functions of the OT and/or V1a receptors in disease states of mammals. It is also an objective of the present invention to provide small molecule chemical compounds for the modulation, preferably the down-regulation or even antagonisation of the oxytocin receptor. Moreover, it is an objective of the present invention to provide methods for preparing said small molecule chemical compounds. It is furthermore an object of the present invention to provide a new category of pharmaceutical formulations for the treatment of preterm labor and dysmenorrhea, and/or diseases mediated by the oxytocin receptor. It is finally an object of the present invention to provide a method of treating or prevent disorders mediated by the oxytocin receptor, like preterm labor, inappropriate secretion of vasopressin, congestive heart failure, arterial hypertension, liver cirrhosis, nephrotic syndrome, dysmenorrhea and ocular hypertension with oxytocin and/or vasopressin antagonists, acting for example by antagonising the binding of oxytocin and/or vasopressin to their receptor.

DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, such as, for example, benzyl, phenethyl and the like.

"Heteroaryl" refers to a monocyclic heteromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrehydroisoquinolyl, purinyl, pteridinyl, carbazolyl, xanthenyl or benzoquinolyl and the like.

"$C_1$-$C_6$-alkyl heteroaryl" refers to $C_1$-$C_6$-alkyl groups having a heteroaryl substituent, such as, for example, 2-furylmethyl, 2-thienylmethyl, 2-(1H-indol-3-yl)ethyl and the like.

"Alkenyl" refers to alkenyl groups preferably having from 2 to 6 carbon atoms and having one or more sites of alkenyl unsaturation. Preferred alkenyl groups include ethenyl (—CH═CH$_2$), n-2-propenyl (allyl, —CH$_2$CH═CH$_2$) and the like.

"Alkynyl" refers to alkynyl groups preferably having from 2 to 6 carbon atoms and having one or more sites of alkynyl unsaturation. Preferred alkynyl groups include ethynyl (—C≡CH), propargyl (—CH$_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R'is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to a group "—SO$_2$—R" wherein R is selected from H, "$C_1$-$C_6$-alkyl", "$C_1$-$C_6$-alkyl" optionally substituted with halogens, such as, for example, an —SO$_2$—CF$_3$ group, "aryl", "heteroaryl", "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alyl", "$C_1$-$C_6$-alkyl" optionally substituted with halogens, such as, for example, an —SO—CF$_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-aryl aryl", "$C_1$-$C_6$-alkyl heteroaryl", "$C_2$-$C_6$-alkenyl", "$C_2$-$C_6$-alkynyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of Formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the Formula —NR,R',R" $^+$ Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phos-phate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have the inventive set out activity as OT-R antagonists.

The term "preterm labor" or the term "premature labor" shall mean expulsion from the uterus of a viable infant before the normal end of gestation, or more particularly, onset of labor with effacement and dilation of the cervix before the $37^{th}$ week of gestation. It may or may not be associated with vaginal bleeding or rupture of the membranes.

The term "dismenorrhea" shall mean painful menstruation.

The term "cesarean delivery" shall mean incision through the abdominal and uterine walls for delivery of a fetus.

It has now been found that sulfanilide derivatives according to Formula I, set out below, are suitable pharmaceutically active agents, by effectively modulating, in particular by effectively inhibiting the OT-R function and more specifically by antagonising the oxytocin receptor. When compounds according to Formula I are used, oxytocin is antagonised by being prevented to interact with its receptor and is therefore unable to exert its biologic or pharmacological effects. The compounds of the present invention are therefore particularly useful in the treatment and/or prevention of oxytocin-related disorders of mammals and in particular of humans. Disorders mediated by the oxytocin receptor are primarily preterm labor and dysmenorrhea.

The present invention thus provides the use of sulfanilides of Formula I:

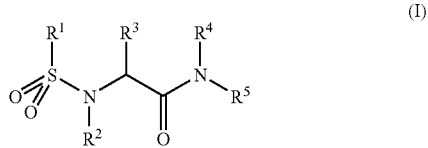

(I)

for the treatment of preterm labor, premature birth, dysmenorrhea, inappropriate secretion of vasopressin, congestive heart failure, arterial hypertension, liver cirrhosis, nephrotic syndrome and ocular hypertension.

Compounds of Formula (I) include also their geometrical isomers, their optically active forms as enantiomers, diastereomers and its racemate forms, as well as pharmaceutically acceptable salts thereof, wherein:

$R^1$ and $R^2$ are "aryl" or "heteroaryl" groups, which may be fused with 1-2 further cycloalkyl or aryl or heteroaryl groups.

Said "aryl" or "heteroaryl" may be substituted with 1 to 5 substituents independently selected from the group consisting of: "$C_1$-$C_6$-alkyl", "$C_1$-$C_6$-alkyl aryl", "$C_1$-$C_6$-alkyl heteroaryl", "$C_1$-$C_6$-alkyl cycloalkyl", "$C_2$-$C_6$-alkenyl", "$C_2$-$C_6$-alkynyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl, 2-alkoxyethoxy, 2-(2-alkoxyethoxy)ethoxy, 2-hydroxyethoxy, 2-(2-hydroxyethoxy)ethoxy, 2-(dimethylamino)ethoxy, 2-(2-(dimethylamino)ethoxy)ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl]ethoxy, 2-[(2-hydroxyethyl)sulfanyl]ethoxy, 2-[(2-carboxyethyl)sulfanyl]ethoxy, 2-[(2-carboxymethyl)sulfanyl]ethoxy, 2-[(2-sulfoxyethyl)sulfanyl]ethoxy and the like.

$R^3$ is selected from the group consisting of H, "$C_1$-$C_6$-alkyl", such as, e.g., hydroxymethyl, 1-hydroxyethyl, 2-hydroxyethyl, carboxymethyl, (aminocarbonyl)methyl, 2-carboxyethyl, 2-aminocarbonylethyl, 3-aminopropyl, 4-aminobutyl, 3-guanidinopropyl and the like, "$C_1$-$C_6$-alkyl aryl", such as, e.g. phenylmethyl, 2-phenylethyl, hydroxy (phenyl)methyl and the like, "$C_1$-$C_6$-alkyl heteroaryl", such as, e.g., (imidazol-4-yl)methyl, (indol-3-yl)methyl, (pyrid-2-yl)methyl, (pyrid-3-yl)methyl, (pyrid-4-yl)methyl, (thien-2-yl)methyl, (thien-3-yl)methyl and the like, "$C_2$-$C_6$-alkenyl", "$C_2$-$C_6$-alkynyl". Preferred are H and "$C_1$-$C_6$-alkyl", like a methyl or a ethyl group.

$R^4$ and RW are independently selected from the group consisting of hydrogen, $C_1$-$C_6$ alkyl, $C_2$-$C_6$ alkenyl, $C_2$-$C_6$ alkynyl, saturated or unsaturated 3-8-membered cycloalkyl which may contain 1 to 3 heteroatoms selected from N, O, S, aryl, heteroaryl, $C_1$-$C_6$-alkyl aryl, $C_1$-$C_6$-alkyl heteroaryl and the like.

Alternatively, $R^4$ and $R^5$ may form together with the N atom—to which they are attached—a 3-8 membered saturated or unsaturated heterocyclic ring which may contain 1-2 further heteroatoms. Said heteroatoms are preferably selected from N, S and O. Said heterocyclic ring may optionally be fused with an aryl, heteroaryl or 3-8 membered saturated or unsaturated cycloalkyl ring.

According to a further embodiment, $R^4$ can be H or $C_1$-$C_6$ alkyl, and $R^5$ may be —N=$CR^6R^7$, wherein:

$R^6$ is an "aryl" or a "heteroaryl" group optionally substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups, "acyl", "acyloxy", "acylamino", "amino-carbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl, 2-alkoxyethoxy, 2-(2-alkoxyethoxy)ethoxy, 2-hydroxyethoxy, 2-(2-hydroxyethoxy)ethoxy, 2-(dimethylamino) ethoxy, 2-(2-(dimethyl-amino)ethoxy)ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl]ethoxy, 2-[(2-hydroxyethyl)sulfanyl]ethoxy, 2-[(2-carboxyethyl)sulfanyl]ethoxy, 2-[(2-carboxymethyl)-sulfanyl]ethoxy, 2-[(2-sulfoxyethyl)sulfanyl] ethoxy and the like;

$R^7$ is selected from the group consisting of H, "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", "acyl", "aminocarbonyl", "alkoxycarbonyl", "aryl", "heteroaryl", carboxyl, cyano, sulfonyl and the like.

Alternatively, $R^6$ and $R^7$ may form together with the C atom to which they are attached a 3-8 membered saturated or unsaturated heterocyclic ring which may contain 1-2 further heteroatoms selected from N, S and O and which is optionally fused with an aryl, heteroaryl or 3-8 membered saturated or unsaturated cycloalkyl ring.

Preferably, the compounds according to Formula I are suitable for the modulation of the oxytocin and/or vasopressin (in particular the $V_{1a}$) function, thus specifically allowing the treatment and/or prevention of disorders which are mediated by the oxytocin and/or vasopressin receptor. Said treatment involves the modulation—in particular the down regulation or the antagonisation—of the oxytocin and/or vasopressin receptor.

More specifically, the compounds of the present invention are useful for the treatment of preterm labor, premature birth, dysmenorrhea, inappropriate secretion of vasopressin, congestive heart failure, arterial hypertension, liver cirrhosis, nephrotic syndrome, ocular hypertension and for stopping labor prior to cesarean delivery. The compounds of the present invention are in particular useful for the treatment of preterm labor, premature birth, dysmenorrhea.

Preferred $R^1$ and $R^2$ groups are aryl and heteroaryl rings, whereby either or both of said rings are substituted with 1 or 2 substituents selected from the group consisting of halogens, cyano, $C_1$-$C_6$-alkyl, primary, secondary amines or $C_1$-$C_6$-alkoxy groups. Particularly preferred substituents are alkoxy groups such as, for example, methoxy, ethoxy groups and substituted ethoxy groups such as, for example, 2-alkoxyethoxy, 2-(2-alkoxyethoxy)ethoxy, 2-hydroxyethoxy, 2-(2-hydroxyethoxy)ethoxy, 2-(dimethylamino)ethoxy, 2-(2-(dimethylamino)ethoxy)ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl]ethoxy, 2-[(2-hydroxyethyl)sulfanyl]ethoxy, 2-[(2-carboxyethyl)sulfanyl]ethoxy, 2-[(2-carboxymethyl)sulfanyl]ethoxy, 2-[(2-sulfoxyethyl)sulfanyl]ethoxy.

Preferred sulfanilide derivatives are compounds according to Formula I, wherein $R^1$ and $R^2$ are unsubstituted or substituted aryl and mor particularly preferred are sulfanilides of Formula I wherein $R^1$ and $R^2$ are unsubstituted or substituted phenyl.

Particularly preferred sulfanilides are compounds according to Formula I wherein $R^1$ and $R^2$ are unsubstituted or substituted phenyl rings, $R^3$ and $R^4$ are H, and $R^5$ is a group $N=CR^6R^7$ thus giving sulfanilides of the Formula II:

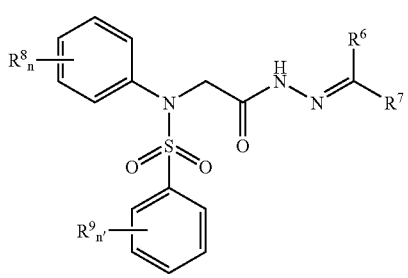

(II)

Formula (II) also comprises tautomeric forms, such as, for example, the keto-enol form of the carbonyl group or the different forms of the group —$N=CR^6R^7$, its geometrical isomers, its optically active forms as enantiomers, diastereomers and its racemate forms, as well as pharmaceutically acceptable salts thereof. In Formula (II) the substituents are as follows:

$R^6$ is an "aryl" or "heteroaryl" group.

$R^7$ of Formula II is selected from the group consisting of H, "$C_1$-$C_6$-alkyl", "$C_1$-$C_6$-alkyl aryl", "$C_1$-$C_6$-alkyl heteroaryl", "$C_1$-$C_6$-alkyl cycloalkyl, "$C_2$-$C_6$-alkenyl", "$C_2$-$C_6$-alkynyl", "acyl", "aminocarbonyl", "alkoxycarbonyl", "aryl", "heteroaryl", carboxyl, cyano, sulfonyl.

Alternatively, $R^6$ and $R^7$ form together with the C atom to which they are attached a 3-8 membered saturated or unsaturated heterocyclic ring which may contain 1-2 further heteroatoms selected from N, S and O and which may be fused with an aryl, heteroaryl or 3-8 membered cycloalkyl ring.

Further particularly preferred sulfanilide derivatives of Formula II are compounds wherein $R^6$ is an phenyl and $R^7$ is hydrogen or $C_1$-$C_6$-alkyl; or $R^1$ and $R^7$ form together a tetrahydroisoquinoline or oxindole group. Most preferred are compounds of Formula II wherein or $R^6$ and $R^7$ are together an oxindole group.

$R^8$ and $R^9$ selected from the group consisting of "$C_1$-$C_6$-alkyl", "$C_1$-$C_6$-alkyl aryl", "$C_1$-$C_6$-alkyl heteroaryl", "$C_1$-$C_6$-alkyl cycloalkyl, "$C_2$-$C_6$-alkenyl", "$C_2$-$C_6$-alkynyl", primary, secondary or tertiary amino groups or quarternary ammonium moieties, "acyl", "acyloxy", "acylamino", "aminocarbonyl", "aLkoxycarbonyl", "aryl", "heteroaryl", carbonyl, carboxyl, cyano, halogen, hydroxy, mercapto, nitro, sulfoxy, sulfonyl, $C_1$-$C_6$-alkoxy, thioalkoxy, with the proviso that $R^8$ is not a carbonyl moiety in the 2 position (ortho).

Alternatively, 2 substituents of $R^8$ and/or of $R^9$ may undergo ring closure, in particular when vicinal functional substituents are involved, thus forming e.g. lactams, lactons, cyclic anhydrides, but also acetals, thioacetals, aminals formed by ring closure for instance in an effort to obtain a protective group. n and n' are independently selected from 1 to 5.

More preferred $R^8$ and $R^9$ are halogen, $C_1$-$C_6$-alkyl or $C_1$-$C_6$-alkoxy groups. Particularly preferred are alkoxy groups such as, for example, methoxy, ethoxy groups and substituted ethoxy groups such as, for example, 2-aloxyethoxy, 2-(2-alkoxyethoxy)ethoxy, 2-hydroxyethoxy, 2-(2-hydroxyethoxy)ethoxy, 2-(dimethylamino)ethoxy, 2-(2-(dimethylamino)ethoxy)ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl]ethoxy, 2-[(2-hydroxyethyl)sulfanyl]ethoxy, 2-[(2-carboxyethyl)sulfanyl]ethoxy, 2-[(2-carboxymethyl)sulfanyl]ethoxy, 2-[(2-sulfoxyethyl)sulfanyl]ethoxy.

Further particularly preferred sulfanilides are compounds according to Formula I wherein $R^1$ and $R^2$ are unsubstituted or substituted phenyl rings, $R^3$ is H thus giving sulfanilides of the Formula Ia:

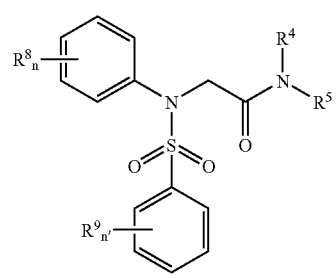

(Ia)

$R^4$ and $R^5$ of Formula Ia are independently selected from the group consisting of H, "$C_1$-$C_6$-alkyl", "$C_1$-$C_6$-alkyl aryl", "$C_1$-$C_6$-alkyl heteroaryl", "$C_1$-$C_6$-alkyl cycloalkyl, "$C_2$-$C_6$-alkenyl", "$C_2$-$C_6$-alkynyl", "acyl", "aminocarbonyl", "alkoxycarbonyl", "aryl", "heteroaryl", carboxyl, cyano, sulfonyl.

Alternatively, $R^4$ and $R^5$ form together with the C atom to which they are attached a 3-8 membered saturated or unsaturated heterocyclic ring which may contain 1-2 further heteroatoms selected from N, S and O and which may be fused with an aryl, heteroaryl or 3-8 membered cycloalkyl ring.

Further particularly preferred sulfanilide derivatives of Formula Ia are compounds wherein $R^4$ is hydrogen or "$C_1$-$C_6$-alkyl", and $R^5$ is an acetamide, propionic amide, propionic acid moiety, being substituted by "$C_1$-$C_6$-alkyl", "$C_1$-$C_6$-alkoxy", "$C_1$-$C_6$-alkyl aryl", "$C_1$-$C_6$-alkyl heteroaryl", "$C_1$-$C_6$-alkyl cycloalkyl. Alternatively preferred compounds of Formula (Ia) are those wherein $R^4$ and $R^5$ form together a pyrrolidine, piperidine, tetrahydroisoquinoline, isoindole or indole ring, optionally carrying an acetamide, propionic amide or propionic acid moiety and which may be substituted by "$C_1$-$C_6$-alkyl", "$C_1$-$C_6$-alkoxy", "$C_1$-$C_6$-alkyl aryl", "$C_1$-$C_6$-alkyl heteroaryl", "$C_1$-$C_6$-alkyl cycloalkyl.

$R^8$ and $R^9$ are selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarternary ammonium moieties, "acyl", "acyloxy", "acylamino", "aminocarbonyl", "alkoxycarbonyl", "aryl", "heteroaryl", carbonyl, carboxyl, cyano, halogen, hydroxy, mercapto, nitro, sulfoxy, sulfonyl, $C_1$-$C_6$-alkoxy, thioalkoxy.

Alternatively, $R^8$ and $R^9$ may undergo ring closure, in particular when vicinal functional substituents are involved, thus forming e.g. lactams, lactons, cyclic anhydrides, but also acetals, thioacetals, aminals formed by ring closure for instance in an effort to obtain a protective group n and n' are independently selected from 1 to 5.

More preferred $R^8$ and $R^9$ are halogen, $C_1$-$C_6$-alkyl or $C_1$-$C_6$-alkoxy groups. Particularly preferred are alkoxy groups such as, for example, methoxy, ethoxy groups and substituted ethoxy groups such as, for example, 2-alkoxyethoxy, 2-(2-alkoxyethoxy)ethoxy, 2-hydroxyethoxy, 2-(2-hydroxyethoxy)ethoxy, 2-(dimethylamino)ethoxy, 2-(2-(dimethylamino)ethoxy)ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl]ethoxy, 2-[(2-hydroxyethyl)sulfanyl]ethoxy, 2-[(2-carboxyethyl)sulfanyl]ethoxy, 2-[(2-carboxymethyl)sulfanyl]ethoxy, 2-[(2-sulfoxyethyl)sulfanyl]ethoxy.

Preferred pharmaceutically acceptable salts of compounds of Formulae I, Ia and II containing a basic residue such as, for example, a primary, secondary, or tertiary amine or a pyridyl moiety, are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The compounds of Formulae I, Ia and II may contain one or more asymmetric centers and may therefore exist as enantiomers or diastereoisomers. It is to be understood that the invention includes both mixtures and separate individual isomers or enantiomers of the compounds of Formula I and Formula II. In a particularly preferred embodiment the sulfanilide derivatives according to Formula I or Formula II containing an asymmetric centre are obtained in an enantiomeric excess of at least 52% ee, preferably of at least 92-98% ee. Also both mixtures and separate individual E/Z geometrical isomers with regard to the sulfanilide derivatives of the present invention, for example hydrazones of Formula II wherein $R^8$ and $R^9$ are are different from each other, are comprised within the scope of the present invention. Tautomeric forms with regard to the sulfanilides of the present invention, such as those present in the hydrazones or in the keto-enol forms of the carbonyl of compounds of Formula II, are also comprised within the scope of the present invention.

A further aspect of the present invention consists in the actually novel compounds of Formula I. They are specified by the ensuing Formulae (IIa) and (Ib):

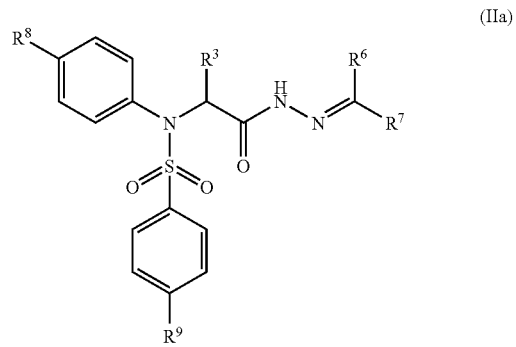

(IIa)

whereby:

$R^3$ is either H or "$C_1$-$C_6$-alkyl", more preferred H.

$R^6$, $R^7$ of Formula II are independently selected from the group consisting of H, "$C_1$-$C_6$-alkyl", "$C_1$-$C_6$-alkyl aryl", "$C_1$-$C_6$-alkyl heteroaryl", "$C_1$-$C_6$-alkyl cycloalkyl", "$C_2$-$C_6$-alkenyl", "$C_2$-$C_6$-alkynyl", "acyl", "aminocarbonyl", "alkoxycarbonyl", "aryl", "heteroaryl", carboxyl, cyano, sulfonyl.

Alternatively, $R^6$ and $R^7$ form together with the C atom to which they are attached a 3-8 membered saturated or unsaturated cyclic or heterocyclic ring which may contain 1-2 further heteroatoms selected from N, S and O and which may be fused with an aryl, heteroaryl or 3-8 membered cycloalkyl ring.

Further particularly preferred sulfanilide derivatives of Formula II are compounds wherein $R^1$ is phenyl and $R^7$ is hydrogen or $C_1$-$C_6$-alkyl; or $R^6$ and $R^7$ form together a tetrahydroisoquinoline or oxindole group. Most preferred are compounds of Formula IIa wherein or $R^6$ and $R^7$ form together an oxindole ring.

$R^8$ is H, halogen or "$C_1$-$C_6$-alkyl".

$R^9$ is selected from the group consisting of —X—($C_1$-$C_6$-alkyl)-Y, whereby X is a bond, O, NR, —CONR; Y is a 3-8-membered cycloalkyl, a 3-8-membered cycloalkyl containing 1-3 heteroatoms selected from N, O, S, aryl, heteroaryl, OR, NRR', —(C=O)—NRR', with R, R' independently being H, "$C_1$-$C_6$-alkyl", "$C_1$-$C_6$-alkyl aryl", "$C_1$-$C_6$-alkyl heteroaryl", "$C_1$-$C_6$-alkyl cycloalkyl", "$C_1$-$C_6$-alkoxy" or R, R' form together with the N atom—to which they are attached—a 3-8 membered saturated or unsaturated heterocyclic ring which may contain 1-2 further heteroatoms selected from N, S and O and which may be fused with an aryl, heteroaryl or 3-8 membered cycloalkyl ring.

Novel compounds of Formula Ib are as follows:

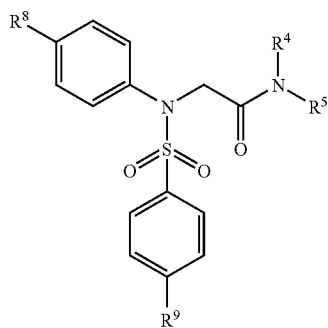

(Ib)

$R^8$ and $R^9$ are independently selected from H, halogen, "$C_1$-$C_6$-alkoxy" or "$C_1$-$C_6$-alkyl".

$R^4$ is hydrogen or "$C_1$-$C_6$-alkyl" and $R^5$ is an acetamide, a propionic amide, a propionic acid moiety, being substituted by "$C_1$-$C_6$-alkyl", "$C_1$-$C_6$-alkyl aryl", "$C_1$-$C_6$-alkyl heteroaryl", "$C_1$-$C_6$-alkoxy".

Alternatively, $R^4$ and $R^5$ form together with the nitrogen atom—to which they are attached—a pyrrolidine, piperidine, tetrahydroisoquinoline, isoindole or indole ring carrying an acetamide, propionic amide or propionic acid moiety. Said acetamide, propionic amide or propionic acid moiety may be substituted by "$C_1$-$C_6$-alkyl", "$C_1$-$C_6$-alkyl aryl", "$C_1$-$C_6$-alkyl heteroaryl", "$C_1$-$C_6$-alkoxy".

Specific examples of compounds of Formula I include the following:

4-ethoxy-N-(2-{(2E)-2-[1-(2-hydroxyphenyl)ethylidene]hydrazino}-2-oxoethyl)-N-(4-methylphenyl)benzenesulfonamide 4-ethoxy-N-(4-methylphenyl)-N-{2-oxo-2-[(2Z)-2-(2-oxo-1,2-dihydro-3H-indol-3-ylidene)hydrazino]ethyl}benzenesulfonamide 4-ethoxy-N-{2-oxo-2-[(2E)-2-(2-oxo-1,2-dihydro-3H-indol-3-ylidene)hydrazino]ethyl}-N-phenylbenzenesulfonamide 4-ethoxy-N-[2-((2E)-2-{5-[hydroxy(oxido)amino]-2-oxo-1,2-dihydro-3H-indol-3-ylidene}hydrazino)-2-oxoethyl]-N-phenylbenzenesulfonamide 4-ethoxy-N-{2-[(2E)-2-(5-iodo-2-oxo-1,2-dihydro-3H-indol-3-ylidene)hydrazino]-2-oxoethyl}-N-phenylbenzenesulfonamide 4-ethoxy-N-(2-hydrazino-2-oxoethyl)-N-(4-methylphenyl)benzenesulfonamide N-(4-methylphenyl)-N-{2-oxo-2-[(2E)-2-(2-oxo-1,2-dihydro-3H-indol-3-ylidene)hydrazino]ethyl}-1-naphthalenesulfonamide N-(4-methylphenyl)-N-{2-oxo-2-[(2E)-2-(2-oxo-1,2-dihydro-3H-indol-3-ylidene)hydrazino]ethyl}-2-naphthalenesulfonamide 4-chloro-N-(4-methylphenyl)-N-{2-oxo-2-[(2E)-2-(2-oxo-1,2-dihydro-3H-indol-3-ylidene)hydrazino]ethyl}benzenesulfonamide 4-methoxy-N-(4-methylphenyl)-N-{2-oxo-2-[(2E)-2-(2-oxo-1,2-dihydro-3H-indol-3-ylidene)hydrazino]ethyl}benzenesulfonamide 4-methyl-N-(4-methylphenyl)-N-{2-oxo-2-[(2E)-2-(2-oxo-1,2-dihydro-3H-indol-3-ylidene)hydrazino]ethyl}benzenesulfonamide 4-cyano-N-(4-methylphenyl)-N-{2-oxo-2-[(2E)-2-(2-oxo-1,2-dihydro-3H-indol-3-ylidene)hydrazino]ethyl}benzenesulfonamide 4-ethoxy-N-{2-[(2Z)-2-(2-fluorobenzylidene)hydrazino]-2-oxoethyl}-N-(4-methylphenyl)benzenesulfonamide (3E)-3-[({[(4-ethoxyphenyl)sulfonyl]-4-methylanilino}acetyl)hydrazono]-2-oxo-2,3-dihydro-1H-indole-5-sulfonic acid N-(4-methylphenyl)-N-{2-oxo-2-[(2E)-2-(2-oxo-1,2-dihydro-3H-indol-3-ylidene)hydrazino]ethyl}[1,1'-biphenyl]-4-sulfonamide N-(4-methylphenyl)-N-{2-oxo-2-[(2E)-2-(2-oxo-1,2-dihydro-3H-indol-3-ylidene)hydrazino] ethyl}-4-phenoxybenzenesulfonamide 4-ethoxy-N-{2-[(2Z)-2-(2-hydroxybenzylidene)hydrazino]-2-oxoethyl}-N-(4-methylphenyl)benzenesulfonamide N-(2-{(2Z)-2-[4-(diethylamino)-2-hydroxybenzylidene]hydrazino}-2-oxoethyl)-4-ethoxy-N-(4-methylphenyl)benzenesulfonamide 4-ethoxy-N-(2-{(2Z)-2-[(2-hydroxy-1-naphthyl)methylene]hydrazino}-2-oxoethyl)-N-(4-methylphenyl)benzenesulfonamide 4-ethoxy-N-(4-methylphenyl)-N-{2-oxo-2-[(2Z)-2-(3-oxo-2,3-dihydro-1H-inden-1-ylidene)hydrazino]ethyl}benzenesulfonamide 4'-methoxy-N-(4-methylphenyl)-N-{2-oxo-2-[(2Z)-2-(2-oxo-1,2-dihydro-3H-indol-3-ylidene)hydrazino]ethyl}[1,1'-biphenyl]4-sulfonamide 4-ethoxy-N-{2-[(2Z)-2-(1-methyl-2-oxo-1,2-dihydro-3H-indol-3-ylidene)hydrazino]-2-oxoethyl}-N-(4-methylphenyl)benzenesulfonamide N-(2-{(2E)-2-[1-(2,4-dihydroxyphenyl)ethylidene]hydrazino}-2-oxoethyl)-4-ethoxy-N-(4-methylphenyl)benzenesulfonamide 3,4-dimethoxy-N-(4-methylphenyl)-N-{2-oxo-2-[(2E)-2-(2-oxo-1,2-dihydro-3H-indol-3-ylidene)hydrazino]ethyl}benzenesulfonamide 4-ethoxy-N-(2-{(2Z)-2-[1-(2-hydroxy-1-naphthyl)ethylidene]hydrazino}-2-oxoethyl)-N-(4-methylphenyl)benzenesulfonamide 4-ethoxy-N-(2-{(2E)-2-[1-(1-hydroxy-2-naphthyl)ethylidene]hydrazino}-2-oxoethyl)-N-(4-methylphenyl)benzenesulfonamide 4-tert-butyl-N-(4-chlorophenyl)-N-{2-oxo-2-[(2E)-2-(2-oxo-1,2-dihydro-3H-indol-3-ylidene)hydrazino]ethyl}benzenesulfonamide N-(4-chlorophenyl)-3,4-diinethoxy-N-{2-oxo-2-[(2E)-2-(2-oxo-1,2-dihydro-3H-indol-3-ylidene)hydrazino]ethyl}benzenesulfonamide 4-tert-butyl-N-(4-methylphenyl)-N-{2-oxo-2-[(2E)-2-(2-oxo-1,2-dihydro-3H-indol-3-ylidene)hydrazino]ethyl}benzenesulfonamide N-(4-methylphenyl)-N-{2-oxo-2-[(2E)-2-(2-oxo-1,2-dihydro-3H-indol-3-ylidene)hydrazino]ethyl}4-propylbenzenesulfonamide 4-butoxy-N-(4-methylphenyl)-N-{2-oxo-2-[(2E)-2-(2-oxo-1,2-dihydro-3H-indol-3-ylidene)hydrazino]ethyl}benzenesulfonamide 4-butoxy-N-(4-chlorophenyl)-N-{2-oxo-2-[(2Z)-2-(2-oxo-1,2-dihydro-3H-indol-3-ylidene)hydrazino]ethyl}benzenesulfonamide N-(4-chlorophenyl)-N-{2-oxo-2-[(2Z)-2-(2-oxo-1,2-dihydro-3H-indol-3-ylidene)hydrazino]ethyl}-4-propoxybenzenesulfonamide N-(4-methylphenyl)-N-{2-oxo-2-[(2Z)-2-(2-oxo-1,2-dihydro-3H-indol-3-ylidene)hydrazino]ethyl}-4-tert-pentylbenzenesulfonamide N-(4-methylphenyl)-N-{2-oxo-2-[(2Z)-2-(2-oxo-1,2-dihydro-3H-indol-3-ylidene)hydrazino]ethyl}-4-propoxybenzenesulfonamide N-(4-methylphenyl)-N-{2-oxo-2-[(2Z)-2-(2-oxo-1,2-dihydro-3H-indol-3-ylidene)hydrazino]ethyl}-2-thiophenesulfonamide N-(4-chlorophenyl)-N-{2-oxo-2-[(2Z)-2-(2-oxo-1,2-dihydro-3H-indol-3-ylidene)hydrazino]ethyl}-2-thiophenesulfonamide N-(4-chlorophenyl)-N-{2-[(2E)-2-(2-hydroxybenzylidene)hydrazino]-2-oxoethyl}-3,4-dimethoxybenzenesulfonamide N-(4-chlorophenyl)-4-ethoxy-N-{2-[(2E)-2-(2-hydroxybenzylidene)hydrazino]-2-oxoethyl}benzenesulfonamide N-(4-chlorophenyl)-N-{2-oxo-2-[(2Z)-2-(2-oxo-1,2-dihydro-3H-indol-3-ylidene)hydrazino]ethyl}-4-tert-pentylbenzenesulfonamide N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide N-(4-chlorophenyl)-N-{2-oxo-2-[(2Z)-2-(2-oxo-1,2-dihydro-3H-indol-3-ylidene)hydrazino]ethyl}benzenesulfonamide N-(4-chlorophenyl)-N-{2-oxo-2-[(2Z)-2-(2-oxo-1,2-dihydro-3H-indol-3-ylidene)hydrazino]ethyl}4-propylbenzenesulfonamide 4-ethoxy-N-{1-methyl-2-oxo-2-[(2Z)-2-(2-oxo-1,2-dihydro-3H-indol-3-ylidene)hydrazino]ethyl}-N-(4-methylphenyl)benzenesulfonamide 4-ethoxy-N-{1-(hydroxymethyl)-2-oxo-2-[(2Z)-2-(2-oxo-1,2-dihydro-3H-indol-3-ylidene)hydrazino]ethyl}-N-(4-methylphenyl)benzenesulfonamide N-(4-chlorophenyl)-4-ethoxy-N-{2-[(2E)-2-(1H-imidazol-2-ylmethylene)hydrazino]-2-oxoethyl}benzenesulfonamide N-(4-chlorophenyl)-4-ethoxy-N-{2-oxo-2-[(2E)-2-(2-pyridinylmethylene)hydrazino]ethyl}benzenesulfonamide 4-fluoro-N-(4-methylphenyl)-N-{2-oxo-2-[(2Z)-2-(2-oxo-1,2-dihydro-3H-indol-3-ylidene)hydrazino]ethyl}benzenesulfonamide 4-fluoro-N-{2-[(2E)-2-(2-hydroxybenzylidene)hydrazino]-2-oxoethyl}-N-(4-methylphenyl)benzenesulfonamide 4-ethoxy-N-[2-((2E)-2-{2-[hydroxy(oxido)aminobenzylidene}hydrazino)-2-oxoethyl]-N-(4-methylphenyl)benzenesulfonamide N-{2-[(2E)-2-(2-aminobenzylidene)hydrazino]-2-oxoethyl}-4-ethoxy-N-(4-methylphenyl)benzenesulfonamide N-(2-{(E)-[2-(2-{[(4-ethoxyphenyl)sulfonyl]-4-methylanilino}acetyl)hydrazono]methyl}phenyl)acetamide N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide N-(4-methylphenyl)-4-[2-(4-morpholinyl)ethoxy]-N-{2-oxo-2-[(2Z)-2-(2-oxo-1,2-dihydro-3H-indol-3-ylidene)hydrazino]ethyl}benzenesulfonamide N-(4-chlorophenyl)-4-[2-(dimethylamino)ethoxy]-N-{2-oxo-2-[(2Z)-2-(2-oxo-1,2-dihydro-3H-indol-3-ylidene)hydrazino]ethyl}benzenesulfonamide 4-[2-(dimethylamino)ethoxy]-N-(4-methylphenyl)-N-{2-oxo-2-[(2Z)-2-(2-oxo-1,2-dihydro-3H-indol-3-ylidene)hydrazino]ethyl}benzenesulfonamide 4-[3-(dimethylamino)propoxy]-N-(4-methylphenyl)-N-{2-oxo-2-[(2Z)-2-(2-oxo-1,2-dihydro-3H-indol-3-ylidene)hydrazino]ethyl}benzenesulfonamide N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide N-(4-chlorophenyl)-4-ethoxy-N-{2-oxo-2-[(2Z)-2-(2-oxo-1,2-dihydro-3H-pyrrolo[3,2-c]pyridin-3-ylidene)hydrazino]ethyl}benzenesulfonamide N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide 3-{4-[(4-methyl{2-oxo-2-[(2Z)-2-(2-oxo-1,2-dihydro-3H-indol-3-ylidene)hydrazino]ethyl{anilino)sulfonyl]phenyl}propanamide N-(4-chlorophenyl)-N-{2-oxo-2-[(2Z)-2-(2-oxo-1,2-dihydro-3H-indol-3-ylidene)hydrazino]ethyl}-4-(2-thienylmethoxy)benzenesulfonamide N-(4-chlorophenyl)-4-[2-(2-methoxyethoxy)ethoxy]-N-{2-oxo-2-[(2Z)-2-(2-oxo-1,2-dihydro-3H-indol-3-ylidene)hydrazino]ethyl}benzenesulfonamide N-(4-chlorophenyl)-4-(2-methoxyethoxy)-N-{2-oxo-2-[(2Z)-2-(2-oxo-1,2-dihydro-3H-indol-3-ylidene)hydrazino]ethyl}benzenesulfonamide N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide N-(4-chlorophenyl)-N-{2-oxo-2-[(2Z)-2-(2-oxo-1,2-dihydro-3H-indol-3-ylidene)hydrazino]ethyl}-4-[3-(2-pyridinyl)propoxy]benzenesulfonamide 4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide 4-ethoxy-N-{2-[(2E)-2-(1H-indol-3-ylmethylene)hydrazino]-2-oxoethyl}-N-(4-methylphenyl)benzenesulfonamide 4-ethoxy-N-(2-{(2E)-2-[(2-methyl-1H-indol-3-yl)methylene]hydrazino}-2-oxoethyl)-N-(4-methylphenyl)benzenesulfonamide N-(4-chlorophenyl)-4-[3-(dimethylamino)propoxy]-N-{2-oxo-2-[(2Z)-2-(2-oxo-1,2-dihydro-3H-pyrrolo[3,2-c]pyridin-3-ylidene)hydrazino]ethyl}benzenesulfonamide (3Z)-3-({[4-chloro({4-[3-(dimethylamino)propoxy]phenyl}sulfonyl)anilino]acetyl}hydrazono)-2-oxo-2,3-dihydro-1H-indole-7-carboxylic acid methyl (3Z)-3-({[4-chloro({4-[3-(dimethylamino)propoxy]phenyl}sulfonyl)anilino]acetyl}hydrazono)-2-oxo-2,3-dihydro-1H-indole-7-carboxylate 4-ethoxy-N-{2-oxo-2-[(2Z)-2-(2-oxo-1,2-dihydro-3H-indol-3-ylidene)hydrazino]ethyl}-N-(2-pyrimidinyl)benzenesulfonamide 3-{4-[(4-chloro{2-oxo-2-[(2Z)-2-(2-oxo-1,2-dihydro-3H-indol-3-ylidene)hydrazino]ethyl}anilino)sulfonyl]phenyl}-N-[3-(dimethylamino)propyl]propanamide N-(4-chlorophenyl)-4-[3-(4-methyl-1-piperazinyl)-3-oxopropyl]-N-{2-oxo-2-[(2Z)-2-(2-oxo-1,2-dihydro-3H-indol-3-ylidene)hydrazino]ethyl}benzenesulfonamide 3-(benzyloxy)-2-[({4-chloro[(3,4-dimethoxyphenyl)sulfonyl]anilino}acetyl)amino]propanamide 3-(benzyloxy)-2-({[4-chloro(phenylsulfonyl)anilino]acetyl}amino)propanamide 2-[({[(4-ethoxyphenyl)sulfonyl]-4-methylanilino}acetyl)amino]-2-phenylacetamide 3-(3,4-dichlorophenyl)-2-[({[(4-fluorophenyl)sulfonyl]-4-methoxyanilino}acetyl)amino]propanamide 2-[2-({[(4-ethoxyphenyl)sulfonyl]-4-methoxyanilino}acetyl)-1,2,3,4-tetrahydro-3-isoquinolinyl]acetamide 2-({[(4-ethoxyphenyl)sulfonyl]-4-methoxyanilino}acetyl)-1-isoindolinecarboxamide 2-[2-({[(3,4-diinethoxyphenyl)sulfonyl]-4-methoxyanilino}acetyl)-1,2,3,4-tetrahydro-3-isoquinolinyl]acetamide
N-({4-chloro[(4-ethoxyphenyl)sulfonyl]anilino}acetyl)valine
2-[({[(4-ethoxyphenyl)sulfonyl]-4-fluoroanilino}acetyl)amino]-3-(1H-indol-3-yl)propanamide
2-[({[(4-ethoxyphenyl)sulfonyl]-4-fluoroanilino}acetyl)amino]-2-phenylacetamide N-({[(3,4-dimethoxyphenyl)sulfonyl]-4-fluoroanilino}acetyl)valine 1-({[(4-ethoxyphenyl)sulfonyl]-4-methylanilino}acetyl)-5-phenyl-2-pyrrolidinecarboxamide
2-[2-({[(4-ethoxyphenyl)sulfonyl]anilino}acetyl)-1,2,3,4-tetrahydro-3-isoquinolinyl]acetamide
2-[2-({[(4-ethoxyphenyl)sulfonyl]-4-methylanilino}acetyl)-1,2,3,4-tetrahydro-3-isoquinolinyl]acetamide 2-[({[(4-ethoxyphenyl)sulfonyl]4-methoxyanilino}acetyl)amino]-4-phenylbutanamide
2-({[(4-ethoxyphenyl)sulfonyl]-4-methoxyanilino}acetyl)-1,2,3,4-tetrahydro-3-isoquinolinecarboxamide
2-[({[(4-ethoxyphenyl)sulfonyl]-4-methoxyanilino}acetyl)amino]-3-(1H-indol-3-yl)propanamide
1-({[(4-ethoxyphenyl)sulfonyl]-4-fluoroanilino}acetyl)-5-phenyl-2-pyrrolidinecarboxamide
3-(3,4-dichlorophenyl)-2-({[4-fluoro(phenylsulfonyl)anilino]acetyl}amino)propanamide A further object of the present invention is a process for preparing the sulfanilide derivatives according to Formula I, Ia, Ib and Formula II as well as IIa.

The sulfanilide derivatives exemplified in this invention may be prepared from readily available or previously described starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the parti-cular reactants or solvents used, but such conditions can be determined by one skilled in the art by routine optimisation procedures.

Generally, the sulfanilide derivatives according to the general Formula I and/or II may be obtained by several processes, using both solution-phase and solid-phase chemistry protocols. Depending on the nature of $R^1$-$R^9$, certain processes will, in some instances, be preferred over others, and it is assumed that the choice of the most suitable process will be known to the practitioner skilled in the art.

According to one process, sulfanilide derivatives according to the general Formula I, whereby C(O)—NR⁴R⁵ represents an amide moiety, with $R^4$ and $R^5$ being defined as above, are prepared from the corresponding carboxylic acids III (R═H) and primary or secondary amines IV, following solution-phase chemistry protocols such as described in the Examples and shown in Scheme 1, using conditions and methods well known to those skilled in the art to prepare an amide bond from an amine and a carboxylic acid or a carboxylic acid derivative, with standard peptide coupling agents, such as e.g. DIC, EDC, TBTU, DECP, or others.

According to another process, sulfanilide derivatives according to the general Formula I, whereby C(O)—NR⁴R⁵ represents an acyl hydrazone moiety C(O)—NH—N═CR⁸R⁹ (general Formula II, with $R^8$ and $R^9$ being defined as above, are prepared from the corresponding $C_1$-$C_6$-alkyl esters III (R═Me, for example), which are first converted to the corresponding hydrazides by treatment with hydrazine, followed by reaction with ketones or aldehydes V, using standard solution-phase chemistry protocols such as those described in the Examples and shown in Scheme 1. The ketones or aldehydes, V, are either commercial or can be prepared from readily available starting materials according to published litterature procedures (see e.g., Rivalle, C.; Bisagni, E. *J. Heterocyclic Chem.* 1997, 34, 441. Deady, L. W.; Kaye, A. J.; Finlay, G. J.; Baguley, B. C.; Denny, W. A. *J. Med. Chem.* 1997, 40, 2040), standard protocols, as hereinafter described in the Examples, or by other current methods well known to the practitioner skilled in the art.

Other derivatives of Formula I and/or of Formula II are prepared using known modifications to the Scheme 1 reaction sequence.

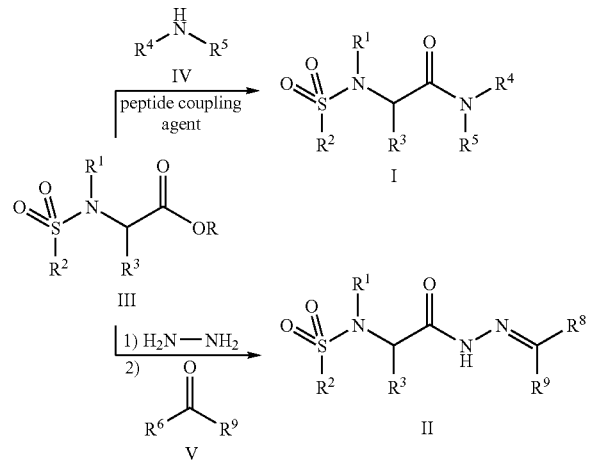

Scheme 1

Compounds of Formula III may be converted to alternative compounds III*, if $R_2$ is bearing an appropriate reactive group G and by employing suitable interconversion techniques as described in Scheme 2 and hereinafter in the Examples. G can be substituted by activated unsaturated chains, using Pd catalysed Heck reaction under usual reaction conditions described in the litterature as shown in Scheme 2 and reported hereinafter in the Examples. This unsaturated substituted alkyl chain, such as in compound IIIa, can optionally be hydrogenated and further transformed (reduction, saponification, amide formation, substitution, etc) following standard conditions well known to the person skilled in the art and as it is described below in the Examples. Resulting alternative intermediate III* can be converted into I or II following procedures described on Scheme 1 and hereinafter described in the Examples.

Scheme 2

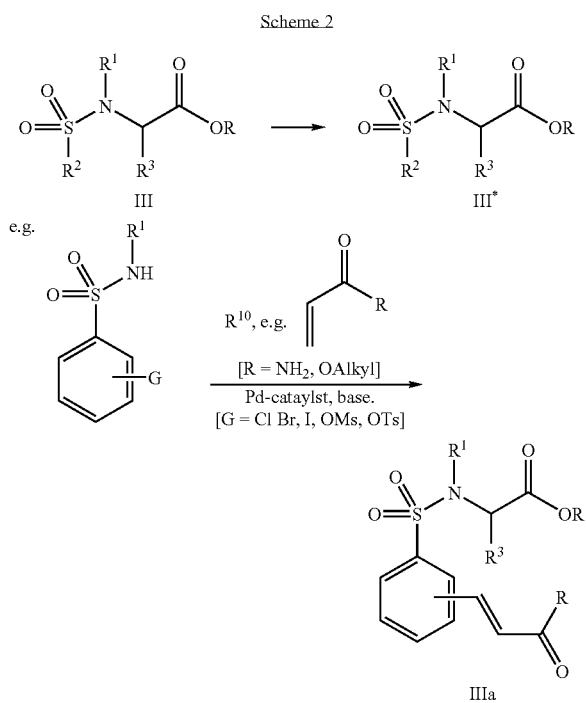

Compounds of Formula III, whereby the substituents $R^1$, $R^1$ and $R^3$ are as above defined, can be prepared from the corresponding N-aryl- or N-heteroaryl α-aminoacids or aminoacid esters, VI, by sulfonylation with aryl or heteroaryl sulfonyl chlorides VII, using standard synthetic techniques, as hereinafter described in the Examples and shown in Scheme 2. The aryl or heteroaryl sulfonyl chlorides, VII, are either commercial or may be prepared from readily available starting materials according to standard protocols, such as by chlorosulfonylation (see e.g., Ramage, R.; Green, J.; Blake, A. J. *Tetrahedron*, 1991, 47, 6353), as hereinafter described in the Examples, or by other current methods well known to the practitioner skilled in the art.

The corresponding N-aryl- or N-heteroaryl α-aminoacids or aminoacid esters, VI, can be prepared from the corresponding N-unsubstituted precursors VIII, using a variety of synthetic strategies, of which some selected examples are shown in Scheme 3 and described hereinafter in the Examples. Thus, the amino group of compounds of Formula VIII can for example be cross-coupled with aryl or heteroaryl halides and sulfonates, DX, using a base and an appropriate Pd-catalyst, the correct choice of will depend on the molecular context, as appreciated by one skilled in the art and as recently reviewed in extenso (Wolfe, J. P.; Tomori, H.; Sadighi, J. P.; Yin, J.; Buchwald, S. L. *J. Org. Chem.*, 2000, 65, 1158). The N-unsubstituted precursors VIII are notably naturally occuring and/or synthetic α-amino acids including Glycine, Serine, Tyrosine, Alanine, Valine, Leucine etc.

Alternatively, to get access to compounds of general Formula VI, compounds of Formula VIII can be reacted with electron-deficient aryl or heteroaryl fluorides and/or chlorides, X, under conditions suitable for $S_NAr$-type reactions. If the aryl component X contains a nitro-group, as shown in Scheme 3 and described hereinafter in the Examples, the resulting compound VI can optionally be carried on to nitro group reduction and further functionalization (acylation, sulfonylation, alkylation) of the resulting primary amino group, before eventually being converted to III by sulfonylation with VII.

As a further alternative, compounds of general Formula VI can be prepared from corresponding precursors of general Formula XI containing a suitable leaving group Z, by displacement of the latter with aryl or heteroaryl amines (e.g. anilines), XII, under standard conditions well known to the person skilled in the art. Compounds of Formula XI are either commercially available per se or readily accessible from commercial starting materials. In one particularly preferred synthetic approach, compounds of Formula XI whereby Z=Br and n=1 are made from suitably side-chain protected α-amino acids by treatment with $NaNO_2$ and HBr, as shown in Scheme 3 and described hereinafter in the Examples (see e.g., Souers, A. J.; Schuerer, S.; Kwack, H.; Virgilio, A. A.; Ellman, J. A. *Synthesis*, 1999, 583).

Scheme 3

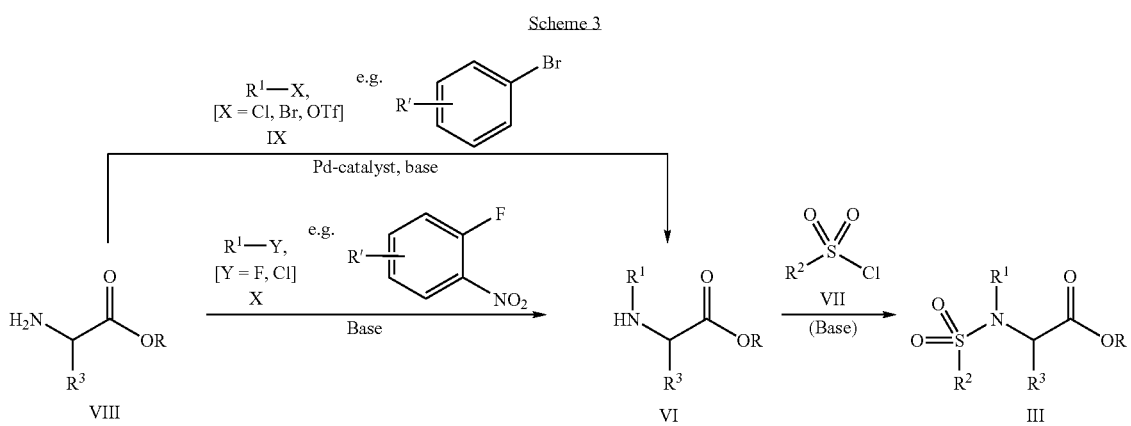

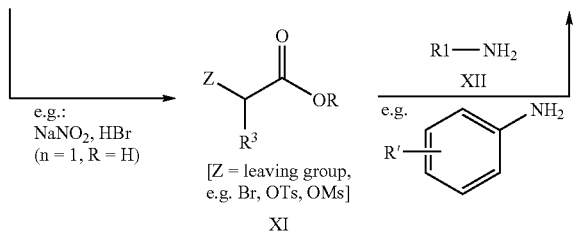

As a further alternative, compounds of general Formula m can be prepared from intermediates of general Formula XI (see Scheme 2) containing a suitable leaving group Z, by displacement of the latter with preformed anions of N-sulfonylated aryl or heteroaryl amines or heteroaryl amines, XIII, using standard synthetic techniques as shown in Scheme 4 and hereinafter described in the Examples. Alternatively, compounds of general Formula III can be prepared from N-sulfonylated aryl or heteroaryl amines or heteroaryl amines, XIII, with intermediates of general Formula XIa by Mitsunobu reaction, using standard reaction conditions, as depicted in Scheme 4.

bearing an appropriate reactive group G and by employing suitable interconversion techniques as described in Scheme 5 and hereinafter in the Examples. Under conditions suitable for $S_NAr$-type reactions, G can be displaced by preformed anions of the appropriate alkohol or amine $R^{10}$, as shown in Scheme 5 (compound XIIIb) and hereinafter described in the Examples. Alternatively, G can be substituted by activated unsaturated chains, using Pd catalysed Heck reaction under usual reaction conditions described in the litterature as shown in Scheme 5 and reported hereinafter in the

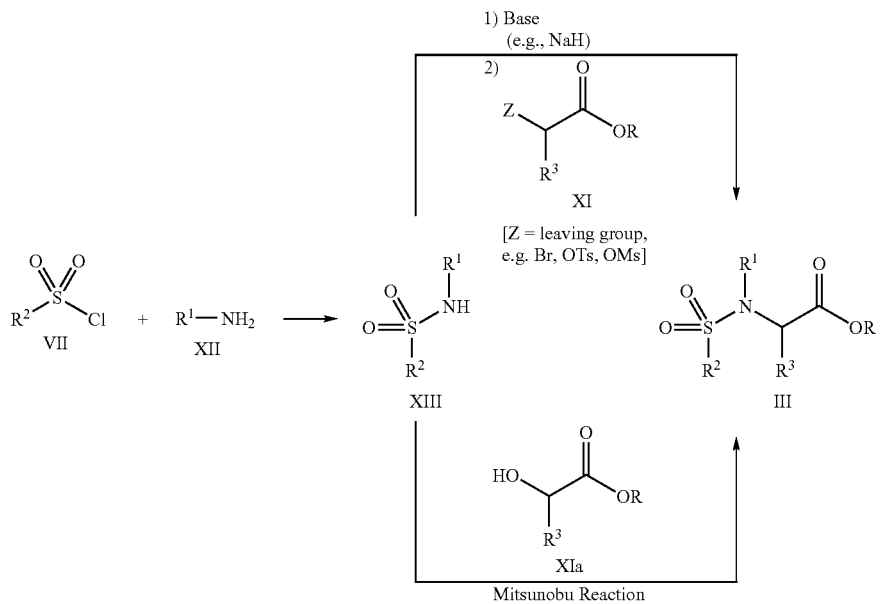

Said N-sulfonylated aryl or heteroaryl amines or heteroaryl amines, XIII, are obtained from reactions between aryl or heteroaryl sulfonyl chlorides, VII, and aryl or heteroaryl amines, XII, using conditions and methods well known to those skilled in the art to form a sulfonamide bond from an amine and a sulfonyl chloride, as shown in Scheme 4 and hereinafter described in the Examples.

According to a further general process, intermediate XIII can be converted to alternative intermediate XIII*, if $R_2$ is Examples. This unsaturated substituted alkyl chain, such as in compound XIIIb, can optionally be hydrogenated and further transformed (reduction, saponification, amide formation, substitution, etc) following standard conditions well known to the person skilled in the art and as it is described below in the Examples. Resulting alternative intermediate XIII or XIII* can be converted into III following procedures described on Scheme 5 and hereinafter described in the Examples.

Scheme 5

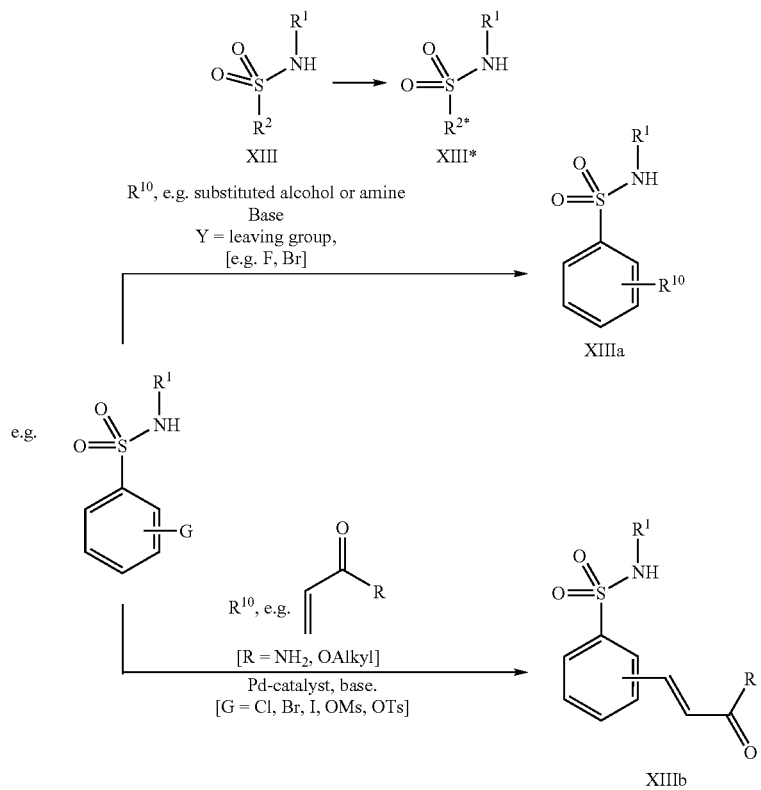

According to another process, compounds of Formula III, whereby the substituents $R^1$, $R^2$ and $R^3$ are as above defined, are prepared from the corresponding N-sulfonylated α-aminoacid esters, XIV (R=Me), by N-arylation, using cuprate/boronic acid methodologies (see e.g., Combs, A. P. et al. *J. Comb. Chem.*, 2000, 2, 29), as shown in Scheme 6 and described hereinafter in the Examples. The appropriate N-sulfonylated Ca-aminoacid esters, XIV, are obtained from reactions between aryl or heteroaryl sulfonyl chlorides, VII, and α-aminoacid esters, VIII (R=Me) using conditions and methods well known to those skilled in the art to form a sulfonamide bond from an amino group and a sulfonyl chloride.

Scheme 6

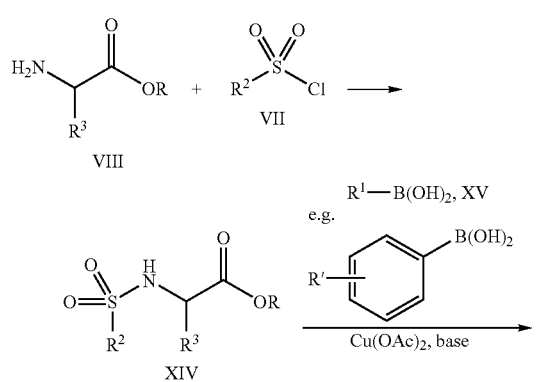

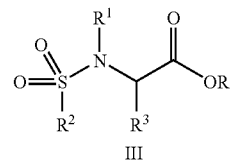

-continued

The processes hitherto presented provide compounds of general Formula e I and II by initial elaboration of the N-terminal portion of the central α-aminoacid core, followed by ultimate transformation of the carboxy terminus into the corresponding amides and/or acylhydrazones. As will be appreciated by the person skilled in the art, it may, depending on the molecular context, sometimes be preferable to inverse the order of the above reaction sequence. Thus, suitably N-protected x-aminoacids or amino acid esters, XVI, are subjectd to the reaction conditions outlined in Scheme 1 and the associated text, to provide the corresponding N-protected amides and/or acyl hydrazones XVII, as shown in Scheme 7. After N-deprotection, the resulting free amino groups are then elaborated according to the conditions and methods summarized in Schemes 3 and 6 and the associated text above, to afford the final products of general Formulae I, Ia, Ib, II, IIa.

By virtue of analogy, compounds of general Formula XI containing a suitable leaving group Z, which are either commercially available per se or readily accessible from commercial starting materials, as described in Scheme 3 and the associated text, may first be subjected to the reaction conditions outlined in Scheme 1 (see also the inserted text), to provide the corresponding amides and/or acyl hydrazones of Formula XVIII, as shown in Scheme 7 below. Subsequent displacement of the leaving group Z from compounds XVIII, either using aryl or heteroaryl amines (e.g. anilines), XII (Scheme 3), followed by N-sulfonylation, or using preformed anions of N-sulfonylated aryl or heteroaryl amines or heteroaryl amines, XIII (Scheme 4), affords the final products of general Formulae I, Ia, Ib, II, IIa.

heteroaryl fluorides and/or chlorides, X, under conditions suitable for $S_NAr$-type reactions. If the aryl component X contains a nitro-group, as shown in Scheme 8 and described hereinafter in the Examples, the resulting compound VIa can optionally be carried on to nitro group reduction and further functionalization (acylation, sulfonylation, alkylation) of the resulting primary amino group, before eventually being converted to III by sulfonylation with VII, and subsequent acid-catalyzed cleavage from the resin. The resulting acids III can directly be captured onto a further, nucleophile-

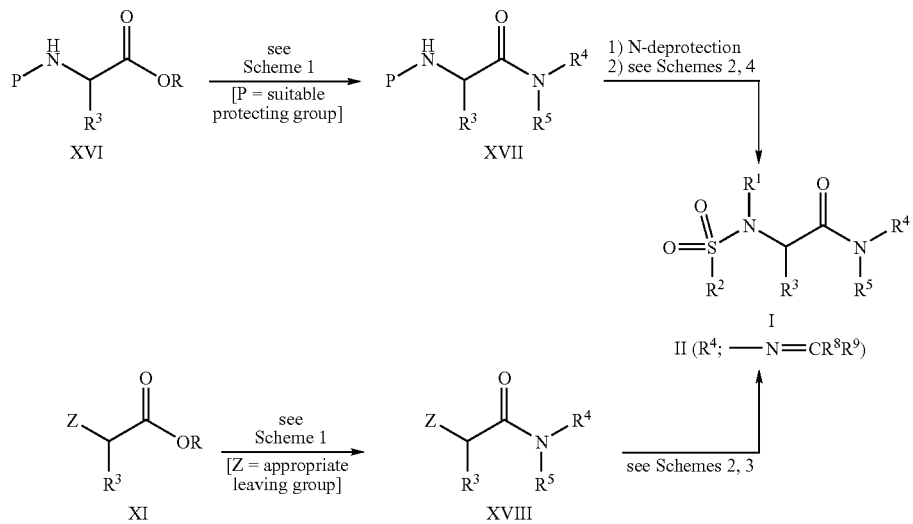

According to yet another process, sulfanilide derivatives according to the general Formula e I and/or II, whereby the substituents $R^1$-$R^9$ are as above defined, are prepared by solid-phase and/or mixed solid-/solution-phase synthesis protocols such as, e.g., those described in the examples and shown in Schemes 8 and 9 below. It will be appreciated by the practitioner skilled in the art that basically the same conditions, methods and reagents as above described in Schemes 1-4 for the solution-phase synthesis of compounds of Formula e I and/or II can be applied to the solid-phase and/or mixed solid-/solution-phase synthesis of said compounds. In the context of such a solid-phase and/or mixed solid-/solution-phase synthesis protocol, the R-group contained in the C(O)—OR moiety of the compounds In, VI, VIII, XI and XIV shown in Schemes 1-4, represents a suitable resin comprising the appropriate cleavable linker. The circles within the below Schemes 8 and 9 illustrate the resin beads to which the corresponding compounds are linked during the solid phase synthesis. It is to be understood that further to the below mentioned resin types, other suitable reagents, notably resins, known to a person skilled in the art, could be employed for the solid-phase synthesis of compounds of general Formula e I and/or II.

Thus, in one preferred scenario, suitably N-protected x-aminoacids are coupled to an acid-labile resin, such as, e.g., Wang resin, XIX, using standard carbodiimide-mediated coupling conditions well known to the practitioner skilled in the art, followed by N-deprotection, to afford resin-bound intermediates of Formula VIIIa. According to the methods outlined in Scheme 2, the latter intermediates VIIIa can then be reacted with electron-deficient aryl or labile, resin, such as, e.g. Kaiser oxime resin, XX, to give intermediates of Formula IIIb, which upon cleavage with either primary or secondary amines IV, and/or hydrazones of Formula XXI, will yield compounds of general Formula I and/or II, respectively, as shown in Scheme 8 and described hereinafter in the Examples.

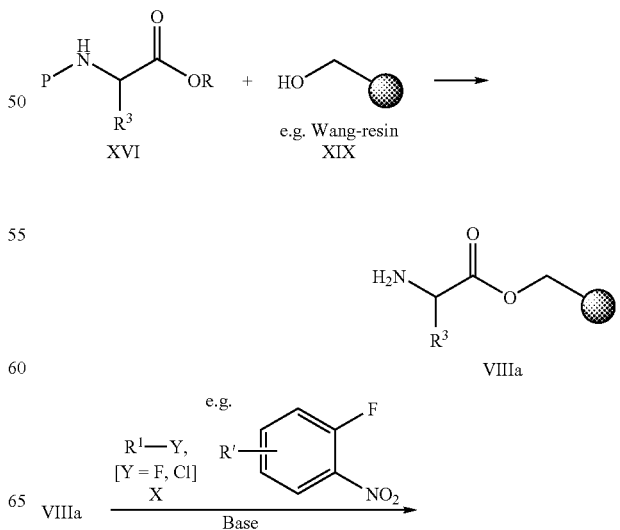

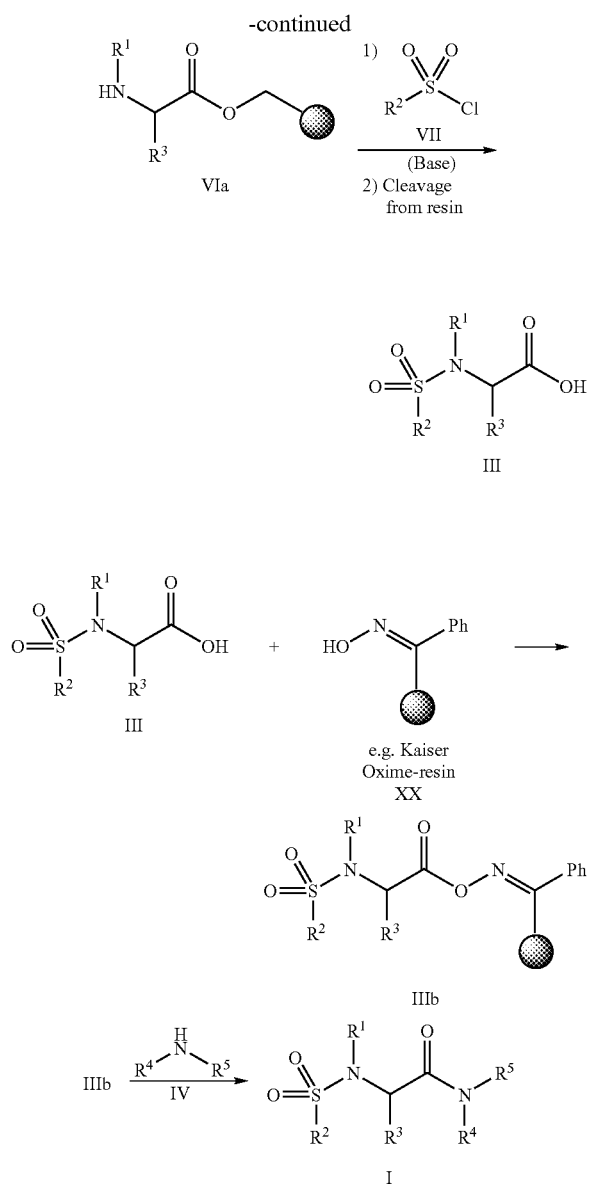

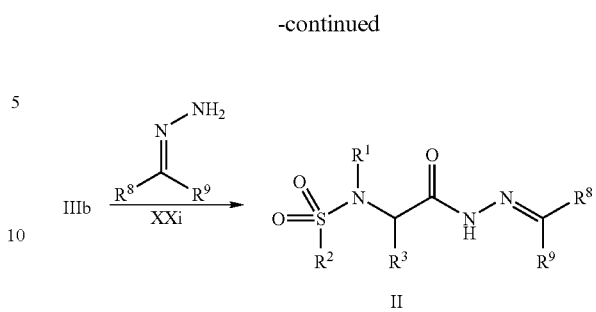

According to another preferred process, compounds of general Formula XI containing a suitable leaving group Z, which are either commercially available per se or readily accessible from commercial starting materials, as described in Scheme 3 and the associated text, can first be coupled to a resin presenting a hydroxyalkyl moiety, XXII, such as, e.g., TentaGel S OH, or hydroxymethyl-PS, using standard carbodiimide-mediated coupling conditions well known to the practitioner skilled in the art. Subsequent displacement of the leaving group Z from the resulting resin-bound intermediates XIc, either using aryl or heteroaryl, amines (e.g. anilines), XII (Scheme 2), followed by N-sulfonylation, or using preformed anions of N-sulfonylated aryl or heteroaryl amines or heteroaryl amines, XIII (Scheme 3), affords the resin-bound intermediates of general Formula IIIc. Cleavage from the resin is effected, e.g. by hydrazine, affording the corresponding hydrazides, XXIII, which can ultimately be transformed into the corresponding acyl hydrazones, II, by treatment with a ketone and/or aldehyde component, V, as described hereinafter in the Examples and shown in Scheme 9.

Scheme 9

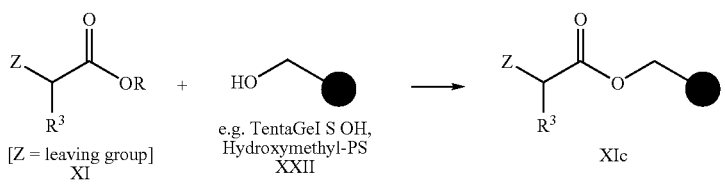

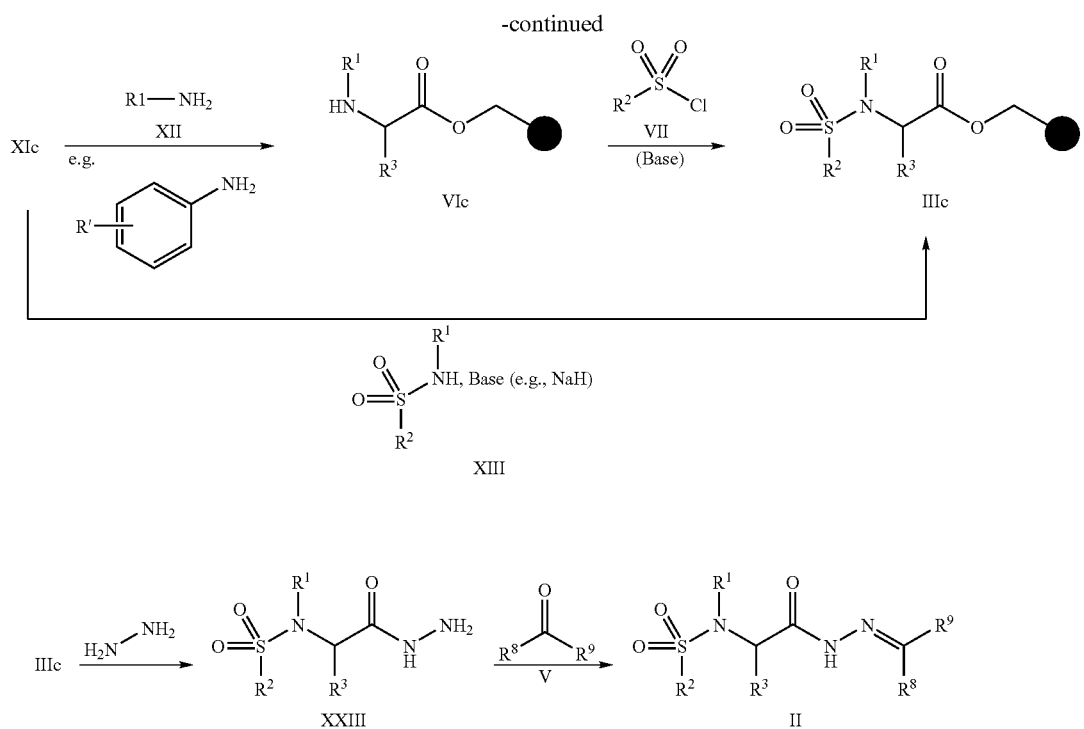

According to another preferred process, Fmoc-protected α-, β-, γ-, cyclic and acylic amino acids, which are either commercially available per se or readily accessible from commercial starting materials, as described in Scheme 10, may first be coupled to a resin presenting a amine moiety, XXV, such as, e.g., Rink resin, using standard carbodiimide-mediated coupling conditions well known to the practitioner skilled in the art. Subsequent Fmoc deprotection and coupling with carboxylic acid XIa, using stardard carbodiimide-mediated coupling conditions, are affording intermediate XXVI. Displacement of the leaving group Z from the resulting resin-bound intermediates XXVI, either using aryl or heteroaryl amines (e.g. anilines), XII (Scheme 2), followed by N-sulfonylation, or using preformed anions of N-sulfonylated aryl or heteroaryl amines or heteroaryl amines, XIII (Scheme 3), affords the resin-bound intermediates of general Formula XXVIII. Cleavage from the resin is effected under acidic conditions, affording the corresponding acetamide IIa as described hereinafter in the Examples and shown in Scheme 10.

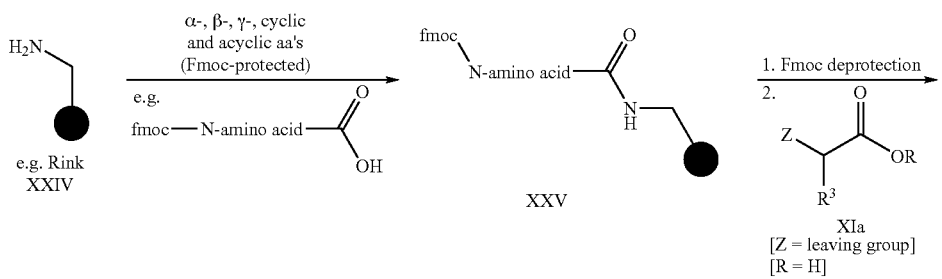

-continued

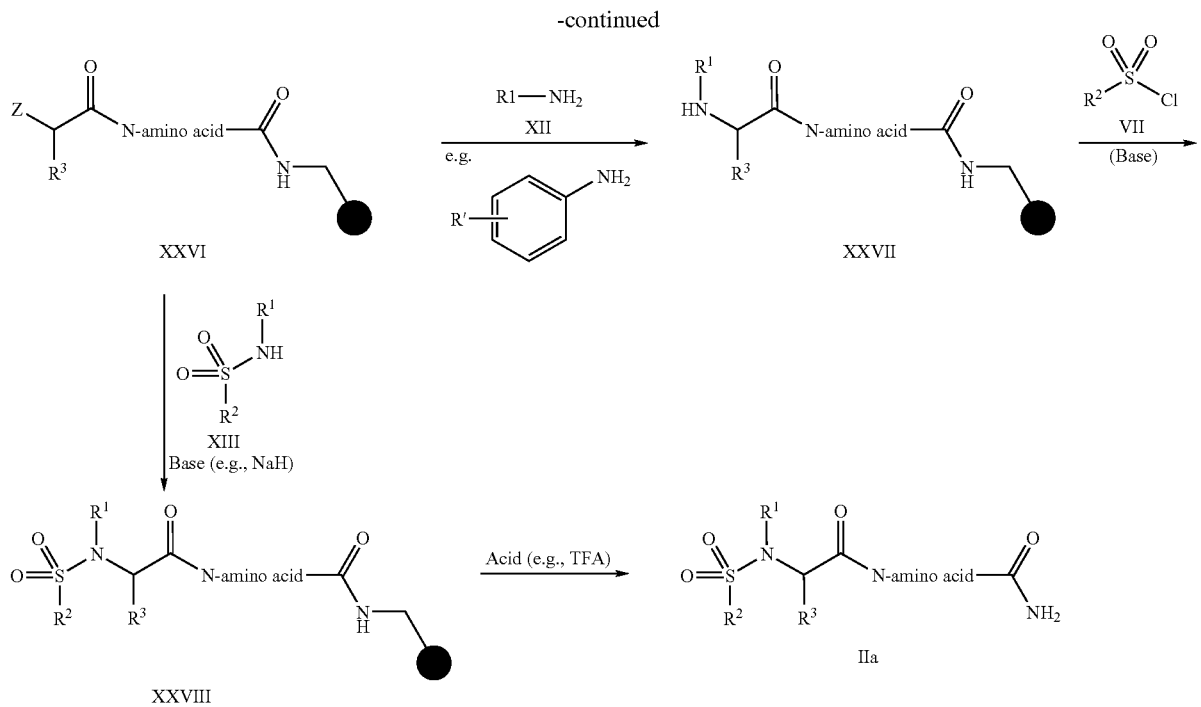

The term "fmoc-N-amino acid-COOH" as used in the above Scheme 10, denotes an α-, β-, γ-, cyclic and acylic amino acid which is protected by the protective group "Fmoc".

The reaction sequences outlined in the above Schemes provides enantiomerically pure compounds of Formula I, if enantiomerically pure starting materials are used. (R) as well as (S) enantiomers can be obtained depending upon whether (R) or (S) forms of commercially available starting materials are used.

According to a further general process, compounds of Formula I can be converted to alternative compounds of Formula I, employing suitable interconversion techniques such as hereinafter described in the Examples.

If the above set out general synthetic methods are not applicable for obtaining compounds according to Formula I and/or necessary intermediates for the synthesis of compounds of Formula I, suitable methods of preparation known by a person skilled on the art should be used. In general, the synthesis pathways for any individual compound of Formula I will depend on the specific substitutents of each molecule and upon the ready availability of intermediates necessary; again such factors being appreciated by those of ordinary skill in the art. For all the protection, de-protection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley-Interscience, 1991.

Compounds of this invention can be isolated in association with solvent molecules by crystallization from evaporation of an appropriate solvent. The pharmaceutically acceptable acid addition salts of the compounds of Formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula I with a suitable base. Both types of salt may be formed or interconverted using ion-exchange resin techniques.

A final aspect of the present invention relates to the use of the compounds according to Formula I and Formula H for the preparation of pharmaceutical compositions for the modulation of the oxytocin receptor and/or the vasopressin receptor as well as the Formula tions containing the active compounds according to Formula I and Formula II. The modulation of the oxytocin receptor is viewed as a suitable approach for the treatment of preterm labor and dysmenorrhea. The modulation of the vasopressin receptor is viewed as a suitable approach for the treatment of congestive heart failure, arterial hypertension, liver cirrhosis, nephrotic syndrome and ocular hypertension. When employed as pharmaceuticals, the sulfanilide derivatives of the present invention are typically administered in the form of a pharmaceutical composition. Hence, pharmaceutical compositions comprising a compound of Formula I and a pharmaceutically acceptable carrier, diluent or excipient therefore are also within the scope of the present invention. A person skilled in the art is aware of a whole variety of such carrier, diluent or excipient compounds suitable to Formula te a pharmaceutical composition. Also, the present invention provides compounds for use as a medicament. In particular, the invention provides the compounds of Formula I for use as antagonists of the oxytocin receptor, for the treatment or prevention of disorders mediated by the oxytocin receptor in mammals, particularly in humans, either alone or in combination with other medicaments, e.g. in combination with a further OT antagonist.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous)

use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the sulfanilide derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably Formula ted as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the sulfanilide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the sulfanilide derivatives of Formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, 17th Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

The present invention shall be illustrated by means of the following examples which are not construed to be viewed as limiting the scope of the invention. The HPLC, NMR and MS data provided in the examples described below were obtained as followed. The following abbreviations are hereinafter used in the accompanying examples: min (minute), hr (hour), g (gram), mmol (millimole), m.p. (melting point), eq (equivalents), mL (milliliter), μL (microliters), mL (milliliters), ACN (Acetonitrile), CDCl$_3$ (deuterated chloroform), cHex (Cyclohexanes), DCM (Dichloromethane), DECP (Diethylcyanophosphonate), DIC (Diisopropyl carbodiimide), DMAP (4-Dimethylaminopyridine) DMF (Dimethylformamide), DMSO (Dimethylsulfoxide), DMSO-d$_6$ (deuterated dimethylsulfoxide), EDC (1-(3-Dimethyl-amino-propyl)-3-ethylcarbodiimide), EtOAc (Ethyl acetate), Et$_2$O (Diethyl ether), HOBt (1-Hydroxybenzotriazole), K$_2$CO$_3$ (potassium carbonate), NaH (Sodium hydride), NaHCO$_3$ (Sodium bicarbonate), nBuLi (n Butyllithium), TBTU (O-Benzotriazolyl-N,N,N',N'-tetramethyluronium-tetrafluoroborate), TEA (Triethyl amine), TFA (Trifluoro-acetic acid), THE (Tetrahydrofuran), MgSO$_4$ (Magnesium sulfate), PetEther (Petroleum ether), rt (room temperature).

EXAMPLES

Intermediate 1:

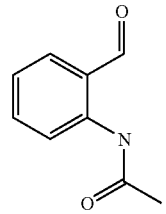

N-Acetyl-2-amino Benzaldehyde a) Synthesis of 2-Aminobenzyl Alcohol

To a solution of 2-nitrobenzyl alcohol (500 g, 3.2 mol) in MeOH (2.5 L) was added Pd/C (40 g) under N$_2$ and refluxed for 30 min. Hydrazine hydrate (500 mL) was added slowly with stirring. The resulting mixture was stirred under reflux for another 2 h. The solid formed was filtered, concentrated and the crude residue was extracted with ethyl acetate (2×500 mL). The organic layer was washed with brine and dried over MgSO$_4$. After evaporation of the solvents, 2-aminobenzyl alcohol (357 g, 89% yield) was isolated as pale yellow solid.

b) Synthesis of N-Acetyl-O-acetyl-2-aminobenzyl Alcohol

Et$_3$N (132 g, 1.3 mol) was added to a solution of 2-aminobenzyl alcohol (40 g, 0.33 mol) in dry CH$_2$Cl$_2$ (400 mL). The mixture was stirred for 20 min. and acetic anhydride (100 g, 0.98 mol) was added slowly. After 12 h stirring at room temperature, the reaction mixture was washed with water, brine and dried over MgSO4. The solvents were removed under vacuum to give the crude N-acetyl-O-acetyl-2-aminobenzyl alcohol (55 g, 88% yield).

c) Synthesis of N-Acetyl-2-aminobenzyl Alcohol

To a solution of N-acetyl-O-acetyl-2-aminobenzyl alcohol (55 g, 0.25 mol) in MeOH (550 mL) was added K$_2$CO$_3$ (200 g, 1.42 mol). After 2 h at room temperature, the resulting solid was filtered and concentrated. The crude product was dissolved in CH$_2$Cl$_2$ (250 mL), washed with water, brine and dried over MgSO$_4$. The solvent was removed under vacuum, affording N-acetyl-2-aminobenzylalcohol (20 g, 47% yield).

d) Synthesis of N-Acetyl-2-anzinobenzaldehlyde

To a stirred solution of N-acetyl-2-amino-benzylalcohol (20 g) in dry CHCl$_3$ (500 mL) was added MnO$_2$ (160 g, 8 equivalents) and allowed to stir at room temperature for 12 h. The reaction mixture was filtered through celite and concentrated. The crude product was recrystallised from CHCl$_3$/petrol ether to give N-acetyl-2-aminobenzaldehyde (14 g, 73%).

$^1$H NMR (300 MHz, DMSO-d$_6$): 2.01 (s, 3H), 7.30 (m, 2H, H arom.), 7.65 (m, 2H, H arom.), 7.85 (m, 2H, H arom.), 8.09 (m, 2H, H arom.), 9.95 (s, 1H, CHO), 10.70 (s, 1H, NH).

Example 1

General protocol A for the Solution-Phase Synthesis of Sulfanilide Derivatives of General Formula II with R$^3$=H (Schemes 1, 4): e.g. 3-[({[(4-ethoxyphenyl)sulfonyl]-4-methylanilino}acetyl)hydrazono]-2-oxo-2,3-dihydro-H-indole-5-sulfonic Acid

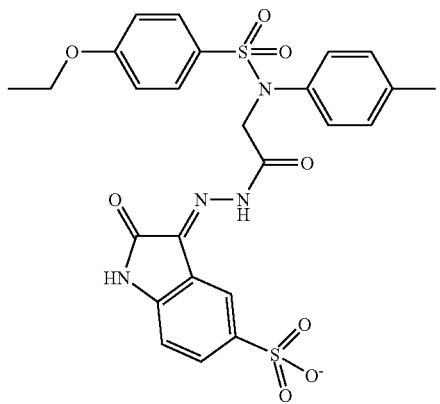

a) Protocol for the Formation of the N-aryl-benzenesulfonamide Building Block, XIII (Scheme 4); e.g. 4-ethoxy-N-(4-methylphenyl)benzenesulfonamide 1-Amino-4-methylbenzene (1.821 g, 17.0 mmol) was dissolved in DCM (25 mL). N,N-Diisopropylethylamine (3.1 mL, 18.1 mmol) and 4-ethoxy-benzenesulfonyl chloride (2.50 g, 11.3 mmol) were added successively. The reaction mixture was stirred at room temperature overnight and then washed with 10% HCl (2×20 mL) and brine (1×20 mL). Organic phase was dried with sodium sulfate before filtering and removal of solvent. The desired product, e.g. 4-ethoxy-N-(4-methylphenyl)benzenesulfonamide (3.087 g, 94%), was obtained as a colorless solid, in 99.2% purity by HPLC (MaxPlot detection between 230 and 400 nm).

$^1$H NMR (300 MHz, CDCl$_3$): 1.39 (t, J=7.0 Hz, 3H, OCH$_2$CH$_3$), 2:24 (s, 3H, CH$_3$), 4.02 (q, J=7.0 Hz, 2H, OCH$_2$CH$_3$), 6.35 (br s, 1H, NH), 6.84 (m, 2H, H arom.), 6.91 (m, 2H, H arom.), 7.01 (m, 2H, H arom.), 7.63 (m, 2H, H arom.); M$^+$(ESI$^+$): 292; M$^-$(ESI$^-$): 290.

b) Protocol for the Displacement of the Leaving Group in XI (Scheme 4); e.g. methyl{[(4-ethoxyphenyl)sulfonyl]-4-methylanilino}acetate The crude N-aryl-benzenesulfonamide building block XIII, e.g. 4-ethoxy-N-(4-methylphenyl)benzenesulfonamide (3.087 g, 10.6 mmol), was dissolved in DMF (10 mL) and was added to a suspension of NaH (13.6 mmol, 0.593 mg of NaH 55-65% in oil) in DMF (30 mL). The mixture was stirred 45 min at room temperature. 2-Bromoacetic acid methyl ester (1.45 mL, 15.9 mmol) was added dropwise. The resulting mixture was stirred at room temperature overnight. The solvents were evaporated, affording the desired product, e.g. methyl{[(4-ethoxyphenyl)sulfonyl]-4-methylanilino}acetate (3.816 g, quantitative crude yield) as a light yellow solid, in 96.1% purity by HPLC (MaxPlot detection between 230 and 400 nm).

$^1$H NMR (300 MHz, CDCl$_3$): 1.42 (t, J=7.0 Hz, 3H, OCH$_2$CH$_3$), 2.29 (s, 3H, CH$_3$), 3.67 (s, 3H, OCH$_3$), 4.06 (q, J=7.0 Hz, 2H, OCH$_2$CH$_3$), 4.36 (s, 2H, NCH$_2$CO), 6.87 (m, 2H, H arom.), 7.05 (br s, 4H, H arom.), 7.58 (m, 2H, H arom.); M$^+$(APCI$^+$): 364; M$^-$(APCI$^-$): 362.

c) Protocol for the Transformation of the Carboxylic Acid Ester into the Hydrazide (Scheme 1); e.g. 4-ethoxy-N-(2-hydrazino-2-oxoethyl)-N-(4-methylphenyl)benzenesulfonamide The crude carboxylic acid methyl ester, e.g. methyl{[(4-ethoxyphenyl)sulfonyl]-4-methylanilino}acetate (3.816 g, 10.5 mmol), was dissolved in MeOH (30 mL). Hydrazine hydrate was added (3.3 mL). The reaction mixture was stirred overnight at room temperature. A white precipitate was formed. It was isolated by filtration and rinsed with cold MeOH. From mother liquors some more compound could be recovered, affording the desired product, e.g. 4-ethoxy-N-(2-hydrazino-2-oxoethyl)-N-(4-methylphenyl)benzenesulfonamide (2.745 g, 72%) as a colorless solid in 99.8% purity by HPLC (MaxPlot detection between 230 and 400 nm).

M.p. 117.5-118.5° C.; IR (neat) σ 3326, 2926, 1595, 1344, 1154 cm$^{-1}$; $^1$H NMR (300 MHz, DMSO-d$_6$): 1.34 (t, J=7.0 Hz, 3H, OCH$_2$CH$_3$), 2.26 (s, 3H, CH$_3$), 4.10 (q, J=7.0 Hz, 2H, OCH$_2$CH$_3$), 4.11 (s, 2H, NCH$_2$CO), 4.18 (br s, 2H, N—NH$_2$), 6.95-7.15 (m, 6H, H arom.), 7.51 (m, 2H, H arom.); M$^-$(APCI$^-$): 362. Analysis calculated for C$_{17}$H$_{21}$N$_3$O$_4$S 07H$_2$O: C, 54.30; H, 6.00; N, 11.17. Found: C, 53.97; H, 5.97; N, 11.03.

d) Protocol for the Formation of the Acyl Hydrazone, II (Scheme 1), e.g. 3-[({[(4-ethoxyphenyl)sulfonyl]-4-niethylanilino}acetyl)hydrazono]-2-oxo-2,3-dihydro-1H-indole-5-sulfonic Acid Hydrazide obtained in the precedent step, e.g. 4-ethoxy-N-(2-hydrazino-2-oxoethyl)-N-(4-methylphenyl)benzenesulfonamide (73 mg, 0.2 mmol), was dissolved in EtOH/5% AcOH (4 mL). Isatin-5-sulfonic acid sodium salt dihydrate (57 mg, 0.2 mmol) was added. The reaction mixture was stirred overnight at 76° C. A yellow precipitate was formed. It was collected by filtration, washed with cold EtOH and dried under vacuo at 40° C., affording the desired product, e.g. 3-[(([(4-ethoxyphenyl)sulfonyl]-4-methylanilino}acetyl)hydrazono]-2-oxo-2,3-dihydro-]H-indole-5-sulfonic acid (38 mg, 32%) as a yellow solid in 98.4% purity by HPLC (MaxPlot detection between 230 and 400 nm).

M.p. 318-319° C., decomposition; IR (neat) σ 2988, 1698, 1595, 1500, 1354, 1222, 1091 cm$^{-1}$; $^1$H NMR (300 MHz, DMSO-d$_6$): 1.42 (t, J=7.0 Hz, 3H, OCH$_2$CH$_3$), 2.33 (s, 3H, CH$_3$), 4.20 (m, 2H, OCH$_2$CH$_3$), 4.55 (br s, 2H, NCH$_2$CO, minor isomer (45%)), 4.55 (br s, 2H, NCH$_2$CO, major isomer (55%)), 6.95 (m, 1H, H arom.), 7.06-7.30 (m, 6H, H arom.), 7.50-7.90 (m, 4H, H arom.), 11.38 (s, 1H, NH), 12.54 (br s, 1H, CONHN, major isomer (55%)), 13.64 (br s, 1H, CONHN, minor isomer (45%)); M$^-$(APCI$^-$): 571.

Analysis calculated for $C_{25}H_{24}N_4O_8S_2Na$ 0.5$H_2O$: C, 49.75; H, 4.01; N, 9.28. Found: C, 49.58; H, 3.93; N, 9.24.

Example 2

4-ethoxy-N-{2-oxo-2-[2-(2-oxo-1,2-dihydro-3H-indol-3-ylidene)hydrazino]-ethyl}-N-phenylbenzenesulfonamide

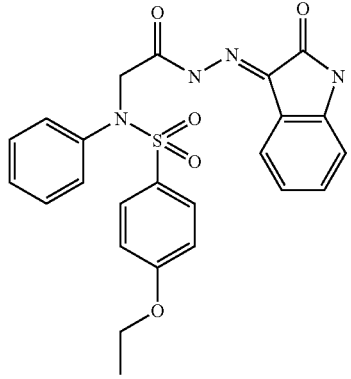

Following the general method as outlined in Example 1, starting from 4-ethoxybenzenesulfonyl chloride, aniline, methyl bromoacetate and 1H-indole-2,3-dione, the title compound was precipitated with the addition of water and recrystallized from MeOH. A bright yellow solid (74 mg, 62%) was isolated in 99.6% purity by HPLC (MaxPlot detection between 230 and 400 nm).

M.p. 135.5-136.5° C.; IR (neat) σ 3168, 1688, 1595, 1495, 1337, 1155, 1122, 1091 cm$^{-1}$; $^1$H NMR (300 MHz, DMSO-d$_6$): 1.34 (t, J=7.0 Hz, 3H, OCH$_2$CH$_3$), 4.11 (q, J=7.0 Hz, 2H, OCH$_2$CH$_3$), 4.51 (br s, 2H, NCH$_2$CO, major isomer (65%)), 5.00 (br s, 2H, NCH$_2$CO, minor isomer (35%)), 6.95 (m, 1H, H arom.), 7.03-7.17 (m, 3H, H arom.), 7.19-7.43 (m, 6H, H arom.), 7.43-7.70 (m, 3H, H arom.), 11.27 (s, 1H, NH), 12.50 (br s, 1H, CONBN, minor isomer (35%)), 13.66 (br s, 1H, CONHN, major isomer (65%)); M$^-$(APCI$^-$): 477. Analysis calculated for $C_{24}H_{22}N_4O_5S$ 1$H_2O$: C, 58.05; H, 4.87; N, 11.28. Found: C, 57.71; H, 4.92; N, 11.03.

Example 3

4-ethoxy-N-{2-[2-(5-nitro-2-oxo-1,2-dihydro-3H-indol-3-ylidene)hydrazino]-2-oxoethyl}-N-phenyl-benzenesulfonamide

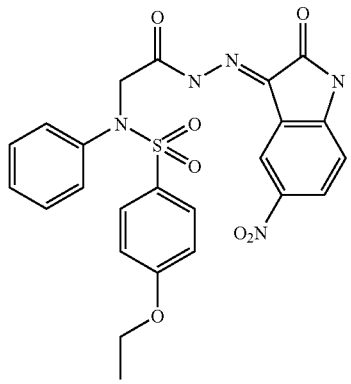

Following the general method as outlined in Example 1, starting from 4-ethoxybenzenesulfonyl chloride, aniline, methyl bromoacetate and 5-nitro-1H-indole-2,3-dione, the title compound was precipitated with the addition of water and recrystallized in THF/H$_2$O. A yellow powder (48 mg, 40%) was isolated in 98.9% purity by HPLC (MaxPlot detection between 230 and 400 nm).

M.p. 252-253° C.; IR (neat) σ 3107, 1734, 1721, 1624, 1595, 1518, 1337, 1154, 1118, 1084 cm$^{-1}$; $^1$H NMR (300 MHz, DMSO-d$_6$): 1.34 (t, J=7.0 Hz, 3H, OCH$_2$CH$_3$), 4.20 (q, J=7.0 Hz, 2H, OCH$_2$CH$_3$), 4.68 (br s, 2H, NCH$_2$CO, major isomer (55%)), 5.14 (br s, 2H, NCH$_2$CO, minor isomer (45%)), 7.12-7.27 (m, 3H, H arom.), 7.30-7.48 (m, 5H, H arom.), 7.52-7.77 (m, 2H, H arom.), 8.23-8.46 (m, 2H, H arom.), 11.95 (s, 1H, NH), 12.48 (br s, 1H, CONHN, minor isomer (45%)), 13.58 (br s, 1H, CONHN, major isomer (55%)); M$^-$(APCI$^-$): 522. Analysis calculated for $C_{24}H_{21}N_5O_7S$: C, 55.06; H, 4.04; N, 13.38. Found: C, 54.92; H, 4.09; N, 13.27.

Example 4

4-ethoxy-N-{2-[2-(5-iodo-2-oxo-1,2-dihydro-3H-indol-3-ylidene)hydrazino]-2-oxoethyl}-N-phenyl-benzenesulfonamide

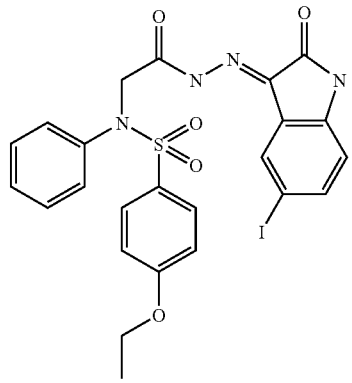

Following the general method as outlined in Example 1, starting from 4-ethoxybenzenesulfonyl chloride, aniline, methyl bromoacetate and 5-iodo-1H-indole-2,3-dione, the title compound was precipitated with the addition of water and recrystallized in EtOH. A yellow solid (65 mg, 47%) was isolated in 95.1% purity by HPLC (MaxPlot detection between 230 and 400 nm).

M.p. 233-234° C.; IR (neat) σ 3371, 2976, 1719, 1693, 1594, 1534, 1338, 1156, 1094 cm$^{-1}$; $^1$H NMR (300 MHz, DMSO-d$_6$): 1.13 (t, J=7.0 Hz, 3H, OCH$_2$CH$_3$), 3.89 (q, J=7.0 Hz, 2H, OCH$_2$CH$_3$), 4.31 (br s, 2H, NCH$_2$CO, major isomer (55%)), 1.80 (br s, 2H, NCH$_2$CO, minor isomer (45%)), 6.79 (m, 1H, H arom.), 7.07 (m, 2H, H arom.), 7.19-7.41 (m, 5H, H arom.), 7.41-7.92 (m, 4H, H arom.), 11.35 (s, 1H, NH), 12.42 (br s, 1H, CONHN, minor isomer (45%)), 13.58 (br s, 1H, CONHN, major isomer (55%)); M$^-$(APCI$^-$): 603. Analysis calculated for $C_{24}H_{21}IN_4O_5S$ 0.1$H_2O$: C, 47.55; H, 3.52; N, 9.24. Found: C, 47.20; H, 3.58; N, 9.26.

Example 5

4-ethoxy-N-(4-methylphenyl)-N-{2-oxo-2-[2-(2-oxo-1,2-dihydro-3H-indol-3-ylidene)hydrazino]ethyl}benzenesulfonamide

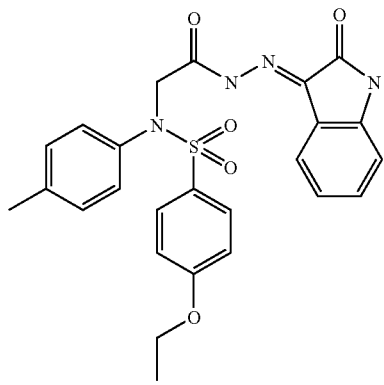

Following the general method as outlined in Example 1, starting from 4-ethoxybenzenesulfonyl chloride, p-toluidine, methyl bromoacetate and 1H-indole-2,3-dione, the title compound was precipitated with the addition of water and recrystallized in MeOH. A bright yellow solid (197 mg, 58%) was isolated in 98.9% purity by HPLC (MaxPlot detection between 230 and 400 nm).

M.p. 130-131° C.; IR (neat) σ 3170, 1682, 1598, 1335, 1262, 1152, 1091 cm$^{-1}$; $^1$H NMR (300 MHz, DMSO-d$_6$): 1.16 (t, J=7.0 Hz, 3H, OCH$_2$CH$_3$), 2.07 (s, 3H, CH$_3$), 3.93 (q, J=7.0 Hz, 2H, OCH$_2$CH$_3$), 4.29 (br s, 2H, NCH$_2$CO, major isomer (67%)), 4.78 (br s, 2H, NCH$_2$CO, minor isomer (33%)), 6.77 (m, 1H, H arom.), 7.01-7.20 (m, 7H, H arom.), 7.20 (m, 1H, H arom.), 7.43-7.68 (m, 3H, H arom.), 11.09 (s, 1H, NH), 12.31 (br s, 1H, CONHN, minor isomer (33%)), 13.46 (br s, 1H, CONHN, major isomer (67%)); M$^+$(ESI$^+$): 493; M$^-$(ESI$^-$): 491. Analysis calculated for C$_{25}$H$_{24}$N$_4$O$_5$S 1H$_2$O: C, 58.81; H, 5.13; N, 10.97. Found: C, 58.41; H, 5.19; N, 10.98.

Example 6

N-(4-methylphenyl)-N-{2-oxo-2-[2-(2-oxo-1,2-dihydro-3H-indol-3-ylidene)hydrazino]ethyl}-1-naphthalenesulfonamide

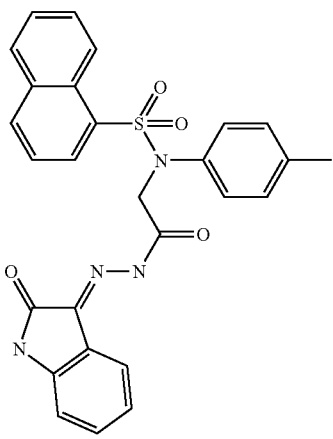

Following the general method as outlined in Example 1, starting from 1-naphthalenesulfonyl chloride, p-toluidine, methyl bromoacetate and 1H-indole-2,3-dione, the title compound was isolated by evaporation of the solvents and purified by recrystallization in MeOH. A yellow powder (52 mg, 52%) was obtained in 98.5% purity by HPLC (MaxPlot detection between 230 and 400 nm).

M.p. 138-139° C.; IR (neat) σ 3431, 1698, 1621, 1494, 1465, 1336, 1193, 1161, 1162 cm$^{-1}$; $^1$H NMR (300 MHz, DMSO-d$_6$): 2.27 (s, 3H, CH$_3$), 4.66 (br s, 2H, NCH$_2$CO, major isomer (60%)), 5.14 (br s, 2H, NCH$_2$CO, minor isomer (40%)), 6.98 (m, 1H, H arom.), 6.99-7.15 (m, 5H, H arom.), 7.30-7.70 (m, 5H, H arom.), 8.02-8.19 (m, 2H, H arom.), 8.21-8.45 (m, 2H, H arom.), 11.30 (s, 1H, NH), 12.54 (br s, 1H, CONHN, minor isomer (40%)), 13.56 (br s, 1H, CONHN, major isomer (60%)); M$^-$(APCI$^-$): 497. Analysis calculated for C$_{27}$H$_{22}$N$_4$O$_4$S 0.5H$_2$O: C, 63.89; H, 4.57; N, 11.04. Found: C, 63.73; H, 4.48; N, 11.34.

Example 7

N-(4-methylphenyl)-N-{2-oxo-2-[2-(2-oxo-1,2-dihydro-3H-indol-3-ylidene)hydrazino]ethyl}-2-naphthalenesulfonamide

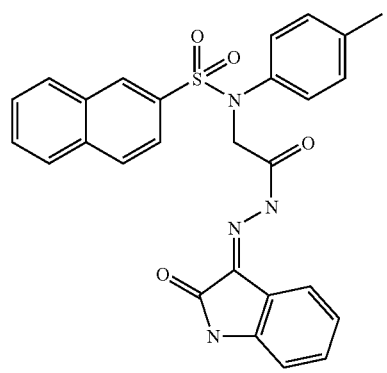

Following the general method as outlined in Example 1, starting from 2-naphthalenesulfonyl chloride, p-toluidine, methyl bromoacetate and 1H-indole-2,3-dione, the title compound was isolated by evaporation of the solvents and purified by recrystallization in MeOH. An orange powder (52 mg, 55%) was obtained in 94.7% purity by HPLC (MaxPlot detection between 230 and 400 nm).

$^1$H NMR (300 MHz, DMSO-d$_6$): 2.24 (s, 3H, CH$_3$), 4.60 (br s, 2H, NCH$_2$CO, major isomer (65%)), 5.06 (br s, 2H, NCH$_2$CO, minor isomer (35%)), 6.82-7.19 (m, 6H, H arom.), 7.38 (m, 1H, H arom.), 7.46-7.61 (m, 2H, H arom.), 7.61-7.79 (m, 2H, H arom.), 8.02-8.20 (m, 3H, H arom.), 8.38 (s, 1H, H arom.), 11.27 (s, 1H, NH), 12.51 (br s, 1H, CONHN, minor isomer (35%)), 13.66 (br s, 1H, CONBN, major isomer (65%)); M$^-$(APCI$^-$): 497.

Example 8

4-chloro-N-(4-methylphenyl)-N-{2-oxo-2-[2-(2-oxo-1,2-dihydro-3H-indol-3-ylidene)hydrazino]ethyl}benzenesulfonamide

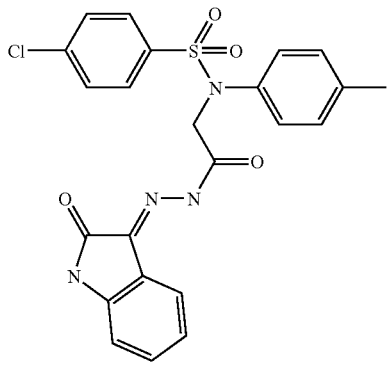

Following the general method as outlined in Example 1, starting from 4-chlorobenzenesulfonyl chloride, p-toluidine, methyl bromoacetate and 1H-indole-2,3-dione, the title compound was isolated by evaporation of the solvents and purified by recrystallization in MeOH. A yellow powder (50 mg, 51%) was obtained in 98.7% purity by HPLC (MaxPlot detection between 230 and 400 nm).

M.p. 234-235° C.; IR (neat) σ 3352, 1717, 1693, 1614, 1509, 1463, 1332, 1192, 1152, 1127, 1087 cm$^{-1}$; $^1$H NMR (300 MHz, DMSO-d$_6$): 2.26 (s, 3H, CH$_3$), 4.56 (br s, 2H, NCH$_2$CO, major isomer (60%)), 5.00 (br s, 2H, NCH$_2$CO, minor isomer (40%)), 6.94 (m, 1H, H arom.), 7.03-7.19 (m, 5H, H arom.), 7.38 (m, 1H, H arom.), 7.46-7.71 (m, 5H, H arom.), 11.27 (s, 1H, NH), 12.49 (br s, 1H, CONHN, minor isomer (40%)), 13.59 (br s, 1H, CONHN, major isomer (60%)); M$^{-1}$(APCI$^-$): 481. Analysis calculated for C$_{23}$H$_{19}$ClN$_4$O$_4$S 0.4H$_2$O: C, 56.36; H, 4.07; N, 11.43. Found: C, 56.54; H, 4.11; N, 11.43.

Example 9

4-methoxy-N-(4-methylphenyl)-N-{2-oxo-2-[2-(2-oxo-1,2-dihydro-3H-indol-3-ylidene)hydrazino]ethyl}benzenesulfonamide

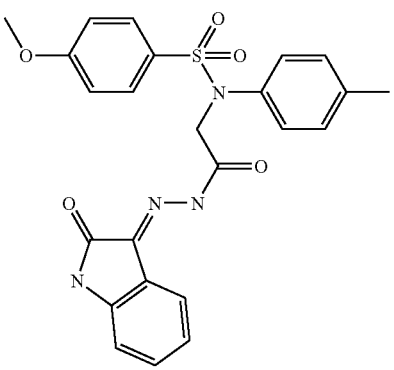

Following the general method as outlined in Example 1, starting from 4-methoxybenzenesulfonyl chloride, p-toluidine, methyl bromoacetate and 1H-indole-2,3-dione, the title compound was isolated by evaporation of the solvents and purified by recrystallization in MeOH. A yellow powder (60 mg, 63%) was obtained in 97.0% purity by HPLC (MaxPlot detection between 230 and 400 nm).

M.p. 134-135° C.; IR (neat) σ 3353, 1691, 1613, 1503, 1464, 1334, 1152, 1123, 1089 cm$^{-1}$; $^1$H NMR (300 MHz, DMSO-d$_6$): 2.25 (s, 3H, CH$_3$), 3.84 (s, 3H, OCH$_3$), 4.47 (br s, 2H, NCH$_2$CO, major isomer (67%)), 4.96 (br s, 2H, NCH$_2$CO, minor isomer (33%)), 6.84-7.01 (m, 1H, H arom.), 7.06-7.18 (m, 7H, H arom.), 7.38 (m, 1H, H arom.), 7.44-7.68 (m, 3H, H arom.), 11.27 (s, 1H, NH), 12.49 (br s, 1H, CONHN, minor isomer (33%)), 13.65 (br s, 1H, CONHN, major isomer (67%)); M$^+$(APCI$^+$): 479; M$^-$(APCI$^-$): 477. Analysis calculated for C$_{24}$H$_{22}$N$_4$O$_5$S 1.5H$_2$O: C, 57.02; H, 4.98; N, 11.08. Found: C, 57.02; H, 4.93; N, 11.10.

Example 10

4-methyl-N-(4-methylphenyl)-N-{2-oxo-2-[2-(2-oxo-1,2-dihydro-3H-indol-3-ylidene)hydrazino]ethyl}benzenesulfonamide

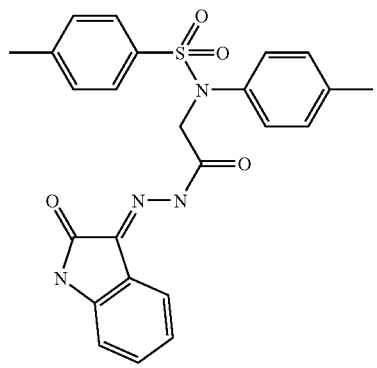

Following the general method as outlined in Example 1, starting from 4-methylbenzenesulfonyl chloride, p-toluidine, methyl bromoacetate and 1H-indole-2,3-dione, the title compound was isolated by evaporation of the solvents and purified by recrystallization in MeOH. A yellow powder (37 mg, 40%) was obtained in 98.0% purity by HPLC (MaxPlot detection between 230 and 400 nm).

M.p. 243-244° C.; IR (neat) σ 3350, 1715, 1692, 1614, 1508, 1462, 1328, 1150, 1124, 1091 cm$^{-1}$; $^1$H NMR (300 MHz, DMSO-d$_6$): 2.25 (s, 3H, CH$_3$), 2.39 (s, 3H, CH$_3$), 4.49 (br s, 2H, NCH$_2$CO, major isomer (65%)), 4.97 (br s, 2H, NCH$_2$CO, minor isomer (35%)), 6.95 (m, 1H, H arom.), 7.04-7.19 (m, 5H, H arom.), 7.34-7.64 (m, 6H, H arom.), 11.27 (s, 1H, NH), 12.49 (br s, 1H, CONHN, minor isomer (35%)), 13.63 (br s, 1H, CONHN, major isomer (65%)); M$^+$(APCI$^+$): 463; M$^-$(APCI$^-$): 461. Analysis calculated for C$_{24}$H$_{22}$N$_4$O$_4$S 0.3H$_2$O: C, 61.60; H, 4.87; N, 11.97. Found: C, 61.48; H, 4.87; N, 12.02.

Example 11

4-cyano-N-(4-methylphenyl)-N-{2-oxo-2-[2-(2-oxo-1,2-dihydro-3H-indol-3-ylidene)hydrazino]ethyl}benzenesulfonamide

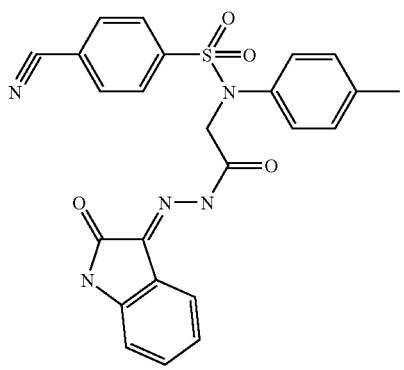

Following the general method as outlined in Example 1, starting from 4-cyanobenzenesulfonyl chloride, p-toluidine, methyl bromoacetate and 1H-indole-2,3-dione, the title compound was isolated by evaporation of the solvents and purified by recrystallization in MeOH. A yellow powder (59 mg, 63%) was obtained in 93.0% purity by HPLC (MaxPlot detection between 230 and 400 nm).

$^1$H NMR (300 MHz, DMSO-d$_6$): 2.25 (s, 3H, CH$_3$), 4.62 (br s, 2H, NCH$_2$CO, major isomer (57%)), 5.04 (br s, 2H, NCH$_2$CO, minor isomer (43%)), 6.94 (m, 1H, H arom.), 7.03-7.22 (m, 5H, H arom.), 7.38 (m, 1H, H arom.), 7.46-7.62 (m, 1H, H arom.), 7.72-7.92 (m, 2H, H arom.), 8.08 (m, 2H, H arom.), 11.27 (s, 1H, NH), 12.49 (br s, 1H, CONBN, minor isomer (43%)), 13.52 (br s, 1H, CONHN, major isomer (57%)); M$^-$(APCI$^-$): 472.

Example 12

4-ethoxy-N-{2-[2-(2-fluorobenzylidene)hydrazino]-2-oxoethyl}-N-(4-methylphenyl)benzenesulfonamide

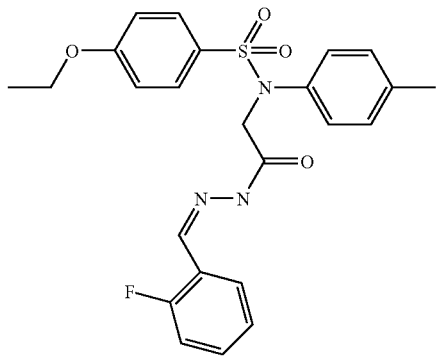

Following the general method as outlined in Example 1, starting from 4-ethoxybenzenesulfonyl chloride, p-toluidine, methyl bromoacetate and 2-fluorobenzaldehyde, the title compound precipitate in the reaction mixture. It was collected by filtration, washed with cold EtOH and dried under vacuo at 40° C., affording a colorless powder (72 mg, 77%) in 96% purity by HPLC (MaxPlot detection between 230 and 400 nm).

M.p, 183-184° C.; IR (neat) σ 3286, 2987, 1673, 1594, 1537, 1454, 1343, 1256, 1152, 1091, 1073 cm$^{-1}$; $^1$H NMR (300 MHz, DMSO-d$_6$): 1.34 (t, J=7.0 Hz, 3H, OCH$_2$CH$_3$), 2.24 (s, 3H, CH$_3$), 4.10 (q, J=7.0 Hz, 2H, OCH$_2$CH$_3$), 4.31 (s, 2H, NCH$_2$CO, minor isomer (38%)), 4.80 (s, 2H, NCH$_2$CO, major isomer (62%)), 6.95-7.15 (m, 6H, H arom.), 7.20-7.33 (m, 2H, H arom.), 7.42-7.64 (m, 3H, H arom.), 7.75-7.95 (m, 1H, H arom.), 8.15 (s, 1H, CH=N, major isomer (62%)), 8.42 (s, 1H, CH=N, minor isomer (38%)), 11.56 (s, 1H, CONHN, major isomer (62%)), 11.60 (s, 1H, CONHN, minor isomer (38%)); M$^-$(APCI$^-$): 468. Analysis calculated for C$_{24}$H$_{24}$FN$_3$O$_4$S 0.1H$_2$O: C, 61.16; H, 5.17; N, 8.92. Found: C, 60.92; H, 5.21; N, 8.95.

Example 13

N-(4-methylphenyl)-N-{2-oxo-2-[2-(2-oxo-1.2-dihydro-3H-indol-3-ylidene)hydrazino]ethyl}[1,1'-biphenyl]-4-sulfonamide

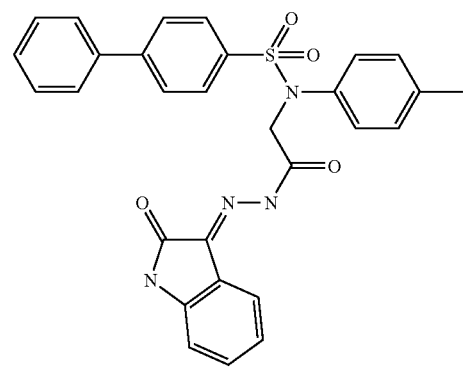

Following the general method as outlined in Example 1, starting from 4-phenylbenzenesulfonyl chloride, p-toluidine, methyl bromoacetate and 1H-indole-2,3-dione, the title compound precipitate in the reaction mixture. It was collected by filtration, washed with cold EtOH and dried under vacuo at 40° C., affording a yellow-orange powder (76 mg, 70%) in 99% purity by HPLC (MaxPlot detection between 230 and 400 nm).

M.p. 246-247° C.; IR (neat) σ 3098, 1698, 1616, 1506, 1468, 1317, 1148, 1117 cm$^{-1}$; $^1$H NMR (300 MHz, DMSO-d$_6$): 2.26 (s, 3H, CH$_3$), 4.57 (br s, 2H, NCH$_2$CO, major isomer (65%)), 5.04 (br s, 2H, NCH$_2$CO, minor isomer (35%)), 6.94 (m, 1H, H arom.), 7.08 (m, 1H, H arom.), 7.16 (m, 4H, H arom.), 7.34-7.60 (m, 5H, H arom.), 7.60-7.83 (m, 4H, H arom.), 7.90 (m, 2H, H arom.), 11.27 (s, 1H, NH), 12.52 (br s, 1H, CONIIN, minor isomer (35%)), 13.64 (br s, 1H, CONBN, major isomer (65%)); M$^-$(APCI$^-$): 523. Analysis calculated for C$_{29}$H$_{24}$N$_4$O$_4$S: C, 66.40; H, 4.61; N, 10.68. Found: C, 66.25; H, 4.63; N, 10.59.

Example 14

N-(4-methylphenyl)-N-{2-oxo-2-[2-(2-oxo-1,2-dihydro-3H-indol-3-ylidene)hydrazino]ethyl}-4-phenoxybenzenesulfonamide

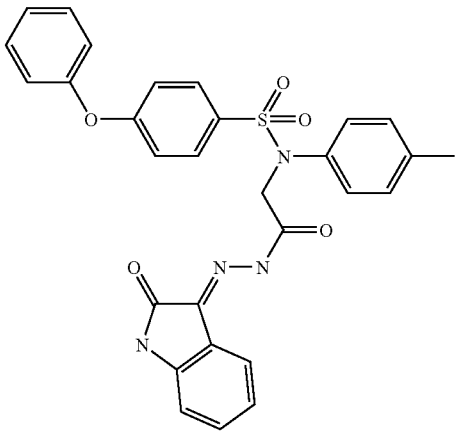

Following the general method as outlined in Example 1, starting from 4-phenoxybenzenesulfonyl chloride, p-toluidine, methyl bromoacetate and 1H-indole-2,3-dione, the title compound precipitate in the reaction mixture. It was collected by filtration, washed with cold EtOH and dried under vacuo at 40° C., affording a yellow powder (84 mg, 78%) in 98% purity by BPLC (MaxPlot detection between 230 and 400 nm).

M.p. 245-246° C.; IR (neat) σ 2987, 1698, 1616, 1506, 1468, 1317, 1248, 1148, 1117, 1078 cm$^{-1}$; $^1$H NMR (300 MHz, DMSO-d$_6$): 2.26 (s, 3H, CH$_3$), 4.57 (br s, 2H, NCH$_2$CO, major isomer (63%)), 5.04 (br s, 2H, NCH$_2$CO, minor isomer (37%)), 6.95 (m, 1H, H arom.), 7.08 (m, 1H, H arom.), 7.16 (m, 4H, H arom.), 7.34-7.61 (m, 5H, H arom.), 7.61-7.84 (m, 4H, H arom.), 7.90 (m, 2H, H arom.), 11.27 (s, 1H, NH), 12.52 (br s, 1H, CONHN, minor isomer (37%)), 13.64 (br s, 1H, CONHN, major isomer (63%)); [M-CH$_3$]$^-$(APCI$^-$): 523.

Example 15

4-ethoxy-N-{2-[2-(2-hydroxybenzylidene)hydrazino]-2-oxoethyl}-N-(4-methylphenyl)benzenesulfonamide

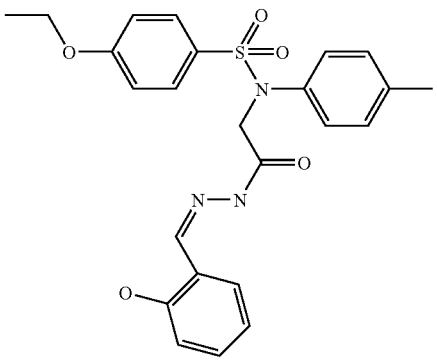

Following the general method as outlined in Example 1, starting from 4-ethoxybenzenesulfonyl chloride, p-toluidine, methyl bromoacetate and 2-hydroxybenzaldehyde, the title compound precipitate in the reaction mixture. It was collected by filtration, washed with cold EtOH and dried under vacuo at 40° C., affording a colorless powder (63 mg, 68%) in 83% purity by IPLC (MaxPlot detection between 230 and 400 nm).

$^1$H NMR (300 MHz, DMSO-d$_6$): 1.34 (t, J=7.0 Hz, 3H, OCH$_2$CH$_3$), 2.24 (s, 3H, CH$_3$), 4.10 (q, J=7.0 Hz, 2H, OCH$_2$CH$_3$), 4.32 (s, 2H, NCH$_2$CO, major isomer (63%)), 4.77 (s, 2H, NCH$_2$CO, minor isomer (37%)), 6.81-7.16 (m, 8H, H arom.), 7.18-7.31 (m, 1H, H arom.), 7.45-7.72 (m, 3H, H arom.), 8.23 (s, 1H, CH=N, minor isomer (37%)), 8.39 (s, 1H, CH=N, major isomer (63%)), 9.98 (s, 1H, OH, minor isomer (37%)), 10.92 (s, 1H, OH, major isomer (63%)), 11.37 (s, 1H, CONBN, minor isomer (37%)), 11.68 (s, 1H, CONJN, minor isomer (38%)); M$^-$(APCI$^-$): 466.

Example 16

N-(2-{2-[4-(diethylamino)-2-hydroxybenzylidene]hydrazino}-2-oxoethyl)-4-ethoxy-N-(4-methylphenyl)benzenesulfonamide

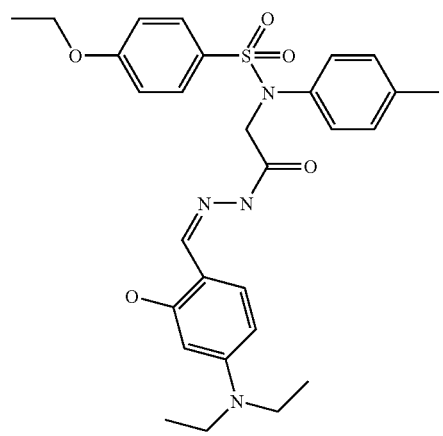

Following the general method as outlined in Example 1, starting from 4-ethoxybenzenesulfonyl chloride, p-toluidine, methyl bromoacetate and 4-(diethylamino)-2-hydroxybenzaldehyde, the title compound precipitate in the reaction mixture. It was collected by filtration, washed with cold EtOH and dried under vacuo at 40° C., affording a peach powder (91 mg, 85%) in 98% purity by HPLC (MaxPlot detection between 230 and 400 nm).

M.p. 227-228° C.; IR (neat) σ 3338, 2978, 1687, 1633, 1592, 1510, 1338, 1242, 1154, 1092, 1043 cm$^{-1}$; $^1$H NMR (300 MHz, DMSO-d$_6$): 1.00-1.17 (m, 6H, NCH$_2$CH$_3$), 1.34 (t, J=7.0 Hz, 3H, OCH$_2$CH$_3$), 2.24 (s, 3H, CH$_3$), 3.20-3.43 (m, 4H, NCH$_2$CH$_3$), 4.10 (q, J=7.0 Hz, 2H, OCH$_2$CH$_3$), 4.27 (s, 2H, NCH$_2$CO, major isomer (75%)), 4.68 (s, 2H, NCH$_2$CO, minor isomer (25%)), 6.06 (s, 1H, H arom, major isomer (75%)), 6.10 (s, 1H, H arom, minor isomer (25%)), 6.22 (m, 1H, H arom.), 6.95-7.40 (m, 7H, H arom.), 7.45-7.65 (m, 2H, H arom.), 8.02 (s, 1H, CH=N, minor isomer (25%)), 8.15 (s, 1H, CH=N, major isomer (75%)), 9.75 (s, 1H, OH, minor isomer (25%)), 11.06 (s, 1H, OH, major isomer (75%)), 11.10 (s, 1H, CONHN, minor isomer (25%)), 11.36 (s, 1H, CONHN, major isomer (75%)); M$^-$(APCI$^-$): 537. Analysis calculated for C$_{28}$H$_{34}$N$_4$O$_5$S: C, 62.43; H, 6.36; N, 10.40. Found: C, 62.31; H, 6.40; N, 10.41.

Example 17

4-ethoxy-N-(2-{2-[(2-hydroxy-1-naphthyl)methylene]hydrazino}-2-oxoethyl)-N-(4-methylphenyl)benzenesulfonamide

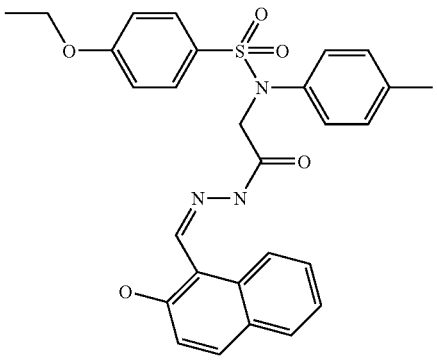

Following the general method as outlined in Example 1, starting from 4-ethoxybenzenesulfonyl chloride, p-toluidine, methyl bromoacetate and 2-hydroxy-1-naphthaldehyde, the title compound precipitate in the reaction mixture. It was collected by filtration, washed with cold EtOH and dried under vacuo at 40° C., affording a bright yellow powder (71 mg, 68%) in 92% purity by HPLC (MaxPlot detection between 230 and 400 nm).

$^1$H NMR (300 MHz, DMSO-$d_6$): 1.34 (t, J=7.0 Hz, 3H, OCH$_2$CH$_3$), 2.25 (s, 3H, CH$_3$), 4.11 (q, J=7.0 Hz, 2H, OCH$_2$CH$_3$), 4.39 (s, 2H, NCH$_2$CO, major isomer (76%)), 4.81 (s, 2H, NCH$_2$CO, minor isomer (24%)), 7.05-7.65 (m, 11H, H arom.), 7.82-7.95 (m, 2H, H arom.), 8.25 (m, 1H, H arom., major isomer (76%)), 8.64 (m, 1H, H arom., minor isomer (24%)), 8.78 (s, 1H, CH=N, minor isomer (24%)), 9.26 (s, 1H, CH=N, major isomer (76%)), 10.70 (s, 1H, OH, minor isomer (24%)), 11.41 (s, 1H, CONHN, minor isomer (24%)), 11.77 (s, 1H, OH, major isomer (76%)), 11.33 (s, 1H, CONHN, major isomer (76%)); M$^-$(APCI$^-$): 516.

Example 18

4-ethoxy-N-(4-methylphenyl)-N-{2-oxo-2-[2-(3-oxo-2,3-dihydro-1H-inden-1-ylidene)hydrazino]ethyl}benzenesulfonamide

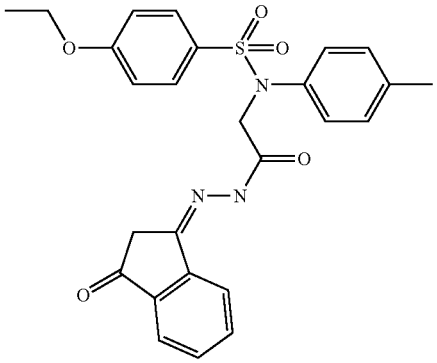

Following the general method as outlined in Example 1, starting from 4-ethoxybenzenesulfonyl chloride, p-toluidine, methyl bromoacetate and 1H-indene-1,3(2H)-dione, the title compound precipitate in the reaction mixture. It was collected by filtration, washed with cold EtOH and dried under vacuo at 40° C., affording a grey brown powder (60 mg, 62%) in 93% purity by HPLC (MaxPlot detection between 230 and 400 nm).

$^1$H NMR (300 MHz, DMSO-$d_6$): 1.35 (t, J=7.0 Hz, 3H, OCH$_2$CH$_3$), 2.24 (s, 3H, CH$_3$), 3.39 (m, 2H, (C=N)CH$_2$(C=O)), 4.11 (q, J=7.0 Hz, 2H, OCH$_2$CH$_3$), 4.44 (s, 2H, NCH$_2$CO, minor isomer (38%)), 4.88 (s, 2H, NCH$_2$CO, major isomer (62%)), 6.98-7.16 (m, 6H, H arom.), 7.51-7.68 (m, 3H, H arom.), 7.70-7.86 (m, 2H, H arom.), 7.90 (m, 1H, H arom., minor isomer (38%)), 7.99 (m, 1H, H arom., major isomer (62%)), 10.52 (s, 1H, CONHN, minor isomer (38%)), 10.92 (s, 1H, CONHN, major isomer (62%)); M$^-$(APCI$^-$): 490.

Example 19

4'-methoxy-N-(4-methylphenyl)-N-{2-oxo-2-[2-(2-oxo-1,2-dihydro-3H-indol-3-ylidene)hydrazino]ethyl}[1,1'-biphenyl]-4-sulfonamide

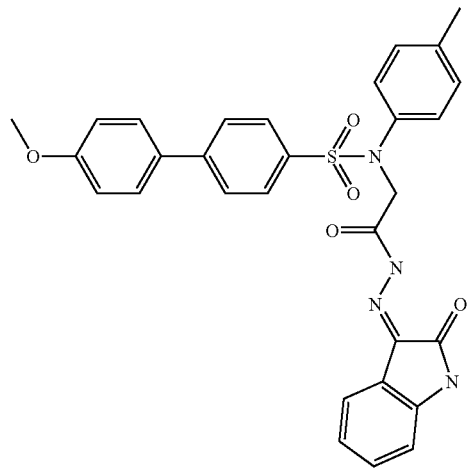

Following the general method as outlined in Example 1, starting 4'-methoxy[1,1'-biphenyl]-4-sulfonyl chloride, p-toluidine, methyl bromoacetate and 1H-indole-2,3-dione, the title compound precipitate in the reaction mixture. It was collected by filtration, washed with cold EtOH and dried under vacuo at 40° C., affording a yellow-orange powder (106 mg, 92%) in 98% purity by HPLC (MaxPlot detection between 230 and 400 nm).

M.p. 235-236° C.; IR (neat) σ 3204, 1717, 1688, 1595, 1504, 1466, 1337, 1249, 1155, 1125, 1092 cm$^{-1}$; $^1$H NMR (300 MHz, DMSO-$d_6$): 2.26 (s, 3H, CH$_3$), 3.81 (s, 3H, OCH$_3$), 4.55 (br s, 2H, NCH$_2$CO, major isomer (63%)), 5.03 (br s, 2H, NCH$_2$CO, minor isomer (37%)), 6.95 (m, 1H, H arom.), 7.01-7.22 (m, 7H, H arom.), 7.38 (m, 1H, H arom.), 7.46-7.78 (m, 5H, H arom.), 7.85 (m, 2H, H arom.), 11.27 (s, 1H, NH), 12.51 (br s, 1H, CONHN, minor isomer (37%)); 13.64 (br s, 1H, CONHN, major isomer (63%)); M$^-$(APCI$^-$): 553. Analysis calculated for $C_{30}H_{26}N_4O_5S$: C, 64.97; H, 4.73; N, 10.10. Found: C, 64.60; H, 4.70; N, 9.94.

Example 20

4-ethoxy-N-{2-[2-(1-methyl-2-oxo-1,2-dihydro-3H-indol-3-ylidene)hydrazino]-2-oxoethyl}-N-(4-methylphenyl)benzenesulfonamide

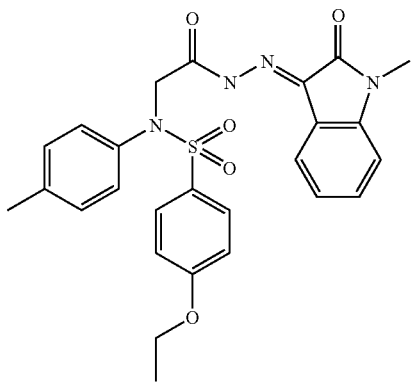

Following the general method as outlined in Example 1, starting from 4-ethoxybenzenesulfonyl chloride, p-toluidine, methyl bromoacetate and 1-methylisatin, the title compound was isolated by evaporation of the solvents and purified by recrystallization in MeOH. A yellow powder (79 mg, 79%) was obtained in 99% purity by HPLC (MaxPlot detection between 230 and 400 nm).

M.p. 109-110° C.; IR (neat) σ 2987, 1694, 1616, 1592, 1505, 1470, 1356, 1338, 1261, 1153, 1116, 1097, 1041 cm$^{-1}$; $^1$H NMR (300 MHz, DMSO-d$_6$): 1.34 (t, J=7.0 Hz, 3H, OCH$_2$CH$_3$), 2.26 (s, 3H, CH$_3$), 3.31 (s, 3H, CH$_3$), 4.11 (q, J=7.0 Hz, 2H, OCH$_2$CH$_3$), 4.48 (s, 2H, NCH$_2$CO, major isomer (70%)), 4.96 (s, 2H, NCH$_2$CO, major isomer (30%)), 7.02-7.23 (m, 8H, H arom.), 7.43-7.67 (m, 4H, H arom.), 12.42 (s, 1H, CONHN, minor isomer (30%)), 13.60 (s, 1H, CONHN, major isomer (70%)); M$^-$(APCI$^-$): 505. Analysis calculated for C$_{26}$H$_{26}$N$_4$O$_5$S 0.2H$_2$O: C, 61.21; H, 5.22; N, 10.98. Found: C, 60.96; H, 5.23; N, 10.92.

Example 21

N-(2-{2-[1-(2,4-dihydroxyphenyl)ethylidene]hydrazino}-2-oxoethyl)-4-ethoxy-N-(4-methylphenyl)benzenesulfonamide

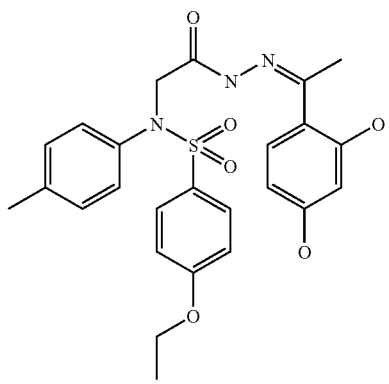

Following the general method as outlined in Example 1, starting from 4-ethoxybenzenesulfonyl chloride, p-toluidine, methyl bromoacetate and 2,4-dihydroxyacetophenone, the title compound was isolated by evaporation of the solvents and purified by recrystallization in MeOH. A light yellow powder (33 mg, 33%) was obtained in 93% purity by HPLC (MaxPlot detection between 230 and 400 nm).

$^1$H NMR (300 MHz, DMSO-d$_6$): 1.34 (t, J=7.0 Hz, 3H, OCH$_2$CH$_3$), 2.21 (s, 3H, CH$_3$), 2.25 (s, 3H, CH$_3$), 4.10 (q, J=7.0 Hz, 2H, OCH$_2$CH$_3$), 4.45 (s, 2H, NCH$_2$CO), 6.20 (m, 1H, H arom.), 6.28 (m, 1H, H arom.), 6.95-7.18 (m, 6H, H arom.), 7.35 (m, 1H, H arom.), 7.55 (m, 2H, H arom.), 9.81 (s, 1H, OH), 10.79 (s, 1H, OH), 13.12 (s, 1H, CONHN); M$^-$(APCI$^-$): 496.

Example 22

4-ethoxy-N-(2-{2-[1-(2-hydroxyphenyl)ethylidene]hydrazino}-2-oxoethyl)-N-(4-methylphenyl)benzenesulfonamide

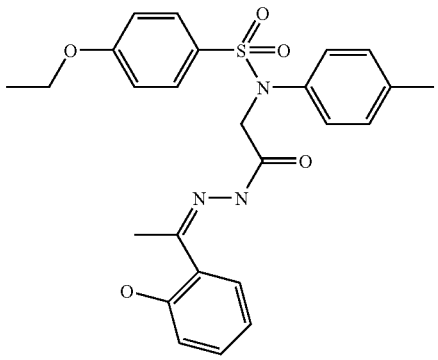

Following the general method as outlined in Example 1, starting from 4-ethoxybenzenesulfonyl chloride, p-toluidine, methyl bromoacetate and 2-hydroxyacetophenone, the title compound was isolated by evaporation of the solvents and purified by recrystallization in MeOH. A colorless powder (59 mg, 61%) was obtained in 99% purity by HPLC (MaxPlot detection between 230 and 400 nm).

M.p. 199-200° C.; IR (neat) σ 2986, 1669, 1592, 1534, 1493, 1351, 1304, 1244, 1203, 1161, 1084 cm$^{-1}$; $^1$H NMR (300 MHz, DMSO-d$_6$): 1.34 (t, J=7.0 Hz, 3H, OCH$_2$CH$_3$), 2.25 (s, 3H, CH$_3$), 2.30 (s, 3H, CH$_3$), 4.10 (q, J=7.0 Hz, 2H, OCH$_2$CH$_3$), 4.49 (s, 2H, NCH$_2$CO, major isomer (93%)), 4.72 (s, 2H, NCH$_2$CO, minor isomer (7%)), 6.81-6.90 (m, 2H, H arom.), 7.00-7.16 (m, 6H, H arom.), 7.26 (m, 1H, H arom.), 7.55 (m, 3H, H arom.), 10.77 (s, 1H, CH=N, minor isomer (7%)), 10.98 (s, 1H, CH=N, major isomer (93%)), 12.94 (s, 1H, CONHN); M$^-$(APCI$^-$): 480. Analysis calculated for C$_{25}$H$_{27}$N$_3$O$_5$S: C, 62.35; H, 5.65; N, 8.73. Found: C, 62.16; H, 5.60; N, 8.74.

Example 23

3,4-dimethoxy-N-(4-methylphenyl)-N-{2-oxo-2-[2-(2-oxo-1,2-dihydro-3H-indol-3-ylidene)hydrazino]ethyl}benzenesulfonamide

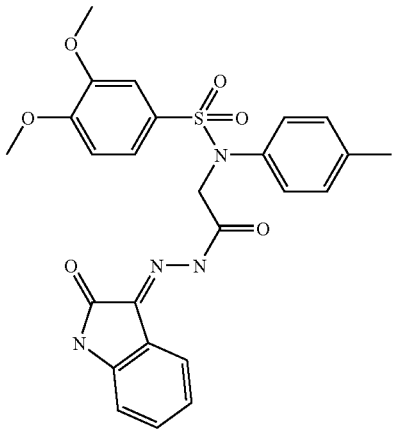

Following the general method as outlined in Example 1, starting from 3,4-dimethoxybenzenesulfonyl chloride, p-toluidine, methyl bromoacetate and 1H-indole-2,3-dione, the title compound was isolated by evaporation of the solvents and purified by recrystallization in EtOAc. A dark orange powder (35 mg, 35%) was obtained in 92% purity by HPLC (MaxPlot detection between 230 and 400 nm).

$^1$H NMR (300 MHz, DMSO-$d_6$): 2.08 (s, 3H, $CH_3$), 3.54 (s, 3H, $OCH_3$), 3.66 (s, 3H, $OCH_3$), 4.31 (s, 2H, $NCHCO$, major isomer (70%)), 4.79 (s, 2H, $NCH_2CO$, minor isomer (30%)), 6.68-6.85 (m, 2H, H arom.), 6.85-7.10 (m, 7H, H arom.), 7.20 (m, 1H, H arom.), 7.35 (m, 1H, H arom.), 11.09 (s, 1H, NH), 12.32 (s, 1H, CONHN, minor isomer (30%)), 13.48 (s, 1H, CONHN, major isomer (70%)); $M^+(APCI^+)$: 509, $M^-(APCI^-)$: 507.

Example 24

4-ethoxy-N-(2-{2-[1-(2-hydroxy-1-naphthylethylidene]hydrazino}-2-oxoethyl)-N-(4-methylphenyl)benzenesulfonamide

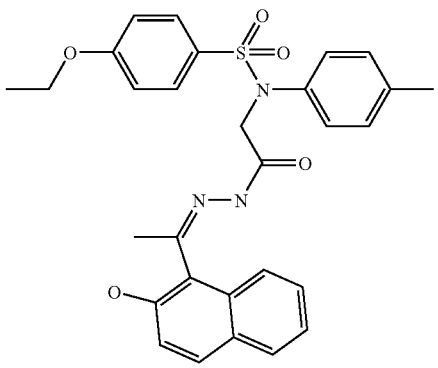

Following the general method as outlined in Example 1, starting from 4-ethoxybenzenesulfonyl chloride, p-toluidine, methyl bromoacetate and 2-hydroxy-1-acetonaphthone, the title compound was isolated by evaporation of the solvents and purified by recrystallization in AcOEt. A light yellow powder (55 mg, 52%) was obtained in 90% purity by HPLC (MaxPlot detection between 230 and 400 nm).

$^1$H NMR (300 MHz, DMSO-$d_6$): 1.34 (m, 3H, $OCH_2CH_3$), 2.25 (m, 6H, 2 $CH_3$), 3.90-4.15 (m, 4H, $OCH_2CH_3$ and $NCH_2CO$, minor isomer (30%)), 4.79 (s, 2H, $NCH_2CO$, major isomer (70%)), 6.25 (m, 1H, H arom.), 6.80 (m, 1H, H arom.), 6.88-7.65 (m, 10H, H arom.), 7.76-8.04 (m, 2H, H arom.), 9.13 (s, 1H, OH, minor isomer (30%)),9.30 (s, 1H, OH, major isomer (70%)), 10.07 (s, 1H, CONHN, minor isomer (30%)), 10.23 (s, 1H, CONHN, major isomer (70%)); $M^-(APCI^-)$: 530.

Example 25

4-Ethoxy-N-(2-{(2E)-2-[1-(1-hydroxy-2-naphthyl)ethylidene]hydrazino}-2-oxoethyl)-N-(4-methylphenyl)benzenesulfonamide

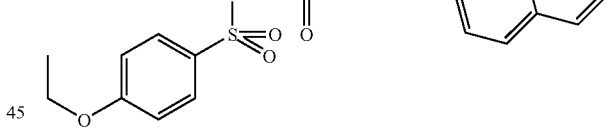

Following the general method as outlined in Example 1, starting from 4-ethoxybenzenesulfonyl chloride, 4-toluidine, methyl bromoacetate and 1'-hydroxy-2'-acetophenone, the title compound was isolated by evaporation of the solvents and purified by crystallization in EtOH/AcOH 5%. A light beige solid (18.9 mg, 18%) was obtained in 98.18% purity by HPLC (MaxPlot detection between 230 and 400 nm).

$^1$H NMR (DMSO-$d_6$, 300 MHz) d 1.37 (t, 3H, J=6.8 Hz), 2.22 (s, 3H), 2.43 (s, 3H), 4.14 (q, 2H, J=6.8 Hz), 4.56 (s, 2H), 7.05-7.18 (m, 6H), 7.39 (m, 1H), 7.47-7.70 (m, 5H), 7.85 (m, 1H), 8.29 (m, 1H), 11.1 (s, 1H, OH). $(APCI^-)$: 530.2. $(APCI^+)$: 532.2.

Example 26

4-tert-Butyl-N-(4-chlorophenyl)-N-{2-oxo-2-[(2E)-2-(2-oxo-1,2-dihydro-3H-indol-3-ylidene)hydrazino]ethyl}benzenesulfonamide

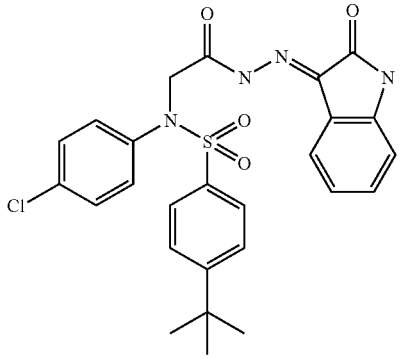

Following the general method as outlined in Example 1, starting from 4-tert-butylbenzenesulfonyl chloride, 4-chloroaniline, methyl bromoacetate and isatine, the title compound was isolated by evaporation of the solvents and purified by crystallization in MeOH. A yellow powder (72.7 mg, 69%) was obtained in 99.35% purity by HPLC (MaxPlot detection between 230 and 400 nm).

M.p. 194-195° C. IR (neat) σ 2966, 1698, 1620, 1469, 1366, 1170, 1084 cm$^{-1}$. $^1$H NMR (DMSO-d$_6$, 300 MHz) d 1.30 (s, 9H), 4.57 (br s, 2H, NCH2CO, major isomer (60%)), 5.04 (br s, 2H, NCH2CO, minor isomer (40%)), 6.94 (m, 1H), 7.09 (m, 1H), 7.25-7.67 (m, 10H), 11.27 (s, 1H, NH), 12.52 (br s, 1H, CONHN, minor isomer (40%)), 13.56 (br s, 1H, CONHN, major isomer (60%)). (ESI$^-$): 523. Analysis calculated for C$_{26}$H$_{25}$ClN$_4$O$_4$S.0.5H$_2$° C., 58.48; H, 4.91; N, 10.49. Found: C, 58.37; H, 4.97; N, 10.57.

Example 27

N-(4-chlorophenyl)-3,4-dimethoxy-N-{2-oxo-2-[(2E)-2-(2-oxo-1,2-dihydro-3H-indol-3-ylidene)hydrazino]ethyl}benzenesulfonamide

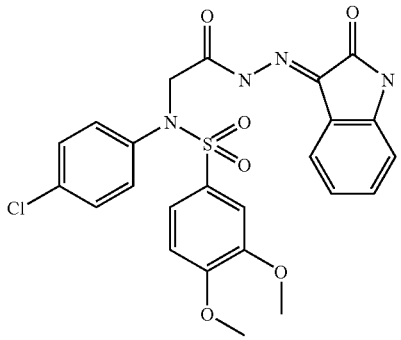

Following the general method as outlined in Example 1, starting from 3,4-dimethoxybenzenesulfonyl chloride, 4-chloroaniline, methyl bromoacetate and isatine, the title compound was isolated by evaporation of the solvents and purified by crystallization in MeOH. A yellow powder (91.0 mg, 86%) was obtained in 97.58% purity by HPLC (Max-Plot detection between 230 and 400 nm).

M.p. 132-133° C. IR (neat) σ 3188, 2966, 1714, 1622, 1506, 1464, 1337, 1139, 1016 cm$^{-1}$. $^1$H NMR (DMSO-d$_6$, 300 MHz) d 3.74 (s, 3H, OCH3), 3.83 (s, 3H, OCH3), 4.55 (br s, 2H, NCH2CO, major isomer (60%)), 5.03 (br s, 2H, NCH2CO, minor isomer (40%)), 6.90-7.60 (m, 11H, H arom.), 11.27 (s, 1H, NH), 12.52 (br s, 1H, CONHN, minor isomer (40%)), 13.62 (br s, 1H, CONHN, major isomer (60%)). Analysis calculated for C$_{24}$H$_{21}$ClN$_4$O$_6$S.1.8H$_2$° C., 51.35; H, 4.42; N, 9.98. Found: C, 51.12; H, 4.08; N, 10.05.

Example 28

4-tert-Butyl-N-(4-methylphenyl)-N-{2-oxo-2-[(2E)-2-(2-oxo-1,2-dihydro-3H-indol-3-ylidene)hydrazino]ethyl}benzenesulfonamide

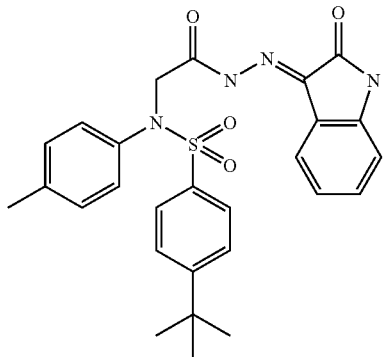

Following the general method as outlined in Example 1, starting from 4-tert-butylbenzenesulfonyl chloride, 4-toluidine, methyl bromoacetate and isatine, the title compound was isolated by evaporation of the solvents and purified by crystallization in MeOH. A yellow powder (49.9 mg, 49%) was obtained in 99.44% purity by HPLC (MaxPlot detection between 230 and 400 nm).

M.p. 139-140° C. IR (neat) σ 3188, 2968, 1698, 1506, 1465, 1338, 1160, 1084 cm$^{-1}$. $^1$H NMR (DMSO-d$_6$, 300 MHz) d 1.30 (s, 9H), 2.25 (s, 3H), 4.50 (br s, 2H, NCH2CO, major isomer (60%)), 4.98 (br s, 2H, NCH2CO, minor isomer (40%)), 6.94 (m, 1H), 7.02-7.20 (m, 5H), 7.38 (m, 1H), 7.47-7.70 (m, 5H), 11.27 (s, 1H, NH), 12.52 (br s, 1H, CONHN, minor isomer (40%)), 13.56 (br s, 1H, CONHN, major isomer (60%)). (ESI$^-$): 503. (ESI$^+$): 505.

Example 29

N-(4-methylphenyl)-N-{2-oxo-2-[(2E)-2-(2-oxo-12-dihydro-3H-indol-3-ylidene)hydrazino]ethyl}-4-propylbenzenesulfonamide

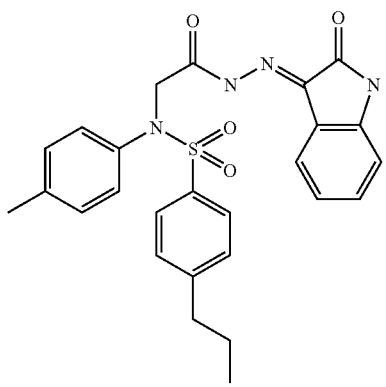

Following the general method as outlined in Example 1, starting from 4-n-propylbenzenesulphonyl chloride, 4-toluidine, methyl bromoacetate and isatine, the title compound was isolated by evaporation of the solvents and purified by crystallization in MeOH. A orange powder (44.5 mg, 45%) was obtained in 96.59% purity by HPLC (MaxPlot detection between 230 and 400 nm).

M.p. 198-199° C. IR (neat) σ 3207, 2966, 1698, 1619, 1467, 1314, 1245, 1143, 1116 cm$^{-1}$. $^1$H NMR (DMSO-d$_6$, 300 MHz) d 0.88 (t, 3H, J=7.54 Hz), 1.60 (sex, 2H, J=7.54 Hz), 2.25 (s, 3H), 2.64 (t, 2H, J=7.54 Hz), 4.50 (s, 2H, NCH2CO, major isomer (60%)), 4.97 (br s, 2H, NCH2CO, minor isomer (40%)), 6.94 (m, 1H), 7.05-7.20 (m, 5H), 7.30-7.65 (m, 6H), 11.28 (s, 1H, NH), 12.49 (br s, 1H, CONHN, minor isomer (40%)), 13.63 (br s, 1H, CONHN, major isomer (60%)). (ESI$^-$): 489.2. Analysis calculated for C26H26N4O4SC, 63.66; H, 5.34; N, 11.42. Found: C, 63.60; H, 5.36; N, 11.49.

Example 30

4-Butoxy-N-(4-methylphenyl)-N-{2-oxo-2-[(2E)-2-(2-oxo-1,2-dihydro-3H-indol-3-ylidene)hydrazino]ethyl}benzenesulfonamide

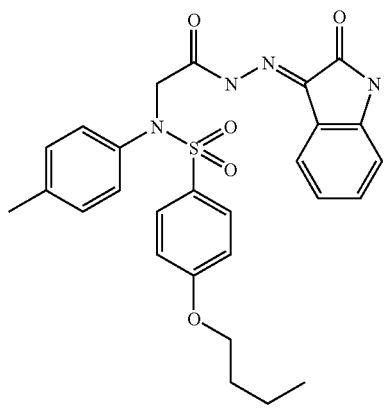

Following the general method as outlined in Example 1, starting from 4-(n-butoxy)benzenesulfonyl chloride, 4-toluidine, methyl bromoacetate and isatine, the title compound was isolated by evaporation of the solvents and purified by crystallization in MeOH. A yellow powder (61.4 mg, 59%) was obtained in 99.39% purity by HPLC (MaxPlot detection between 230 and 400 nm).

M.p. 111-112° C. IR (neat) σ 2962, 1693, 1622, 1594, 1497, 1466, 1347, 1257, 1152, 1092 cm$^{-1}$. $^1$H NMR (DMSO-d$_6$, 300 MHz) d 0.93 (t, 3H, J=7.53 Hz), 1.43 (sex, 2H, J=7.53 Hz), 1.71 (m, 2H), 2.26 (s, 3H), 4.05 (t, 2H, J=6.39 Hz), 4.47 (s, 2H, NCH2CO, major isomer (65%)), 4.95 (br s, 2H, NCH2CO, minor isomer (35%)), 6.95 (n, 1H), 7.05-7.26 (m, 7H), 7.36 (m, 1H), 7.38-7.70 (m, 3H), 11.28 (s, 1H, NH), 12.49 (br s, 1H, CONHN, minor isomer (35%)), 13.65 (br s, 1H, CONHN, major isomer (65%)). (ESI$^-$): 519.2. (ESI$^+$): 521.2. Analysis calculated for C27H28N4O5SC, 62.29; H, 5.42; N, 10.76. Found: C, 62.19; H, 5.44; N, 10.67.

Example 31

4-Butoxy-N-(4-chlorophenyl)-N-{2-oxo-2-[(2Z)-2-(2-oxo-1,2-dihydro-3H-indol-3-ylidene)hydrazino]ethyl}benzenesulfonamide

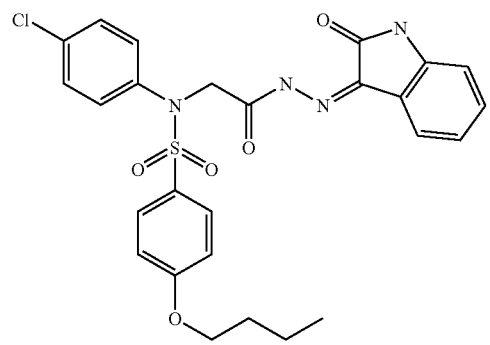

Following the general method as outlined in Example 1, starting from 4-(n-butoxy)benzenesulfonyl chloride, 4-chloroaniline, methyl bromoacetate and isatine, the title compound was isolated by evaporation of the solvents and purified by crystallization in MeOH. A yellow powder (26.3 mg, 25%) was obtained in 96.1% purity by HPLC (MaxPlot detection between 230 and 400 nm).

$^1$H NMR (DMSO-d$_6$, 300 MHz) d 0.93 (t, 3H, J=7.5 Hz), 1.43 (sex, 2H, J=7.5 Hz), 1.71 (m, 2H), 4.05 (t, 2H, J=6.40 Hz), 4.52 (s, 2H, NCH2CO, major isomer (65%)), 5.01 (br s, 2H, NCH2CO, minor isomer (35%)), 6.95 (m, 1H), 7.03-7.14 (m, 3H), 7.22-7.68 (m, 8H), 11.28 (s, 1H, NH), 12.51 (br s, 1H, CONHN, minor isomer (35%)), 13.60 (br s, 1H, CONHN, major isomer (65%)). (APCI$^-$): 539. (APCI$^+$): 541.

Example 32

N-(4-chlorophenyl)-N-{2-oxo-2-[(2Z)-2-(2-oxo-1,2-dihydro-3H-indol-3-ylidene)hydrazino]ethyl}-4-propoxybenzenesulfonamide

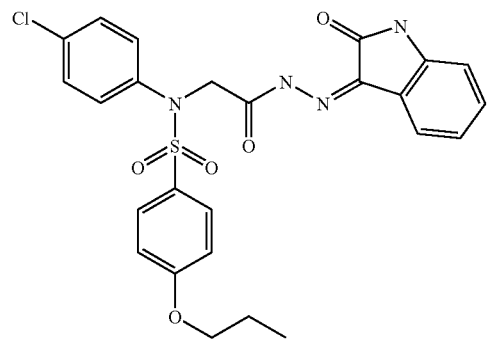

Following the general method as outlined in Example 1, starting from 4-n-propoxy-1-benzenesulfonyl chloride, 4-chloroaniline, methyl bromoacetate and isatine, the title compound was isolated by evaporation of the solvents and purified by flash chromatography, using a mixture cyclohexane/ethyl acetate 3:1 as eluent. A yellow powder (46.8 mg, 44.4%) was obtained in 98.92% purity by HPLC (MaxPlot detection between 230 and 400 nm).

¹H NMR (DMSO-d₆, 300 MHz) d 0.98 (t, 3H, J=7.53 Hz), 1.75 (m, 2H), 4.02 (t, 2H, J=6.40 Hz), 4.53 (s, 2H, NCH2CO, major isomer (65%)), 5.02 (br s, 2H, NCH2CO, minor isomer (35%)), 6.95 (m, 1H), 7.05-7.16 (m, 3H), 7.28 (m, 2H), 7.35-7.70 (m, 6H), 11.28 (s, 1H, NH), 12.52 (br s, 1H, CONHN, minor isomer (35%)), 13.61 (br s, 1H, CONHN, major isomer (65%)). (APCI⁻): 525.2. (APCI⁺): 527.2.

Example 33

N-(4-methylphenyl)-N-{2-oxo-2-[(2Z)-2-(2-oxo-1,2-dihydro-3H-indol-3-ylidene)hydrazino]ethyl}-4-tert-pentylbenzenesulfonamide

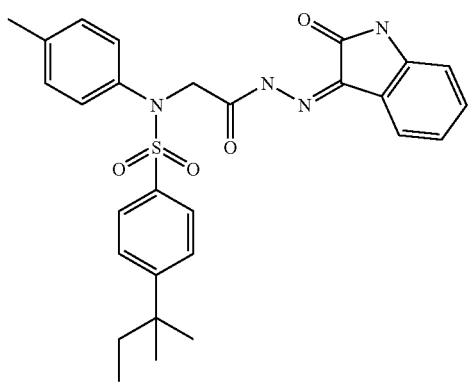

Following the general method as outlined in Example 1, starting from 4-tert-amylbenzenesulfonyl chloride, 4-toluidine, methyl bromoacetate and isatine, the title compound was isolated by evaporation of the solvents and purified by crystallization in EtOH. A orange-yellow powder (14.7 mg, 14.2%) was obtained in 88.22% purity by HPLC (MaxPlot detection between 230 and 400 nm).

¹H NMR (DMSO-d₆, 300 MHz) d 0.98 (t, 3H, J=7.53 Hz), 1.26 (s, 6H), 1.63 (q, 2H, J=7.53 Hz), 2.25 (s, 3H), 4.51 (s, 2H, NCH2CO, major isomer (65%)), 4.98 (br s, 2H, NCH2CO, minor isomer (35%)), 6.95 (m, 1H), 7.02-7.18 (m, 5H), 7.38 (m, 1H), 7.46-7.67 (m, 5H), 11.27 (s, 1H, NH), 12.49 (br s, 1H, CONHN, minor isomer (35%)), 13.62 (br s, 1H, CONHN, major isomer (65%)). (APCI⁻): 517. (APCI⁻): 519.2.

Example 34

N-(4-methylphenyl)-N-{2-oxo-2-[(2Z)-2-(2-oxo-1,2-dihydro-3H-indol-3-ylidene)hydrazino]ethyl}-4-propoxybenzenesulfonamide

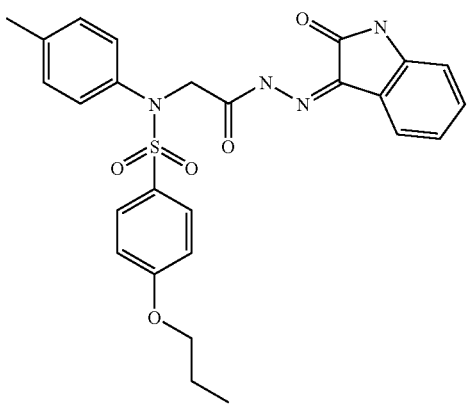

Following the general method as outlined in Example 1, starting from 4-n-propoxy-1-benzenesulfonyl chloride, 4-toluidine, methyl bromoacetate and isatine, the title compound was isolated by evaporation of the solvents and purified by flash chromatography, using a mixture cyclohexane/ethyl acetate 3:1 as eluent. A yellow powder (46.9 mg, 46.3%) was obtained in 99.6% purity by HPLC (MaxPlot detection between 230 and 400 nm).

¹H NMR (DMSO-d₆, 300 MHz) d 0.97 (t, 3H, J=7.34 Hz), 1.74 (m, 2H), 2.25 (s, 3H), 4.01 (t, 2H, J=6.40 Hz), 4.47 (s, 2H, NCH2CO, major isomer (70%)), 4.95 (br s, 2H, NCH2CO, minor isomer (30%)), 6.95 (m, 1H), 7.03-7.18 (m, 7H), 7.38 (m, 1H), 7.44-7.68 (m, 6H), 11.28 (s, 1H, NH), 12.49 (br s, 1H, CONHN, minor isomer (30%)), 13.65 (br s, 1H, CONHN, major isomer (70%)). (APCI⁻): 505. (APCI⁺): 507.2.

Example 35

N-(4-methylphenyl)-N-{2-oxo-2-[(2Z)-2-(2-oxo-1,2-dihydro-3H-indol-3-ylidene)hydrazino]ethl}-2-thiophenesulfonamide

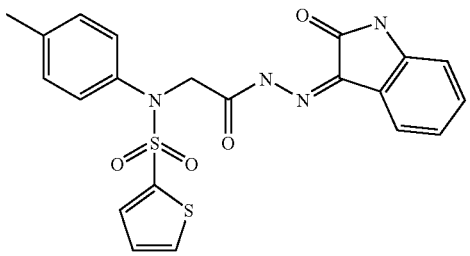

Following the general method as outlined in Example 1, starting from 2-thiophenesulfonyl chloride, 4-toluidine, methyl bromoacetate and isatine, the title compound was isolated by evaporation of the solvents and purified by crystallization in EtOH. A brown powder (12.9 mg, 14.2%) was obtained in 58.4% purity by IPLC (MaxPlot detection between 230 and 400 nm).

(APCI⁻): 453. (APCI⁺): 455.

Example 36

N-(4-chlorophenyl)-N-{2-oxo-2-[(2Z)-2-(2-oxo-1,2-dihydro-3H-indol-3-ylidene)hydrazino]ethyl}-2-thiophenesulfonamide

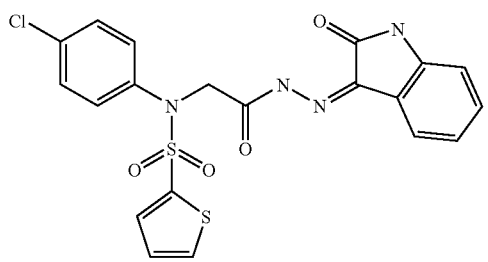

Following the general method as outlined in Example 1, starting from 2-thiophenesulfonyl chloride, 4-chloroaniline, methyl bromoacetate and isatine, the title compound was isolated by evaporation of the solvents and purified by flash chromatography, using a mixture cyclohexane/ethyl acetate 3:1 as eluent. A yellow powder (21.8 mg, 23%) was obtained in 99.2% purity by HPLC (MaxPlot detection between 230 and 400 nm).

$^1$H NMR (DMSO-$d_6$, 300 MHz) d 4.59 (s, 2H, NCH2CO, major isomer (60%)), 5.03 (br s, 2H, NCH2CO, minor isomer (40%)), 6.94 (m, 1H), 7.09 (m, 1H), 7.21-7.59 (m, 7H), 7.64 (m, 1H), 8.05 (m, 1H), 11.28 (s, 1H, NH), 12.52 (br s, 1H, CONHN, minor isomer (40%)), 13.62 (br s, 1H, CONHN, major isomer (60%)). (APCI$^-$): 473. (APCI$^+$): 475.

Example 37

N-(4-chlorophenyl)-N-{2-[(2E)-2-(2-hydroxybenzylidene)hydrazino]-2-oxoethyl}-3,4-dimethoxybenzenesulfonamide

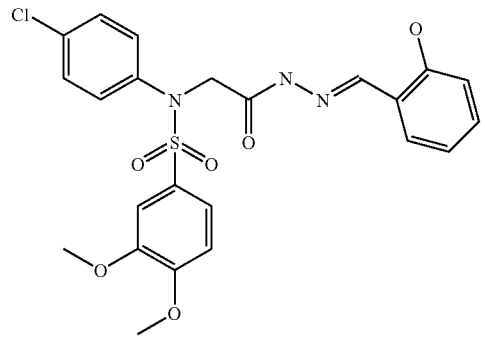

Following the general method as outlined in Example 1, starting from 3,4-dimethoxybenzenesulfonyl chloride, 4-chloroaniline, methyl bromoacetate and salicylaldehyde, the title compound was isolated by evaporation of the solvents and purified by crystallization in EtOH/5% AcOH. A colorless solid (232 mg, 80.4%) was obtained in 99.52% purity by HPLC (MaxPlot detection between 230 and 400 nm).

M.p. 188-189° C. IR (neat) σ 2962, 1673, 1507, 1488, 1351, 1241, 1137, 1020 cm$^{-1}$. $^1$H NMR (DMSO-$d_6$, 300 MHz) d 3.74 (s, 3H), 3.77 (s, 3H), 4.39 (s, 2H, NCH2CO, major isomer (54%)), 4.85 (br s, 2H, NCH2CO, minor isomer (46%)), 6.80-6.93 (m, 2H), 7.05-7.15 (m, 2H), 7.17-7.31 (m, 4H), 7.34-7.45 (m, 2H), 7.50 (m, 1H, major isomer (54%)), 7.67 (m, 1H, minor isomer (46%)), 8.24 (s, 1H, minor isomer (46%)), 8.41 (s, 1H, major isomer (54%)), 10.00 (s, 1H, minor isomer (46%)), 10.90 (s, 1H, major isomer (54%)), 11.46 (s, 1H, minor isomer (46%)), 11.74 (s, 1H, major isomer (54%)). (APCI$^-$): 502.

(APCI$^+$): 504.2. Analysis calculated for C23H22ClN3O6SC, 54.82; H, 4.40; N, 8.34. Found: C, 54.48; H, 4.44; N, 8.31.

Example 38

N-(4-chlorophenyl)-4-ethoxy-N-{2-[(2E)-2-(2-hydroxybenzylidene)hydrazino]-2-oxoethyl}benzenesulfonamide

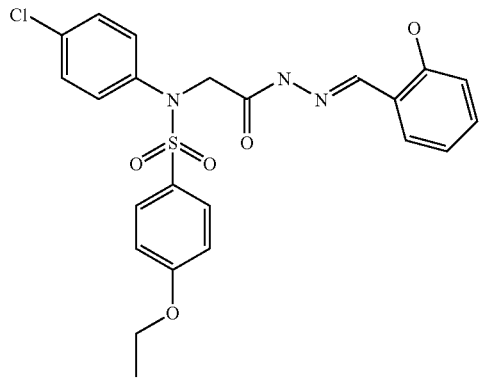

Following the general method as outlined in Example 1, starting from 4-ethoxybenzenesulfonyl chloride, 4-chloroaniline, methyl bromoacetate and salicylaldehyde, the title compound was isolated by evaporation of the solvents and purified by crystallization in EtOH. A colorless powder (64.6 mg, 66.2%) was obtained in 92.2% purity by HPLC (MaxPlot detection between 230 and 400 nm).

IR (neat) σ 2988, 1632, 1488, 1351, 1262, 1155, 1084 cm$^{-1}$. $^1$HNMR (DMSO-$d_6$, 300 MHz) d 1.34 (t, 3H, J=7.14 Hz), 4.10 (q, 2H, J=7.14 Hz), 4.37 (s, 2H, NCH2CO, major isomer (55%)), 4.82 (br s, 2H, NCH2CO, minor isomer (45%)), 6.81-7.14 (m, 4H), 7.16-7.32 (m, 3H), 7.35-7.44 (m, 2H), 7.46-7.73 (m, 3H), 8.24 (s, 1H, minor isomer (45%)), 8.40 (s, 1H, major isomer (55%)), 9.99 (s, 1H, minor isomer (45%)), 10.90 (s, 1H, major isomer (55%)), 11.42 (s, 1H, minor isomer (45%)), 11.74 (s, 1H, major isomer (55%)). (APCI$^-$): 486. (APCI$^+$): 488.

Example 39

N-(4-chlorophenyl-N-{2-oxo-2-[(2Z)-2-(2-oxo-1,2-dihydro-3H-indol-3-ylidene)hydrazino]ethyl}-4-tert-pentylbenzenesulfonamide

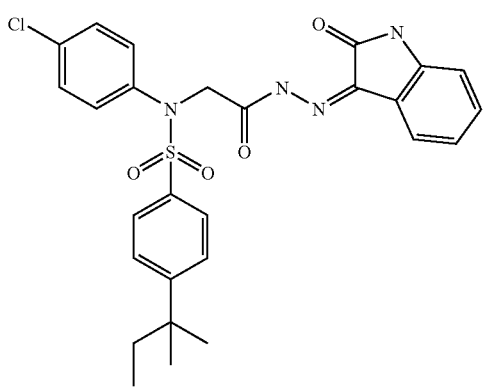

Following the general method as outlined in Example 1, starting from 4-tert-amylbenzenesulfonyl chloride, 4-chloroaniline, methyl bromoacetate and isatine, the title compound was isolated by evaporation of the solvents and purified by crystallization in EtOH. A brown-orange powder (59.3 mg, 55%) was obtained in 76% purity by HPLC (MaxPlot detection between 230 and 400 nm).

(APCI$^-$): 537. (APCI$^+$): 539.2.

Example 40

N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide

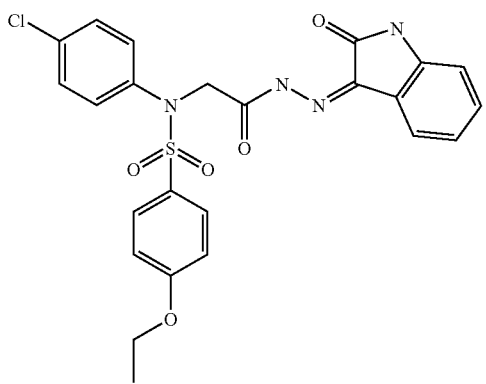

Following the general method as outlined in Example 1, starting from 4-ethoxybenzenesulfonyl chloride, 4-chloroaniline, methyl bromoacetate and isatine, the title compound was isolated by evaporation of the solvents and purified by flash chromatography, using a mixture cyclohexane/ethyl acetate 3:1 as eluent. A orange powder (60.3 mg, 59%) was obtained in 95.48% purity by HPLC (MaxPlot detection between 230 and 400 nm).

$^1$H NMR (DMSO-d$_6$, 300 MHz) d 1.34 (t, 3H, J=6.78 Hz), 4.10 (q, 2H, 3=6.78 Hz), 4.52 (s, 2H, NCH2CO, major isomer (60%)), 5.01 (br s, 2H, NCH2CO, minor isomer (40%)), 6.94 (m, 1H), 7.02-7.14 (m, 3H), 7.26 (m, 2H), 7.33-7.71 (m, 6H), 11.28 (s, 1H, NH), 12.52 (br s, 1H, CONHN, minor isomer (40%)), 13.61 (br s, 1H, CONHN, major isomer (60%)). (APCI$^-$): 511. (APCI$^+$): 513.

Example 41

N-(4-chlorophenyl)-N-{2-oxo-2-[(2Z)-2-(2-oxo-1,2-dihydro-3H-indol-3-ylidene)hydrazino]ethyl}benzenesulfonamide

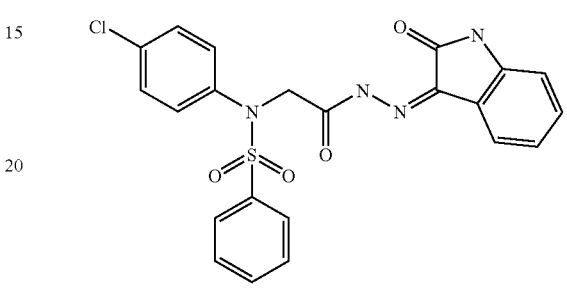

Following the general method as outlined in Example 1, starting from benzene-sulfonyl chloride, 4-chloroaniline, methyl bromoacetate and isatine, the title compound was isolated by evaporation of the solvents and purified by flash chromatography, using a mixture cyclohexane/ethyl acetate 3:1 as eluent. A yellow powder (15.5 mg, 16.5%) was obtained in 98% purity by HPLC (MaxPlot detection between 230 and 400 nm).

$^1$H NMR (DMSO-d$_6$, 300 MHz) d 4.59 (s, 2H, NCH2CO, major isomer (55%)), 5.06 (br s, 2H, NCH2CO, minor isomer (45%)), 6.94 (m, 1H), 7.09 (m, 1H), 7.26 (m, 2H), 7.33-7.47 (m, 3H), 7.49-7.78 (m, 6H), 11.28 (s, 1H, 1H), 12.53 (br s, 1H, CONHN, minor isomer (45%)), 13.58 (br s, 1H, CONHN, major isomer (55%)). (APCI$^-$): 466.8. (APCI$^+$): 469.

Example 42

N-(4-chlorophenyl)-N-{2-oxo-2-[(2Z)-2-(2-oxo-1,2-dihydro-3H-indol-3-ylidene)hydrazino]ethyl}-4-propylbenzenesulfonamide

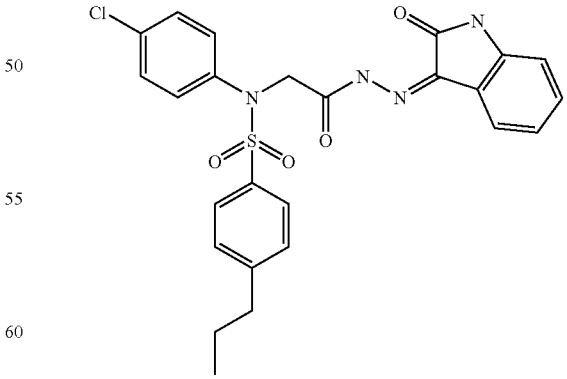

Following the general method as outlined in Example 1, starting from 4-n-propoxy-1-benzenesulfonyl chloride, 4-chloroaniline, methyl bromoacetate and isatine, the title compound was isolated by evaporation of the solvents and purified by flash chromatography, using a mixture cyclohexane/ethyl acetate 3:1 as eluent. A yellow powder (32.8 mg, 32%) was obtained in 67.9% purity by HPLC (MaxPlot detection between 230 and 400 nm).

(APCI⁻): 508.8. (APCI⁺): 511.2.

Example 43

N-(4-chlorophenyl)-4-ethoxy-N-{2-[(2E)-2-(1H-imidazol-2-ylmethylene)hydrazino]-2-oxoethyl}benzenesulfonamide

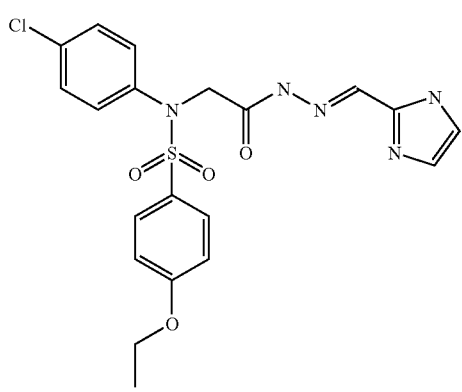

Following the general method as outlined in Example 1, starting from 4-ethoxybenzenesulfonyl chloride, 4-chloroaniline, methyl bromoacetate and 2-imidazolecarboxaldehyde, the title compound was isolated by evaporation of the solvents and purified by crystallization in EtOH/5% AcOH. A colorless powder (34 mg, 74%) was obtained in 98.73% purity by HPLC (MaxPlot detection between 230 and 400 nm).

$^1$H NMR (DMSO-$d_6$, 300 MHz) d 1.34 (t, 3H, J=6.0 Hz), 4.10 (q, 2H, J=6.0 Hz), 4.35 (s, 2H, NCH2CO, minor isomer (35%)), 4.89 (br s, 2H, NCH2CO, major isomer (65%)), 6.98-7.44 (m, 8H), 7.54 (m, 2H, minor isomer (35%)), 7.64 (m, 2H, major isomer (65%)), 7.82 (s, 1H, major isomer (65%)), 8.07 (s, 1H, minor isomer (35%)), 11.50 (s, 1H, NH), 12.55 (br s, 1H, CONHN, major isomer (65%)), 12.72 (br s, 1H, CONHN, minor isomer (35%)). (APCI⁻): 459.8. (APCI⁺): 462.

Example 44

N-(4-chlorophenyl)-4-ethoxy-N-{2-oxo-2-[(2E)-2-(2-pyridinylmethylene)hydrazino]ethyl}benzenesulfonamide

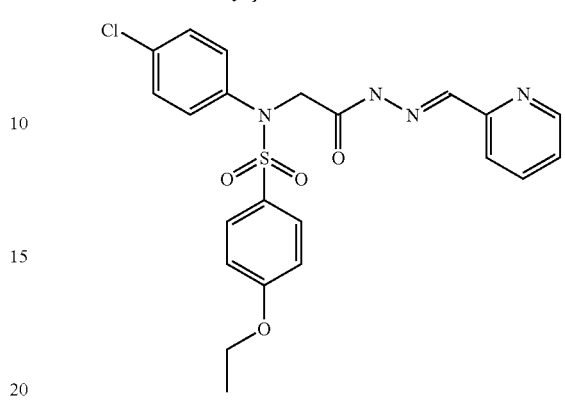

Following the general method as outlined in Example 1, starting from 4-ethoxybenzenesulfonyl chloride, 4-chloroaniline, methyl bromoacetate and 2-pyridinecarboxaldehyde, the title compound was isolated by evaporation of the solvents and purified by crystallization in EtOH/5% AcOH. A colorless powder (26.9 mg, 57%) was obtained in 96.4% purity by HPLC (MaxPlot detection between 230 and 400 nm).

$^1$H NMR (DMSO-$d_6$, 300 MHz) d 1.34 (t, 3H, J=6.0 Hz), 4.11 (q, 2H, J=6.0 Hz), 4.38 (s, 2H, NCH2CO, minor isomer (35%)), 4.88 (br s, 2H, NCH2CO, major isomer (65%)), 7.01-7.66 (m, 9H), 7.80-8.22 (m, 3H), 8.58 (m, 1H), 11.71 (m, 1H). (APCI⁻): 471. (APCI⁺): 473.

Example 45

4-Fluoro-N-(4-methylphenyl)-N-{2-oxo-2-[(2Z)-2-(2-oxo-1,2-dihydro-3H-indol-3-ylidene)hydrazino]ethyl}benzenesulfonamide

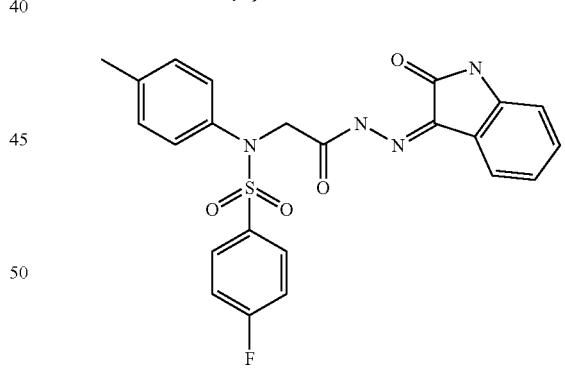

Following the general method as outlined in Example 1, starting from 4-fluorobenzenesulfonyl chloride, 4-toluidine, methyl bromoacetate and isatine, the title compound was isolated by evaporation of the solvents and purified by crystallization in EtOH/5% AcOH. A yellow powder (26 mg, 59%) was obtained in 94.7% purity by HPLC (MaxPlot detection between 230 and 400 nm).

$^1$H NMR (DMSO-$d_6$, 300 MHz) d 2.27 (s, 3H), 4.54 (s, 2H, NCH2CO, major isomer (68%)), 5.01 (br s, 2H, NCH2CO, minor isomer (32%)), 6.94 (m, 1H), 7.03-7.22 (m, 5H), 7.33-7.85 (m, 6H), 11.28 (s, 1H, NH), 12.49 (br s, 1H, CONHN, minor isomer (32%)), 13.61 (br s, 1H, CONHN, major isomer (68%)). (ESI⁻): 464.8.

Example 46

4-Fluoro-N-{2-[(2E)-2-(2-hydroxybenzylidene)hydrazino]-2-oxoethyl}-N-(4-methylphenyl)benzenesulfonamide

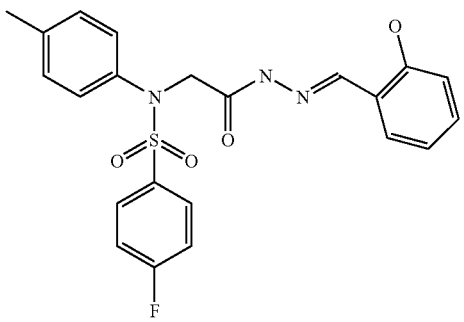

Following the general method as outlined in Example 1, starting from 4-fluorobenzenesulfonyl chloride, 4-toluidine, methyl bromoacetate and salicylaldehyde, the title compound was isolated by evaporation of the solvents and purified by crystallization in EtOH/5% AcOH. A colorless powder (33.5 mg, 76%) was obtained in 87.3% purity by HPLC (MaxPlot detection between 230 and 400 nm).

$^1$H NMR (DMSO-$d_6$, 300 MHz) d 2.25 (s, 3H), 4.37 (s, 2H, NCH2CO, major isomer (56%)), 4.81 (br s, 2H, NCH2CO, minor isomer (44%)), 6.81-6.91 (m, 2H), 7.02-7.32 (m, 5H), 7.36-7.78 (m, 5H), 8.24 (s, 1H, minor isomer (44%)), 8.40 (s, 1H, major isomer (56%)), 9.98 (s, 1H, minor isomer (44%)), 10.90 (s, 1H, major isomer (56%)), 11.40 (s, 1H, minor isomer (44%)), 11.71 (s, 1H, major isomer (56%)). (ESI$^-$): 440.

Example 47

4-Ethoxy-N-[2-((2E)-2-{2-[hydroxy(oxido)amino]benzylidene}hydrazino)-2-oxoethyl]-N-(4-methylphenyl)benzenesulfonamide

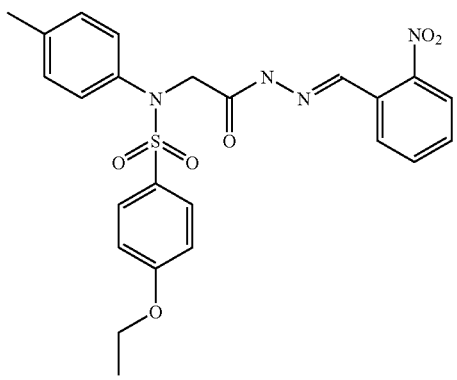

Following the general method as outlined in Example 1, starting from 4-ethoxybenzenesulfonyl chloride, 4-toluidine, methyl bromoacetate and 2-nitrobenzaldehyde, the title compound was isolated by evaporation of the solvents and purified by crystallization in AcOH. A colorless powder (418.3 mg, 84%) was obtained in 98.62% purity by HPLC (MaxPlot detection between 230 and 400 nm).

$^1$H NMR (DMSO-$d_6$, 300 MHz) d 1.34 (t, 3H, J=6.0 Hz), 2.24 (s, 3H), 4.10 (q, 2H, J=6.0 Hz), 4.34 (s, 2H, NCH2CO, minor isomer (38%)), 4.78 (br s, 2H, NCH2CO, major isomer (62%)), 6.88-7.20 (m, 6H), 7.50-7.70 (m, 3H), 7.77 (m, 1H), 7.95-8.10 (m, 2H), 8.29 (s, 1H, major isomer (62%)), 8.58 (s, 1H, minor isomer (38%)), 11.74 (s, 1H, major isomer (62%)), 11.81 (s, 1H, minor isomer (38%)), 11.93 (s, 1H). (APCI$^-$): 494.8. (APCI$^+$): 496.8.

Example 48

N-{2-[(2E)-2-(2-aminobenzylidene)hydrazino]-2-oxoethyl}-4-ethoxy-N-(4-methylphenyl)benzenesulfonamide

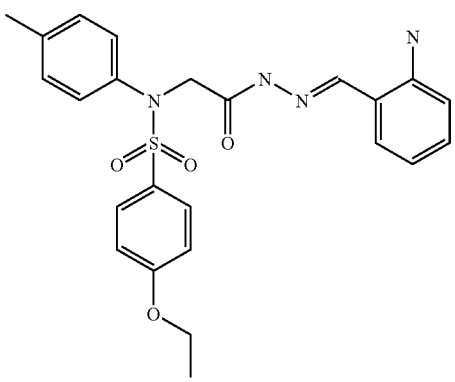

4-ethoxy-N-(4-methylphenyl)-N-{2-[(2E)-2-(2-nitrobenzylidene)hydrazino]-2-oxoethyl}benzenesulfonamide (99 mg, 0.2 mmol) was dissolved in methylene chloride. Palladium 5% on charcoal was added (10 mol %). The mixture was stirred under H$_2$ at athmospheric pressure at room temperature overnight. It was filtered on Celite and solvents were evaporated. The expected product, e.g. N-{2-[(2E)-2-(2-aminobenzylidene)hydrazino]-2-oxoethyl}-4-ethoxy-N-(4-methylphenyl)benzenesulfonamide (71.2 mg, 76%), was obtained as a light yellow solid, in 90.9% purity by HPLC (MaxPlot detection between 230 and 400 nm).

$^1$H NMR (300 MHz, CDCl$_3$): 1.38 (t, J=6.0 Hz, 3H, OCH$_2$CH$_3$), 2.26 (s, 3H, CH$_3$), 3.5 (br s, 2H), 4.01 (q, J=6.0 Hz, 2H, OCH$_2$CH$_3$), 4.14 (s, 2H), 6.62 (m, 1H), 6.76-6.91 (m, 5H, H arom.), 6.93-7.07 (m, 4H, H arom.), 7.40 (m, 2H, H arom.), 7.85 (br s, 1H).

Example 49

N-(2-{(E)-[2-(2-{[(4-ethoxyphenyl)sulfonyl]-4-methylanilino}acetyl)hydrazono]methyl}phenyl)acetamide

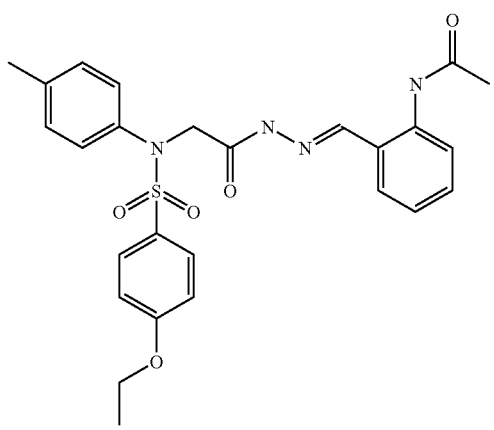

Following the general method as outlined in Example 1, starting from 4-ethoxybenzenesulfonyl chloride, 4-toluidine, methyl bromoacetate and N-acetyl-2-aminobenzaldehyde, the title compound was isolated by evaporation of the solvents and purified by flash chromatography, using a mixture cyclohexane/ethyl acetate 4:1 as eluent. A light yellow solid (18.3 mg, 18%) was obtained in 93.6% purity by HPLC (MaxPlot detection between 230 and 400 nm).

$^1$H NMR (DMSO-$d_6$, 300 MHz) d 1.44 (t, 3H, J=6.0 Hz), 2.26 (s, 3H), 2.32 (s, 3H), 4.08 (q, 2H, J=6.0 Hz), 4.29 (s, 2H, NCH2CO), 6.81-7.16 (m, 7H), 7.24 (m, 1H), 7.38 (m, 1H), 7.50 (m, 2H), 8.13 (s, 1H), 8.69 (d, 1H, J=6 Hz), 9.82 (s, 1H), 11.59 (s, 1H). (ESI$^-$): 507.

Example 50

N-(4-chlorophenyl)-4-ethoxy-N-{2-oxo-2-[(2Z)-2-(2-oxo-1,2-dihydro-3H-pyrrolo[3,2-c]pyridin-3-ylidene)hydrazino]ethyl}benzenesulfonamide

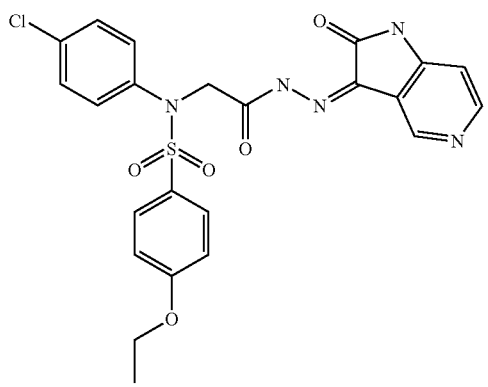

Following the general method as outlined in Example 1, starting from 4-ethoxybenzenesulfonyl chloride, 4-chloroaniline, methyl bromoacetate and 5-azaisatine, the title compound was isolated by evaporation of the solvents and purified by flash chromatography, using a mixture DCM/MeOH 20:1 as eluent. A light yellow solid (32.4 mg, 26%) was obtained in 87% purity by HPLC (MaxPlot detection between 230 and 400 nm).

$^1$H NMR (DMSO-$d_6$, 300 MHz) d 1.12 (t, 3H, J=6 Hz), 3.88 (q, 2H, J=6 Hz), 4.35 (s, 2H, NCH2CO, major isomer (63%)), 4.80 (br s, 2H, NCH2CO, minor isomer (37%)), 6.79 (m, 1H), 6.87 (m, 2H), 7.03 (m, 2H), 7.19 (m, 2H), 7.32 (m, 2H), 8.24 (d, 1H, J=3 Hz), 8.40 (br s, 1H), 11.45 (s, 1H, NH), 12.15 (br s, 1H, CONHN, minor isomer (37%)), 13.28 (br s, 1H, CONHN, major isomer (63%)). (ESI$^-$): 511.8. (ESI$^+$): 514.

Example 51

4-Ethoxy-N-{2-[(2E)-2-(1H-indol-3-ylmethylene)hydrazino]-2-oxoethyl}-N-(4-methylphenyl)benzenesulfonamide

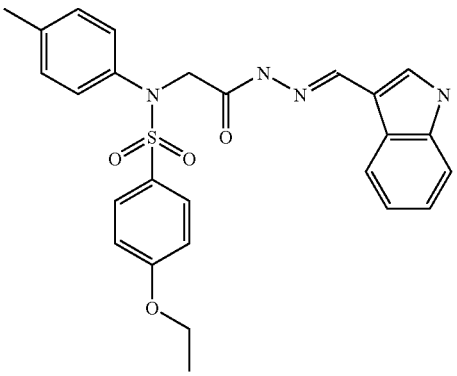

Following the general method as outlined in Example 1, starting from 4-ethoxybenzenesulfonyl chloride, 4-toluidine, methyl bromoacetate and indole-3-carboxyldehyde, the title compound was isolated by evaporation of the solvents and purified by crystallization in ethyl acetate. A beige solid (40 mg, 43.3%) was obtained in 93.2% purity by HPLC (MaxPlot detection between 230 and 400 nm).

$^1$H NMR (DMSO-$d_6$, 300 MHz) d 1.37 (m, 3H), 2.24 (s, 3H), 4.12 (m, 2H), 4.29 (s, 2H, NCH2CO, minor isomer (36%)), 4.80 (br s, 2H, NCH2CO, major isomer (64%)), 7.01-7.26 (m, 1H), 7.42 (m, 1H), 7.57 (m, 2H), 7.77 (m, 1H), 7.99 (m, 1H, major isomer (64%)), 8.10 (br s, 1H, major isomer (64%)), 8.12 (m, 1H, minor isomer (36%)), 8.30 (br s, 1H, minor isomer (36%)), 11.08 (s, 1H, CONHN, minor isomer (36%)), 11.55 (s, 1H, CONHN, major isomer (64%)), 11.55 (br s, 1H, NH). (APCI$^-$): 489. (APCI$^+$): 491.2.

Example 52

4-Ethoxy-N-(2-{(2E)-2-[(2-methyl-1H-indol-3-yl)methylene]hydrazino}-2-oxoethyl)-N-(4-methylphenyl)benzenesulfonamide

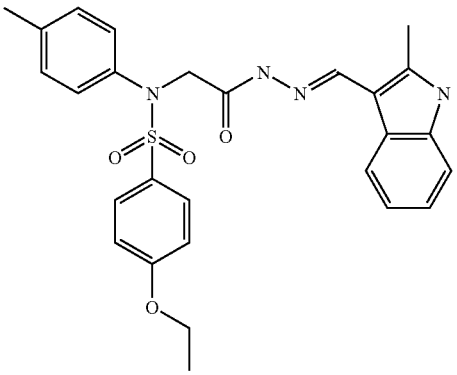

Following the general method as outlined in Example 1, starting from 4-ethoxybenzenesulfonyl chloride, 4-toluidine, methyl bromoacetate and 2-methylindole-3-carboxyldehyde, the title compound was isolated by evaporation of the solvents and purified by crystallization in ethyl acetate. A yellow powder (57.4 mg, 60%) was obtained in 95.2% purity by HPLC (MaxPlot detection between 230 and 400 nm).

¹H NMR (DMSO-d₆, 300 MHz) d 1.36 (m, 3H), 2.24 (s, 3H), 2.43 (s, 3H, major isomer (60%)), 2.45 (s, 3H, minor isomer (40%)), 4.12 (m, 2H), 4.27 (s, 2H, NCH2CO, minor isomer (40%)), 4.78 (br s, 2H, NCH2CO, major isomer (60%)), 6.95-7.18 (m, 8H), 7.32 (m, 1H), 7.56 (m, 2H), 7.77 (m, 1H), 7.88 (m, 1H, major isomer (60%)), 8.04 (m, 1H, minor isomer (40%)), 8.18 (s, 1H, major isomer (60%)), 8.37 (s, 1H, minor isomer (40%)), 11.44 (br s, 1H, minor isomer (40%)), 11.46 (br s, 1H, major isomer (60%)), 11.90 (br s, 1H, NH). (APCI⁻): 503.2. (APCI⁺): 505.2.

Example 53

4-Ethoxy-N-{2-oxo-2-[(2Z)-2-(2-oxo-1,2-dihydro-3H-indol-3-ylidene)hydrazino]ethyl}-N-(2-pyrimidinyl)benzenesulfonamide

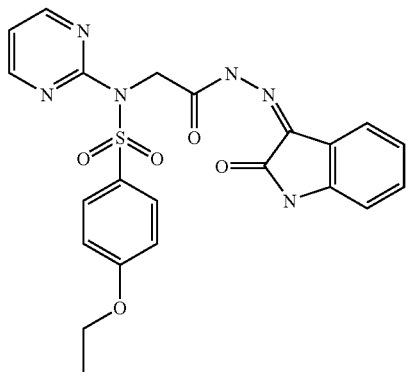

Following the general method as outlined in Example 1, starting from 4-ethoxybenzenesulfonyl chloride, 2-aminopyrimidine, methyl bromoacetate and isatine, the title compound was isolated by evaporation of the solvents and purified by crystallization in AcOH. A yellow solid (61.1 mg, 75%) was obtained in 96.63% purity by BPLC (ax-Plot detection between 230 and 400 nm).

¹H NMR (DMSO-d₆, 300 MHz) d 1.27 (t, 3H, J=6 Hz), 4.05 (q, 2H, J=6 Hz), 5.01 (s, 2H, NCH2CO, minor isomer (20%)), 5.42 (br s, 2H, NCH2CO, major isomer (80%)), 6.89 (m, 1H), 6.94-7.15 (m, 4H), 7.34 (m, 1H), 7.42-7.68 (m, 1H), 8.01 (m, 2H), 8.48 (m, 2H), 11.20 (br s, 1H, major isomer (80%)), 12.55 (br s, 1H, minor isomer (20%)). (ESI⁻): 479.17. (ESI⁺): 481.24.

Example 54

General Protocol B for the Solution-Phase Synthesis of Sulfanilide Derivatives of General Formula II with R³=H (Schemes 3, 5); e.g. 4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide.

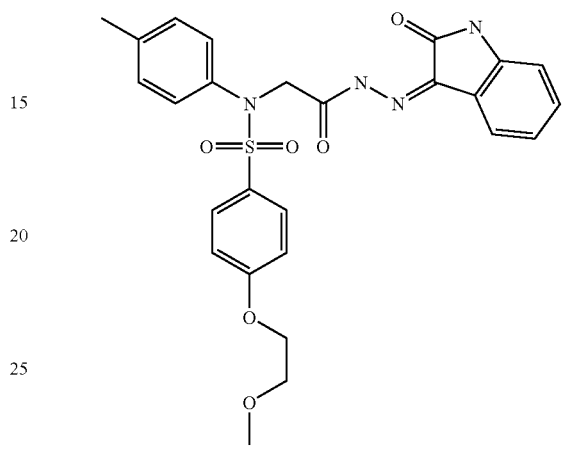

a) Protocol for the Formation of the N-aryl-benzenesulfonamide building block, XIII (Scheme 4 and 5); e.g. 4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide.

4-Toluidine (6.430 g, 60 mmol) was dissolved in pyridine (200 mL). The resulting mixture was cooled down to 0° C. 4-fluoro-benzenesulfonyl chloride (7.784 g, 40 mmol) was added in portions. The mixture was stirred between 0° C. and room temperature overnight. Solvents were evaporated to dryness. The crude oil was dissolved in ethyl acetate (150 mL) and washed with 10% HCl (2×75 mL) and brine (1×75 mL). Organic phase was dried over magnesium sulfate before filtering and removal of solvent. The resulting solid was recrystallized in cyclohexane/ethyl acetate 9:1. The desired product, e.g. 4-fluoro-N-(4-methylphenyl)benzenesulfonamide (9.4754 g, 89%), was obtained as a colorless solid, in 98% purity by HPLC (MaxPlot detection between 230 and 400 nm).

¹H NMR (300 MHz, CDCl₃): 2.26 (s, 3H, CH₃), 6.63 (br s, 1H, NH), 6.92 (m, 2H, H arom.), 6.97-7.14 (m, 4H, H arom.), 7.73 (m, 2H, H arom.); M⁺(ESI⁺): 266.20; M⁻(ESI⁻): 264.18.

b) Protocol for the Transformation of the N-aryl-benzenesulfonamide Building Block XIII into XIII* by Aromatic Nucleophilic Substitution with Sodium Alcoholate (Scheme 5); e.g. 4-(2-methoxyethoxy)-N-(4-methylphenyl)benzenesulfonamide.

To a suspention of NaH (2.2 mmol, 55-65% in oil) in dry dioxane (6 mL) was added 2-methoxyethanol (158 µl, 2 mmol). The mixture was stirred 1 h at room temperature. A solution of 4-fluoro-N-(4-methylphenyl)benzenesulfonamide (265.3 mg, 1 mmol) in dry dioxane (2 mL) was added. The resulting mixture was heated 24 h at 100° C. Solvents were evaporated. NH₄Cl saturated solution in water (5 mL) was added and the desired product was extracted with three portions of ethyl acetate (3×5 mL). Combined organic phases were dried over magnesium sulfate before filtering and removal of solvent. The desired product, e.g. 4-(2-methoxyethoxy)-N-(4-methylphenyl)benzenesulfonamide was obtained as a colorless oil, in 77% purity by HPLC (MaxPlot detection between 230 and 400 nm). This intermediate was used in the next step without further purification.

M$^+$(APCI$^+$): 322.

c) Protocol for the Displacement of the Leaving Group in XI (Scheme 3); e.g. Methyl ({[4-(2-methoxyethoxy)phenyl]sulfonyl}-4-methylanilino)acetate.

The crude N-aryl-benzenesulfonamide building block XIII* resulting from the precedent step, e.g. 4-(2-methoxyethoxy)-N-(4-methylphenyl)benzenesulfonamide (1 mmol), was dissolved in dry dioxane (5 mL) and was added to a suspension of NaH (1.2 mmol, 55-65% in oil) in dry dioxane (1 mL). The mixture was stirred 1 h at room temperature. 2-Bromoacetic acid methyl ester (133 mL, 1.4 mmol) was added dropwise. The resulting mixture was stirred at 60° C. overnight. The solvents were evaporated, affording the desired product, e.g. methyl ({[4-(2-methoxyethoxy)phenyl]sulfonyl}-4-methylanilino)acetate as a light yellow oil, in 74% purity by HPLC (MaxPlot detection between 230 and 400 nm). This intermediate was used in the next step without further purification.

M$^+$(APCI$^+$): 394.

d) Protocol for the Transformation of the Carboxylic Acid Ester into the Hydrazide (Scheme 1); e.g. N-(2-hydrazino-2-oxoethyl)-4-(2-methoxyethoxy)-N-(4-methylphenyl)benzenesulfonamide.

The crude carboxylic acid methyl ester resulting from the precedent step, e.g. methyl ({[4-(2-methoxyethoxy)phenyl]sulfonyl}-4-methylanilino)acetate (1 mmol), was dissolved in MeOH (3.5 mL). Hydrazine hydrate was added (0.385 mL). The reaction mixture was stirred overnight at room temperature. Solvents were evaporated. The crude product was dissolved in ethyl acetate (4 mL) and was washed with water (4 mL). Aqueous phase was extracted with ethyl acetate (3×2 mL) and with methylene chloride (2×2 mL). Combined organic phases were dried over magnesium sulfate, filtrated and solvents were evaporated. The desired product, e.g. N-(2-hydrazino-2-oxoethyl)-4-(2-methoxyethoxy)-N-(4-methylphenyl)benzenesulfonamide was isolated as a light yellow oil, in 86% purity by HPLC (MaxPlot detection between 230 and 400 m). This intermediate was used in the next step without further purification.

M$^+$(ESI$^+$): 394.33. M$^-$(ESI$^-$): 392.18.

e) Protocol for the Formation of the Acyl Hydrazone, II (Scheme 1), e.g. 4-{2-methoxyethoxy)-N-(4-methylphenyl)-N-(2-oxo-2-[(2Z)-2-(2-oxo-1,2-dihydro-3H-indol-3-ylidene)hydrazino]ethyl}benzenesulfonamide.

Hydrazide obtained in the precedent step, e.g. N-(2-hydrazino-2-oxoethyl)-4-(2-methoxyethoxy)-N-(4-methylphenyl)benzenesulfonamide (1 mmol), was dissolved in EtOH/5% AcOH (3 mL). Isatin (118 mg, 0.8 mmol) was added. The reaction mixture was stirred overnight at 75° C. Solvents were evaporated and the desired product was purfied by flash chromatography using a 1:1 mixture of cyclohexane and ethyl acetate. The expected product, e.g. 4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide (135.6 mg, 26% yield over 4 steps) was isolated as a yellow solid in 96% purity by HPLC (MaxPlot detection between 230 and 400 nm).

$^1$H NMR (300 MHz, DMSO-d$_6$): 2.29 (s, 3H, CH$_3$), 3.45 (s, 3H, OCH$_3$), 3.76 (m, 2H), 4.16 (m, 2H), 4.39 (br s, 2H, NCH$_2$CO, major isomer (68%)), 5.00 (br s, 2H, NCH$_2$CO, minor isomer (32%)), 6.87-7.01 (m, 3H, H arom.), 7.02-7.21 (m, 4H, H arom.), 7.32 (m, 1H, H arom.), 7.52 (m, 2H, H arom.), 7.66-7.78 (m, 2H, H arom.), 7.92 (br s, 1H, minor isomer (32%)), 8.34 (br s, 1H, major isomer (68%)), 12.39 (br s, 1H, minor isomer (32%)), 14.00 (br s, 1H, major isomer (68%)); M$^+$(APCI$^+$): 523.0; M$^-$(APCI$^-$): 521.0.

Example 55

N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide

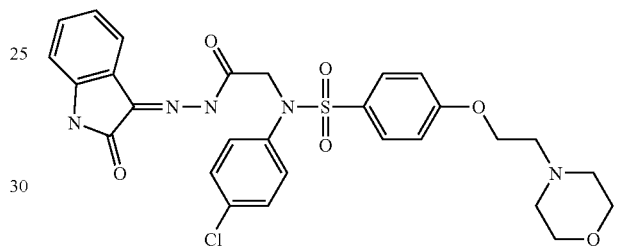

Following the general method as outlined in Example 54, starting from 4-chloroaniline, 2-morpholin-4-yl-ethanol, methyl bromoacetate and isatine, the title compound was isolated by evaporation of the solvents and purified by flash chromatography, using a mixture methylene chloride/MeOH 40:1 as eluent. A yellow powder (342.1 mg, 8.2% over four steps) was obtained in 95% purity by HPLC (MaxPlot detection between 230 and 400 nm).

N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide (342.1 mg, 0.572 mmol) was dissolved in DCM (10 mL). A HCl solution in diethylether (1M, 0.58 mL, 0.580 mmol) was added. Solvents were evaporated and the resulting mass was recrystallized in MeOH. A yellow powder. (307.9 mg, 90% yield of recrystallization) was obtained in 100% purity by HPLC (MaxPlot detection between 230 and 400 nm).

M.p. 255° C. IR (neat) σ 2971, 1682, 1506, 1492, 1350, 1233, 1159, 1089 cm$^{-1}$. $^1$HNMR (DMSO-dr, 300 MHz) δ 3.28 (m, 2H), 3.51-3.74 (m, 4H), 3.84 (m, 2H), 4.04 (m, 2H), 4.48-4.74 (m, 2H+2H, NCH2CO, major isomer (60%)), 5.12 (br s, 2H, NCH2CO, minor isomer (40%)), 7.03 (m, 1H, H arom.), 7.16 (m, 1H, H arom.), 7.25 (m, 2H, H arom.), 7.35 (m, 2H, H arom.), 7.41-7.56 (m, 3H, H arom.), 7.57-7.82 (m, 3H, H arom.), 10.91 (br s, 1H), 11.39 (s, 1H), 12.59 (br s, 1H, CONHN, minor isomer (40%)), 13.68 (br s, 1H, CONHN, major isomer (60%)). (ESI$^-$): 596.4. (ESI$^+$): 598.0.

Example 56

N-(4-methylphenyl)-4-[2-(4-morpholinyl)ethoxy]-N-{2-oxo-2-[(2Z)-2-(2-oxo-1,2-dihydro-3H-indol-3-ylidene)hydrazino]ethyl}benzenesulfonamide

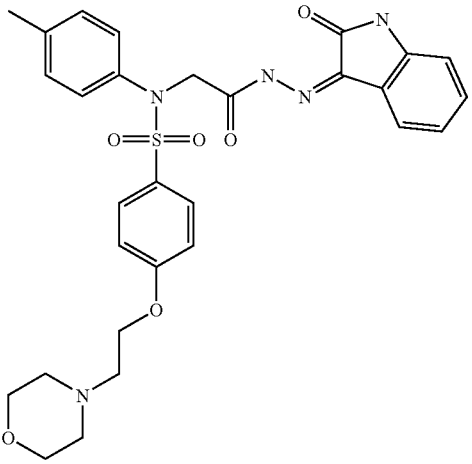

Following the general method as outlined in Example 54, starting from 4-toluidine, 2-morpholin-4-yl-ethanol, methyl bromoacetate and isatine, the title compound was isolated by evaporation of the solvents and purified by flash chromatography, using a mixture methylene chloride/MeOH 40:1 as eluent. A yellow solid. (39.7 mg, 7% over 4 steps) was obtained in 95.38% purity by HPLC (MaxPlot detection between 230 and 400 nm).

$^1$HNMR (CDCl$_3$, 300 MHz) δ 2.28 (s, 3H), 2.58. (m, 4H), 2.83 (m, 2H), 3.73 (m, 4H), 4.15 (m, 2H), 4.40 (s, 2H, NCH2CO, major isomer (70%)), 4.99 (s, 2H, NCH2CO, minor isomer (30%)), 6.86-7.22 (m, 8H, H arom.), 7.29 (m, 1H, H arom.), 7.51 (m, 2H, H arom.), 7.69 (m, 1H, H arom.), 8.85 (s, 1H, minor isomer (40%)), 9.32 (s, 1H, major isomer (60%)), 12.41 (s, 1H, minor isomer (40%)), 14.06 (s, 1H, major isomer (60%)). (ESI$^-$): 576.3. (ESI$^+$): 578.5.

Example 57

N-(4-chlorophenyl)-4-[2-(dimethylamino)ethoxy]-N-{2-oxo-2-[(2Z)-2-(2-oxo-1,2-dihydro-3H-indol-3-ylidene)hydrazino]ethyl}benzenesulfonamide

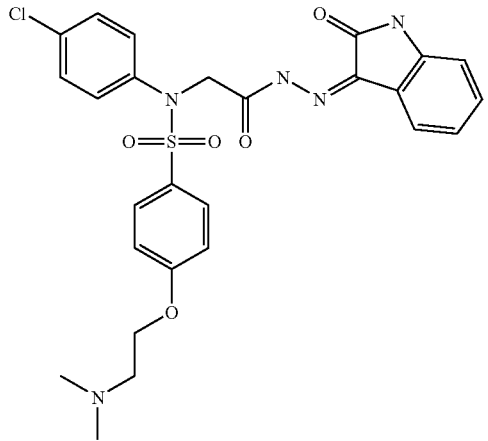

Following the general method as outlined in Example 54, starting from 4-chloroaniline, 2-dimethylamino-ethanol, methyl bromoacetate and isatine, the title compound was isolated by evaporation of the solvents and purified by flash chromatography, using a mixture methylene chloride/MeOH 20:1 as eluent. A yellow oil. (20.0 mg, 8% over 4 steps) was obtained in 97.54% purity by HPLC (MaxPlot detection between 230 and 400 nm).

$^1$H NMR (CDCl$_3$, 300 MHz) δ 2.44 (s, 6H, N(CH3)$_2$), 2.91 (m, 2H), 4.18 (m, 2H), 4.39 (s, 2H, NCH2CO, major isomer (60%)), 4.99 (s, 2H, NCH2CO, minor isomer (40%)), 6.86-6.98 (m, 3H, H arom.), 7.07 (m, 1H, H arom.), 7.12-7.36 (m, 5H, H arom.), 7.49 (m, 2H, H arom.), 7.69 (m, 1H, H arom.), 9.20 (br s, 1H), 12.45 (s, 1H, minor isomer (40%)), 13.98 (s, 1H, major isomer (60%)). (ESI$^-$): 554.1. (ESI$^+$): 556.3.

Example 58

4-[2-(Dimethylamino)ethoxy]-N-(4-methylphenyl)-N-{2-oxo-2-[(2Z)-2-(2-oxo-1,2-dihydro-3H-indol-3-ylidene)hydrazino]ethyl}benzenesulfonamide

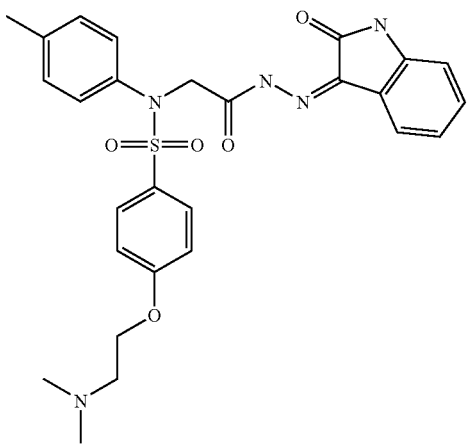

Following the general method as outlined in Example 54, starting from 4-toluidine, 2-dimethylamino-ethanol, methyl bromoacetate and isatine, the title compound was isolated by evaporation of the solvents and purified by flash chromatography, using a mixture methylene chloride/MeOH 20:1 as eluent. A yellow oil. (23.4 mg, 9% over 4 steps) was obtained in 98.42% purity by HPLC (MaxPlot detection between 230 and 400 nm).

$^1$H NMR (CDCl$_3$, 300 MHz) δ 2.42 (s, 6H, N(CH3)2), 2.87 (m, 2H), 4.17 (m, 2H), 4.40 (s, 2H, NCH2CO, major isomer (60%)), 4.99 (s, 2H, NCH2CO, minor isomer (40%)), 6.86-6.98 (m, 3H, H arom.), 7.02-7.22 (m, 5H, H arom.), 7.32 (m, 1H, H arom.), 7.50 (m, 2H, H arom.), 7.72 (m, 1H, H arom.), 8.05 (br s, 1H, minor isomer (40%)), 8.60 (br s, 1H, major isomer (60%)), 12.37 (s, 1H, minor isomer (40%)), 13.95 (s, 1H, major isomer (60%)). (APCI$^-$): 534.0. (APCI$^+$): 536.4.

Example 59

4-[3-(Dimethylamino)propoxy]-N-(4-methylphenyl)-N-{2-oxo-2-[(2Z)-2-(2-oxo-1,2-dihydro-3H-indol-3-ylidene)hydrazino]ethyl}benzenesulfonamide

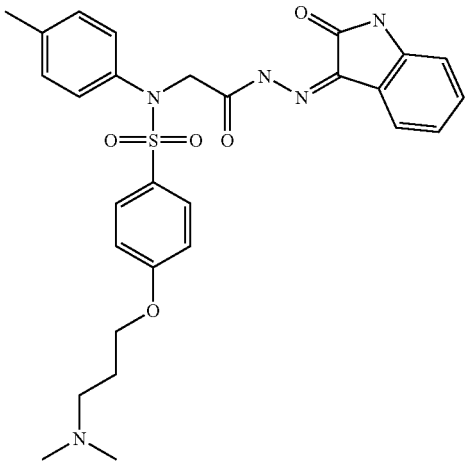

Following the general method as outlined in Example 54, starting from 4-toluidine, 3-dimethylamino-propan-1-ol, methyl bromoacetate and isatine, the title compound was isolated by evaporation of the solvents and purified by flash chromatography, using a mixture methylene chloride/MeOH 10:1 as eluent. A yellow solid (22.9 mg, 7% over 4 steps) was obtained in 97.93% purity by HPLC (MaxPlot detection between 230 and 400

$^1$H NMR (CDCl$_3$, 300 MHz) δ 2.25 (m, 2H), 2.29 (s, 3H, CH3), 2.68 (s, 6H, N(CH3)$_2$), 2.94 (m, 2H, minor isomer (25%)), 2.94 (m, 2H, major isomer (75%)), 4.08 (m, 2H, minor isomer (25%)), 4.15 (m, 2H, major isomer (75%)), 4.32 (s, 2H, NCH2CO, major isomer (75%)), 4.97 (br s, 2H, NCH2CO, minor isomer (25%)), 6.78-7.23 (m, 9H, H arom.), 7.32 (m, 2H, H arom.), 7.70 (m, 1H, H arom.), 8.40 (br s, 1H, minor isomer (25%)), 9.60 (br s, 1H, major isomer (75%)), 12.36 (s, 1H, minor isomer (25%)), 14.08 (s, 1H, major isomer (75%)). (APCI$^-$): 548.0. (APCI$^+$): 550.2.

Example 60

N-(4-chlorophenyl)-N-{2-oxo-2-[(2Z)-2-(2-oxo-1,2-dihydro-3H-indol-3-ylidene)hydrazino]ethyl}-4-(2-thienylmethoxy)benzenesulfonamide

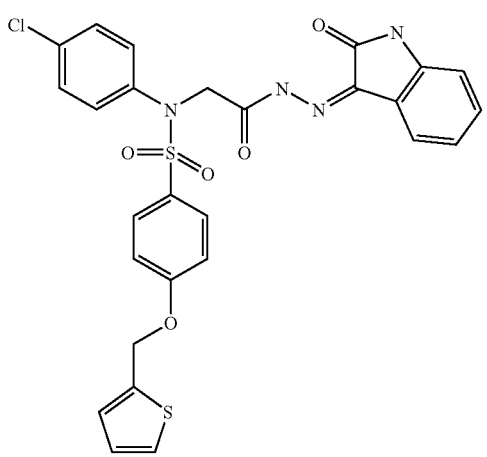

Following the general method as outlined in Example 54, starting from 4-chloroaniline, thiophen-2-yl-methanol, methyl bromoacetate and isatine, the title compound was isolated by evaporation of the solvents and purified by flash chromatography, using a mixture cyclohexane/ethyl acetate 4:1 as eluent. A yellow soild (149.6 mg, 26% over 4 steps) was obtained in 91.11% purity by HPLC (MaxPlot detection between 230 and 400 nm).

$^1$H NMR (CDCl$_3$, 300 MHz) δ 4.38 (s, 2H, NCH2CO, major isomer (53%)), 5.01 (s, 2H, NCH2CO, minor isomer (47%)), 5.26 (m, 2H), 6.90 (m, 1H, H arom.), 7.02 (m, 2H, H arom.), 7.05-7.39 (m, 6H, H arom.), 7.47-7.64 (m, 3H, H arom.), 7.68 (m, 2H, H arom.), 7.77 (m, 1H, H arom.), 12.42 (s, 1H, minor isomer (47%)), 13.92 (s, 1H, major isomer (53%)). (ESI$^-$): 579.0. (ESI$^+$): 581.2.

Example 61

N-(4-chlorophenyl)-4-[2-(2-methoxyethoxy)ethoxy]-N-{2-oxo-2-[(2Z)-2-(2-oxo-1,2-dihydro-3H-indol-3-ylidene)hydrazino]ethyl}benzenesulfonamide

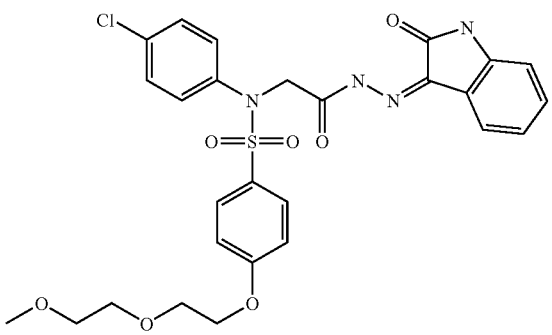

Following the general method as outlined in Example 54, starting from 4-chloroaniline, 2-(2-methoxy-ethoxy)-ethanol, methyl bromoacetate and isatine, the title compound was isolated by evaporation of the solvents and purified by flash chromatography, using a mixture cyclohexane/ethyl acetate 1:1 then 2:3 as eluent. A yellow solid. (447 mg, 38% over 4 steps) was obtained in 95.5% purity by HPLC (MaxPlot detection between 230 and 400 nm).

$^1$H NMR (CDCl$_3$, 300 MHz) δ 3.38 (s, 3H, OCH3), 3.57 (m, 2H), 3.71 (m, 2H), 3.87 (m, 2H), 4.17 (m, 2H), 4.39 (s, 2H, NCH2CO, major isomer (58%)), 4.99 (s, 2H, NCH2CO, minor isomer (42%)), 6.88-6.97 (m, 3H, H arom.), 7.09 (m, 1H, H arom.), 7.14-7.37 (m, 5H, H arom.), 7.52 (m, 2H, H arom.), 7.70 (m, 1H, H arom.), 7.98 (br s, 1H, minor isomer (42%)), 8.28 (br s, 1H, major isomer (58%)), 12.41 (s, 1H, minor isomer (42%)), 13.91 (s, 1H, major isomer (58%)). (ESI$^-$): 586.0. (ESI$^+$): 587.3.

Example 62

N-(4-chlorophenyl)-4-(2-methoxyethoxy)-N-{2-oxo-2-[(2Z)-2-(2-oxo-1,2-dihydro-3H-indol-3-ylidene)hydrazino]ethyl}benzenesulfonamide

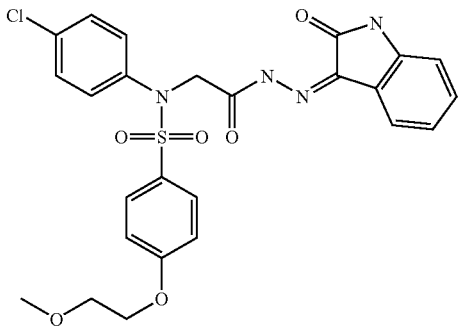

Following the general method as outlined in Example 54, starting from 4-chloroaniline, 2-methoxy-ethanol, methyl bromoacetate and isatine, the title compound was isolated by evaporation of the solvents and purified by flash chromatography, using a mixture cyclohexane/ethyl acetate 1:1 as eluent. A orange solid. (240 mg, 44% over 4 steps) was obtained in 91.3% purity by HPLC (MaxPlot detection between 230 and 400 nm).

$^1$H NMR (CDCl$_3$, 300 MHz) δ 3.45 (s, 3H, OCH$_3$), 3.76 (m, 2H), 4.16 (m, 2H), 4.38 (s, 2H, NCH2CO, major isomer (56%)), 4.99 (s, 2H, NCH$_2$CO, minor isomer (44%)), 6.87-7.01 (m, 3H, H arom.), 7.03-7.29 (m, 5H, H arom.), 7.33 (m, 1H, H arom.), 7.53 (m, 2H, H arom.), 7.61 (m, 1H, H arom.), 7.82 (br s, 1H, minor isomer (44%)), 8.11 (br s, 1H, major isomer (56%)), 12.42 (s, 1H, minor isomer (44%)), 13.94 (s, 1H, major isomer (56%)). (APCI$^-$): 540.6. (APCI$^+$): 543.0.

Example 63

N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide

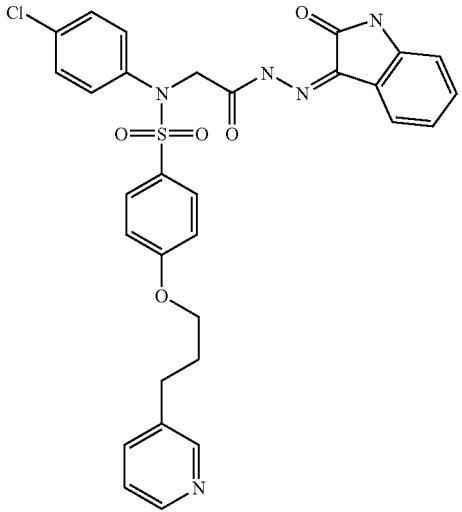

Following the general method as outlined in Example 54, starting from 4-chloroaniline, 3-pyridin-3-yl-propan-1-ol, methyl bromoacetate and isatine, the title compound was isolated by evaporation of the solvents and purified by flash chromatography, using pure ethyl acetate as eluent. A yellow solid. (88.9 mg, 15% over 4 steps) was obtained in 99.67% purity by HPLC (MaxPlot detection between 230 and 400 nm).

$^1$H NMR (CDCl$_3$, 300 MHz) δ 2.16 (m, 2H), 2.89 (m, 2H), 4.02 (m, 2H), 4.42 (s, 2H, NCH$_2$CO, major isomer (64%)), 5.00 (s, 2H, NCH$_2$CO, minor isomer (36%)), 6.83-6.99 (m, 4H, H arom.), 6.08 (m, 1H, H arom.), 7.14-7.44 (m, 5H, H arom.), 7.46-7.58 (m, 2H, H arom.), 7.63-7.77 (m, 3H, H arom.), 8.17 (s, 1H, minor isomer (36%)), 8.55 (s, 1H, H arom.), 9.18 (s, 1H, major isomer (64%)), 12.43 (s, 1H, minor isomer (36%)), 13.92 (s, 1H, major isomer (64%)). (ESI$^-$): 602.06. (ESI$^+$): 604.11.

Example 64

N-(4-chlorophenyl)-N-{2-oxo-2-[(2Z)-2-(2-oxo-1,2-dihydro-3H-indol-3-ylidene)hydrazino]ethyl}-4-[3-(2-pyridinyl)propoxy]benzenesulfonamide

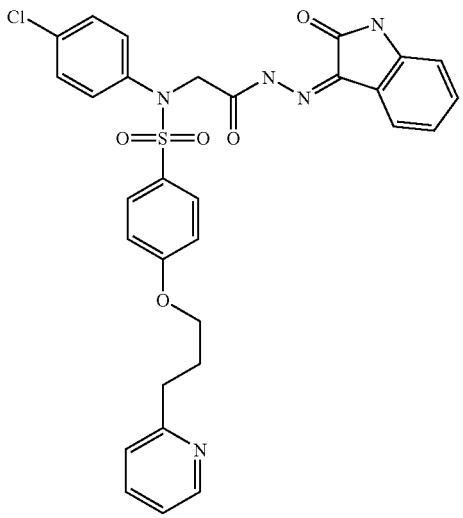

Following the general method as outlined in Example 54, starting from 4-chloroaniline, 3-pyridin-2-yl-propan-1-ol, methyl bromoacetate and isatine, the title compound was isolated by evaporation of the solvents and purified by flash chromatography, using a mixture cyclohexane/ethyl acetate 1:1 to 1:4 as eluent. A yellow solid (59.4 mg, 10% over 4 steps) was obtained in 95.15% purity by HPLC (MaxPlot detection between 230 and 400 nm).

$^1$H NMR (CDCl$_3$, 300 MHz) δ 2.27 (m, 2H), 3.02 (m, 2H), 4.06 (m, 2H), 4.42 (s, 2H, NCH2CO, major isomer (60%)), 4.99 (s, 2H, NCH2CO, minor isomer (40%)), 6.83-6.94 (m, 3H, H arom.), 7.03-7.38 (m, 8H, H arom.), 7.46-7.80 (m, 4H, H arom.), 8.01 (br s, 1H, minor isomer (40%)), 8.55 (m, 1H, H arom.), 8.72 (br s, 1H, major isomer (60%)), 12.42 (s, 1H, minor isomer (40%)), 13.86 (s, 1H, major isomer (60%)). (ESI$^-$): 601.98. (ESI$^+$): 604.06.

Example 65

General Protocol C for the Solution-Phase Synthesis of Sulfanilide Derivatives of General Formula II with R³=H (Schemes 3, 5); e.g. N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide

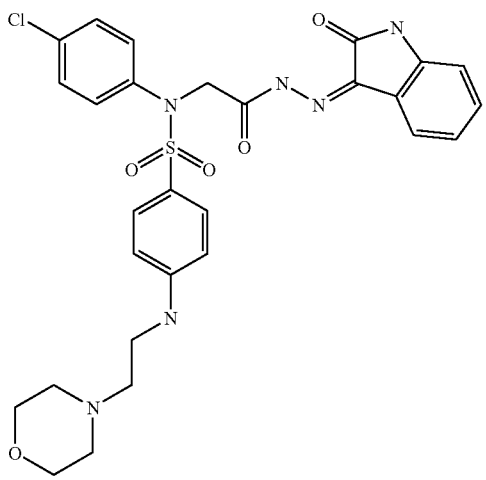

a) Protocol for the Formation of the N-aryl-benzenesulfonamide Building Block, XIII (Scheme 5); e.g. 4-fluoro-N-(4-chlorophenyl)benzenesulfonamide.

4-Chloroaniline (6.697 g, 52 mmol) was dissolved in pyridine (250 mL). The resulting mixture was cooled down to 0° C. 4-fluoro-benzenesulfonyl chloride (7.775 g, 40 mmol) was added in portions. The mixture was stirred between 0° C. and room temperature overnight. Solvents were evaporated to dryness. The crude oil was dissolved in ethyl acetate (150 mL) and washed with 10% HCl (2×75 mL) and brine (1×75 mL). Organic phase was dried over magnesium sulfate before filtering and removal of solvent. The resulting solid was recrystallized in cyclohexane/ethyl acetate 9:1. The desired product, e.g. 4-fluoro-N-(4-chlorophenyl)benzenesulfonamide (6.630 g, 58%), was obtained as a colorless solid, in 97.3% purity by HPLC (MaxPlot detection between 230 and 400 nm).

$^1$H NMR (300 MHz, CDCl$_3$): 7.05 (m, 2H, H arom.), 7.15 (m, 2H, H arom.), 7.24 (m, 2H, H arom.), 7.81 (m, 2H, H arom.); M$^-$(ESI$^-$): 284.12.

b) Protocol for the Transformation of the N-aryl-benzenesulfonamide Building Block XIII into XIII* by aromatic nucleophilic substitution with lithium amide (Scheme 5); e.g. N-(4-chlorophenyl)-4-{[2-(4-morpholinyl)ethyl]amino}benzenesulfonamide.

N-(2aminoethyl)morpholine (293 µL, 2.25 mmol) was dissolved in THF (7.5 mL) and was cooled down to −78° C. A 2.5N solution of nBuLi in hexane (1 mL, 2.5 mmol) was added dropwise. After 5 min. at −78° C., the mixture was stirred 1 h at −40° C. N-aryl-benzenesulfonamide building block XIII, e.g. 4-fluoro-N-(4-chlorophenyl)benzenesulfonamide (214 mg, 0.75 mmol), was added as a solid. The reaction mixture was stirred 2 h at room temperature, then overnight at 60° C. The reaction was quenched at room temperature with NH$_4$Cl saturated solution in water (5 mL). The desired product was extracted with three portions of ethyl acetate (3×10 mL). Combined organic phases were dried over magnesium sulfate before filtering and removal of solvent. The crude product was purified by flash chromatography, using pure ethyl acetate as eluent. The desired product, e.g. N-(4-chlorophenyl)-4-{[2-(4-morpholinyl)ethyl]amino}benzenesulfonamide (184.2 mg, 62% yield) was obtained as a colorless oil, in 97% purity by BPLC (MaxPlot detection between 230 and 400 nm). This intermediate was used in the next step without further purification.

$^1$H NMR (300 MHz, CDCl$_3$): 2.30 (m, 4H), 2.46 (m, 2H), 3.00 (m, 2H), 3.55 (m, 4H), 4.74 (br s, 1H), 6.35 (m, 2H, H arom.), 6.51 (br s, 1H), 6.84 (m, 2H, H arom.), 7.01 (m, 2H, H arom.), 7.37 (m, 2H, H arom.); M$^-$(ESI$^-$): 394.

c) Protocol for the Formation of the Acyl Hydrazone, II (Scheme 1), e.g. N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide The crude N-aryl-benzenesulfonamide building block XIII* resulting from the precedent step, e.g. N-(4-chlorophenyl)-4-{[2-(4-morpholinyl)ethyl]amino}benzenesulfonamide (0.465 mmol), was submitted to the procedure described in the general protocol B point c). Expected product, e.g. methyl{4-chloro[(4-{[2-(4-morpholinyl)ethyl]amino}phenyl)sulfonyl]anilino}acetate, was obtained as a colorless oil, in 87% purity by HPLC (MaxPlot detection between 230 and 400 nm). This intermediate was used in the next step without further purification.

$^1$H NMR (300 MHz, CDCl$_3$): 2.48 (m, 4H), 2.64 (m, 2H), 3.18 (m, 2H), 3.68 (s, 3H, OCH$_3$), 3.72 (m, 4H), 4.34 (s, 2H, NCH$_2$CO), 4.92 (br s, 1H, NH), 6.52 (m, 2H, H arom.), 7.13 (m, 2H, H arom.), 7.23 (m, 2H, H arom.), 7.42 (m, 2H, H arom.); M$^+$(ESI$^+$): 468.3; M$^-$(ESI$^-$): 466.3.

The crude carboxylic acid methyl ester resulting from the precedent step, e.g. methyl{4-chloro[(4-{[2-(4-morpholinyl)ethyl]amino}phenyl)sulfonyl]anilino}acetate (0.465 mmol), was transformed in the corresponding hydrazide following the procedure described in the general protocol B point d). Expected product, e.g. N-(4-chlorophenyl)-N-(2-hydrazino-2-oxoethyl)-4-{[2-(4-morpholinyl)ethyl]amino}benzenesulfonamide, was obtained as a colorless oil, in 96% purity by HPLC (MaxPlot detection between 230 and 400 nm). This intermediate was used in the next step without further purification.

M$^+$(APCI$^+$): 468.0; M$^-$(APCI$^-$): 465.6.

Hydrazide obtained in the precedent step, e.g. N-(4-chlorophenyl)-N-(2-hydrazino-2-oxoethyl)-4-{[2-(4-morpholinyl)ethyl]amino}benzenesulfonamide (0.465 mmol), was dissolved in EtOH/5% AcOH (8 mL). Isatin (65 mg, 0.442 mmol) was added. The reaction mixture was stirred overnight at 77° C. Temperature was cooled down to room temperature, and the desired product, e.g. N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide (220.9 mg, 84% yield), crystallised in the reaction mixture. It was isolated by filtration as an orange-yellow solid, in 98% purity by HPLC (MaxPlot detection between 230 and 400 nm).

$^1$H NMR (300 MHz, DMSO-d$_6$): 2.9-3.78 (m, 10H), 3.93 (m, 2H), 4.40 (br s, 2H, NCH$_2$CO, major isomer (65%)), 4.93 (br s, 2H, NCH$_2$CO, major isomer (35%)), 6.64 (m, 2H, H arom.), 6.77 (br s, 1H, NH minor isomer (35%)), 6.90 (m, 1H, H arom.), 7.03 (m, 1H, H arom.), 7.15-7.55 (m, 8H, H arom.), 11.38 (s, 1H, NH, major isomer (65%)), 11.22 (s, 1H, NH), 12.46 (br s, 1H, CONBN, minor isomer (35%)), 13.60 (br s, 1H, CONHN, major isomer (65%)); M⁻(ESI⁻): 595.0.

Example 66

General Protocol D for the Solution-Phase Synthesis of Sulfanilide Derivatives of General Formula II with R³=H (Schemes 2 and 3); e. 3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide.

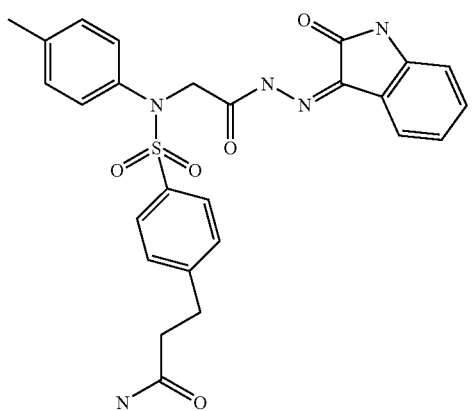

a) Formation of the Carboxylic Acid Methyl Ester Building Block, III (Scheme 3); e.g. methyl{[(4-bromophenyl)sulfonyl]-4-metlylanilino}acetate.

Following the general protocol A as outlined in Example 1, points a) and b), starting from 4-bromobenzene-sulfonyl chloride, p-toluidine and methyl bromoacetate, the title compound was isolated as a light yellow oil (3.347 g, quantitative yield) in 98% purity by HPLC (MaxPlot detection between 230 and 400 nm).

¹H NMR (300 MHz, DMSO-d₆): 2.29 (s, 3H), 3.63 (s, 3H), 4.53 (s, 2H), 7.07 (m, 2H, H arom.), 7.17 (m, 2H, H arom.), 7.58 (m, 2H, H arom.), 7.82 (m, 2H, H arom.); M⁺(APCI⁺): 400.0.

b) Protocol for the Transformation of the Carboxylic Acid Methyl Ester Building Block, 1H into III* by Heck Reaction Followed by Hydrogenation (Scheme 2); e.g. Methyl ({[4-(3-amino-3-oxopropyl)phenyl]sulfonyl}-4-methylanilino)acetate Sodium acetate was dissolved in water (0.5 mL). The carboxylic acid methyl ester building lock III, e.g. methyl{[(4-bromophenyl)sulfonyl]-4-methylanilino}acetate (398 mg, 1 mmol), in DMW (3.5 mL) was added, followed by acrylamide (78 mg, 1.11 mmol), triphenylphosphine (26.2 mg, 0.11 mmol, 10 mol %) and palladium diacetate (11.2 mg, 0.05 mmol, 5 mol %). The resulting mixture was degazed for 5 min with argon and was heated at 80° C. for 3 h. It was filtrated through celite. Water (5 mL) was added and the desired product was extracted with ethyl acetate (3×7 mL). Combined organic phases were dried over magnesium sulfate before filtering and removal of solvent The desired product, e.g. methyl[({4-[(1E)-3-amino-3-oxo-1-propenyl]phenyl}sulfonyl)-4-methylanilino]acetate was obtained as a colorless oil, in 88% purity by HPLC (MaxPlot detection between 230 and 400 nm). This intermediate was used in the next step without further purification.

¹H NMR (300 MHz, CDCl₃): 2.20 (s, 3H), 3.58 (s, 3H, OCH₃), 4.29 (s, 2H), 5.60-5.90 (m, 2H, CONH₂), 6.92-7.03 (m, 4H), 7.43 (m, 2H), 7.50-7.62 (m, 4H); M⁺(ESI⁺): 389.2; M⁻(ES⁻): 387.1.

The crude product resulting from the precedent step, e.g. methyl[({4-[(1E)-3-amino-3-oxo-1-propenyl]phenyl}sulfonyl)-4-methylanilino]acetate (1 mmol) was dissolved in DMF (5 mL). Palladium 10% on charcoal (100 mg, 0.09 mmol) was added. The mixture was heated 4 days under 45 bar of H₂ at 60° C. The solution was filtered through celite and solvents were evaporated. The desired product, e.g. methyl ({[4-(3-amino-3-oxopropyl)phenyl]sulfonyl}-4-methylanilino)acetate (308 mg, 79% yield over two steps), was obtained as a colorless oil, in 79% purity by HPLC (MaxPlot detection between 230 and 400 nm). This intermediate was used in the next step without further purification.

¹H NMR (300 MHz, CDCl₃): 2.25 (s, 3H), 2.47 (t, 2H, J=6.0 Hz), 2.97 (t, 2H, J=6.0 Hz), 3.62 (s, 3H, OCH₃), 4.31 (s, 2H), 5.33 (br s, 2H, CONH₂), 6.95-7.05 (m, 4H, H arom.), 7.21 (m, 2H, H arom.), 7.52 (m, 2H, H arom.); M⁺(ESI⁺): 391.5; M⁻(ESI⁻): 389.2.

c) Protocol for the Formation of the Acyl Hydrazone, II (Scheme 1), e.g. 3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide.

The crude carboxylic acid methyl ester resulting from the precedent step III*, e.g. methyl ({[4-(3-amino-3-oxopropyl)phenyl]sulfonyl}-4-methylanilino)acetate (308 mg, 0.789 mmol), was transformed in the corresponding hydrazide following the procedure described in the general protocol B point d). Expected product, e.g. 3-(4-{[(2-hydrazino-2-oxoethyl)-4-methylanilino]sulfonyl}phenyl)propanamide (197.3 mg, 64%) was obtained as a colorless oil, in 79% purity by HPLC (MaxPlot detection between 230 and 400 nm). This intermediate was used in the next step without further purification.

¹H NMR (300 MHz, MeOH-d₄): 2.21 (s, 3H, CH₃), 2.44 (t, 2H, J=7.5 Hz), 2.90 (t, 2H, J=7.5 Hz), 4.13 (s, 2H, NCH₂CO), 6.90 (m, 2H, H arom.), 7.01 (m, 2H, H arom.), 7.30 (m, 2H, H arom.), 7.41 (m, 2H, H arom.); M⁺(ESI⁺): 391.4; M⁻(ESI⁻): 389.2.

Hydrazide obtained in the precedent step, e.g. 3-(4-{[(2-hydrazino-2-oxoethyl)-4-methylanilino]sulfonyl}phenyl)propanamide (197 mg, 0.505 mmol), was dissolved in EtOH/5% AcOH (8 mL). Isatin (71 mg, 0.480 mmol) was added. The reaction mixture was stirred overnight at 77° C. Solvents were evaporated and the crude product was recrystallized in EtOH. The desired product, e.g. 3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide (171.3 mg, 69% yield), was isolated by filtration as a yellow solid, in 94% purity by HPLC (MaxPlot detection between 230 and 400 nm).

¹H NMR (300 MHz, DMSO-d₆): 2.25 (s, 3H, CH₃), 2.38 (t, 2H, J=7.5 Hz), 2.89 (t, 2H, J=7.5 Hz), 4.50 (br s, 2H, NCH₂CO, major isomer (65%)), 4.97 (br s, 2H, NCH₂CO, minor isomer (35%)), 6.80 (br s, 1H), 6.94 (m, 1H, H arom.), 7.03-7.17 (m, 5H, H arom.), 7.30 (br, s 1H), 7.34-7.64 (m, 6H, H arom.), 11.27 (s, 1H, NH), 12.50 (br s, 1H, CONHN, minor isomer (35%)), 13.64 (br s, 1H, CONBN, major isomer (65%)); M⁺(ESI⁺): 520.3; M⁻(ESI⁻): 518.3.

Example 67

General Protocol E for the Solution-Phase Synthesis of Sulfanilide Derivatives of General Formula II with $R^3$=H (Schemes 1, 4, 5); e.g. N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide

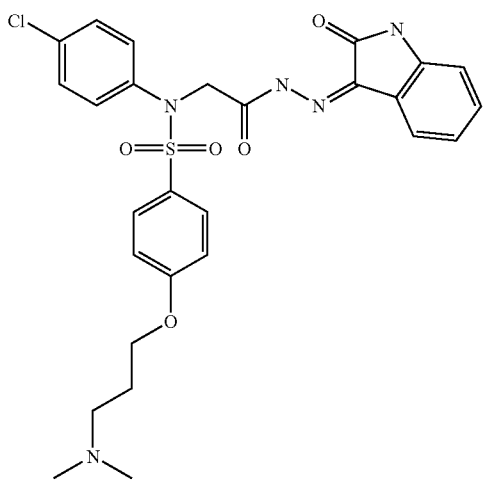

a) Protocol for the Transformation of the N-aryl-benzenesulfonamide Building Block: XIII into XIII* by aromatic nucleophilic substitution with sodium alcoholate (Scheme 5); e.g. N-(4-chlorophenyl)-4-[3-(dimethylamino)propoxy]benzenesulfonamide.

To a suspension of NaH (100 mmol, 55-65% in oil) in dry dioxane (140 mL) was added 3-dimethylamino-1-propanol (11.90 mL, 100 mmol). The mixture was stirred 1 h at room temperature. A solution of 4-fluoro-N-(4-chlorophenyl)benzenesulfonamide (9.53 g, 33.35 mmol, preparation described in example 66) in dry dioxane (35 mL) was added. The resulting mixture was heated 24 h at 100° C. Solvents were evaporated. NH$_4$Cl saturated solution in water (75 mL) was added and the desired product was extracted with three portions of ethyl acetate (3×100 mL). Combined organic phases were dried over magnesium sulfate before filtering and removal of solvent. The desired product, e.g. N-(4-chlorophenyl)-4-[3-(dimethylamino)propoxy]benzenesulfonamide was obtained as a colorless oil, in 96% purity by HPLC (MaxPlot detection between 230 and 400 nm). This intermediate was used in the next step without further purification.

$^1$H NMR (300 MHz, CDCl$_3$): 1.99 (m, 2H, CH$_2$CH$_2$CH$_2$), 2.29 (s, 6H, N(CH$_3$)$_2$), 2.50 (m, 2H, NCH$_2$CH$_2$), 4.01 (m, 2H, OCH$_2$CH$_2$), 6.84 (m, 2H, H arom.), 7.01 (m, 2H, H arom.), 7.14 (m, 2H, H arom.), 7.65 (m, 2H, H arom.); M$^+$(ESI$^-$): 369.17; M$^-$(ESI$^-$): 366.86.

b) Protocol for the Mitsunobu Reaction (Scheme 4); e.g. Methyl[4-chloro({4-[3-(dimethylamino)propoxy]phenyl}sulfonyl)anilino]acetate.

The crude N-aryl-benzenesulfonamide building block XIII* resulting from the precedent step, e.g. N-(4-chlorophenyl)-4-[3-(dimethylamino)propoxy]benzenesulfonamide (33.35 mmol), was dissolved in dry THF (500 mL). Triphenyl phosphine (33.689 g, 128.44 mmol) was added, and the resulting mixture was cooled down to 0° C. Diethyl azodicarboxylate (19.97 n2L, 128.44 mmol) was added dropwise. After 15 min at room temperature, methyl glycolate in THF (100 mL) was added dropwise. The mixture was stirred 30 min. at room temperature. Solvents were evaporated and th resulting crude oil was dissolved in ethyl acetate (100 mL). It was extracted with 30% citric acid solution in water (2×70 mL). Combined aqueous layers were extracted with diethyl ether (2×50 mL). They were then basified with NaOH 2M until pH 10, and extracted with EtOAc (3×70 mL). Combined organic layers were dried over magnesium sulfate, filtrated and evaporated. The desired product, e.g. methyl[4-chloro({4-[3-(dimethylamino)propoxy]phenyl}sulfonyl)anilino]acetate (12.235 g, 83% yield over 2 steps) was obtained as a colorless oil, in 90% purity by HPLC (MaxPlot detection between 230 and 400 nm). This intermediate was used in the next step without further purification.

$^1$H NMR (300 MHz, CDCl$_3$): 2.03 (m, 2H, CH$_2$CH$_2$CH$_2$), 2.29 (s, 6H, N(CH$_3$)$_2$), 2.49 (m, 2H, NCH$_2$CH$_2$), 3.72 (s, 3H, OCH$_3$), 4.09 (m, 2H, OCH$_2$CH$_2$), 4.39 (s, 2H), 6.93 (m, 2H, H arom.), 7.16 (m, 2H, H arom.), 7.28 (m, 2H, H arom.), 7.60 (m, 2H, H arom.); M$^+$(ESI$^+$): 441.09.

c) Protocol for the Transformation of the Carboxylic Acid Ester into the Hydrazide (Scheme 1); e.g. N-(4-chlorophenyl)-4-[3-(dimethylamino)propoxy]-N-(2-hydrazino-2-oxoethyl)benzenesulfonamide.

The crude carboxylic acid methyl ester resulting from the precedent step, e.g. methyl[4-chloro({4-[3-(dimethylamino)propoxy]phenyl}sulfonyl)aniilino]acetate (12.235 g, 27.75 mmol), was dissolved in MeOH (95 mL). Hydrazine hydrate was added (10 mL). The reaction mixture was stirred 1 h at room temperature. Solvents were evaporated. The crude product was dissolved in ethyl acetate (50 mL) and It was extracted with 30% citric acid solution in water (2×70 mL). Combined aqueous layers were extracted with diethyl ether (2×50 mL). They were then basified with NaOH 2M until pH 10, and extracted with EtOAc (3×70 mL). Combined organic layers were dried over magnesium sulfate, filtrated and evaporated. The desired product, e.g. N-(4-chlorophenyl)-4-[3-(dimethylamino)propoxy]-N-(2-hydrazino-2-oxoethyl)benzenesulfonamide (8.772 g, 72% yield) was obtained as a colorless solid, in 87% purity by HPLC (MaxPlot detection between 230 and 400 nm).

A fraction of this crude intermediate (842 mg) was recrystallized in EtOH. The expected product, e.g. N-(4-chlorophenyl)-4-[3-(dimethylamino)propoxy]-N-(2-hydrazino-2-oxoethyl)benzenesulfonamide (283 mg, 34% yield) was was isolated as a colorless solid, in 97% purity by HPLC (MaxPlot detection between 230 and 400 nm).

$^1$H NMR (300 MHz, CDCl$_3$): 1.79 (m, 2H, CH$_2$CH$_2$CH$_2$), 2.07 (s, 6H, N(CH$_3$)$_2$), 2.28 (m, 2H, NCH$_2$CH$_2$), 3.24 (s, 2H), 4.00 (m, 2H, OCH$_2$CH$_2$), 4.09 (s, 2H), 4.12 (br s, 1H), 7.01 (m, 2H, H arom.), 7.10 (m, 2H, H arom.), 7.33 (m, 2H, H arom.), 7.45 (m, 2H, H arom.); M$^+$(ESI$^+$): 441.12; M$^-$(ESI$^-$): 439.12.

d) Protocol for the formation of the Acyl Hydrazone, II (Scheme 1), e.g. N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide.

Hydrazide obtained in the precedent step, e.g. N-(4-chlorophenyl)-4-[3-(dimethylamino)propoxy]-N-(2-hydrazino-2-oxoethyl)benzenesulfonamide, was dissolved in EtOH/5% AcOH (40 mL). Isatin (2.029 g, 13.8 mmol) was added. The reaction mixture was stirred overnight at 75° C. Solvents were evaporated and the desired product was purfied by flash chromatography using a mixture methylene chloride/MeOH 40:1 to 40:3 as eluent. Two fractions of the expected product, e.g. N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide (855 mg in 92.2% purity and 5.141 g in 74% purity by HPLC ((MaxPlot detection between 230 and 400 nm) were isolated as a yellow solid (61% yield).

One fraction of the final product (5.141 g, 9.018 mmol, 74% pure) was transformed in the corresponding HCl salt, by dissolution in methylene chloride (120 mL) and addition of one equivalent of a 1N HCl solution in diethyl ether (9.5 mL). After evaporation of the solvents, the crude salt was recrystallized in EtOH. The expected product, e.g. HCl salt of N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide (1.734 g, 32% yield), was isolated as a yellow solid, in 98% purity by HPLC (MaxPlot detection between 230 and 400 nm).

M.p. 232° C.; IR (neat) σ 3060, 1694, 1596, 1467, 1353, 1267, 1158 cm$^{-1}$; $^1$H NMR (300 MHz, DMSO-d$_6$): 2.16 (m, 2H), 2.77 (s, 6H, N(CH$_3$)$_2$), 3.20 (m, 2H), 4.15 (m, 2H), 4.54 (br s, 2H, NCH$_2$CO, major isomer (60%)), 5.03 (br s, 2H, NCH$_2$CO, minor isomer (40%)), 6.96 (m, 1H, H arom.), 7.03-7.17 (m, 3H, H arom.), 7.10 (m, 2H, H arom.), 7.33-7.74 (m, 6H, H arom.), 10.55 (br s, 1H), 11.35 (s, 1H), 12.52 (br s, 1H, CONHN, minor isomer (40%)), 13.61 (br s, 1H, CONHN, major isomer (60%)); M$^+$(APCI$^+$): 570.2; M$^-$(APCI$^-$): 568.0. Analysis calculated for C$_{27}$H$_{29}$Cl$_2$N$_5$O$_5$S.0.5H$_2$O: C, 52.69; H, 4.91; N, 11.38; Cl, 11.52. Found: C, 53.01; H, 4.95; N, 11.45; Cl, 11.57.

Example 68

N-(4-chlorophenyl)-4-[3-(dimethylamino)propoxy]-N-{2-oxo-2-[(2Z)-2-(2-oxo-1,2-dihydro-3H-pyrrolo[3,2-c]pyridin-3-ylidene)hydrazino]ethyl}benzenesulfonamide

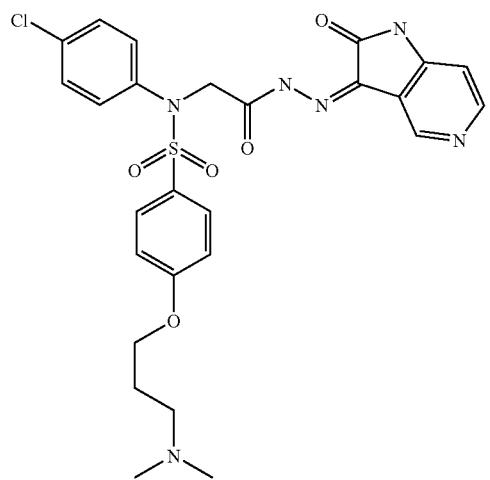

Following the general method as outlined in Example 67, starting from 4-chloroaniline, 3-dimethylamino-propan-1-ol, methyl bromoacetate and 1H-pyrrolo[3,2-c]pyridine-2,3-dione, the title compound was isolated by evaporation of the solvents and purified by flash chromatography, using a mixture methylene chloride/MeOH 10:1 to 5:1 as eluent. A light yellow powder (296.4 mg, 43%) was obtained in 94% purity by HPLC (MaxPlot detection between 230 and 400 nm). It was further purified by preparative HPLC with a gradient of H$_2$O/0.1% TFA and MeCN/1% TFA as eluent. A beige powder. (234.4, %) was obtained in 99.68% purity by HPLC (MaxPlot detection between 230 and 400 nm).

IR (neat) σ 1718, 1674, 1651, 1487, 1195, 1123 cm$^{-1}$. $^1$HNMR (DMSO-d$_6$, 300 MHz) 2.11 (m, 2H), 2.82 (s, 3H, N(CH3)2), 2.22 (m, 2H), 4.01 (br s, 2H, major isomer (65%)), 4.13 (m, 2H), 4.70 (m, 2H, minor isomer (35%)), 7.00 (m, 2H, H arom.), 7.17-7.34 (m, 3H, H arom.), 7.43 (m, 2H, H arom.), 7.59 (m, 2H), 8.57 (m, 1H, H arom.), 9.49 (s, 1H), 11.06 (br s, 1H), 12.19 (s, 1H, major isomer (65%)), 13.38 (s, 1H, minor isomer (35%)). (ESI$^-$): 569.48. (ESI$^+$): 571.47.

Example 69

(3Z)-3-({[4-chloro({4-[3-(dimethylamino)propoxy]phenyl}sulfonyl anilino]acetyl}hydrazono)-2-oxo-2,3-dihydro-1H-indole-7-carboxylic Acid

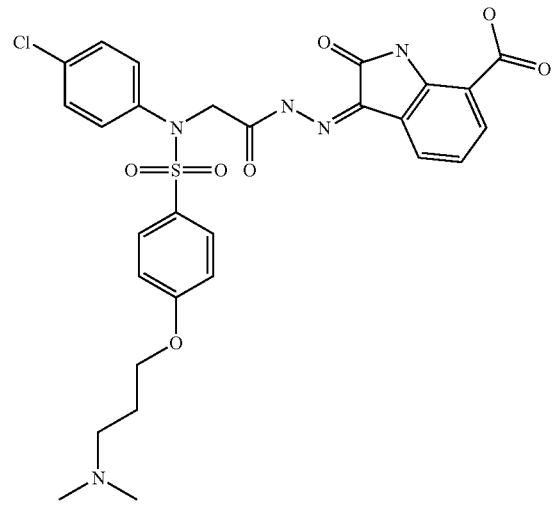

Following the general method as outlined in Example 67, starting from 4-chloroaniline, 3-dimethylamino-propan-1-ol, methyl bromoacetate and 2,3-dioxo-2,3-dihydro-1H-indole-7-carboxylic acid, the title compound was isolated by evaporation of the solvents and purified by flash chromatography, using a mixture methylene chloride/MeOH 10:1 to 5:1 as eluent. A yellow solid. (39.7 mg, 35%) was obtained in 92.02% purity by HPLC (MaxPlot detection between 230 and 400 nm).

$^1$H NMR (DMSO-d$_6$, 300 MHz) δ 1.94 (m, 2H), 2.23 (s, 3H, N(CH3)2), 2.60 (m, 2H), 4.09 (m, 2H), 4.54 (br s, 2H, major isomer (65%)), 5.01 (m, 2H, minor isomer (35%)), 7.02-7.13 (m, 4H, H arom.), 7.28 (m, 2H, H arom.), 7.40 (m, 2H, H arom.), 7.46-7.67 (m, 3H), 7.79 (m, 1H), 11.06 (br s, 1H), 12.51 (s, 1H, minor isomer (35%)), 13.60 (s, 1H, major isomer (65%)). (ESI$^-$): 611.89. (ESI$^+$): 614.03.

Example 70

Methyl (3Z)-3-({[4-chloro({4-[3-(dimethylamino)propoxy]phenyl}sulfonyl)anilino]acetyl}hydrazono)-2-oxo-2,3-dihydro-1H-indole-7-carboxylate

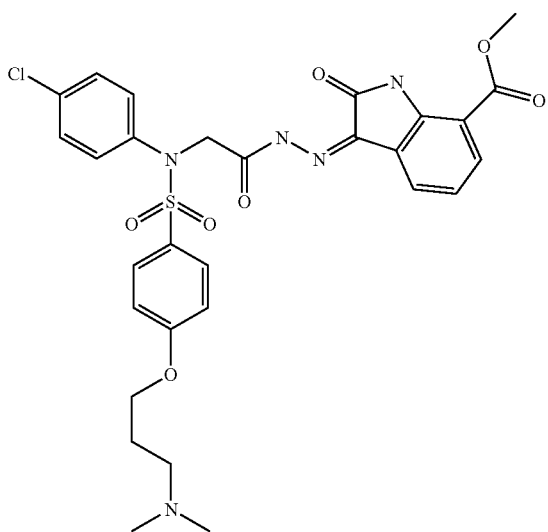

Following the general method as outlined in Example 67, starting from 4-chloroaniline, 3-dimethylamino-propan-1-ol, methyl bromoacetate and 2,3-dioxo-2,3-dihydro-1H-indole-7-carboxylic acid methyl ester, the title compound was isolated by evaporation of the solvents and purified by flash chromatography, using a mixture methylene chloride/MeOH 20:1 as eluent. A yellow solid. (83.8 mg, 77%) was obtained in 92.52% purity by HPLC (MaxPlot detection between 230 and 400 rn).

$^1$H NMR (D)MSO-d, 300 MHz) δ 1.85 (m, 2H), 2.13 (s, 3H, N(CH3)2), 2.34 (m, 2H), 3.89 (s, 3H, OCH3), 4.07 (m, 2H), 4.57 (br s, 2H, major isomer (65%)), 5.02 (m, 2H, minor isomer (35%)), 7.03-7.15 (m, 2H, H arom.), 7.17-7.33 (m, 3H, H arom.), 7.37-7.46 (m, 2H, H arom.), 7.55 (m, 2H, H arom.), 7.81 (m, 1H, H arom.), 7.89 (m, 1H, H arom.), 11.17 (br s, 1H), 12.45 (br s, 1H, minor isomer (35%)), 13.58 (br s, 1H, major isomer (65%)). (ESI$^-$): 626.15. (ESI$^+$): 628.22.

Example 71

General Protocol F for the Solution-Phase Synthesis of Sulfanilide Derivatives of General Formula II with R$^3$=H (Schemes 3, 5): e., 3-{4-[(4-chloro{2-oxo-2-[(2Z)-2-(2-oxo-1,2-dihydro-3H-indol-3-ylidene)hydrazino]ethyl}anilino)sulfonyl]phenyl]}-N-[3-(dimethylamino)propyl]propanamide a) Protocol for the Formation of the N-aryl-benzenesulfonamide Building Block, XIII (Scheme 4); e.g. methyl 3-{4-[(4-chloroanilino)sulfonyl]phenyl}propanoate 4-Chloroaniline (957 mg, 7.5 mmol) was dissolved in pyridine (25 mL). The resulting mixture was cooled down to 0° C. Methyl 3-(4-chlorosulphonyl)phenylpropionate (1.314 g, 5.0 mmol) was added in portions. The mixture was stirred between 0° C. and room temperature overnight. Solvents were evaporated to dryness. The crude oil was dissolved in ethyl acetate (30 mL) and washed with 10% HCl (2×15 mL) and brine (1×15 mL). Organic phase was dried over magnesium sulfate before filtering and removal of solvent. The desired product, e.g. methyl 3-{4-[(4-chloroanilino)sulfonyl]phenyl}propanoate (1.458 g, 82.4%), was obtained as a colorless solid, in 98.5% purity by HPLC (MaxPlot detection between 230 and 400 nm).

$^1$H NMR (300 MHz, CDCl$_3$): 2.65 (t, 2H, J=7.0 Hz), 3.00 (t, 2H, J=7.0 Hz), 3.67 (s, 3H, OCH$_3$), 6.91 (br s, 1H, NH), 7.04 (m, 2H, H arom.), 7.22 (m, 2H, H arom.), 7.30 (m, 2H, H arom.), 7.70 (m, 2H, H arom.); M$^-$(ESI$^-$): 351.4.

b) Protocol for the Transformation of the N-aryl-benzenesulfonamide Building Block: XIII into XIII* by Saponification Followed by Amide Bond Formation (Scheme 5); e.g. 3-{4-[(4-chloroanilino)sulfonyl]phenyl}-N-[3-(dimethylamino)propyl]propanamide.

A solution of sodium hydroxide (560 mg, 14.0 mmol) in water (7.0 mL) was added to the intermediate resulting from the precedent step, e.g. methyl 3-{4-[(4-chloroanilino)sulfonyl]phenyl}propanoate (1.458 g, 4.12 mmol) in 3:1 dioxane:water (30 ml). The resulting mixture was stirred overnight at room temperature. The reaction mixture was acidified to pH 2 with 2N solution of HCl in water. It was extracted with ethyl acetate (3×30 mL). Combined organic phases were dried over magnesium sulphate, filtered and evaporated. The expected product, e.g. 3-{4-[(4-chloroanilino)sulfonyl]phenyl}-N-[3-(dimethylamino)propyl]propanamide (1.410 g, quantitative yield) was obtained as a colorless oil, in 95% purity by HPLC (MaxPlot detection between 230 and 400 nm). This intermediate was used in the next step without further purification.

$^1$H NMR (300 MHz, DMSO-d$_6$): 2.53 (t, 2H, J=7.0 Hz), 2.84 (t, 2H, J=7.0 Hz), 7.08 (m, 2H, H arom.), 7.28 (m, 2H, H arom.), 7.40 (m, 2H, H arom.), 7.64 (m, 2H, H arom.), 10.40 (s, 1H), 12.16 (s, 1H); M+(ESI+): 340.11; M−(ESI−): 338.10.

Intermediate resulting from the precedent step, e.g. 3-{4-[(4-chloroanilino)sulfonyl]phenyl}-N-[3-(dimethylamino) propyl]propanamide (2.06 mmol) was dissolved in THF (10 mL) and cooled down to −25° C. N-methyl morpholine (0.57 mL, 5.15 mmol) and isobutylchloroformate (0.29 mL, 2.27 mmol) were added successively. The resulting mixture was stirred at −25° C. for 30 min. N,N-dimethyl-1,3-propanediamine (316 mg, 3.09 mmol) was added and the mixture was allowed to gradually warm to room temperaure. After 16 h, solvents were removed. The crude residue was dissolved in EtOAc and washed with water and with a 10% solution of NaHCO3 in water. Organic layer was dried over Na2SO4 filtrated and evaporated. The desired product, e.g. 3-{4-[(4-chloroanilino)sulfonyl]phenyl}-N-[3-(dimethylamino)propyl]propanamide (816.2 mg, 98%), was obtained as a colorless oil, in 94.3% purity by HPLC (MaxPlot detection between 230 and 400 nm).

$^1$H NMR (300 M, CDCl$_3$): 1.61 (m, 2H), 2.23 (s, 6H, N(CH$_3$)$_2$), 2.35 (m, 2H), 2.42 (m, 2H), 2.96 (m, 2H), 3.26 (m, 2H), 7.04 (m, 2H, H arom.), 7.16 (m, 2H, H arom.), 7.24 (m, 2H, H arom.), 7.64 (m, 2H, H arom.); M+(ESI+): 424.22; M−(ES−): 422.16.

c) Protocol for the Formation of the Acyl Hydrazone, II (Scheme 1), e.g. 3-{4-[(4-chloro{2-oxo-2-[(2Z)-2-(2-oxo-1,2-dihydro-3H-indol-3-ylidene)hyrazino]ethyl}anilino)-sulfonyl]phenyl}-N-[3-(dimethylamino)propyl]propanamide The crude N-aryl-benzenesulfonamide building block XIII* resulting from the precedent step, eg. 3-{4-[(4-chloroanilino)sulfonyl]phenyl})-N-[3-(dimethylamino)propyl]-propanamide (1.925 mmol), was submitted to the Mitsunobu reaction following the procedure described in the general protocol C point c). Expected product, e.g. methyl (4-chloro{[4-(3-{[3-(dimethylamino)propyl]amino}-3-oxopropyl)phenyl]sulfonyl}-anilino)acetate (664.5 mg, 69% yield) was obtained as a colorless oil, in 84% purity by HPLC (MaxPlot detection between 230 and 400 nm). This intermediate was used in the next step without further purification.

$^1$H NMR (300 MHz, CDCl$_3$): 1.57 (m, 2H), 2.20 (s, 6H, N(CH$_3$)$_2$), 2.29 (m, 2H), 2.38 (m, 2H), 2.94 (m, 2H), 3.22 (m, 2H), 3.61 (s, 3H, OCH$_3$), 4.29 (s, 2H), 7.06 (m, 2H, H arom.), 7.14-7.29 (m, 4H, H arom.), 7.48 (m, 2H, H arom.); M+(APCI+): 496.2.

The crude carboxylic acid methyl ester resulting from the precedent step, e.g. methyl (4-chloro{[4-(3-{[3-(dimethylamino)propyl]amino}-3-oxopropyl)phenyl] sulfonyl}anilino)acetate (0.70 mmol), was transformed in the corresponding hydrazide following the procedure described in the general protocol C point d). Expected product, eg. 3-(4-{[4-chloro(2-hydrazino-2-oxo ethyl) amino]sulfonylphenyl)-N-[3-(dimethylamino)propyl]-propanamide (1170.2 mg, 49% yield) was obtained as a colorless oil, in 75% purity by HPLC (MaxPlot detection between 230 and 400 nm). This intermediate was used in the next step without further purification.

$^1$H NMR (300 MHz, MeOH-d$_4$): 1.64 (m, 2H), 2.24 (s, 6H, N(CH$_3$)$_2$), 2.29 (m, 2H), 2.54 (m, 2H), 3.03 (m, 2H), 3.18 (m, 2H), 4.28 (s, 2H), 7.18 (m, 2H, H arom.), 7.34 (m, 2H, H arom.), 7.42 (m, 2H, H arom.), 7.56 (m, 2H, H arom.); M+(APCI+): 496.

Hydrazide obtained in the precedent step, e.g. 3-(4-{[4-chloro(2-hydrazino-2-oxoethyl)anilino]sulfonyl}phenyl)-N-[3-(dimethylamino)propyl]propanamide (170 mg, 0.34 mmol), was dissolved in AcOH (3.5 mL). Isatin (48 mg, 0.33 mmol) was added. The reaction mixture was stirred 1 h at 100° C. Solvents were evaporated and the desired product was purfied by preparative HPLC (reverse phase, H$_2$O 0.1% TFA/MeCN 0.1% TFA gradient between 100:1 and 45:55). After lyophilisation, the TFA salt of the expected product, e.g. 3-{4-[(4-chloro{2-oxo-2-[(2Z)-2-(2-oxo-1,2-dihydro-3H-indol-3-ylidene)hydrazino]ethyl}-anilino)sulfonyl]phenyl}-N-[3-(dimethylamino)propyl]propanamide (107.9 mg, 44% yield), was isolated as a yellow solid, in 98% purity by HPLC (MaxPlot detection between 230 and 400 nm).

$^1$H NMR (300 MHz, DMSO-d$_6$): 1.68 (m, 2H), 2.42 (m, 2H), 2.73 (s, 3H, N(CH$_3$)$_2$), 2.88-2.96 (m, 4H), 3.06 (m, 2H), 4.56 (br s, 2H, NCH$_2$CO, major isomer (60%)), 5.05 (br s, 2H, NCH$_2$CO, minor isomer (40%)), 6.95 (m, 1H, H arom.), 7.09 (m, 1H, H arom.), 7.25 (m, 2H, H arom.), 7.34-7.68 (m, 8H), 8.00 (m, 1H),), 9.19 (br s, 1H),), 11.28 (s, 1H), 12.52 (br s, 1H, CONHN, minor isomer (40%)), 13.58 (br s, 1H, CONHN, major isomer (60%)); M+(APCI+): 625.2 M−(APCI−): 623.0. Analysis calculated for C$_{30}$H$_{33}$ClN$_6$O$_5$S 0.5 H$_2$O 1.7 TFA: C, 48.45; H, 4.35; N, 10.15. Found: C, 48.39; H, 4.64; N, 10.33.

Example 72

N-(4-chlorophenyl)-4-[3-(4-methyl-1-piperazinyl)-3-oxopropyl]-N-{2-oxo-2-[(2Z)-2-(2-oxo-1,2-dihydro-3H-indol-3-ylidene)hydrazino] ethyl}benzenesulfonamide

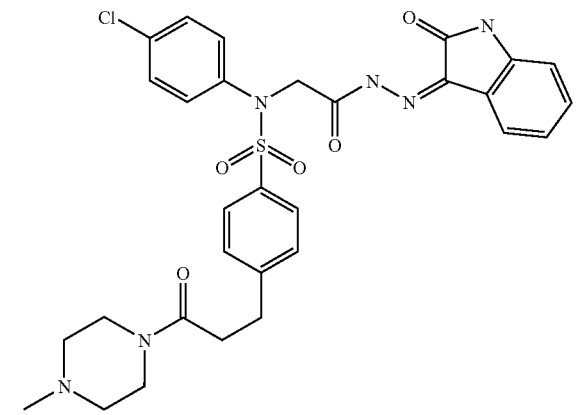

Following the general method as outlined in Example D1, starting from methyl 3-(4-chlorosulphonyl)phenylpropionate, 4-chloroaniline, 1-methylpiperazine, methyl glycolate and isatine, the title compound was isolated by evaporation of the solvents and purified by preparative HPLC (reverse phase, H$_2$O 0.1% TFA/MeCN 0.1% TFA gradient between 100:1 and 45:55). After lyophilisation, the TFA salt of the expected product, e.g. N-(4-chlorophenyl)-4-[3-(4-methyl-1-piperazinyl)-3-oxopropyl]-N-{2-oxo-2-[(2Z)-2-(2-oxo-1,2-dihydro-3H-indol-3-ylidene)hydrazino] ethyl}benzenesulfonamide (68.9 mg, 27.5% yield), was isolated as a yellow solid, in 98% purity by HPLC (MaxPlot detection between 230 and 400 nm).

$^1$H NMR (300 MHz, DMSO-d$_6$): 2.65-3.05 (m, 8H), 2.79 (s, 3H, NCH$_3$), 3.25-3.45 (m, 2H), 4.05 (m, 1H), 4.43 (m, 1H), 4.57 (br s, 2H, NCH$_2$CO, major isomer (60%)), 5.06 (br s, 2H, NCH$_2$CO, minor isomer (40%)), 6.95 (m, 1H, H arom.), 7.09 (m, 1H, H arom.), 7.28 (m, 2H, H arom.), 7.34-7.72 (m, 8H, H arom.), 9.79 (br s, 1H), 11.29 (s, 1H), 12.52 (br s, 1H, CONHN, minor isomer (40%)), 13.57 (br s, 1H, CONHN, major isomer (60%)); M$^+$(ESI$^-$): 623.12; M$^-$(ESI$^-$): 621.18.

Example 73

General Protocol for the Solution-Phase Synthesis of Sulfanilide Derivatives of General Formula II with R$^3$=Me (Schemes 1, 2, 3); e.g. 4-ethoxy-N-{1-methyl-2-oxo-2-[(2Z)-2-(2-oxo-1,2-dihydro-3H-indol-3-ylidene)hydrazino]ethyl}-N-(4-methylphenyl)benzene-sulfonamide

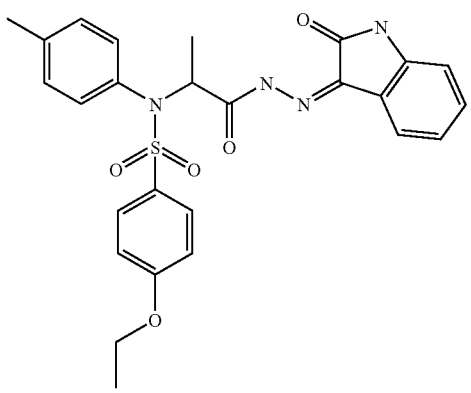

a) Protocol for the Displacement of the Leaving Group in XI (Scheme 3); e.g. methyl 2-{[(4-ethoxyphenyl)sulfonyl]-4-methylanilino}propanoate.

The crude N-aryl-benzenesulfonamide building block XIII, e.g. 4-ethoxy-N-(4-methylphenyl)benzenesulfonamide (204 mg, 0.70 mmol, preparation described in example 1, step a)), was dissolved in DMF (5 mL). Methyl-2-bromopropionate (0.117 mL, 1.05 mmol) and potassium carbonate (193 mg, 1.40 mmol) were added. The mixture was heated overnight at 60° C. Solvents were evaporated. The crude residue was suspended in ethyl acetate (10 mL) and was washed with 1N HCl solution (7 mL) and with brine (7 mL). Organic phase was dried over MgSO$_4$, fltrated and evaporated. The desired product, e.g. methyl 2-{[(4-ethoxyphenyl)sulfonyl]-4-methylanilino}propanoate (276 mg, quantitative crude yield) was isolated as a light yellow oil, in 94.3% purity by HPLC (MaxPlot detection between 230 and 400 nm).

$^1$H NMR (300 MHz, CDCl$_3$): 1.42 (t, 3H, J=7.1 Hz), 2.30 (s, 3H), 3.65 (s, 3H), 4.01-4.17 (m, 3H), 6.85 (m, 2H, H arom.), 6.98-7.10 (m, 4H, H arom.), 7.58 (m, 2H, H arom.); M$^+$(APCI$^+$): 378.

b) Protocol for the Transformation of the Carboxylic Acid Ester into the Hydrazide (Scheme 1); e.g. 4-ethoxy-N-(2-hydrazino-1-methyl-2-oxoethyl)-N-(4-methylphenyl)benzenesulfonamide.

The crude carboxylic acid methyl ester, e.g. methyl 2-{[(4-ethoxyphenyl)sulfonyl]-4-methylanilino}propanoate (264 mg, 0.70 mmol), was dissolved in MeOH (2 mL). Hydrazine hydrate was added (0.44 mL). The reaction mixture was stirred overnight at 60° C. Solvents were evaporated. The crude mass was redissolved in MeOH and solvents were evaporated again. This process was repeated three times. The desired product, e.g. 4-ethoxy-N-(2-hydrazino-1-methyl-2-oxoethyl)-N-(4-methylphenyl)benzenesulfonamide (138.4 mg, 52%) was isolated as a colorless solid in 91.1% purity by HPLC (MaxPlot detection between 230 and 400 nm).

$^1$H NMR (300 MHz, CDCl$_3$): 1.13 (d, 3H, J=7.2 Hz), 1.45 (t, 3H, J=7.0 Hz), 2.36 (s, 3H), 3.34 (m, 1H), 4.15 (q, 2H, J=7.0 Hz), 7.03 (m, 2H, H arom.), 7.09 (m, 2H, H arom.), 7.15 (m, 2H, H arom.), 7.63 (m, 2H, H arom.); M$^+$(APCI$^+$): 378.0; M$^-$(APCI$^-$): 376.0.

c) Protocol for the Formation of the Acyl Hydrazone, II (Scheme 1), e.g. 4-ethoxy-N-(1-methyl-2-oxo-2-[(2Z)-2-(2-oxo-1,2-dihydro-3H-indol-3-ylidene)hydrazino]ethyl}-N-(4-methylphenyl)benzenesulfonamide.

Hydrazide obtained in the precedent step, e.g. 4-ethoxy-N-(2-hydrazino-1-methyl-2-oxoethyl)-N-(4-methylphenyl) benzenesulfonamide 4-ethoxy-N-(2-hydrazino-1-methyl-2-oxoethyl)-N-(4-methylphenyl)benzenesulfonamide (138 mg, 0.37 mmol), was dissolved in EtOH/5% AcOH (8 mL). Isatin (54 mg, 0.37 mmol) was added. The reaction mixture was stirred overnight at 76° C. Solvents were evaporated and the crude mixture was purified by flash chromatography, using a mixture cyclohexane/ethyl acetate 6:4 as eluent. The desired product, e.g. 4-ethoxy-N-{1-methyl-2-oxo-2-[(2Z)-2-(2-oxo-1,2-dihydro-3H-indol-3-ylidene)hydrazino]ethyl}-N-(4-methylphenyl)benzenesulfonamide (86 mg, 46%) was isolated as a yellow solid in 89% purity by HPLC (MaxPlot detection between 230 and 400 nm).

$^1$H NMR (300 MHz, CDCl$_3$): 1.28 (d, J=7.2 Hz, 3H), 1.41 (m, 3H, OCH$_2$CH$_3$), 4.04 (m, 2H, OCH$_2$CH$_3$), 5.05 (m, 1H, NCHCO, major isomer (65%)), 6.11 (m, 1H, NCHCO, minor isomer (35%)), 6.72-6.95 (m, 3H, H arom.), 6.98-7.22 (m, 5H, H arom.), 7.29 (m, 1H, H arom.), 7.52-7.80 (m, 3H, H arom.), 8.23 (br s, 1H, CONHN, minor isomer (35%)), 8.67 (br s, 1H, CONHN, major isomer (65%)), 12.40 (br s, 1H, CONHN, minor isomer (35%)), 13.83 (br s, 1H, CONHN, major isomer (65%)); M$^+$(APCI$^+$): 507; M$^-$(APCI$^-$): 505.

Example 74

General Protocol for the Solution-Phase Synthesis of Sulfanilide Derivatives of General Formula II with R$^3$=CH$_2$OH (Schemes 1, 3): e.g. 4-ethoxy-N-{1-(1(hydroxymethyl)-2-oxo-2-[(2Z)-2-(2-oxo-1,2-dihydro-3H-indol-3-ylidene)hydrazino]ethyl}-N-(4-methylphenyl)benzenesulfonamide

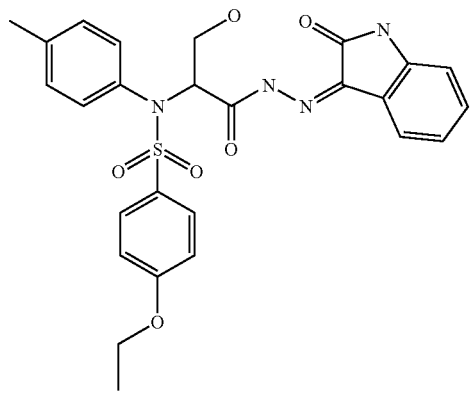

a) Protocol for the Preparation of Intermediate XI with R³=CH₂OʹBu (Scheme 3); e.g. 2-bromo-3-tert-butoxypropanoic Acid.

A mixture of potassium bromide (6.830 g, 57.39 mmol) and 0.75 M HBr solution (91 mL, 68.24 mmol) was cooled down to −7° C. Sodium nitrite (2.093 g, 29.47 mmol) and L-serine tert-butyl ether (2.50 g, 15.51 mmol) were added successively and the mixture was stirred 3 h at room temperature. The mixture was cooled down to 0° C., and was extracted with ethyl acetate (3×100 mL). Combined organic phases were washed with brine (2×180 mL), dried over MgSO₄, filtrated and evaporated. The expected product, e.g. 2-bromo-3-tert-butoxypropanoic acid (3.481 g, quantitative yield), was isolated as a light yellow oil. This intermediate was used in the next step without further purification.

¹H NMR (300 MHz, MeOH-d₄): 1.21 (s, 9H), 3.68 (m, 1H), 3.84 (m, 1H), 4.22 (m, 1H); M⁺(APCI⁺): 168.4.

The bromo acid isolated in the precedent step, e.g. 2-bromo-3-tert-butoxypropanoic acid (1.276 g, 5.67 mmol), was dissolved in a 3:1 chloroform/MeOH mixture (81 mL). Tirmethylsilyl diazomethane (8.505 mL, 17.01 mmol) was added dropwise. The yellow resulting mixture was stirred overnight at room temperature. The solvents were evaporated at atmospheric pressure, affording the desired product, e.g. methyl 2-bromo-3-tert-butoxypropanoate (1.482 g), in quantitative yield. This intermediate was used in the next step without further purification.

¹H NMR (300 MHz, CDCl₃): 1.01 (s, 9H), 3.51 (m, 1H), 3.67 (s, 3H, OCH₃), 3.69 (m, 1H), 4.05 (m, 1H); M⁺(APCI⁺): 240.

b) Protocol for the Displacement of the Leaving Group in with R³=CH₂OʹBu (Scheme 3); e.g. Methyl 3-tert-butoxy-2-{[(4-ethoxyphenyl)sulfonyl]-4-methylanilino}propanoate The crude N-aryl-benzenesulfonamide building block XIII, e.g. 4-ethoxy-N-(4-methylphenyl)benzenesulfonamide (388 mg, 1.33 mmol, preparation described in example 1, step a)), was dissolved in DMF (5 mL). Intermediate XI with R³=CH₂OʹBu, e.g. methyl 2-bromo-3-tert-butoxypropanoate (478 mg, 2 mmol) and potassium carbonate (368 mg, 2.66 mmol) were added. The mixture was heated overnight at 60° C. Solvents were evaporated. The crude residue was suspended in ethyl acetate (10 mL) and was washed with 1N HCl solution (7 mL) and with brine (7 mL). Organic phase was dried over MgSO4, fitrated and evaporated. The crude mixture was purified by flash chromatography, using a 8:2 mixture cyclohexane/ethyl acetate as eluent. The desired product, e.g. methyl 3-tert-butoxy-2-{[(4-ethoxyphenyl)sulfonyl]-4-methylanilino}propanoate (157 mg, 26.3%) was isolated as a light yellow oil, in 96.4% purity by HPLC (MaxPlot detection between 230 and 400 nm).

¹H NMR (300 MHz, CDCl₃): 1.28 (s. 9H), 1.61 (t, 3H, J=7.1 Hz), 2.49 (s, 3H), 3.50 (t, 1H, J=9.4 Hz), 3.85 (dd, 1H, J=4.9, 9.4 Hz), 3.92 (s, 3H), 4.25 (q, 2H, J=7.1 Hz), 5.33 (dd, 1H, J=4.9, 9.4 Hz), 7.03 (m, 2H, H arom.), 7.23 (m, 2H, H arom.), 7.28 (m, 2H, H arom.), 7.87 (m, 2H, H arom.); M⁺(APCI⁺): 450.

c) Protocol for the Transformation of the Carboxylic Acid Ester into the Hydrazide (Scheme 1); e.g. N-[1-(tert-butoxymethyl)-2-hydrazino-2-oxoethyl]-4-ethoxy-N-(4-methylphenyl)benzenesulfonamide.

The crude carboxylic acid methyl ester, e.g. methyl 3-tert-butoxy-2-{[(4-ethoxyphenyl)sulfonyl]-4-methylanilino}propanoate (157 mg, 0.35 mmol), was dissolved in MeOH (1 mL). Hydrazine hydrate was added (0.11 mL). The reaction mixture was stirred 3 days at 60° C. By cooling down the reaction mixture, the desired product, e.g. N-[1-(tert-butoxymethyl)-2-hydrazino-2-oxoethyl]-4-ethoxy-N-(4-methylphenyl)benzenesulfonamide (40.5 mg, 25%) crystallised. It was isolated by filtration as a colorless solid in 86% purity by HPLC (MaxPlot detection between 230 and 400 nm).

¹H NMR (300 MHz, MeOH-d₄): 1.21 (s. 9H), 1.60 (t, 3H, J=7.1 Hz), 2.51 (s, 3H), 3.43 (m, 1H), 3.53 (s, 2H), 3.62 (m, 1H), 3.79 (m, 1H), 4.29 (q, 2H, J=7.1 Hz), 7.15 (m, 2H, H arom.), 7.29 (m, 4H, H arom.), 7.82 (m, 2H, H arom.); M⁺(APCI⁺): 450.2.

d) Formation of the Acyl Hydrazonze, II (Scheme 1), e.g. 4-ethoxy-N-{1-(hydroxymethyl)-2-oxo-2-[(2Z)-2-(2-oxo-1,2-dihydro-3H-indol-3-ylidene)hydrazillo]ethyl}-N-(4-methylphenyl)benzenesulfonamide Hydrazide obtained in the precedent step, e.g. N-[1-(tert-butoxymethyl)-2-hydrazino-2-oxoethyl]4-ethoxy-N-(4-methylphenyl)benzenesulfonamide (40 mg, 0.09 mmol), was dissolved in EtOH/5% AcOH (2 mL). Isatin (13 mg, 0.09 mmol) was added. The reaction mixture was stirred overnight at 76° C. Solvents were evaporated and the crude mixture was dissolved in methylene chloride (1 mL). Trifluoroacetic acid (0.5 mL) was added at 0° C. The reaction mixture was stirred 3 days at room temperature and the solvents were evaporated. The crude product was purified by flash chromatography, using a mixture cyclohexane/ethyl acetate 1:1 as eluent. The desired product, e.g. 4-ethoxy-N-{1-(hydroxymethyl)-2-oxo-2-[(2Z)-2-(2-oxo-1,2-dihydro-3H-indol-3-ylidene)hydrazino]ethyl}-N-(4-methylphenyl)benzenesulfonamide (17.2 mg, 36%) was isolated as an orange solid in 90% purity by HPLC (MaxPlot detection between 230 and 400 nm).

¹H NMR (300 MHz, MeOH-d₄): 1.16 (m, 3H, OCH₂CH₃), 2.20 (s, 3H, CH₃), 3.56 (m, 1H), 3.64-3.81 (m, 1H), 3.84-4.02 (m, 2H), 4.86 (m, 1H, NCHCO, major isomer (68%)), 5.22 (m, 1H, NCHCO, minor isomer (32%)), 6.77-6.87 (m, 3H, H arom.), 7.93-7.04 (m, 5H, H arom.), 7.26 (m, 1H), 7.44-7.72 (m, 3H, H arom.). M⁻(APCI⁻): 521.

Example 75

General Protocol for the Solid-Phase Synthesis of Sulfanilide Derivatives of General Formula I with R³=H (Scheme 10); e.g. 3-(3,4-Dichlorophenyl)-2-({[4-fluoro(phenylsulfonyl)anilino]acetyl}amino)propanamide

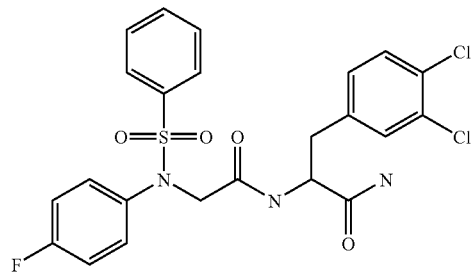

a) Protocol for the Preparation of the Rink Amine Resume, XXIV, by Fmoc Deprotection of Fmoc-Rink Amide Resin.

Fmoc-Rink amide resin (0.84 mmol/g) was suspended in 10 mL/g of 20% piperidine in DMF and was shaken for 30 min. The resin was filtered and washed with DMF, DCM, DMF, DCM, MeOH and twice with Et₂O. It was finally dried on sinter. The disappearance of the C=O stretch in the IR indicated a complete deprotection of the Fmoc-Rink amide.

b) Protocol for the Loading of, Fmoc-Protected Amino Acids on Rink Amine Resine, XXIV, e.g. Loading of N-fmoc-2-amino-3-(3,4-dichloro-phenyl)-propionic Acid.

The resin resulting from the precendent step, the Rink amine resine, XXIV, was suspended in DMF (10 ml/g) fmoc-protected amino acid (3 eq) was added, together with diisopropylcarbodiimide (3 eq). The suspention was shaken overnight at room temperature. The resin was washed with DMF, DCM, DMF, DCM, MeOH and twice with Et₂O. It was finally dried on sinter. The formation of this new amide bond could be checked by negative ninhydrin test and the apparition of new C=O stretches in IR.

c) Protocol for Fmoc Deprotection of the Amino Acid Loaded Oil Rink Resine, XXV.

Fmoc-protected amino acid loaded on Rink resin (0.84 mmol/g) was suspended in 10 mL/g of 20% piperidine in DMF and was shaken for 30 min. The resin was filtered and washed with DMF, DCM, DMF, DCM, MeOH and twice with Et₂O. It was finally dried on sinter. The lost of the C=O stretch in IR indicated a complete deprotection of the amino acid.

d) Protocol for Amide Bond Formation Between Amino Acid and XIa with R³=H (Scheme 10); Formation of XXVI.

Resin amine recovered from the precendent step was suspended in DMF (10 mL/g). Carboxylic acid XIa (3 eq), e.g. bromoacetic acid, and diisopropylcarbodiimide (3 eq) were added and the mixture was shaken overnight at room temperature. The resin was washed with DAV, DCM, DMF, DCM, MeOH and twice with Et₂O. It was finally dried on sinter. The formation of this new amide bond could be checked by negative ninhydrin test and the apparition of new C=O stretches in IR.

e) Protocol for the Displacement of the Leaving Group in XIa with R³=H with XII (Scheme 10); Formation of XXVII.

Amine XII, e.g. 4-fluoroaniline (25 eq), was dissolved in DMSO (10 mL/g of resin). This solution was added to the resin resulting from the precendent step and the mixture was shaken overnight at room temperature. The resin was recovered and washed with DMF, DCM, DMF, DCM, MeOH and twice with Et₂O. It was finally dried on sinter. The formation of this new amide bond was checked on a sample of resin which was suspended in 50% TFA/DCM for 10 min at room temperature. The resulting solution was analysed by LC-MS and ¹H NMR.

f) Protocol for the Sulfonylation of (Scheme 10); Formation of XXVIII.

Sulfonyl chloride VII, e.g. benzenesulfonyl chloride (5 eq), was dissolved in dichloroethane (10 mL/g of resin) and N-methylmorpholine (5 eq) was added. This solution was added on the resin resulting from the precedent step. The whole mixture was shaken overnight at 60° C. The resin was recovered and washed with DMF, DCM, DMF, DCM, MeOH and twice with Et₂O. It was finally dried on sinter.

g) Protocol for the Cleavage from the Resin XXVIII of Sulfanilide Derivatives of General Formula I with R³=H (Schemes 10); e.g. 3-(3,4-Dichlorophenyl)-2-({[4-fluoro (phenylsulfonyl)anilino]acetyl}amino)propanamide.

A 50% TFA in DCM solution (3×0.5 mL) was allowed to drip through the resin resulting from the precedent step. This procedure was repeated twice. The combined filtrate was evaporated and analyzed by LC-MS and ¹H NMR. Through this procedure, the desired product, e.g. 3-(3,4-Dichlorophenyl)-2-({[4-fluoro(phenylsulfonyl)anilino]acetyl}amino) propanamide, was isolated in >60% purity by LC/MS. (ESI⁺): 525.

Example 76

3-(Benzyloxy)-2-[({4-chloro[(3,4-dimethoxyphenyl) sulfonyl]anilino}-acetyl)amino]propanamide

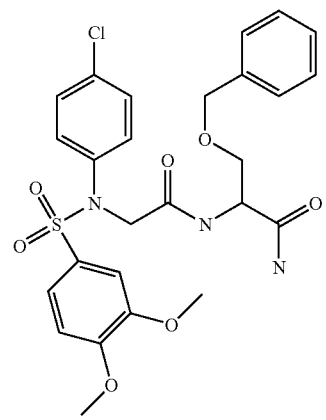

Following the general method as outlined in Example 75, starting from N-fmoc-2-amino-3-benzyloxy-propionic acid, methyl bromoacetate, 4-chloroaniline and 3,4-dimethoxy-benzenesulfonyl chloride, the title compound was obtained in >60% purity by LC/MS. (ESI⁺): 563.

Example 77

3-(Benzyloxy)-2-({[4-chloro(phenylsulfonyl)anilino] acetyl}amino)propanamide

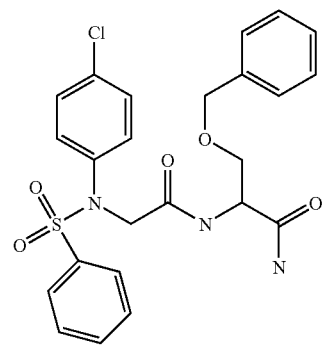

Following the general method as outlined in Example 75, starting from N-fmoc-2-amino-3-benzyloxy-propionic acid, methyl bromoacetate, 4-chloroaniline and benzenesulfonyl chloride, the title compound was obtained in >60% purity by LC/MS. (ESI⁺): 502.

Example 78

2-[({[(4-Ethoxyphenyl)sulfonyl]-4-methylanilino}acetyl)amino]-2-phenylacetamide

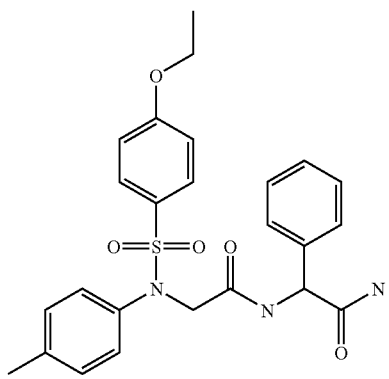

Following the general method as outlined in Example 75, starting from N-fmoc-aminophenyl-acetic acid, methyl bromoacetate, 4-toluidine and 4-ethoxy-benzenesulfonyl chloride, the title compound was obtained in >60% purity by LC/MS. (ESI$^+$): 482.

Example 79

3-(3,4-Dichlorophenyl)-2-[({[(4-fluorophenyl)sulfonyl]-4-methoxyanilino}-acetyl)amino]propanamide

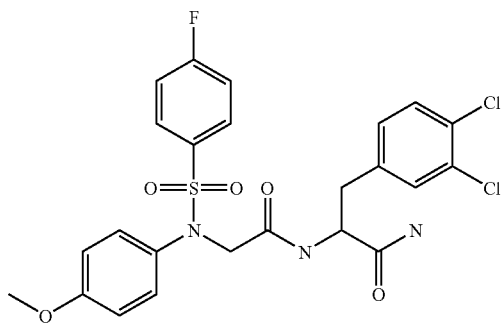

Following the general method as outlined in Example 75, starting from N-fmoc-2-amino-3-(3,4-dichloro-phenyl)-propionic acid, methyl bromoacetate, 4-methoxy-aniline and 4-fluoro-benzenesulfonyl chloride, the title compound was obtained in >60% purity by LC/MS. (ESI$^+$): 555.

Example 80

2-[2-({[(4-Ethoxyphenyl)sulfonyl]-4-methoxyanilino}acetyl)-1,2,3,4-tetrahydro-3-isoquinolinyl]acetamide

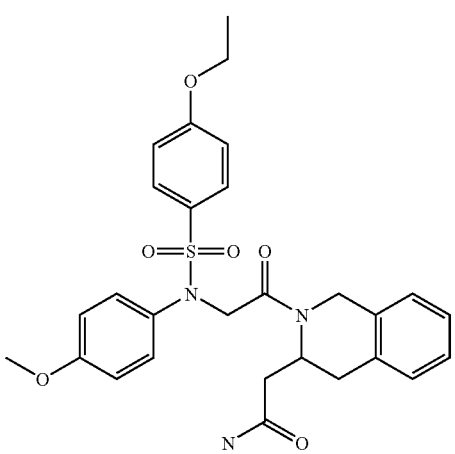

Following the general method as outlined in Example 75, starting from N-fmoc-(1,2,3,4-tetrahydro-isoquinolin-3-yl)-acetic acid, methyl bromoacetate, 4-methoxy-aniline and 4-ethoxy-benzenesulfonyl chloride, the title compound was obtained in >60% purity by LC/MS. (ESI$^+$): 538.

Example 81

2-{[(4-Ethoxyphenyl)sulfonyl]-4-methoxyanilino}acetyl)-1-isoindolinecarboxamide

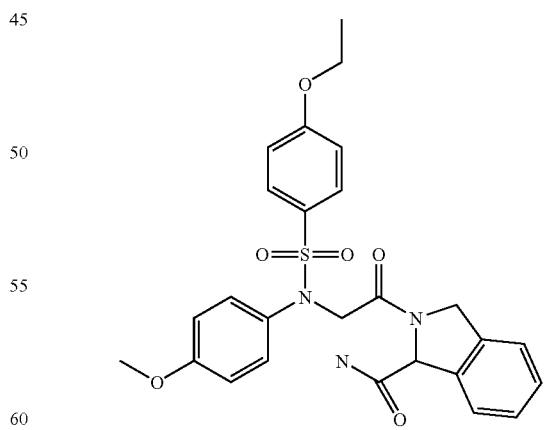

Following the general method as outlined in Example 75, starting from N-fmoc-2,3-dihydro-1H-isoindole-1-carboxylic acid, methyl bromoacetate, 4-methoxy-aniline and 4-ethoxy-benzenesulfonyl chloride, the title compound was obtained in >60% purity by LC/MS. (ESI$^+$): 510.

Example 82

2-[2-({[(3,4-Dimethoxyphenyl)sulfonyl]-4-methoxyanilino}acetyl)-1,2,3,4-tetrahydro-3-isoquinolinyl]acetamide

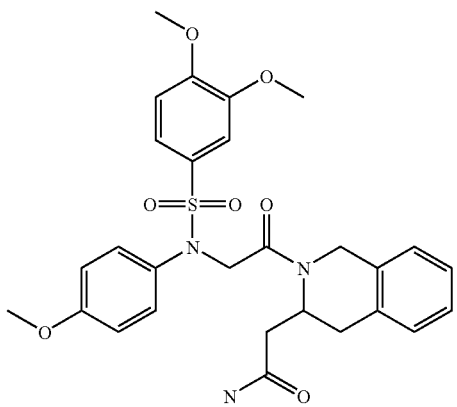

Following the general method as outlined in Example 75, starting from N-fmoc-(1,2,3,4-tetrahydro-isoquinolin-3-yl)-acetic acid, methyl bromoacetate, 4-methoxy-aniline and 3,4-dimethoxy-benzenesulfonyl chloride, the title compound was obtained in >60% purity by LC/MS. (ESI$^+$): 554.

Example 83

N-({4-Chloro[(4-ethoxyphenyl)sulfonyl]anilino}acetyl)valine

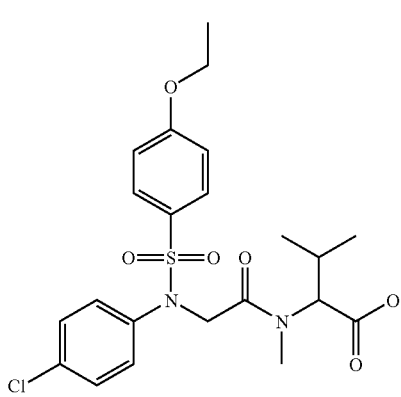

Following the general method as outlined in Example 75, starting from N-fmoc-3-methyl-2-methylamino-butyric acid, methyl bromoacetate, 4-chloroaniline and 4-ethoxy-benzenesulfonyl chloride, the title compound was obtained in >60% purity by LC/MS. (ESI$^+$): 483.

Example 84

2-[({[(4-Ethoxyphenyl)sulfonyl]-4-fluoroanilino}acetyl)amino]-3-(1H-indol-3-yl)propanamide

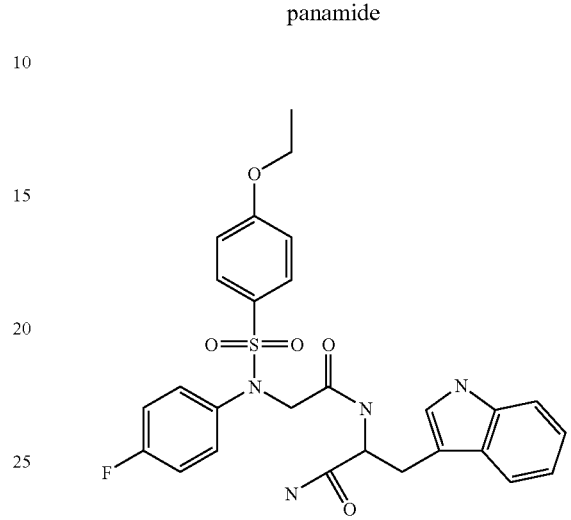

Following the general method as outlined in Example 75, starting from N-fmoc-2-amino-3-(1H-indol-3-yl)-propionic acid, methyl bromoacetate, 4-fluoroaniline and 4-ethoxy-benzenesulfonyl chloride, the title compound was obtained in >60% purity by LC/MS. (ESI$^+$): 539.

Example 85

2-[({[(4-Ethoxyphenyl)sulfonyl]-4-fluoroanilino}acetyl)amino]-2-phenylacetamide

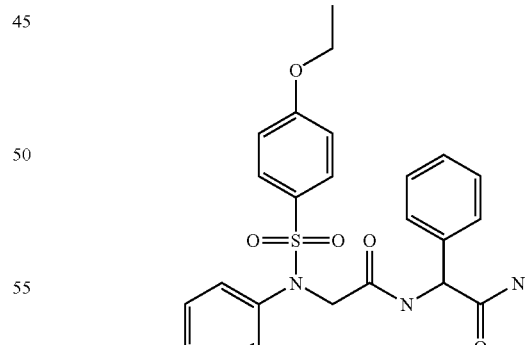

Following the general method as outlined in Example 75, starting from N-fmoc-aminophenyl-acetic acid, methyl bromoacetate, 4-fluoroaniline and 4-ethoxy-benzenesulfonyl chloride, the title compound was obtained in >60% purity by LC/MS. (ESI$^+$): 486.

Example 86

N-({[(3,4-Dimethoxyphenyl)sulfonyl]-4-fluoroanilino}acetyl)valine

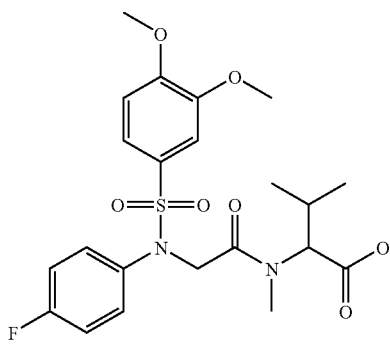

Following the general method as outlined in Example 75, starting from N-fmoc-3-methyl-2-methylamino-butyric acid, methyl bromoacetate, 4-fluoroaniline and 3,4-dimethoxybenzenesulfonyl chloride, the title compound was obtained in >60% purity by LC/MS. (ESI$^+$): 483.

Example 87

1-({[(4-Ethoxyphenyl)sufonyl]-4-methylanilino}acetyl)-5-phenyl-2-pyrrolidinecarboxamide

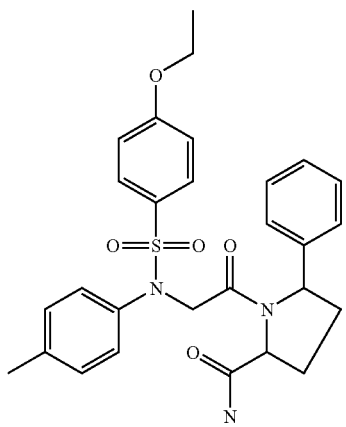

Following the general method as outlined in Example 75, starting from N-fmoc-5-phenylpyrrolidine-2-carboxylic acid, methyl bromoacetate, 4-toluidine and 4-ethoxybenzenesulfonyl chloride, the title compound was obtained in >60% purity by LC/MS. (ESI$^+$): 522.

Example 88

2-[2-({[(4-Ethoxyphenyl)sulfonyl]anilino}acetyl)-12,3,4-tetrahydro-3-isoguinolinyl]acetamide

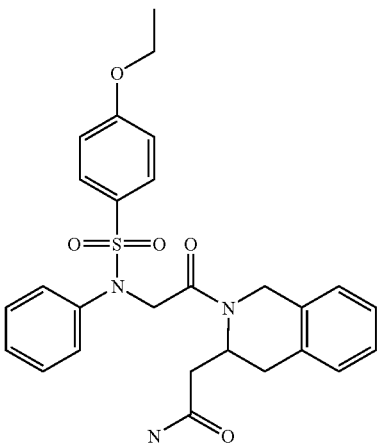

Following the general method as outlined in Example 75, starting from N-fmoc-(1,2,3,4-tetrahydro-isoquinolin-3-yl)-acetic acid, methyl bromoacetate, aniline and 4-ethoxybenzenesulfonyl chloride, the title compound was obtained in >60% purity by LC/MS. (ESI$^+$): 508.

Example 89

2-[2-({[(4-Ethoxyphenyl)sulfonyl]-4-methylanilino}acetyl)-1,2,3,4-tetrahydro-3-isoguinolinyl]acetamide

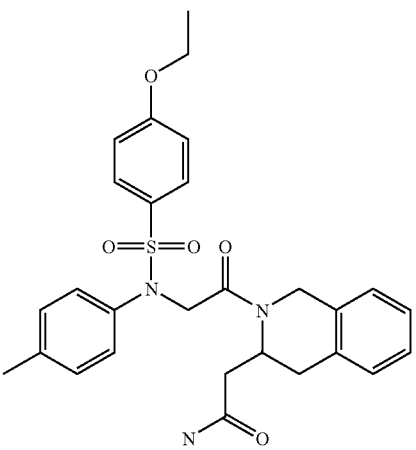

Following the general method as outlined in Example 75, starting from N-fmoc-(1,2,3,4-tetrahydro-isoquinolin-3-yl)-acetic acid, methyl bromoacetate, 4-toluidine and 4-ethoxybenzenesulfonyl chloride, the title compound was obtained in >60% purity by LC/MS. (ESI$^+$): 522.

Example 90

2-[({[(4-Ethoxyphenyl)sulfonyl]-4-methoxyanilino}acetyl)amino]-4-phenylbutanamide

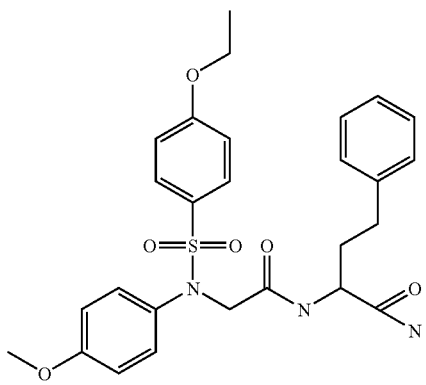

Following the general method as outlined in Example 75, starting from N-fmoc-2-amino-4-phenyl-butyric acid, methyl bromoacetate, 4-methoxy-aniline and 4-ethoxybenzenesulfonyl chloride, the title compound was obtained in >60% purity by LC/MS. (ESI$^+$): 526.

Example 91

2-({[(4-Ethoxyphenyl)sulfonyl]-4-methoxyanilino}acetyl)-1.2,3,4-tetrahydro-3-isoquinolinecarboxamide

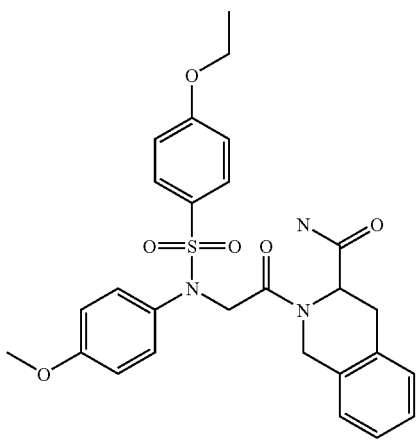

Following the general method as outlined in Example 75, starting from N-fmoc-1,2,3,4-tetrahydroisoquinoline-3-carboxylic acid, methyl bromoacetate, 4-methoxy-aniline and 4-ethoxy-benzenesulfonyl chloride, the title compound was obtained in >60% purity by LC/MS. (ESI$^+$): 524.

Example 92

2-[({[(4-Ethoxyphenyl)sulfonyl]-4-methoxyanilino}acetyl)amino]-3-(1H-indol-3-yl) propanamide

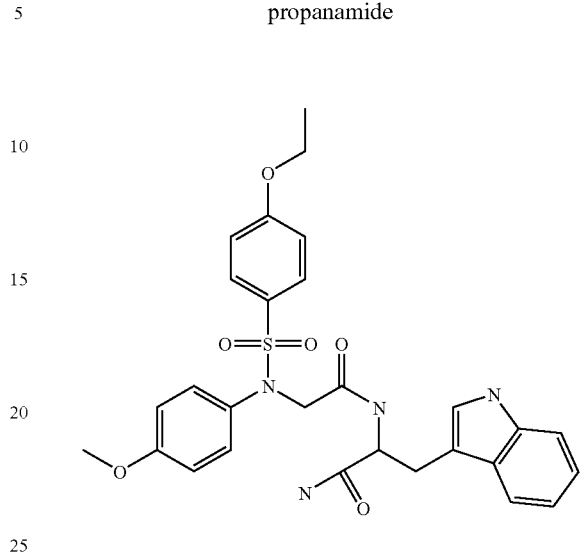

Following the general method as outlined in Example 75, starting from N-fmoc-2-amino-3-(1H-indol-3-yl)-propionic acid, methyl bromoacetate, 4-methoxy-aniline and 4-ethoxybenzenesulfonyl chloride, the title compound was obtained in >60% purity by LC/MS. (ESI$^+$): 551.

Example 93

1-({[(4-Ethoxyphenyl)sulfonyl]-4-fluoroanilino}acetyl)-5-phenyl-2-pyrrolidinecarboxamide

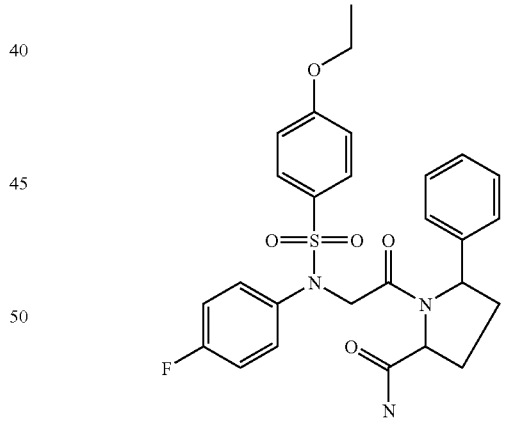

Following the general method as outlined in Example 75, starting from N-fmoc-5-phenylpyrrolidine-2-carboxylic acid, methyl bromoacetate, 4-fluoroaniline and 4-ethoxybenzenesulfonyl chloride, the title compound was obtained in >60% purity by LC/MS. (ESI$^+$): 526.

Example 94

Preparation of a Pharmaceutical Formulation

The following Formulation examples illustrate representative pharmaceutical compositions according to the present invention being not restricted thereto.

Formulation 1—Tablets

A sulfanilide compound of Formula I is admixed as a dry powder with a dry gelatin binder in an approximate 1:2 weight ration. A minor amount of magnesium stearate is added as a lubricant. The mixture is formed into 240-270 mg tablets (80-90 mg of active sulfanilide compound per tablet) in a tablet press.

Formulation 2—Capsules

A sulfanilide compound of Formula I is admixed as a dry powder with a starch diluent in an approximate 1:1 weight ratio. The mixture is filled into 250 mg capsules (125 mg of active sulfanilide compound per capsule).

Formulation 3—Liquid

A sulfanilide compound of Formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A sulfanilide compound of Formula I is admixed as a dry powder with a dry gelatin binder in an approximate 1:2 weight ratio. A minor amount of magnesium stearate is added as a lubricant. The mixture is formed into 450-900 mg tablets (150-300 mg of active sulfanilide compound) in a tablet press.

Formulation 5—Injection

A sulfanilide compound of Formula I is dissolved in a buffered sterile saline injectable aqueous medium to a concentration of approximately 5 mg/ml.

Example 95

Biological Assays

The compounds according to Formula I may be subjected to the following assays:

a) In Vitro Competition Binding Assay on hOT Receptor with Scintillating Proximity Assay (*Pharmaceutical Manufacturing International,* 1992, p. 49-53 by Cook, N. D. et al)

This assays allows to determine the affinity of the test compounds for the OT receptor. Membranes from HEK293EBNA cells expressing the hOT receptor were resuspended in buffer containing 50 mM Tris-HCl, pH 7.4, 5 mM MgCl2 and 0.1% BSA (w/v). The membranes (2-4 µg) were mixed with 0.1 mg wheat-germ aglutinin (WGA) SPA bead (type A) and 0.2 nM of the radiolabel [$^{125}$I]-OVTA (OVTA being Ornithin Vasoactive and is an analogue of OT for competition binding experiments). Non-specific binding was determined in the presence of 1 µM Oxytocin. The total assay volume was 100 µl. The plates (Corning (D NBS plate) were incubated at room temperature for 30 min and counted on a Mibrobeta plate counter. The tests compounds were used in concentrations of 30 µM, 10 µM, 1 µM, 300 nM, 100 nM, 10 nM, 1 nM, 100 pM, 10 pM. The competition binding data were analysed using the iterative, nonlinear, curve-fitting program, "Prism".

The binding affinities to the oxytocin receptor of the sulfanilide derivatives claimed in the formula I were assessed using the above described in vitro biological assay. Representative values for some example compounds are given in Table 1 below. The values refer to the binding affinity (IC$_{50}$; µM) of the example compounds according to formula I to the Oxytocin receptor. From the values shown in Table 1 it can be derived that said test compounds according to formula I do show a significant binding to the oxytocin receptor.

TABLE 1

| Chemical Structure | IUPAC-Name | Binding Affinity Human OT-R Ki (µM) |
|---|---|---|
| 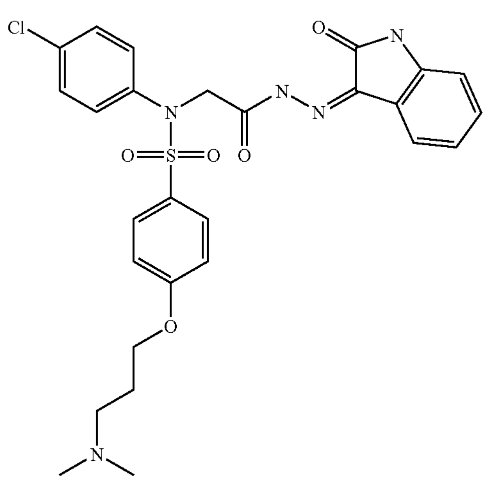 | N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide | 0.0006 |

TABLE 1-continued

| Chemical Structure | IUPAC-Name | Binding Affinity Human OT-R Ki (μM) |
|---|---|---|
| 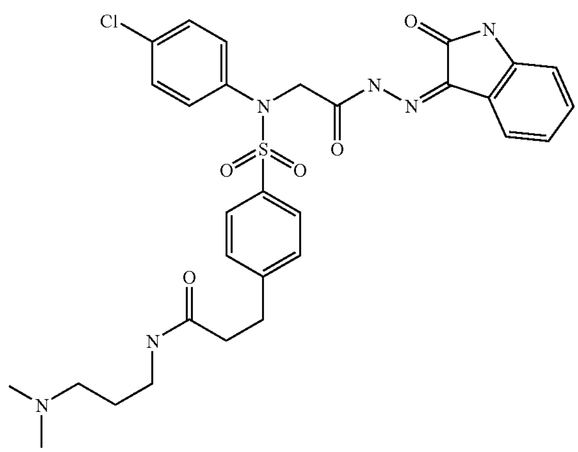 | 3-{4-[(4-chloro{2-oxo-2-[(2Z)-2-(2-oxo-1,2-dihydro-3H-indol-3-ylidene)hydrazino]ethyl}anilino)sulfonyl]phenyl}-N[3-(dimethylamino)propyl]propanamide | 0.0007 |
| 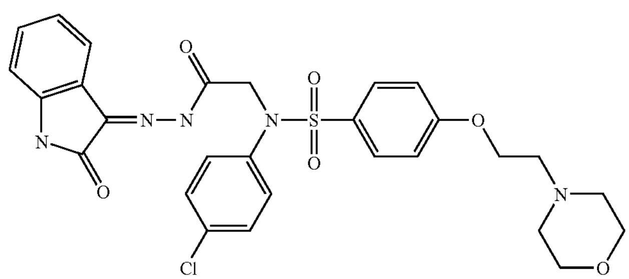 | N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide | 0.0008 |
| 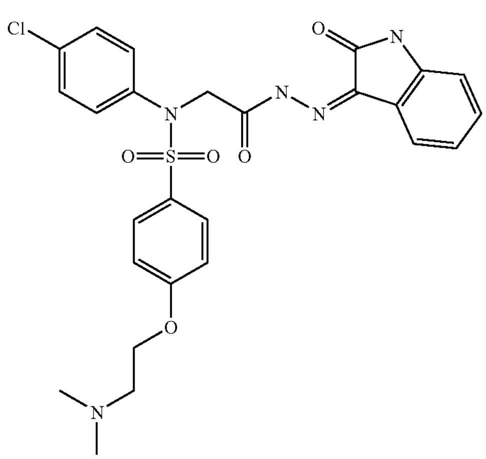 | N-(4-chlorophenyl)-4-[2-(dimethylamino)ethoxy]-N-{2-oxo-2-[(2Z)-2-(2-oxo-1,2-dihydro-3H-indol-3-ylidene)hydrazino]ethyl}benzenesulfonamide | 0.0018 |

TABLE 1-continued

| Chemical Structure | IUPAC-Name | Binding Affinity Human OT-R Ki (μM) |
|---|---|---|
| 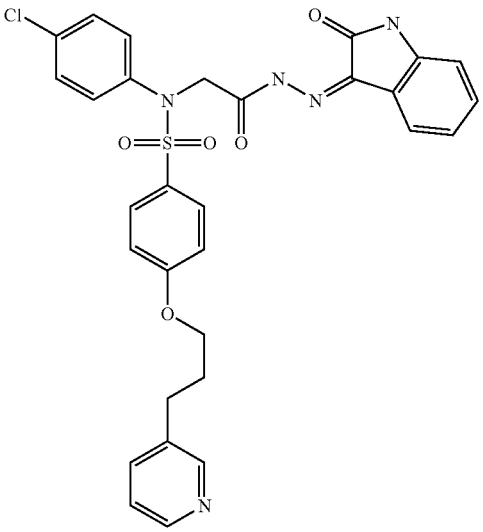 | N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide | 0.0028 |
| 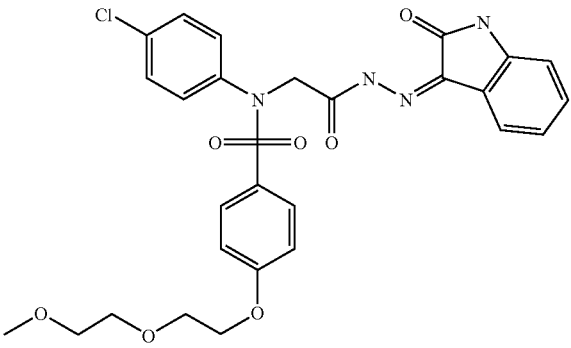 | N-(4-chlorophenyl)-4-[2-{2-methoxyethoxy)ethoxy]-N-{2-oxo-2-[(2Z)-2-(2-oxo-1,2-dihydro-3H-indol-3-ylidene)hydrazino]ethyl}benzenesulfonamide | 0.0029 |
| 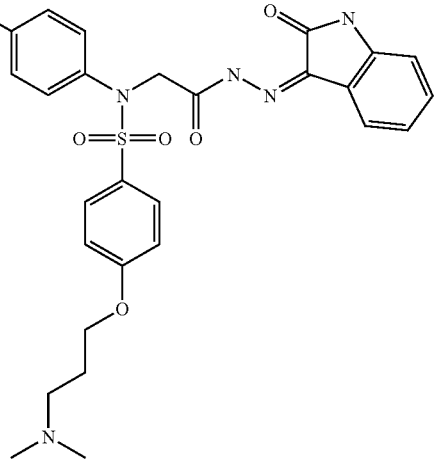 | 4-[3-(dimethylamino)propoxy]-N-(4-methylphenyl)-N-{2-oxo-2-[(2Z)-2-(2-oxo-1,2-dihydro-3H-indol-3-ylidene)hydrazino]ethyl}benzenesulfonamide | 0.0003 |

TABLE 1-continued

| Chemical Structure | IUPAC-Name | Binding Affinity Human OT-R Ki (μM) |
|---|---|---|
| 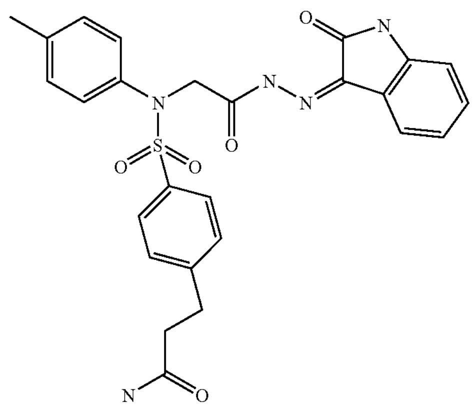 | 3-{4-[(4-methyl{2-oxo-2-[(2Z)-2-(2-oxo-1,2-dihydro-3H-indol-3-ylidene)hydrazino]ethyl}anilino)sulfonyl]phenyl)propanamide | 0.0034 |
| 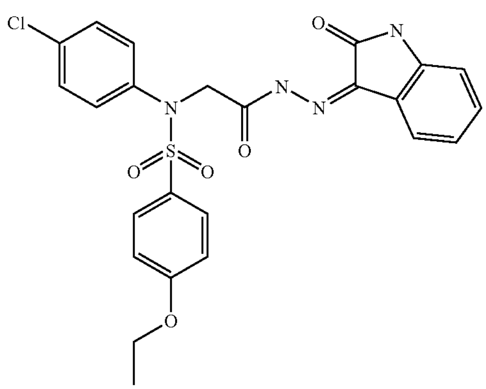 | N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide | 0.0004 |
| 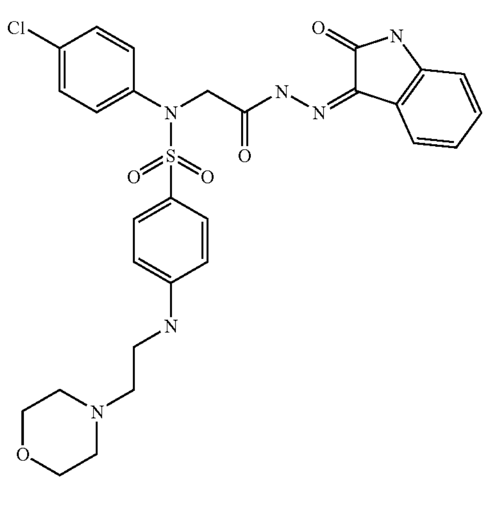 | N-(4-chlorophenyl)-4{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide | 0.0069 |

TABLE 1-continued

| Chemical Structure | IUPAC-Name | Binding Affinity Human OT-R Ki (μM) |
|---|---|---|
| 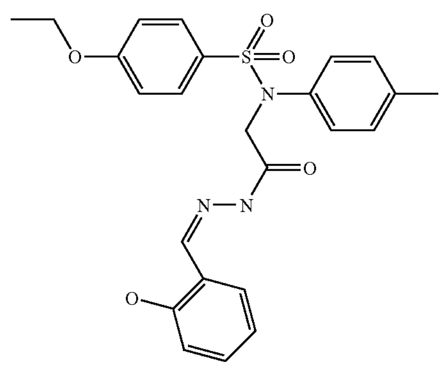 | 4-ethoxy-N-{2-[(2Z)-2-(2-hydroxybenzylidene)hydrazino]-2-oxoethyl}-N-(4-methylphenyl)benzenesulfonamide | 0.0012 |
| 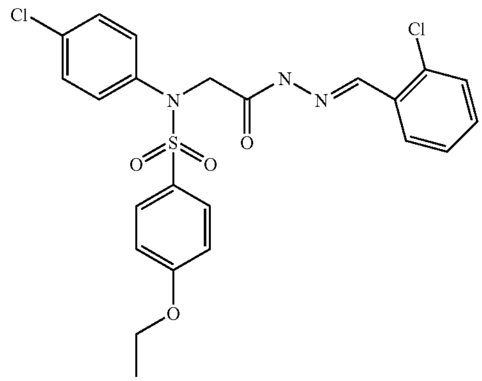 | N-(4-chlorophenyl)-4-ethoxy-N-{2-[(2E)-2-(2-hydroxybenzylidene)hydrazino]-2-oxoethyl)benzenesulfonamide | 0.0148 |
| 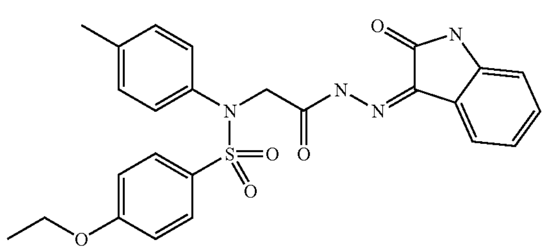 | 4-ethoxy-N-(4-methylphenyl)-N-{2-oxo-2-[(2Z)-2-(2-oxo-1,2-dihydro-3H-indol-3-ylidene)hydrazino]ethyl}benzenesulfonamide | 0.0173 |
| 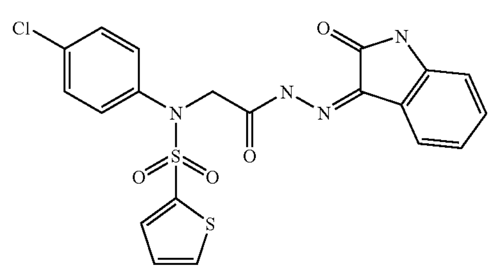 | N-(4-chlorophenyl)-N-{2-oxo-2-[(2Z)-2-(2-oxo-1,2-dihydro-3H-indol-3-ylidene)hydrazino]ethyl}-2-thiophenesulfonamide | 0.0293 |

TABLE 1-continued

| Chemical Structure | IUPAC-Name | Binding Affinity Human OT-R Ki (µM) |
|---|---|---|
| 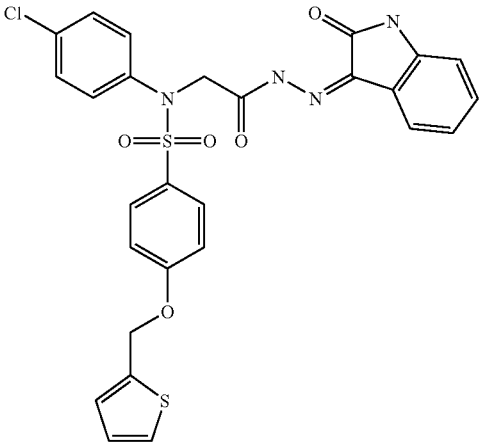 | N-(4-chlorophenyl)-N-{2-oxo-2-[(2Z)-2-(2-oxo-1,2-dihydro-3H-indol-3-ylidene)hydrazino]ethyl}-4-(2-thienylmethoxy)benzenesulfonamide | 0.0533 |
| 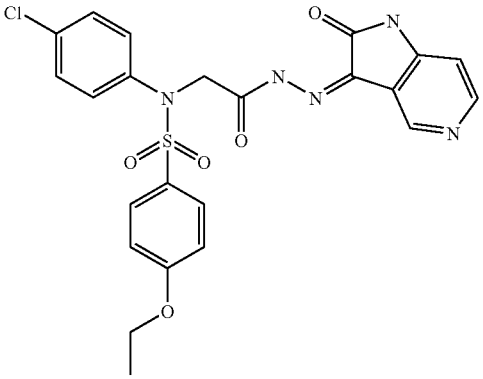 | N-(4-chlorophenyl)-4-ethoxy-N-{2-oxo-2-[(2Z)-2-(2-oxo-1,2-dihydro-3H-pyrrolo[3,2-c]pyridin-3-ylidene)hydrazino]ethyl}benzenesulfonamide | 0.0571 |
| 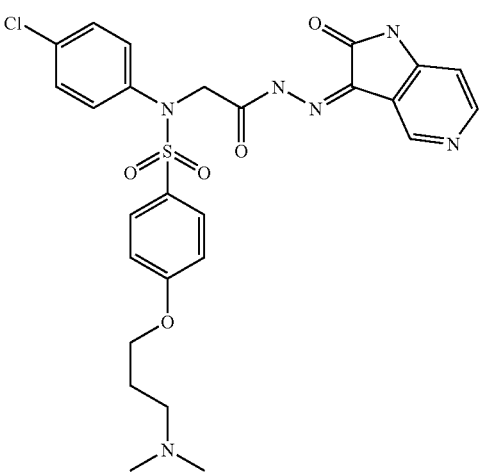 | N-(4-chlorophenyl)-4-[3-(dimethylamino)propoxy]-N-{2-oxo-2-[(2Z)-2-(2-oxo-1,2-dihydro-3H-pyrrolo[3,2-c]pyridin 3-ylidene)hydrazino]ethyl}benzenesulfonamide | 0.0781 |

TABLE 1-continued
| Chemical Structure | IUPAC-Name | Binding Affinity Human OT-R Ki (μM) |
|---|---|---|
| 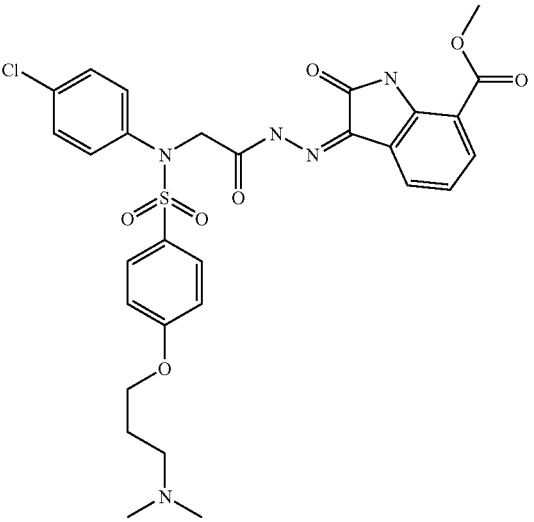 | methyl (3Z)-3-({[4-chloro({4-[3-(dimethylamino)propoxy]phenyl}sulfonyl)anilino]acetyl}hydrazono)-2-oxo-2,3-dihydro-1H-indole-7-carboxylate | 0.1081 |
| 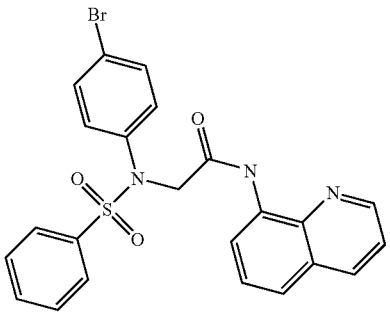 | 2-[Benzenesulfonyl-(4-bromo-phenyl)-amino]-N-quinolin-8-yl-acetamide | 0.192 |
| 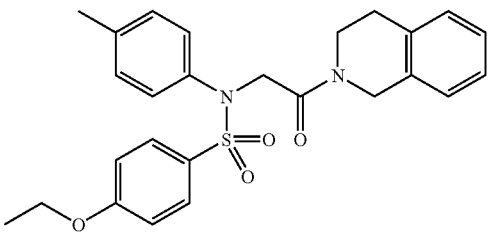 | N-[2-(3,4-Dihydro-1H-isoquinolin-2-yl)-2-oxo-ethyl]-4-ethoxy-N-p-tolyl-benzenesulfonamide | 0.246 |

TABLE 1-continued

| Chemical Structure | IUPAC-Name | Binding Affinity Human OT-R Ki (μM) |
|---|---|---|
| | 2-{2-[(4-Ethoxy-benzenesulfonyl)-(4-methoxy-phenyl)-amino]-acetyl}-1,2,3,4-tetrahydro-isoquinoline-3-carboxylic acid amide | 0.316 |
| 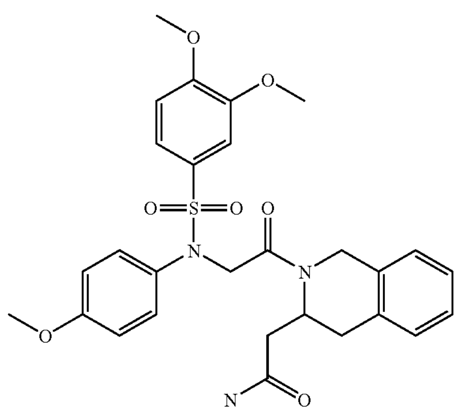 | 2-(2-{2-[(3,4-Dimethoxy-benzenesulfonyl)-(4-methoxy-phenyl)-amino]-acetyl}-1,2,3,4-tetrahydro-isoquinolin-3-yl)-acetamide | 0.465 |
| 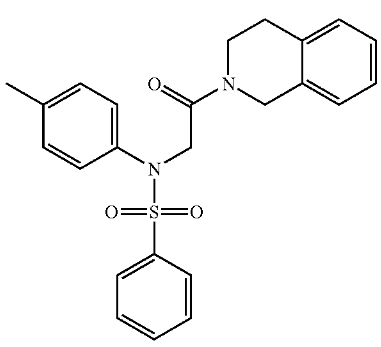 | N-[2-(3,4-Dihydro-1H-isoquinolin-2-yl)-2-oxo-ethyl]-N-p-tolyl-benzenesulfonamide | 0.472 |

TABLE 1-continued

| Chemical Structure | IUPAC-Name | Binding Affinity Human OT-R Ki (µM) |
|---|---|---|
|  | 2-(2-{2-[(4-Ethoxy-benzenesulfonyl)-p-tolyl-amino]-acetyl}-1,2,3,4-tetrahydro-isoquinolin-3-yl)-acetamide | 0.498 | b) In Vitro Competition Binding Assay on hV1a Receptor with Scintillating Proximity Assay This assays allows to determine the affinity of the test compounds for the V1a receptor. Membranes from CHO cells expressing the hV1a receptor were resuspended in buffer containing 50 mM Tris-HCl, pH 7.4, 5 mM MgCl2 and 0.1% BSA (w/v). The membranes (5-10 µg) were mixed with 0.2 mg wheat-germ aglutinin (WGA) SPA bead (type A) and 0.03 nM of the radiolabel [$^{125}$I]-LVA (LVA being Linear Vasopressin Antagonist and is an analogue of AVP for competition binding experiments). Non-specific binding was determined in the presence of 1 µM AVP. The total assay volume was 100 µl. The plates (Corning 0 NBS plate) were incubated at room temperature for 2 hours and counted on a Mibrobeta plate counter. The tests compounds were used in concentrations of 30 µM, 10 µM, 1 µM, 300 nM, 100 nM, 10 nM, 1 nM, 100 pM, 10 pM. The competition binding data were analysed using the iterative, nonlinear, curve-fitting program, Graph pad "Prism".

The binding affinities to the V1a receptor of the sulfanilide derivatives claimed in the formula I were assessed using the above described in vitro biological assay. Representative values for some example compounds are given in Table 1 below. The values refer to the binding affinity (IC$_{50}$; HM) of the example compounds according to formula I to the V$_{1a}$ receptor. From the values shown in Table 1 it can be derived that said test compounds according to formula I do show a significant binding to the V1a receptor.

TABLE 2

| Chemical Structure | IUPAC-Name | Binding Affinity Human V1a Ki (µM) |
|---|---|---|
| 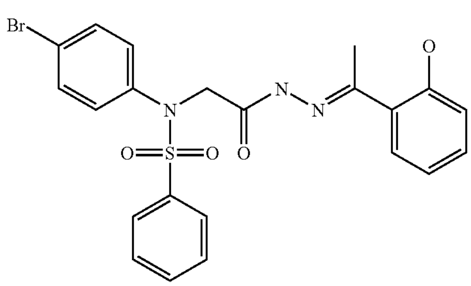 | N-(4-Bromo-phenyl)-N-[1-(2-hydroxy-phenyl)-ethylidene hydrazinocarbonylmethyl]-benzenesulfonamide | 0.391 |

TABLE 2-continued

| Chemical Structure | IUPAC-Name | Binding Affinity Human V1a Ki (μM) |
|---|---|---|
| 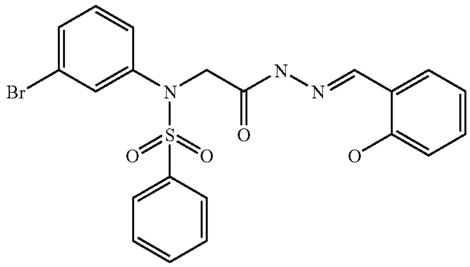 | N-(3-Bromo-phenyl)-N-(2-hydroxy-benzylidene-hydrazinocarbonylmethyl)-benzenesulfonamide | 0.503 |
| 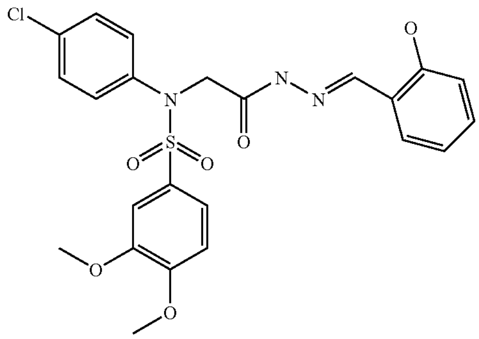 | N-(4-Chloro-phenyl)-N-(2-hydroxy-benzylidene-hydrazinocarbonylmethyl)-3,4-dimethoxy-benzenesulfonamide | 0.55 |
| 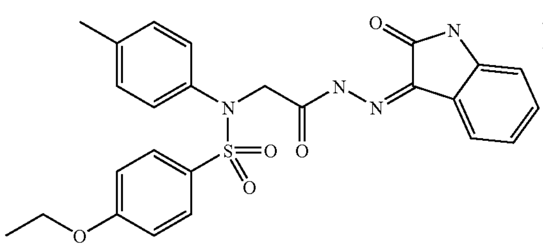 | 4-Ethoxy-N-(2-oxo-1,2-dihydro-indol-3-ylidene-hydrazinocarbonylmethyl)-N-p-totyl-benzenesulfonamide | 0.75 |
| 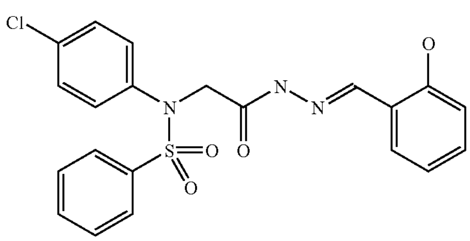 | N-(4-Chloro-phenyl)-N-(2-hydroxy-benzylidene-hydrazinocarbonylmethyl)-benzenesulfonamide | 0.75 |
| 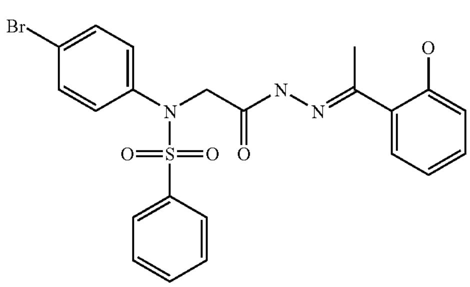 | N-(4-Bromo-phenyl)-N-[1-(2-hydroxy-phenyl)-ethylidene-hydrazinocarbonylmethyl]-benzenesulfonamide | 0.8 |

TABLE 2-continued

| Chemical Structure | IUPAC-Name | Binding Affinity Human V1a Ki (μM) |
|---|---|---|
| 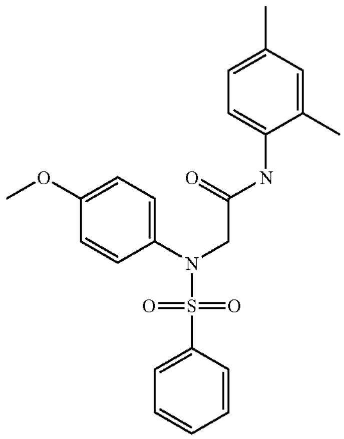 | 2-[Benzenesulfonyl-(4-methoxy-phenyl)-amino]-N-(2,4-dimethyl-phenyl)-acetamide | 0.045 |
| 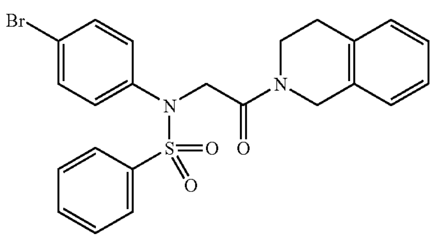 | N-(4-Bromo-phenyl)-N-[2-(3,4-dihydro-1H-isoquinolin-2-yl)-2-oxo-ethyl]-benzenesulfonamide | 0.058 |
| 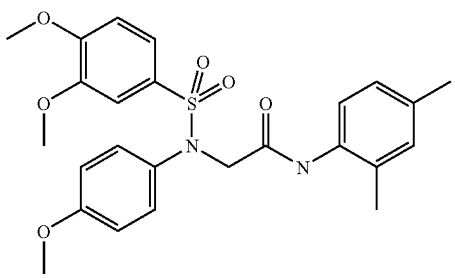 | 2-[(3,4-Dimethoxy-benzenesulfonyl)-(4-methoxy-phenyl)amino]-N-(2,4-dimethyl-phenyl)-acetamide | 0.135 |
| 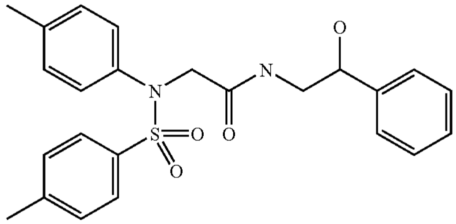 | N-(2-Hydroxy-2-phenyl-ethyl)-2-[(toluene-4-sulfonyl)-p-tolyl-amino]-acetamide | 0.37 |
| 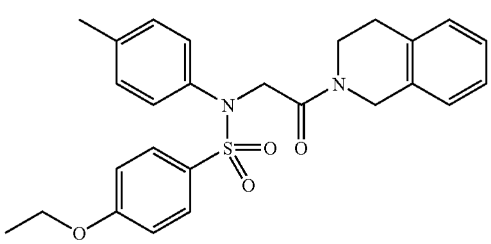 | N-[2-(3,4-Dihydro-1H-isoquinolin-2-yl)-2-oxo-ethyl]-4-ethoxy-N-p-tolyl-benzenesulfonamide | 0.375 |

TABLE 2-continued

| Chemical Structure | IUPAC-Name | Binding Affinity Human V1a Ki (μM) |
|---|---|---|
|  | 2-[(4-Methoxy-phenyl)-(toluene-4-sulfonyl)-amino]-N-[2-(pyridin-2-ylsulfanyl)-ethyl]-acetamide | 0.43 | c) Functional Assay No. 1: Inhibition of Oxytocitn Mediated $Ca^{2+}$-Mobilization by FLIPR (Fluorescent Imaging Plate Reader)

FLIPR is a machine for fluorescence imaging using a laser that is capable of illuminating a 96-well plate and a means of simultaneously reading each well thus enabling rapid measurements on a large number of samples.

This assay intends to show the inhibition of the OT/OT-R mediated calcium mobilisation—being necessary to cause uterine contractions—by using test compounds of formula (I).

Preparing the plates: FLIPR-plates were pre-coated with PLL (Poly-L-Lysine) 10 μg/ml+0.1% gelatine to attach the HEK (Human Embryonic Kidney) cells for 30 min up to 2 days at 37° C. The cells were plated out into 96-well plates (60000 cells/well).

Labelling with fluo-4: 50 kg fluo-4 (fluorescent marker) were dissolved in 20 μl pluronic acid (20% in DMSO). The dissolved fluo-4 was then diluted in 10 ml DMEM (Dubecco's Minimal Essential Medium-F12 medium without FCS (Fetal Calf Serum). The medium was removed from the plates, followed by one wash with DNEM-F12 medium. Now, 100 μl of the DMEM-F12 medium containing fluo-4 were added and the cells incubated for 1.5-2 h (HEK-cells). The cells now contain the fluorescent marker.

Buffer: 145 mM NaCl, 5 mM KCl, 1 mM $MgCl_2$, 10 mM Hepes, 10 mM Glucose, EGTA (Ethylene-bis oxyethylene nitrilo tetraacetic acid). Adjust to pH 7.4.

Performance of the assay: A minimum of 80 μl/well of antagonists (5×) in the above buffer (1×) were prepared (96-well plates). The antagonists were added to the well-plates at different concentrations (30 μM, 10 μM, 1 μM, 300 nM, 100 nM, 10 nM, 1 nM, 100 pM, 10 pM).

OT is added at a concentration of 40 nM.

The fluorescent marker being sensitive to the amount of $Ca^{2+}$ mobilized within the cell may be quantified by the FLIPR machine.

The activities of the sulfanilide derivatives according to formula I were assessed using the above described in vitro biological assay. Representative values for some example compounds are given in Table 3 below. The values refer to the capacity of the example compounds according to formula I to effectively antagonize oxytocin-induced intracellular $Ca^{2+}$-mobilization mediated by the oxytocin receptor. From the values shown in Table 3 it can be derived that said example test compounds according to formula I do exhibit a significant activity as oxytocin receptor antagonists.

TABLE 3

| Structure | IUPAC-Name | Inhibition of Ca2+ mobilization; hOT-R IC50 (μM) |
|---|---|---|
| 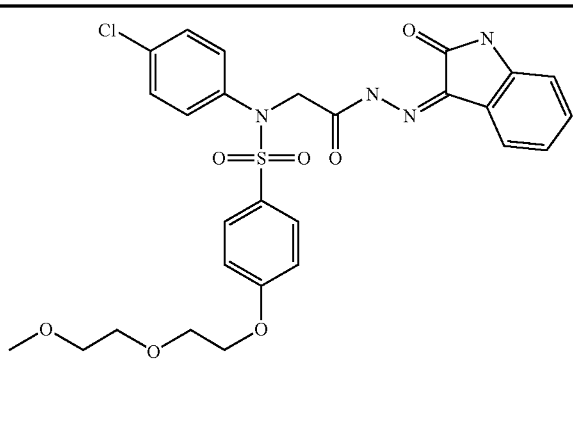 | N-(4-chlorophenyl)-4-[2-(2-methoxyethoxy)ethoxy]-N-{2-oxo-2-[(2Z)-2-(2-oxo-1,2-dihydro-3H-indol-3-ylidene)hydrazino]ethyl}benzenesulfonamide | 0.0069 |

TABLE 3-continued

| Structure | IUPAC-Name | Inhibition of Ca2+ mobilization; hOT-R IC50 (µM) |
|---|---|---|
| 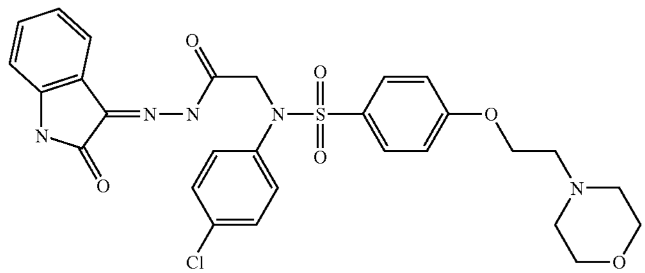 | N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide | 0.007 |
| 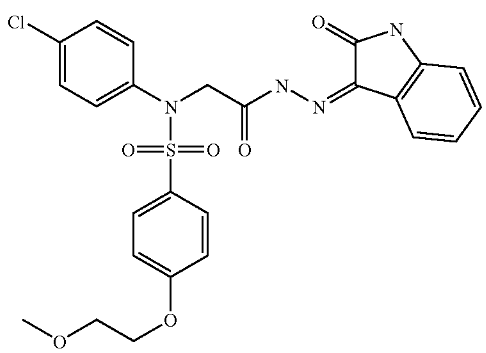 | N-(4-chlorophenyl)-4-(2-methoxyethoxy)-N-{2-oxo-2-[(2Z)-2-(2-oxo-1,2-dihydro-3H-indol-3-ylidene)hydrazino]ethyl}benzenesulfonamide | 0.008 |
| 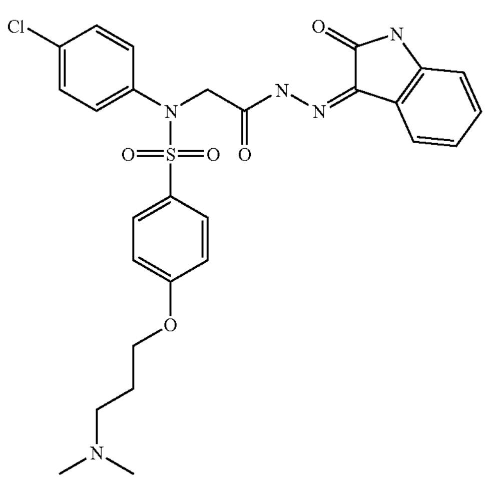 | N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide | 0.0136 |

TABLE 3-continued

| Structure | IUPAC-Name | Inhibition of Ca2+ mobilization; hOT-R IC50 (μM) |
|---|---|---|
| 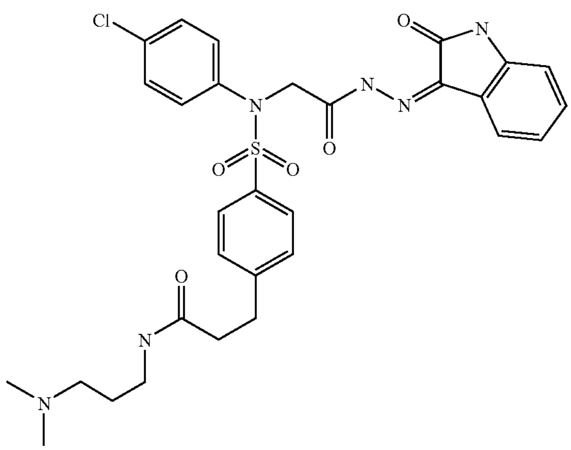 | 3-{4-[(4-chloro{2-oxo-2-[(2Z)-2-(2-oxo-1,2-dihydro-3H-indol-3-ylidene)hydrazino]ethyl}anilino)sulfonyl]phenyl}-N-[3-(dimethylamino)propyl]propanamide | 0.014 |
| 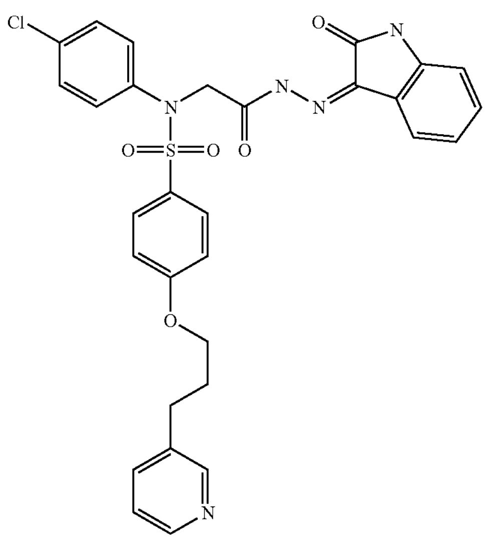 | N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide | 0.017 |
| 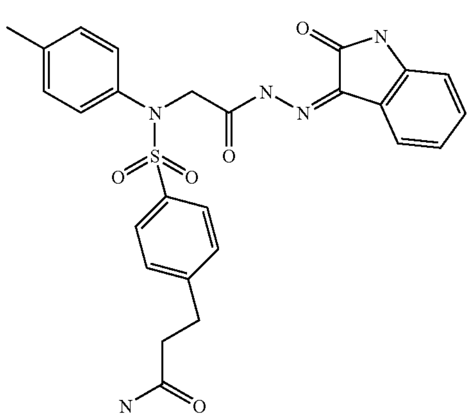 | 3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide | 0.019 |

TABLE 3-continued

| Structure | IUPAC-Name | Inhibition of Ca2+ mobilization; hOT-R IC50 (μM) |
|---|---|---|
| 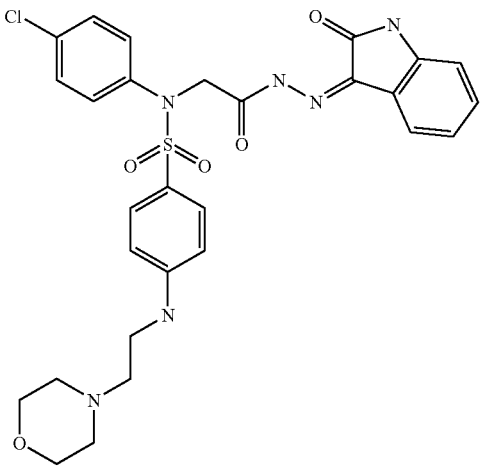 | N-(4-chlorophenyl)-4-{[2-(4-morpholinyl)ethyl]amino)-N-{2-oxo-2-[(2Z)-2-(2-oxo-1,2-dihydro-3H-indol-3-ylidene)hydrazino]ethyl}benzenesulfonamide | 0.049 |
| 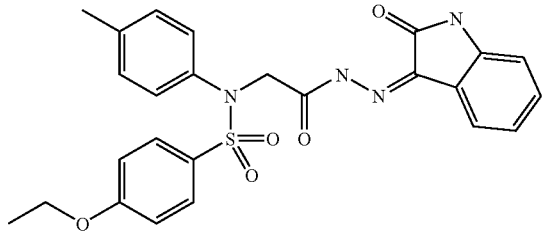 | 4-ethoxy-N-(4-methylphenyl)-N-(2-oxo-2-[(2Z)-2-(2-oxo-1,2-dihydro-3H-indol-3-ylidene)hydrazino]ethyl}benzenesulfonamide | 0.055 |
| 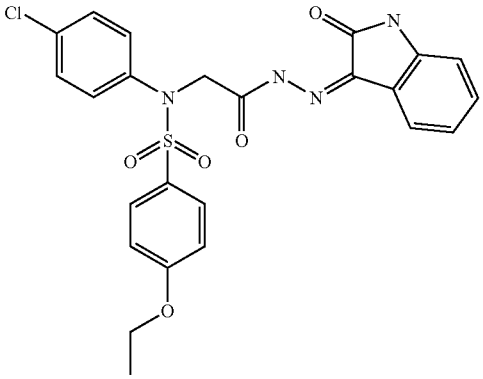 | N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide | 0.102 |

TABLE 3-continued

| Structure | IUPAC-Name | Inhibition of Ca2+ mobilization; hOT-R IC50 (μM) |
|---|---|---|
| 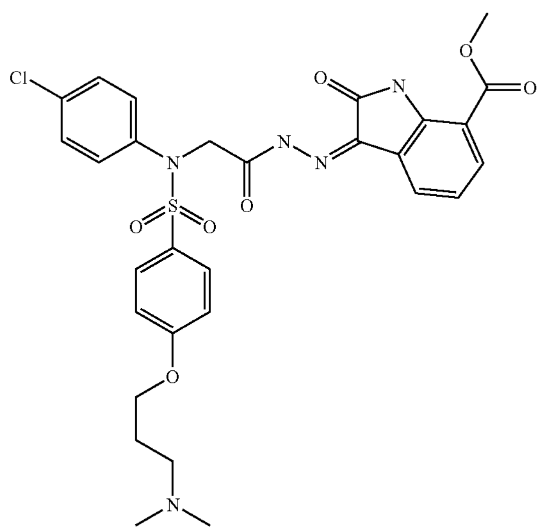 | methyl (3Z)-3-({[4-chloro({4-[3-(dimethylamino)propoxy]phenyl}sulfonyl)anilino]acetyl}hydrazono)-2-oxo-2,3-dihydro-1H-indole 7-carboxylate | 0.393 |
| 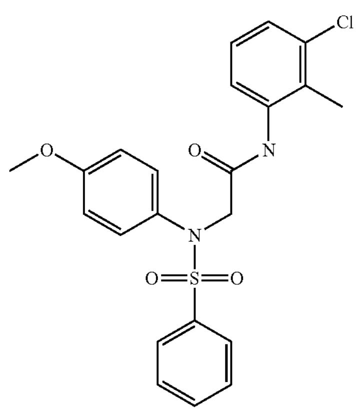 | 2-[Benzenesulfonyl-(4-methoxy-phenyl)-amino]-N-(3-chloro-2-methyl-phenyl)-acetamide | 0.045 |
| 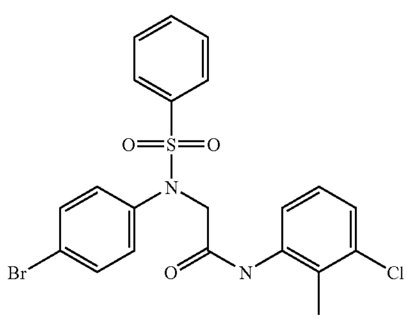 | 2-[Benzenesulfonyl-(4-bromo-phenyl)-amino]-N-(3-chloro-2-methyl-phenyl)-acetamide | 0.353 |

TABLE 3-continued

| Structure | IUPAC-Name | Inhibition of Ca2+ mobilization; hOT-R IC50 (μM) |
|---|---|---|
| 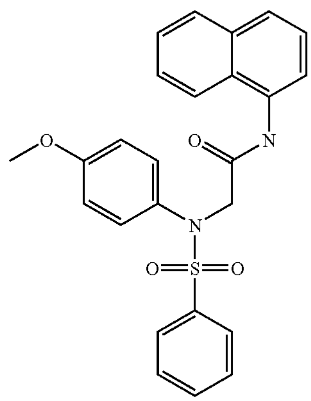 | 2-[Benzenesulfonyl-(4-methoxy-phenyl)-amino]-N-naphthalen-1-yl-acetamide | 0.363 |
| 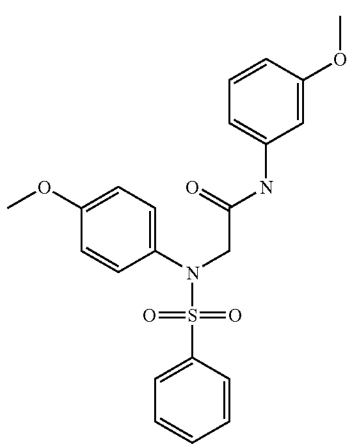 | 2-[Benzenesulfonyl-(4-methoxy-phenyl)-amino]-N-(3-methoxy-phenyl)-acetamide | 0.392 |
| 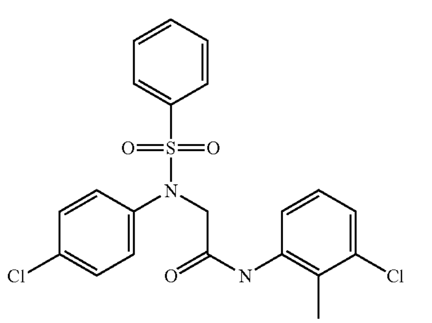 | 2-[Benzenesulfonyl-(4-chloro-phenyl)-amino]-N-(3-chloro-2-methyl-phenyl)-acetamide | 0.443 |
| | N-(2,4-Dichloro-benzyl)-2-[(toluene-4-sulfonyl)-p-tolyl-amino]-acetamide | 0.595 | d) Functional Assay No. 1: Inhibition of Vasopressin-Mediated $Ca^{2+}$-mobilization by FLIPR (Fluorescent Imaging Plate Reader)

FLIPR is a machine for fluorescence imaging using a laser that is capable of illuminating a 96-well plate and a means of simultaneously reading each well thus enabling rapid measurements on a large number of samples.

This assay intends to show the inhibition of the AVP/$V_{1a}$-R mediated calcium mobilisation—being necessary to cause uterine contractions—by using test compounds of formula (1).

Preparing the plates: FLIPR-plates were pre-coated with PLL (Poly-L-Lysine) 10 µg/ml+0.1% gelatine to attach the CHO cells (expessing $hV_{1a}$) for 30 min up to 2 days at 37° C. The cells were plated out into 96-well plates (60000 cells/well).

Labelling with fluo-4: 50 µg fluo-4 (fluorescent marker) were dissolved in 20 µl pluronic acid (20% in DMSO). The dissolved fluo-4 was then diluted in 10 ml DMEM (Dubecco's Minimal Essential Medium-F12 medium without FCS (Fetal Calf Serum). The medium was removed from the plates, followed by one wash with DMEM-F12 medium. Now, 100 µl of the DMEM-F12 medium containing fluo-4 were added and the cells incubated for 1-1.5 h (CHO-cells). The cells now contain the fluorescent marker.

Buffer: 145 mM NaCl, 5 mM KCl, 1 mM $MgCl_2$, 10 mM Hepes, 10 mM Glucose, EGTA (Ethylene-bis oxyethylene nitrilo tetraacetic acid). Adjust to pH 7.4.

Performance of the assay: A minimum of 80 µl/well of antagonists (5×) in the above buffer (1×) were prepared (96-well plates). The antagonists were added to the well-plates at different concentrations (30 µM, 10 µM, 1 µM, 300 nM, 100 nM, 10 nM, 1 nM, 100 pM, 10 pM).

AVP is added at a concentration of 40 nM.

The fluorescent marker being sensitive to the amount of $Ca^{2+}$ mobilized within the cell may be quantified by the FLIPR machine.

The activities of the sulfanilide derivatives according to formula I were assessed using the above described in vitro biological assay. Representative values for some example compounds are given in Table 4 below. The values refer to the capacity of the example compounds according to formula I to effectively antagonize AVP-induced intracellular $Ca^2+$-mobilization mediated by the VIa-receptor. From the values shown in Table 4 it can be derived that said example test compounds according to formula I do exhibit a significant activity as VIa receptor antagonists.

TABLE 4

| Structure | IUPAC-Name | Inhibition of Ca2+ mobilization; hV1a IC50 (µM) |
|---|---|---|
| 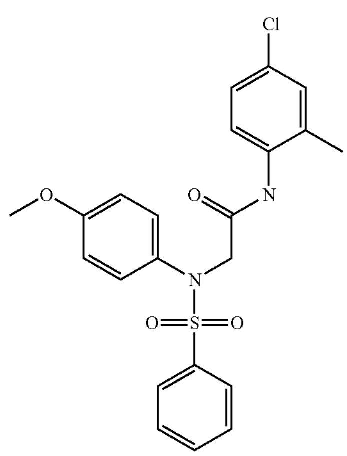 | 2-[Benzenesulfonyl-(4-methoxy-phenyl)-amino]-N-(4-chloro-2-methyl-phenyl)-acetamide | 0.09 |
| 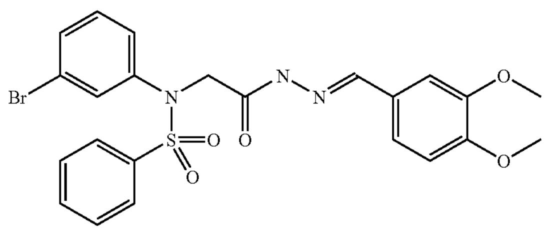 | N-(3-Bromo-phenyl)-N-(3,4-dimethoxy-benzylidene-hydrazinocarbonylmethyl)-benzenesulfonamide | 0.44 |

TABLE 4-continued

| Structure | IUPAC-Name | Inhibition of Ca2+ mobilization; hV1a IC50 (μM) |
|---|---|---|
| 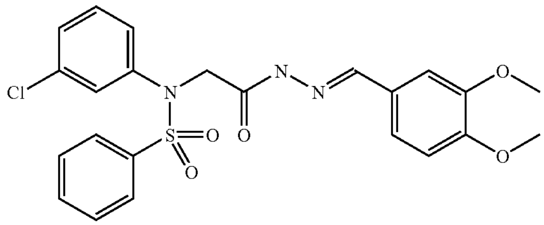 | N-(3-Chloro-phenyl)-N-(3,4-dimethoxy-benzylidene-hydrazinocarbonylmethyl)-benzenesulfonamide | 0.55 |
|  | N-(3-Chloro-phenyl)-N-[1-(2-hydroxy-phenyl)-ethylidene-hydrazinocarbonylmethyl]-benzenesulfonamide | 0.37 | e) Functional Assay No. 2: Inhibition of IP3 (Inositol Tri-Phosphate)-Synthesis in HEK/EBNA-OTR Cells This assay intends to show the inhibition of the OT/OT-R mediated IP3 synthesis—being necessary to cause uterine contractions—by using test compounds of formula (I).

Stimulation of the cells: HEK/EBNA OTR(rat or human) cells were plated out into costar 12-well plates, and equilibrated for 15-24 h with [³H]-inositol radiolabel in medium without inositol supplement, with 1% FCS (0.5 ml/well). 4 μCi/ml were used. After this, the medium containing the label was aspirated. Then was added DMEM (without FCS, inositol), 20 mM Hepes (4-(2-hydroxyethyl)-1-piperazine-ethane-sulphonic acid), 1 mg/ml BSA containing 10 mM LiCl (freshly prepared), for 10-115 min at 37° C. The agonist (i.e. oxytocin used at a concentration of 10 nM) and the antagonists (i.e. the tests compounds of formula (1) used in a concentration of 10 μM, 1 μM, 300 nM, 100 nM, 10 nM, 1 nM, 100 pM, 10 pM, 3 pM) were added for the time required (15-45 min), followed by aspiration of the medium. Due to the antagonization of the OT receptor, the radiolabeled inositol is phosphorylated to yield IP3, the amount of the radiolabeled IP3 may be determined through the ensuing work-up. The reaction was stopped with 1 ml STOP-solution (i.e. 0.4 M perchloric acid), and let sit for 5-10 min at Room Temperature. Then, 0.8 ml were transferred into tubes containing 0.4 ml of neutralizing solution (0.72 M KOH/0.6M KHCO₃), and the tubes vortexed and kept in the cold at least for 2 h.

Separation of IP's: The samples were spun in a table top centrifuge at 3000-4000 rpm for 15 min. 1 ml of the supernatant was transferred to new tubes containing 2.5 ml H₂O. Packed resin (0.8 ml) was equilibrated with 20 ml H₂O, and the whole samples poured onto the chromatography columns, thus separating the mixture. To discard free inositol, two washes with 10 ml H₂O were carried out.

Elution of total IP's: The elution was achieved using 3 ml 1M ammonium formate/0.1M formic acid. The eluant was collected in scintillation counting tubes, followed by addition of 7 ml of scintillation liquid. The amount of IP3 is determined by a scintillating counter.

The activities of the sulfanilide derivatives claimed in the formula I were assessed using the above described in vitro biological assay. Representative values for some example compounds are given in Table 5 below. The values refer to the capacity of the example compounds according to formula I to effectively antagonize oxytocin-induced IP3-synthesis mediated by the oxytocin receptor. From the values shown in Table 5 it can be derived that said example test compounds according to formula I do exhibit a significant activity as oxytocin receptor antagonists.

TABLE 5

| Structure | IUPAC-Name | Inhibition of IP3-Synthesis, ratOT-R IC$_{50}$ (µM) |
|---|---|---|
| 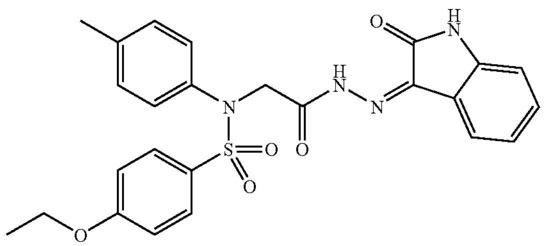 | 4-ethoxy-N-(4-methylphenyl)-N-{2-oxo-2-[2-(2-oxo-1,2-dihydro-3H-indol-3-ylidene)hydrazino]ethyl}benzenesulfonamide | 0.013 |
| 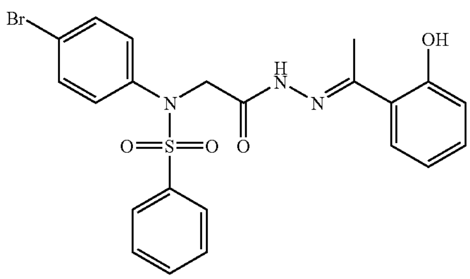 | N-(4-bromophenyl)-N-(2-{2-[1-(2-hydroxyphenyl)ethylidene]hydrazino}-2-oxoethyl)benzenesulfonamide | 0.048 |
| 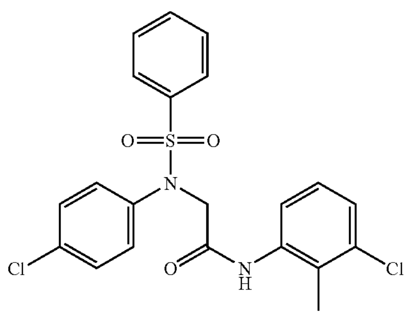 | N-(3-chloro-2-methylphenyl)-2-[4-chloro(phenylsulfonyl)anilino]acetamide | 0.32 |
| 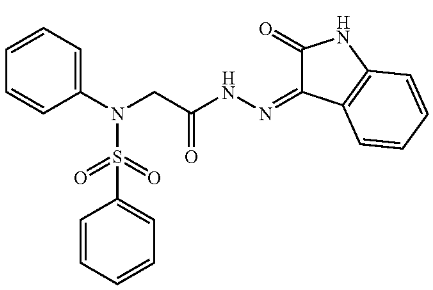 | N-{2-oxo-2-[2-(2-oxo-1,2-dihydro-3H-indol-3-ylidene)hydrazino]ethyl}-N-phenylbenzenesulfonamide | 0.3 |
| | 2-[4-bromo(phenylsulfonyl)anilino]-N-(3-chloro-2-methylphenyl)acetamide | 0.11 | f) In Vivo Model for Inhibition of Uterine Contractions

The assay intends to show the biological effect of tested compounds in an in vivo model of preterm labor, premature birth.

Non-pregnant Charles River CD(SD) BR female rats (9-10 weeks old, 200-250 g) were treated at 18 and 24 hours before the experiment with 250 µg/kg, i.p. diethylstilbestrol (DES). For the assay, the animal was anaesthetised by urethane (1.75 g/kg, i.p.) and placed on an homeothennic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P231D Gould Statham pressure transducer. For the i.v. route of administration of the test compounds, one jugular vein was isolated and cannulated with a PE60 tubing connected to a butterfly needle to allow the administration by a dispensing syringe. In the case of intraduodenal administration of the test compounds, the duodenum was isolated and similarly cannulated through a small incision in its wall. One carotid artery was also isolated and cannulated with PE60 catheter and connected to a suitable syringe for blood sample collection (see below). After a stabilization period, the same dose of oxytocin was repeatedly injected intravenously at 30-min intervals. When comparable contractile responses of the uterus to the selected dose of oxytocin were obtained, the dose of the test or reference compound was administered. Further injections of the same dose of oxytocin were then made for a suitable time after treatment to assess inhibitory effects of the compounds under study. The contractile response of the uterus to oxytocin was quantified by measuring the intra-uterine pressure and the number of contractions. The effect of the reference and test compounds were evaluated by comparing pre- and post-treatment pressure values. In addition, at 2, 30, 90 and 210 minutes after test compound administration, a 0.5-ml blood sample was withdrawn from the cannulated carotid artery of each experimental animal. Plasma was obtained by standard laboratory procedure and the resulting samples were stored at −20° C.

The activities of the sulfanilide derivatives claimed in the Formula I were assessed using the above described in vivo biological assay. Representative values for one example compound are given in Table 4 below. The values refer to the capacity of the example compound according to Formula I to effectively antagonize oxytocin-induced uterine contractions in the rat. From the values shown in Table 6 it can be derived that said example test compound according to Formula I does exhibit a significant activity as tocolytic, i.e. uterine-relaxing, agent.

TABLE 6

| Structure | IUPAC-Name | % Reduction of Uterine Contraction | Doses (mg/kg) |
|---|---|---|---|
| 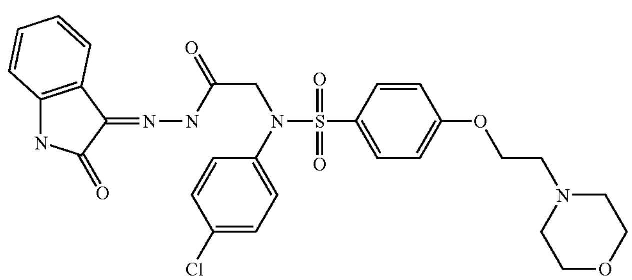 | N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide | 4.3 ± 1.7<br>18.2 ± 3.7<br>39.8 ± 5.1<br>41.7 ± 12.5<br>71.3 ± 6.4 | 0.3<br>1<br>3<br>10<br>30 |
| 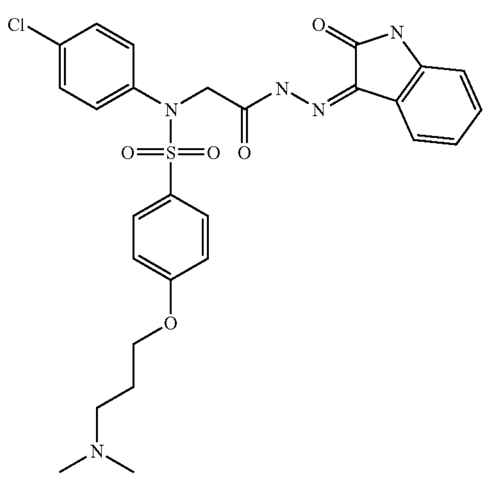 | N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide | 9.3 ± 2.5<br>20.8 ± 2.2<br>34.4 ± 3.9<br>57.1 ± 4.8<br>67.4 ± 7.1 | 0.3<br>1<br>3<br>10<br>30 |

TABLE 6-continued

| Structure | IUPAC-Name | % Reduction of Uterine Contraction | Doses (mg/kg) |
|---|---|---|---|
| 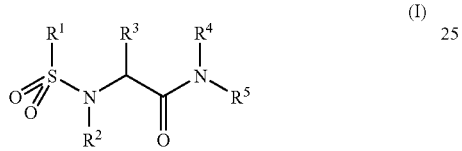 | 4-ethoxy-N-(4-methylphenyl)-N-{2-oxo-2-[(2Z)-2-(2-oxo-1,2-dihydro-3H-indol-3-ylidene)hydrazino]ethyl}benzenesulfonamide | 23.9 ± 4.0<br>40.3 ± 4.2<br>62.6 ± 5.0 | 5<br>7.5<br>10 |

What is claimed is:

1. A method comprising:
administering a composition comprising at least one sulfanilide of Formula I:

(I)

a geometrical isomer thereof, an optically active enantiomer thereof, an optically active diastereomer thereof, a racemate of an optically active enantiomer or diastereomer thereof, or a pharmaceutically acceptable salt thereof, to a mammal in need thereof, wherein:

$R^1$ and $R^2$ are aryl or heteroaryl which may be fused with 1-2 further cycloalkyl or aryl or heteroaryl groups;

$R^3$ is selected from the group consisting of H, $C_1$-$C_6$-alkyl, $C_1$-$C_6$-alkyl aryl, C 1-$C_6$-alkyl heteroaryl, $C_2$-$C_6$-alkenyl, $C_2$-$C_6$-alkynyl;

$R^4$ and $R^5$ are independently selected from the group consisting of hydrogen, $C_2$-$C_6$-alkenyl, $C_2$-$C_6$-alkynyl; saturated or unsaturated 3-8-membered cycloalkyl which may contain 1 to 3 heteroatoms selected from the group consisting of N, 0, S, aryl, heteroaryl, $C_1$-$C_6$-alkyl aryl, and $C_1$-$C_6$-alkyl heteroaryl, or $R^4$ can be H or $C_1$-$C_6$ alkyl, and $R^5$ can be —N=$CR^6R^7$, wherein:

$R^6$ is an aryl or a heteroaryl ring carrying 1 to 5 substituents selected from the group consisting of H, $C_1$-$C_6$-alkyl, $C_1$-$C_6$-alkyl aryl, $C_1$-$C_6$-alkyl heteroaryl, $C_2$-$C_6$-alkenyl, $C_2$-$C_6$-alkynyl, a primary amino group, a secondary amino group, a tertiary amino group, acyl, acyloxy, acylamino, aminocarbonyl, alkoxycarbonyl, aryl, heteroaryl, carboxyl, cyano, halogen, hydroxy, mercapto, nitro, sulfoxy, sulfonyl, $C_1$-$C_6$-alkoxy, thioalkoxy, 2-alkoxyethoxy, 2-(2-alkoxyethoxy)ethoxy, 2-hydroxyethoxy, 2-(2-hydroxyethoxy)-ethoxy, 2-(dimethylamino)ethoxy, 2-(2-(dimethylamino) ethoxy)-ethoxy, 2-carboxyethoxy, 2-(2-carboxyethoxy) ethoxy, carboxymethoxy, 2-sulfoxy-ethoxy, 2-(2-sulfoxyethoxy)ethoxy, 2-[(2-methoxyethyl)sulfanyl] ethoxy, 2-[(2-hydroxyethyl)-sulfanyl]ethoxy, 2-[(2-carboxyethyl)sulfanyl]ethoxy, 2-[(2-carboxymethyl) sulfanyl]-ethoxy, and 2-[(2-sulfoxyethyl)sulfanyl] ethoxy;

$R^7$ is selected from the group consisting of H, $C_1$-$C_6$-alkyl, $C_1$-$C_6$-alkyl aryl, $C_1$-$C_6$-alkyl heteroaryl, $C_2$-$C_6$-alkenyl, $C_2$-$C_6$-alkynyl, acyl, aminocarbonyl, alkoxycarbonyl, aryl, heteroaryl, carboxyl, cyano, and sulfonyl;

or $R^6$ and $R^7$ form together with the C atom to which they are attached a 3-8 membered saturated or unsaturated heterocyclic ring which may contain 1-2 further heteroatoms selected from the group consisting of N, S and 0, and which is optionally fused with an aryl, heteroaryl or 3-8 membered saturated or unsaturated cycloalkyl ring, wherein the mammal is in need of treatment for preterm labor, premature birth, dysmenorrhea, inappropriate secretion of vasopressin, congestive heart failure, arterial hypertension, liver cirrhosis, nephritic syndrome or ocular hypertension.

2. The method according to claim 1, wherein $R^1$ and/or $R^2$ are substituted with from 1 to 5 substituents independently selected from the group consisting of $C_1$-$C_6$-alkyl,$C_1$-$C_6$-alkyl aryl, $C_1$-$C_6$-alkyl heteroaryl, $C_2$-$C_6$-alkenyl, $C_2$-$C_6$-alkynyl, a primary amino group, a secondary amino group, a tertiary amino group, a quaternary ammonium moiety, acyl, acyloxy, acylamino, aminocarbonyl, alkoxycarbonyl, aryl, heteroaryl, carboxyl, cyano, halogen, hydroxy, mercapto, nitro, sulfoxy, sulfonyl, alkoxy, thioalkoxy, 2-alkoxyethoxy, 2-(2-alkoxyethoxy)ethoxy, 2-hydroxyethoxy, 2-(2-hydroxyethoxy)ethoxy, 2-(dimethylamino)ethoxy, 2-(2-(dimethylamino)ethoxy)-ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl] ethoxy, 2-[(2-hydroxyethyl)sulfanyl]ethoxy, 2-[(2-carboxyethyl)sulfanyl]ethoxy, 2-[(2-carboxymethyl)sulfanyl] ethoxy, and 2-[(2-sulfoxy-ethyl)sulfanyl]ethoxy.

3. The method according to claim 1, wherein $R^1$ and $R^2$ are aryl and heteroaryl rings whereby either or both of said rings are substituted with 1 or 2 substituents selected from the group consisting of halogens, cyano, $C_1$-$C_6$-alkyl, primary amines, secondary amines and $C_1$-$C_6$-alkoxy groups.

4. The method according to claim 3, wherein the $C_1$-$C_6$-alkoxy groups are selected from the group consisting of methoxy groups, ethoxy groups and substituted ethoxy groups.

5. The method according to claim 1, wherein $R^1$ and $R^2$ are unsubstituted or substituted phenyl.

6. The method according to claim 1, wherein $R^4$ and $R^5$ are independently selected from the group consisting of phenylmethyl, 2-phenylethyl, hydroxy(phenyl)methyl, (imidazol-4-yl)methyl, (indol-3-yl)methyl, (pyrid-2-yl)methyl, (pyrid-3-yl)methyl, (pyrid-4-yl)methyl, (thien-2-yl)methyl, and (thien-3-yl)methyl.

7. The method according to claim 1, wherein $R^3$ and $R^4$ are H, and $R^5$ is a group N=$CR^6R^7$, and the sulfanilide is of Formula II:

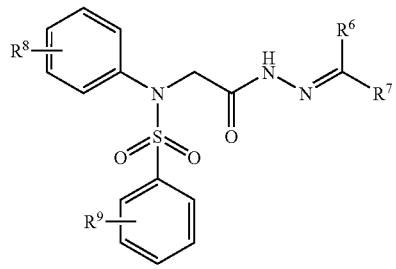

(II)

a tautomeric form thereof, a geometrical isomer thereof, an optically active enantiomer thereof, an optically active diastereomer thereof, a racemate thereof or a pharmaceutically acceptable salt thereof, wherein:

$R^6$ is an aryl or heteroaryl group;

$R^7$ is selected from the group consisting of H, $C_1$-$C_6$-alkyl, $C_1$-$C_6$-alkyl aryl, $C_1$-$C_6$-alkyl heteroaryl, $C_1$-$C_6$-alkyl cycloalkyl, $C_2$-$C_6$-alkenyl, $C_2$-$C_6$-alkynyl, acyl, aminocarbonyl, alkoxycarbonyl, aryl, heteroaryl, carboxyl, cyano, and sulfonyl;

or $R^6$ and $R^7$ form together with the C atom to which they are attached a 3-8 membered, saturated or unsaturated heterocyclic ring which may contain 1-2 further heteroatoms selected from the group consisting of N, S and O, and which is optionally fused with an aryl, heteroaryl or 3-8 membered saturated or unsaturated cycloalkyl ring;

$R^8$ and $R^9$ are selected from the group consisting of $C_1$-$C_6$-alkyl, $C_1$-$C_6$-alkyl aryl, $C_1$-$C_6$-alkyl heteroaryl, $C_1$-$C_6$-alkyl cycloalkyl, $C_2$-$C_6$-alkenyl, $C_2$-$C_6$-alkynyl, a primary amino group, a secondary amino group, a tertiary amino group, a quartemary ammonium moiety, acyl, acyloxy, acylamino, aminocarbonyl, alkoxycarbonyl, aryl, heteroaryl, carbonyl, carboxyl, cyano, halogen, hydroxy, mercapto, nitro, sulfoxy, sulfonyl, $C_1$-$C_6$-alkoxy, and thioalkoxy;

or 2 substituents of $R^8$ andlor of $R^9$ undergo ring closure, and n and n' are independently from 1 to 5.

8. The method according to claim 7, wherein $R^6$ and $R^7$ form an oxindole ring.

9. A sulfanilide of Formula (IIa):

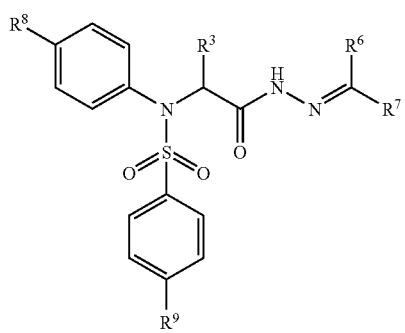

(IIa)

wherein:
$R^3$ is H or $C_1$-$C_6$-alkyl;
$R^6$, $R^7$ are independently selected from the group consisting of H, $C_1$-$C_6$-alkyl, $C_1$-$C_6$-alkyl aryl, $C_1$-$C_6$-alkyl heteroaryl, $C_1$-$C_6$-alkyl cycloalkyl, $C_2$-$C_6$-alkenyl, $C_2$-$C_6$-alkynyl, acyl, aminocarbonyl, alkoxycarbonyl, aryl, heteroaryl, carboxyl, cyano, and sulfonyl;
or, $R^6$ and $R^7$ form together with the C atom to which they are attached a 3-8 membered saturated or unsaturated cyclic or heterocyclic ring which may contain 1-2 further heteroatoms selected from the group consisting of N, S and O, and which may be fused with an aryl, heteroaryl or 3-8 membered cycloalkyl ring;
$R^8$ is H, halogen or $C_1$-$C_6$-alkyl;
$R^9$ is selected from the group consisting of-X-($C_1$-$C_6$-alkyl)-Y, wherein X is a bond, O, NR, or —CONR; Y is a 3-8-membered cycloalkyl, a 3-8-membered cycloalkyl containing 1-3 heteroatoms selected from the group consisting of N, O, S, aryl, heteroaryl, OR, NRR', and —(C=O)—NRR', with R, R' independently H, $C_1$-$C_6$-alkyl, $C_1$-$C_6$-alkyl aryl, $C_1$-$C_6$-alkyl heteroaryl,$C_1$-$C_6$-alkyl cycloalkyl, $C_1$-$C_6$-alkoxy or R, R' form together with the N atom to which they are attached a 3-8 membered saturated or unsaturated heterocyclic ring which may contain 1-2 further heteroatoms selected from the group consisting of N, S and O, and which may be fused with an aryl, heteroaryl or 3-8 membered cycloalkyl ring.

10. The sulfanilide according to claim 9, wherein $R^3$ is H, $R^6$ is phenyl and $R^7$ is H or $C_1$-$C_6$-alkyl.

11. The sulfanilide according to claim 9, wherein R and $R^7$ form together an tetrahydroisoquinoline or an oxindole ring.

12. A sulfanilide of Formula Ib:

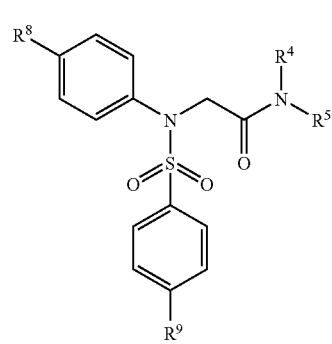

(Ib)

wherein,
$R^8$ and $R^9$ are independently selected from the group consisting of H, halogen, $C_1$-$C_6$-alkoxy or $C_1$-$C_6$-alkyl;
$R^4$ is H or $C_1$-$C_6$-alkyl and $R^5$ is an acetamide, a propionic amide, a propionic acid moiety, substituted by $C_1$-$C_6$-alkyl, $C_1$-$C_6$-alkyl aryl, $C_1$-$C_6$-alkyl heteroaryl, or $C_1$-$C_6$-alkoxy; or
$R^4$ and $R^5$ form together with the nitrogen atom to which they are attached a pyrrolidine, piperidine, tetrahydroisoquinoline, isoindole or indole ring carrying an acetamide, propionic amide or propionic acid moiety, said acetamide, propionic amide or propionic acid moiety may be substituted by $C_1$-$C_6$-alkyl, $C_1$-$C_6$-alkyl aryl, $C_1$-$C_6$-alkyl heteroaryl, or $C_1$-$C_6$-alkoxy.

13. The sulfanilide according to claim 1 selected from the group consisting of:

4-ethoxy-N-(2-{(2E)-2-[1-(2-hydroxyphenyl)ethylidene]hydrazino}-2-oxoethyl)-N-(4-methylphenyl)benzenesulfonamide 4-ethoxy-N-(4-methylphenyl)-N-{2-oxo-2-[(2Z)-2-(2-oxo-1,2-dihydro-3H-indol-3-ylidene)hydrazino]ethyl}benzenesulfonamide, 4-ethoxy-N-{2-oxo-2-[(2E)-2-(2-oxo-1,2-dihydro-3H-indol-3-ylidene)hydrazino]ethyl}-N-phenylbenzenesulfonamide, 4-ethoxy-N-[2-((2E)-2-{5-[hydroxy(oxido)amino]-2-oxo-1,2-dihydro-3H-indol-3-ylidene}hydrazino)-2-oxoethyl]-N-phenylbenzenesulfonamide, 4-ethoxy-N-{2-[(2E)-2-(5-iodo-2-oxo-1,2-dihydro-3H-indol-3-ylidene)hydrazino]-2-oxoethyl}-N-phenylbenzenesulfonamide, 4-ethoxy-N-(2-hydrazino-2-oxoethyl)-N-(4-methylphenyl)benzenesulfonamide, N-(4-methylphenyl)-N-{2-oxo-2-[(2E)-2-(2-oxo-1,2-dihydro-3H-indol-3-ylidene)hydrazino]ethyl}-1-naphthalenesulfonamide, N-(4-methylphenyl)-N-{2-oxo-2-[(2E)-2-(2-oxo-1,2-dihydro-3H-indol-3-ylidene)hydrazino]ethyl}-2-naphthalenesulfonamide, 4-chloro-N-(4-methylphenyl)-N-{2-oxo-2-[(2E)-2-(2-oxo-1,2-dihydro-3H-indol-3-ylidene)hydrazino]ethyl}benzenesulfonamide, 4-methoxy-N-(4-methylphenyl)-N-{2-oxo-2-[(2E)-2-(2-oxo-1,2-dihydro-3H-indol-3-ylidene)hydrazino]ethyl}benzenesulfonamide, 4-methyl-N-(4-methylphenyl)-N-{2-oxo-2-[(2E)-2-(2-oxo-1,2-dihydro-3H-indol-3-ylidene)hydrazino]ethyl}benzenesulfonamide, 4-cyano-N-(4-methylphenyl)-N-{2-oxo-2-[(2E)-2-(2-oxo-1,2-dihydro-3H-indol-3-ylidene)hydrazino]ethyl}benzenesulfonamide, 4-ethoxy-N-{2-[(2Z)-2-(2-fluorobenzylidene)hydrazino]-2-oxoethyl}-N-(4-methylphenyl)benzenesulfonamide, (3E)-3-[({[(4-ethoxyphenyl)sulfonyl]-4-methylanilino}acetyl)hydrazono]-2-oxo-2,3-dihydro-1H-indole-5-sulfonic acid N-(4-methylphenyl)-N-{2-oxo-2-[(2E)-2-(2-oxo-1,2-dihydro-3H-indol-3-ylidene)hydrazino]ethyl}[1,1'-biphenyl]-4-sulfonamide, N-(4-methylphenyl)-N-{2-oxo-2-[(2E)-2-(2-oxo-1,2-dihydro-3H-indol-3-ylidene)hydrazino]ethyl}-4-phenoxybenzenesulfonamide, 4-ethoxy-N-{2-[(2Z)-2-(2-hydroxybenzylidene)hydrazino]-2-oxoethyl}-N-(4-methylphenyl)benzenesulfonamide, N-(2-{(2Z)-2-[4-(diethylamino)-2-hydroxybenzylidene]hydrazino}-2-oxoethyl)-4-ethoxy-N-(4-methylphenyl)benzenesulfonamide, 4-ethoxy-N-(2-{(2Z)-2-[(2-hydroxy-1-naphthyl)methylene]hydrazino}-2-oxoethyl)-N-(4-methylphenyl)benzenesulfonamide, 4-ethoxy-N-(4-methylphenyl)-N-{2-oxo-2-[(2Z)-2-(3-oxo-2,3-dihydro-1H-inden-1-ylidene)hydrazino]ethyl}benzenesulfonamide, 4'-methoxy-N-(4-methylphenyl)-N-{2-oxo-2-[(2Z)-2-(2-oxo-1,2-dihydro-3H-indol-3-ylidene)hydrazino]ethyl}[1,1'-biphenyl]-4-sulfonamide, 4-ethoxy-N-{2-[(2Z)-2-(1-methyl-2-oxo-1,2-dihydro-3H-indol-3-ylidene)hydrazino]-2-oxoethyl}-N-(4-methylphenyl)benzenesulfonamide, N-(2-{(2E)-2-[1-(2,4-dihydroxyphenyl)ethylidene]hydrazino}-2-oxoethyl)-4-ethoxy-N-(4-methylphenyl)benzenesulfonamide, 3,4-dimethoxy-N-(4-methylphenyl)-N-{2-oxo-2-[(2E)-2-(2-oxo-1,2-dihydro-3H-indol-3-ylidene)hydrazino]ethyl}benzenesulfonamide, 4-ethoxy-N-(2-{(2Z)-2-[1-(2-hydroxy-1-naphthyl)ethylidene]hydrazino}-2-oxoethyl)-N-(4-methylphenyl)benzenesulfonamide, 4-ethoxy-N-(2-{(2E)-2-[1-(1-hydroxy-2-naphthyl)ethylidene]hydrazino}-2-oxoethyl)-N-(4-methylphenyl)benzenesulfonamide, 4-tert-butyl-N-(4-chlorophenyl)-N-{2-oxo-2-[(2E)-2-(2-oxo-1,2-dihydro-3H-indol-3-ylidene)hydrazino]ethyl}benzenesulfonamide, N-(4-chlorophenyl)-3,4-dimethoxy-N-{2-oxo-2-[(2E)-2-(2-oxo-1,2-dihydro-3H-indol-3-ylidene)hydrazino]ethyl}benzenesulfonamide, 4-tert-butyl-N-(4-methylphenyl)-N-{2-oxo-2-[(2E)-2-(2-oxo-1,2-dihydro-3H-indol-3-ylidene)hydrazino]ethyl}benzenesulfonamide, N-(4-methylphenyl)-N-{2-oxo-2-[(2E)-2-(2-oxo-1,2-dihydro-3H-indol-3-ylidene)hydrazino]ethyl}-4-propylbenzenesulfonamide, 4-butoxy-N-(4-methylphenyl)-N-{2-oxo-2-[(2E)-2-(2-oxo-1,2-dihydro-3H-indol-3-ylidene)hydrazino]ethyl}benzenesulfonamide, 4-butoxy-N-(4-chlorophenyl)-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-propoxybenzenesulfonamide, N-(4-methylphenyl)-N-{2-oxo-2-[(2Z)-2-(2-oxo-1,2-dihydro-3H-indol-3-ylidene)hydrazino]ethyl}-4-tert-pentylbenzenesulfonamide, N-(4-methylphenyl)-N-{2-oxo-2-[(2Z)-2-(2-oxo-1,2-dihydro-3H-indol-3-ylidene)hydrazino]ethyl}-4-propoxybenzenesulfonamide, N-(4-methylphenyl)-N-{2-oxo-2-[(2Z)-2-(2-oxo-1,2-dihydro-3H-indol-3-ylidene)hydrazino]ethyl}-2-thiophenesulfonamide, N-(4-chlorophenyl)-N-{2-oxo-2-[(2Z)-2-(2-oxo-1,2-dihydro-3H-indol-3-ylidene)hydrazino]ethyl}-2-thiophenesulfonamide, N-(4-chlorophenyl)-N-{2-[(2E)-2-(2-hydroxybenzylidene)hydrazino]-2-oxoethyl}-3,4-dimethoxybenzenesulfonamide, N-(4-chlorophenyl)-4-ethoxy-N-{2-[(2E)-2-(2-hydroxybenzylidene)hydrazino]-2-oxoethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-tert-pentylbenzenesulfonamide, N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-propylbenzenesulfonamide, 4-ethoxy-N-{1-methyl-2-oxo-2-[(2Z)-2-(2-oxo-1,2-dihydro-3H-indol-3-ylidene)hydrazino]ethyl}-N-(4-methylphenyl)benzenesulfonamide, 4-ethoxy-N-{1-(hydroxymethyl)-2-oxo-2-[(2Z)-2-(2-oxo-1,2-dihydro-3H-indol-3-ylidene)hydrazino]ethyl}-N-(4-methylphenyl)benzenesulfonamide, N-(4-chlorophenyl)-4-ethoxy-N-{2-[(2E)-2-(1H-imidazol-2-ylmethylene)hydrazino]-2-oxoethyl}benzenesulfonamide,
N-(4-chlorophenyl)-4-ethoxy-N-{2-oxo-2-[(2E)-2-(2-pyridinylmethylene)hydrazino]ethyl}benzenesulfonamide,
4-fluoro-N-(4-methylphenyl)-N-{2-oxo-2-[(2Z)-2-(2-oxo-1,2-dihydro-3H-indol-3-ylidene)hydrazino]ethyl}benzenesulfonamide,
4-fluoro-N-{2-[(2E)-2-(2-hydroxybenzylidene)hydrazino]-2-oxoethyl}-N-(4-methylphenyl)benzenesulfonamide,
4-ethoxy-N-[2-((2E)-2-{2-[hydroxy(oxido)amino]benzylidene}hydrazino)-2-oxoethyl]-N-(4-methylphenyl)benzenesulfonamide,
N-{2-[(2E)-2-(2-aminobenzylidene)hydrazino]-2-oxoethyl}-4-ethoxy-N-(4-methylphenyl)benzenesulfonamide,
N-(2-{(E)-[2-(2-{[(4-ethoxyphenyl)sulfonyl]-4-methylanilino}acetyl)hydrazono]methyl}phenyl)acetamide,
N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide,
N-(4-methylphenyl)-4-[2-(4-morpholinyl)ethoxy]-N-{2-oxo-2-[(2Z)-2-(2-oxo-1,2-dihydro-3H-indol-3-ylidene)hydrazino]ethyl}benzenesulfonamide,
N-(4-chlorophenyl)-4-[2-(dimethylamino)ethoxy]-N-{2-oxo-2-[(2Z)-2-(2-oxo-1,2-dihydro-3H-indol-3-ylidene)hydrazino]ethyl}benzenesulfonamide,
4-[2-(dimethylamino)ethoxy]-N-(4-methylphenyl)-N-{2-oxo-2-[(2Z)-2-(2-oxo-1,2-dihydro-3H-indol-3-ylidene)hydrazino]ethyl}benzenesulfonamide,
4-[3-(dimethylamino)propoxy]-N-(4-methylphenyl)-N-{2-oxo-2-[(2Z)-2-(2-oxo-1,2-dihydro-3H-indol-3-ylidene)hydrazino]ethyl}benzenesulfonamide,
N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide,
N-(4-chlorophenyl)-4-ethoxy-N-{2-oxo-2-[(2Z)-2-(2-oxo-1,2-dihydro-3H-pyrrolo[3,2-c]pyridin-3-ylidene)hydrazino]ethyl}benzenesulfonamide,
N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide,
3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide,
N-(4-chlorophenyl)-N-{2-oxo-2-[(2Z)-2-(2-oxo-1,2-dihydro-3H-indol-3-ylidene)hydrazino]ethyl}-4-(2-thienylmethoxy)benzenesulfonamide, N-(4-chlorophenyl)-4-[2-(2-methoxyethoxy)ethoxy]-N-{2-oxo-2-[(2Z)-2-(2-oxo-1,2-dihydro-3H-indol-3-ylidene)hydrazino]ethyl}benzenesulfonamide,
N-(4-chlorophenyl)-4-(2-methoxyethoxy)-N-{2-oxo-2-[(2Z)-2-(2-oxo-1,2-dihydro-3H-indol-3-ylidene)hydrazino]ethyl}benzenesulfonamide,
N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide,
N-(4-chlorophenyl)-N-{2-oxo-2-[(2Z)-2-(2-oxo-1,2-dihydro-3H-indol-3-ylidene)hydrazino]ethyl}-4-[3-(2-pyridinyl)propoxy]benzenesulfonamide,
4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide,
4-ethoxy-N-{2-[(2E)-2-(1H-indol-3-ylmethylene)hydrazino]-2-oxoethyl}-N-(4-methylphenyl)benzenesulfonamide,
4-ethoxy-N-(2-{(2E)-2-[(2-methyl-1H-indol-3-yl)methylene]hydrazino}-2-oxoethyl)-N-(4-methylphenyl)benzenesulfonamide,
N-(4-chlorophenyl)-4-[3-(dimethylamino)propoxy]-N-{2-oxo-2-[(2Z)-2-(2-oxo-1,2-dihydro-3H-pyrrolo[3,2-c]pyridin-3-ylidene)hydrazino]ethyl}benzenesulfonamide,
(3Z)-3-({[4-chloro({4-[3-(dimethylamino)propoxy]phenyl}sulfonyl)anilino]acetyl}hydrazono)-2-oxo-2,3-dihydro-1H-indole-7-carboxylic acid
methyl (3Z)-3-({[4-chloro({4-[3-(dimethylamino)propoxy]phenyl}sulfonyl)anilino]acetyl}hydrazono)-2-oxo-2,3-dihydro-1H-indole-7-carboxylate
4-ethoxy-N-{2-oxo-2-[(2Z)-2-(2-oxo-1,2-dihydro-3H-indol-3-ylidene)hydrazino]ethyl}-N-(2-pyrimidinyl)benzenesulfonamide,
3-{4-[(4-chloro{2-oxo-2-[(2Z)-2-(2-oxo-1,2-dihydro-3H-indol-3-ylidene)hydrazino]ethyl}anilino)sulfonyl]phenyl}-N-[3-(dimethylamino)propyl]propanamide,
N-(4-chlorophenyl)-4-[3-(4-methyl-1-piperazinyl)-3-oxopropyl]-N-{2-oxo-2-[(2Z)-2-(2-oxo-1,2-dihydro-3H-indol-3-ylidene)hydrazino]ethyl}benzenesulfonamide,
2-[({[(4-ethoxyphenyl)sulfonyl]-4-methylanilino}acetyl)amino]-2-phenylacetamide,
3-(3,4-dichlorophenyl)-2-[({[(4-fluorophenyl)sulfonyl]-4-methoxyanilino}acetyl)ainino]propanamide,
2-[({[(4-ethoxyphenyl)sulfonyl]-4-fluoroanilino}acetyl)amino]-3-(1H-indol-3-yl)propanamide, 2-[({[(4-ethoxyphenyl)sulfonyl]-4-fluoroanilino}acetyl)amino]-2-phenylacetamide,
2-[({[(4-ethoxyphenyl)sulfonyl]-4-methoxyanilino}acetyl)amino]-4-phenylbutanamide,
2-[({[(4-ethoxyphenyl)sulfonyl]-4-methoxyanilino}acetyl)amino]-3-(1H-indol-3-yl)propanamide, and
3-(3,4-dichlorophenyl)-2-({[4-fluoro(phenylsulfonyl)anilino]acetyl}amino)propanamide.

14. A pharmaceutical composition containing at least one sulfanilide according to claim 9 and a pharmaceutically acceptable carrier, diluent or excipient.

15. A process for the preparation of a sulfanilide according to claim 9:
comprising reacting a compound of formula III with a compound of formula IV in the presence of a peptide coupling agent,

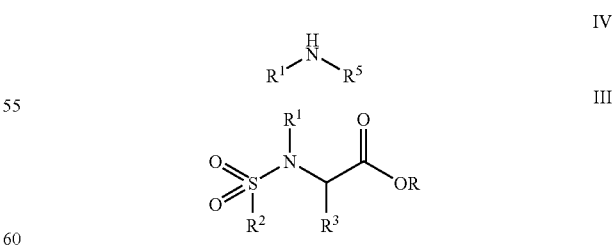

wherein n is an integer from 1 to 3, and R is H or $C_1$-$C_6$-alkyl.

16. A process for the preparation of a sulfanilide according to claim 9:
comprising reacting a compound of formula III with a compound of formula V in the presence of H2N-NH2,

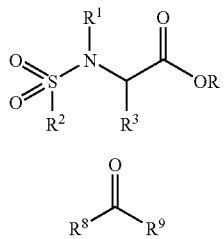

wherein n is an integer from 1 to 3, and R is H or $C_1$-$C_6$-alkyl.

17. A process for the preparation of a sulfanilide according to claim 12:

comprising reacting a compound of formula III with a compound of formula IV in the presence of a peptide coupling reagent,

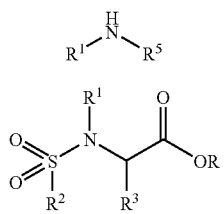

wherein n is an integer from 1 to 3, and R is H or $C_1$-$C_6$-alkyl.

18. A process for the preparation of a sulfanilide according to claim 12:

comprising reacting a compound of formula III with a compound of formula V in the presence of $H_2N$—$NH_2$,

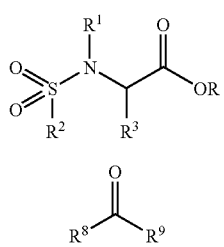

wherein n is an integer from 1 to 3, and R is H or $C_1$-$C_6$-alkyl.

19. A process for the preparation of a sulfanilide according to claim 9:

comprising reacting a compound of formula XVI with a compound of formula XVII then deprotecting the compound of formula XVII,

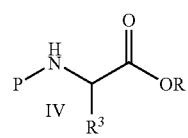

-continued

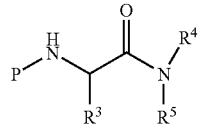

wherein P is a protecting group, n is an integer from 1 to 3, and R is H or $C_1$-$C_6$-alkyl.

20. A process for the preparation of a sulfanilide according to claim 9:

comprising reacting a compound of formula XI to form a compound of formula XVIII, then further reacting the compound of formula XVIII,

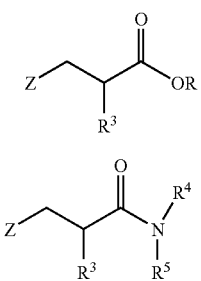

wherein Z is a leaving group, n is an integer from 1 to 3, and R is H or $C_1$-$C_6$-alkyl.

21. A process for the preparation of a sulfanilide according to claim 12:

comprising reacting a compound of formula XI to form a compound of formula XVII, then deprotecting the compound of formula XVII,

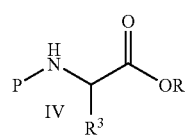

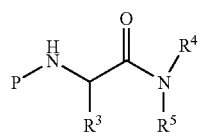

wherein P is a protecting group, n is an integer from 1 to 3, and R is H or $C_1$-$C_6$-alkyl.

22. A process for the preparation of a sulfanilide according to claim 12:

comprising reacting a compound of formula XI to form a compound of formula XVIII, reacting a compound of formula XI to form a compound of formula XVIII then further reacting the compound of formula XVIII,

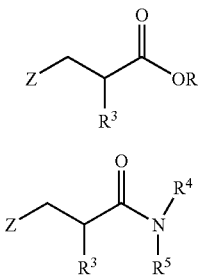

wherein Z is a leaving group, n is an integer from 1 to 3, and R is H or $C_1$-$C_6$-alkyl.

23. The method according to claim 1, wherein the sulfanilide is administered in an amount effective for treating at least one of preterm labor, premature birth, dysmenorrheal, inappropriate secretion of vasopressin, congestive heart failure, arterial hypertension, liver cirrhosis, nephritic syndrome or ocular hypertension.

24. The method of claim 1, wherein the mammal is human.

25. The method of claim 4, wherein the $C_1$-$C_6$-alkoxy group is a substituted ethoxy group selected from the group consisting of 2-alkoxyethoxy, 2-(2-alkoxyethoxy)ethoxy, 2-hydroxy-ethoxy, 2-(2-hydroxyethoxy)ethoxy, 2-(dimethylamino)ethoxy, 2-(2-dimethylamino)-ethoxy)ethoxy, 2-carboxyethoxy, 2-(2-carboxyethoxy)ethoxy, carboxymethoxy, 2-sulfoxyethoxy, 2-(2-sulfoxyethoxy)ethoxy, 2-[(2-methoxyethyl)sulfanyl]ethoxy, 2-[(2-hydroxyethyl)sulfanyl]ethoxy, 2-[(2-carboxyethyl)sulfanyl]ethoxy, and 2-[(2-carboxy-methyl)sulfanyl]ethoxy, 2-[(2-sulfoxyethyl)sulfanyl]ethoxy].

26. The method of claim 7, comprising
administering a tautomeric form of the sulfanilide having a keto-enol form of the carbonyl group or different forms of the group N=$CR^6R^7$.

27. A sulfanilide derivative according to claim 9 selected from the group consisting of:
4-ethoxy-N-(2-{(2E)-2-[1-(2-hydroxyphenyl)ethylidene]hydrazino}-2-oxoethyl)-N-(4-methylphenyl)benzenesulfonamide,
4-ethoxy-N-(4-methylphenyl)-N-{2-oxo-2-[(2Z)-2-(2-oxo-1,2-dihydro-3H-indol-3-ylidene)hydrazino]ethyl}benzenesulfonamide,
4-ethoxy-N-{2-oxo-2-[(2E)-2-(2-oxo-1,2-dihydro-3H-indol-3-ylidene)hydrazino]ethyl}-N-phenylbenzenesulfonamide,
4-ethoxy-N-[2-((2E)-2-{5-[hydroxy(oxido)amino]-2-oxo-1,2-dihydro-3H-indol-3-ylidene}hydrazino)-2-oxoethyl]-N-phenylbenzenesulfonamide,
4-ethoxy-N-{2-[(2E)-2-(5-iodo-2-oxo-1,2-dihydro-3H-indol-3 -ylidene)hydrazino]-2-oxoethyl}-N-phenylbenzenesulfonamide,
4-ethoxy-N-(2-hydrazino-2-oxoethyl)-N-(4-methylphenyl)benzenesulfonamide,
N-(4-methylphenyl)-N-{2-oxo-2-[(2E)-2-(2-oxo-1,2-dihydro-3H-indol-3-ylidene)hydrazino]ethyl}-1-naphthalenesulfonamide,
N-(4-methylphenyl)-N-{2-oxo-2-[(2E)-2-(2-oxo-1,2-dihydro-3H-indol-3-ylidene)hydrazino]ethyl}-2-naphthalenesulfonamide,
4-chloro-N-(4-methylphenyl)-N-{2-oxo-2-[(2E)-2-(2-oxo-1,2-dihydro-3H-indol-3-ylidene)hydrazino]ethyl}benzene sulfonamide,
4-methoxy-N-(4-methylphenyl)-N-{2-oxo-2-[(2E)-2-(2-oxo-1,2-dihydro-3H-indol-3-ylidene)hydrazino]ethyl}benzenesulfonamide,
4-methyl-N-(4-methylphenyl)-N-{2-oxo-2-[(2E)-2-(2-oxo-1,2-dihydro-3H-indol-3-ylidene)hydrazino]ethyl}benzenesulfonamide,
4-cyano-N-(4-methylphenyl)-N-{2-oxo-2-[(2E)-2-(2-oxo-1,2-dihydro-3H-indol-3-ylidene)hydrazino]ethyl}benzenesulfonamide,
4-ethoxy-N-{2-[(2Z)-2-(2-fluorobenzylidene)hydrazino]-2-oxoethyl}-N-(4-methylphenyl)benzenesulfonamide,
(3E)-3-[({[(4-ethoxyphenyl)sulfonyl]-4-methylanilino}acetyl)hydrazono]-2-oxo-2,3-dihydro-1H-indole-5-sulfonic acid,
N-(4-methylphenyl)-N-{2-oxo-2-[(2E)-2-(2-oxo-1,2-dihydro-3H-indol-3-ylidene)hydrazino]ethyl}[1,1'-biphenyl]-4-sulfonamide,
N-(4-methylphenyl)-N-{2-oxo-2-[(2E)-2-(2-oxo-1,2-dihydro-3H-indol-3-ylidene)hydrazino]ethyl}-4-phenoxybenzenesulfonamide,
4-ethoxy-N-{2-[(2Z)-2-(2-hydroxybenzylidene)hydrazino]-2-oxoethyl}-N-(4-methylphenyl)benzenesulfonamide,
N-(2-{(2Z)-2-[4-(diethylamino)-2-hydroxybenzylidene]hydrazino}-2-oxoethyl)-4-ethoxy-N-(4-methylphenyl)benzenesulfonamide,
4-ethoxy-N-(2-{(2Z)-2-[(2-hydroxy-1-naphthyl)methylene]hydrazino}-2-oxoethyl)-N-(4-methylphenyl)benzenesulfonamide,
4-ethoxy-N-(4-methylphenyl)-N-{2-oxo-2-[(2Z)-2-(3-oxo-2,3-dihydro-1H-inden-1-ylidene)hydrazino]ethyl}benzenesulfonamide,
4'-methoxy-N-(4-methylphenyl)-N-{2-oxo-2-[(2Z)-2-(2-oxo-1,2-dihydro-3H-indol-3-ylidene)hydrazino]ethyl}[1,1'-biphenyl]-4-sulfonamide,
4-ethoxy-N-{2-[(2Z)-2-(1-methyl-2-oxo-1,2-dihydro-3H-indol-3-ylidene)hydrazino]-2-oxoethyl}-N-(4-methylphenyl)benzenesulfonamide,
N-(2-{(2E)-2-[1-(2,4-dihydroxyphenyl)ethylidene]hydrazino}-2-oxoethyl)-4-ethoxy-N-(4-methylphenyl)benzenesulfonamide,
3,4-dimethoxy-N-(4-methylphenyl)-N-{2-oxo-2-[(2E)-2-(2-oxo-1,2-dihydro-3H-indol-3-ylidene)hydrazino]ethyl}benzenesulfonamide,
4-ethoxy-N-(2-{(2Z)-2-[1-(2-hydroxy-1-naphthyl)ethylidene]hydrazino}-2-oxoethyl)-N-(4-methylphenyl)benzenesulfonamide,
4-ethoxy-N-(2-{(2E)-2-[1-(1-hydroxy-2-naphthyl)ethylidene]hydrazino}-2-oxoethyl)-N-(4-methylphenyl)benzenesulfonamide,
4-tert-butyl-N-(4-chlorophenyl)-N-{2-oxo-2[-(2E)-2-(2-oxo-1,2-dihydro-3H-indol-3-ylidene)hydrazino]ethyl}benzenesulfonamide,
N-(4-chlorophenyl)-3,4-dimethoxy-N-{2-oxo-2-[(2E)-2-(2-oxo-1,2-dihydro-3H-indol-3-ylidene)hydrazino]ethyl}benzenesulfonamide,
4-tert-butyl-N-(4-methylphenyl)-N-{2-oxo-2-[(2E)-2-(2-oxo-1,2-dihydro-3H-indol-3-ylidene)hydrazino]ethyl}benzenesulfonamide,
N-(4-methylphenyl)-N-{2-oxo-2-[(2E)-2-(2-oxo-1,2-dihydro-3H-indol-3-ylidene)hydrazino]ethyl}-4-propylbenzenesulfonamide, 4-butoxy-N-(4-methylphenyl)-N-{2-oxo-2-[(2E)-2-(2-oxo-1,2-dihydro-3H-indol-3-ylidene)hydrazino]ethyl}benzenesulfonamide,
4-butoxy-N-(4-chlorophenyl)-N-{2-oxo-2-[(2Z)-2-(2-oxo-1,2-dihydro-3H-indol-3-ylidene)hydrazino]ethyl}benzenesulfonamide,
N-(4-chlorophenyl)-N-{2-oxo-2-[(2Z)-2-(2-oxo-1,2-dihydro-3H-indol-3-ylidene)hydrazino]ethyl}-4-propoxybenzenesulfonamide,
N-(4-methylphenyl)-N-{2-oxo-2-[(2Z)-2-(2-oxo-1,2-dihydro-3H-indol-3-ylidene)hydrazino]ethyl}-4-tert-pentylbenzenesulfonamide,
N-(4-methylphenyl)-N-{2-oxo-2-[(2Z)-2-(2-oxo-1,2-dihydro-3H-indol-3-ylidene)hydrazino]ethyl}-4-propoxybenzenesulfonamide,
N-(4-methylphenyl)-N-{2-oxo-2-[(2Z)-2-(2-oxo-1,2-dihydro-3H-indol-3-ylidene)hydrazino]ethyl}-2-thiophenesulfonamide,
N-(4-chlorophenyl)-N-{2-oxo-2-[(2Z)-2-(2-oxo-1,2-dihydro-3H-indol-3-ylidene)hydrazino]ethyl}-2-thiophenesulfonamide,
N-(4-chlorophenyl)-N-{2-[(2E)-2-(2-hydroxybenzylidene)hydrazino]-2-oxoethyl}-3,4-dimethoxybenzenesulfonamide,
N-(4-chlorophenyl)-4-ethoxy-N-{2-[(2E)-2-(2-hydroxybenzylidene)hydrazino]-2-oxoethyl}benzenesulfonamide,
N-(4-chlorophenyl)-N-{2-oxo-2-[(2Z)-2-(2-oxo-1,2-dihydro-3H-indol-3-ylidene)hydrazino]ethyl}-4-tert-pentylbenzenesulfonamide,
N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide,
N-(4-chlorophenyl)-N-{2-oxo-2-[(2Z)-2-(2-oxo-1,2-dihydro-3H-indol-3-ylidene)hydrazino]ethyl}benzenesulfonamide,
N-(4-chlorophenyl)-N-{2-oxo-2-[(2Z)-2-(2-oxo-1,2-dihydro-3H-indol-3-ylidene)hydrazino]ethyl}-4-propylbenzenesulfonamide,
4-ethoxy-N-{1-methyl-2-oxo-2-[(2Z)-2-(2-oxo-1,2-dihydro-3H-indol-3-ylidene)hydrazino]ethyl}-N-(4-methylphenyl)benzenesulfonamide,
4-ethoxy-N-{1-(hydroxymethyl)-2-oxo-2-[(2Z)-2-(2-oxo-1,2-dihydro-3H-indol-3-ylidene)hydrazino]ethyl}-N-(4-methylphenyl)benzenesulfonamide,
N-(4-chlorophenyl)-4-ethoxy-N-{2-[(2E)-2-(1H-imidazol-2-ylmethylene)hydrazino]-2-oxoethyl}benzenesulfonamide,
N-(4-chlorophenyl)-4-ethoxy-N-{2-oxo-2-[(2E)-2-(2-pyridinylmethylene)hydrazino]ethyl}benzenesulfonamide,
4-fluoro-N-(4-methylphenyl)-N-{2-oxo-2-[(2Z)-2-(2-oxo-1,2-dihydro-3H-indol-3-ylidene)hydrazino]ethyl}benzenesulfonamide,
4-fluoro-N-{2-[(2E)-2-(2-hydroxybenzylidene)hydrazino]-2-oxoethyl}-N-(4-methylphenyl)benzenesulfonamide,
4-ethoxy-N-[2-((2E)-2-{2-[hydroxy(oxido)amino]benzylidene}hydrazino)-2-oxoethyl]-N-(4-methylphenyl)benzenesulfonamide,
N-{2-[(2E)-2-(2-aminobenzylidene)hydrazino]-2-oxoethyl}-4-ethoxy-N-(4-methylphenyl)benzenesulfonamide,
N-(2-{(B)-[2-(2-{[(4-ethoxyphenyl)sulfonyl]-4-methylanilino}acetyl)hydrazono]methyl}phenyl)acetamide,
N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide,
N-(4-methylphenyl)-4-[2-(4-morpholinyl)ethoxy]-N-{2-oxo-2-[(2Z)-2-(2-oxo-1,2-dihydro-3H-indol-3-ylidene)hydrazino]ethyl}benzenesulfonamide,
N-(4-chlorophenyl)-4-[2-(dimethylamino)ethoxy]-N-{2-oxo-2-[(2Z)-2-(2-oxo-1,2-dihydro-3H-indol-3-ylidene)hydrazino]ethyl}benzenesulfonamide,
4-[2-(dimethylamino)ethoxy]-N-(4-methylphenyl)-N-{2-oxo-2-[(2Z)-2-(2-oxo-1,2-dihydro-3H-indol-3-ylidene)hydrazino]ethyl}benzenesulfonamide,
4-[3-(dimethylamino)propoxy]-N-(4-methylphenyl)-N-{2-oxo-2-[(2Z)-2-(2-oxo-1,2-dihydro-3H-indol-3-ylidene)hydrazino]ethyl}benzenesulfonamide,
N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide,
N-(4-chlorophenyl)-4-ethoxy-N-{2-oxo-2-[(2Z)-2-(2-oxo-1,2-dihydro-3H-pyrrolo[3,2-c]pyridin-3-ylidene)hydrazino]ethyl}benzenesulfonamide,
N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide,
3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide,
1 N-(4-chlorophenyl)-N-{2-oxo-2-[(2Z)-2-(2-oxo-1,2-dihydro-3H-indol-3-ylidene)hydrazino]ethyl}-4-(2-thienylmethoxy)benzenesulfonamide,
N-(4-chlorophenyl)-4-[2-(2-methoxyethoxy)ethoxy]-N-{2-oxo-2-[(2Z)-2-(2-oxo-1,2-dihydro-3H-indol-3-ylidene)hydrazino]ethyl}benzenesulfonamide,
N-(4-chlorophenyl)-4-(2-methoxyethoxy)-N-{2-oxo-2-[(2Z)-2-(2-oxo-1,2-dihydro-3H-indol-3-ylidene)hydrazino]ethyl}benzenesulfonamide,
N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide,
N-(4-chlorophenyl)-N-{2-oxo-2-[(2Z)-2-(2-oxo-1,2-dihydro-3H-indol-3-ylidene)hydrazino]ethyl}-4-[3-(2-pyridinyl)propoxy]benzenesulfonamide,
4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide,
4-ethoxy-N-{2-[(2E)-2-(1H-indol-3-ylmethylene)hydrazino]-2-oxoethyl}-N-(4-methylphenyl)benzenesulfonamide,
4-ethoxy-N-(2-{(2E)-2-[(2-methyl-1H-indol-3-yl)methylene]hydrazino}-2-oxoethyl)-N-(4-methylphenyl)benzenesulfonamide,
N-(4-chlorophenyl)-4-[3-(dimethylamino)propoxy]-N-{2-oxo-2-[(2Z)-2-(2-oxo-1,2-dihydro-3H-pyrrolo[3,2-c]pyridin-3-ylidene)hydrazino]ethyl}benzenesulfonamide,
(3Z)-3-({[4-chloro({4-[3-dimethylamino)propoxy]phenyl}sulfonyl)anilino]acetyl}hydrazono)-2-oxo-2,3-dihydro-1H-indole-7-carboxylic acid,
methyl (3Z)-3-({[4-chloro({4-[3-(dimethylamino)propoxy]phenyl}sulfonyl)anilino]acetyl}hydrazono)-2-oxo-2,3-dihydro-1H-indole-7-carboxylate,
4-ethoxy-N-{2-oxo-2-[(2Z)-2-(2-oxo-1,2-dihydro-3H-indol-3-ylidene)hydrazino]ethyl}-N-(2-pyrimidinyl)benzenesulfonamide,
3-{4-[(4-chloro{2-oxo-2-[(2Z)-2-(2-oxo-1,2-dihydro-3H-indol-3-ylidene)hydrazino]ethyl}anilino)sulfonyl]phenyl}-N-[3-(dimethylamino)propyl]propanamide, N-(4-chlorophenyl)-4-[3-(4-methyl-1-piperazinyl)-3-oxopropyl]-N-{2-oxo-2-[(2Z)-2-(2-oxo-1,2-dihydro-3H-indol-3-ylidene)hydrazino]ethyl}benzenesulfonamide,
3-(benzyloxy)-2-[({4-chloro[(3,4-dimethoxyphenyl)sulfonyl]anilino}acetyl)amino]propanamide,
3-(benzyloxy)-2-({[4-chloro(phenylsulfonyl)anilino]acetyl}amino)propanamide,
2-[({[(4-ethoxyphenyl)sulfonyl]-4-methylanilino}acetyl)amino]-2-phenylacetamide,
3-(3,4-dichlorophenyl)-2-[({[(4-fluorophenyl)sulfonyl]-4-methoxyanilino}acetyl)amino]propanamide,
2-[2-({[(4-ethoxyphenyl)sulfonyl]-4-methoxyanilino}acetyl)-1,2,3,4-tetrahydro-3-isoquinolinyl]acetamide,
2-({[(4-ethoxyphenyl)sulfonyl]-4-methoxyanilino}acetyl)-1-isoindolinecarboxamide,
2-[2-({[(3,4-dimethoxyphenyl)sulfonyl]-4-methoxyanilino}acetyl)-1,2,3,4-tetrahydro-3-isoquinolinyl]acetamide,
N-({4-chloro[(4-ethoxyphenyl)sulfonyl]anilino}acetyl)valine,
2-[({[(4-ethoxyphenyl)sulfonyl]-4-fluoroanilino}acetyl)amino]-3-(1H-indol-3-yl)propanamide,
2-[({[(4-ethoxyphenyl)sulfonyl]-4-fluoroanilino}acetyl)amino]-2-phenylacetamide,
N-({[(3,4-dimethoxyphenyl)sulfonyl]-4-fluoroanilino}acetyl)valine,
1-({[(4-ethoxyphenyl)sulfonyl]-4-methylanilino}acetyl)-5-phenyl-2-pyrrolidinecarboxamide,
2-[2-({[(4-ethoxyphenyl)sulfonyl]anilino}acetyl)-1,2,3,4-tetrahydro-3-isoquinolinyl]acetamide,
2-[2-({[(4-ethoxyphenyl)sulfonyl]-4-methylanilino}acetyl)-1,2,3,4-tetrahydro-3-isoquinolinyl]acetamide,
2-[({[(4-ethoxyphenyl)sulfonyl]-4-methoxyanilino}acetyl)amino]-4-phenylbutanamide,
2-({[(4-ethoxyphenyl)sulfonyl]-4-methoxyanilino}acetyl)-1,2,3,4-tetrahydro-3-isoquinolinecarboxamide,
2-[({[(4-ethoxyphenyl)sulfonyl]-4-methoxyanilino}acetyl)amino]-3-(1H-indol-3-yl)propanamide,
1-({[(4-ethoxyphenyl)sulfonyl]-4-fluoroanilino}acetyl)-5-phenyl-2-pyrrolidinecarboxamide, and
3-(3,4-dichlorophenyl)-2-({[4-fluoro(phenylsulfonyl)anilino]acetyl}amino)propanamide.

28. A sulfanilide derivative according to claim 12 selected from the group consisting of:
4-ethoxy-N-(2-{(2E)-2-[1-(2-hydroxyphenyl)ethylidene]hydrazino}-2-oxoethyl)-N-(4-methylphenyl)benzenesulfonamide,
4-ethoxy-N-(4-methylphenyl)-N-{2-oxo-2-[(2Z)-2-(2-oxo-1,2-dihydro-3H-indol-3-ylidene)hydrazino]ethyl}benzenesulfonamide,
4-ethoxy-N-{2-oxo-2-[(2E)-2-(2-oxo-1,2-dihydro-3H-indol-3-ylidene)hydrazino]ethyl}-N-phenylbenzenesulfonamide,
4-ethoxy-N-[2-((2E)-2-{5-[hydroxy(oxido)amino]-2-oxo-1,2-dihydro-3H-indol-3-ylidene}hydrazino)-2-oxoethyl]-N-phenylbenzenesulfonamide,
4-ethoxy-N-{2-[(2E)-2-(5-iodo-2-oxo-1,2-dihydro-3H-indol-3-ylidene)hydrazino]-2-oxoethyl}-N-phenylbenzenesulfonamide,
4-ethoxy-N-(2-hydrazino-2-oxoethyl)-N-(4-methylphenyl)benzenesulfonamide,
N-(4-methylphenyl)-N-{2-oxo-2-[(2E)-2-(2-oxo-1,2-dihydro-3H-indol-3-ylidene)hydrazino]ethyl}-1-naphthalenesulfonamide,
N-(4-methylphenyl)-N-{2-oxo-2-[(2E)-2-(2-oxo-1,2-dihydro-3H-indol-3-ylidene)hydrazino]ethyl}-2-naphthalenesulfonamide,
4-chloro-N-(4-methylphenyl)-N-{2-oxo-2-[(2E)-2-(2-oxo-1,2-dihydro-3H-indol-3-ylidene)hydrazino]ethyl}benzenesulfonamide,
4-methoxy-N-(4-methylphenyl)-N-{2-oxo-2-[(2E)-2-(2-oxo-1,2-dihydro-3H-indol-3-ylidene)hydrazino]ethyl}benzenesulfonamide,
4-methyl-N-(4-methylphenyl)-N-{2-oxo-2-[(2E)-2-(2-oxo-1,2-dihydro-3H-indol-3-ylidene)hydrazino]ethyl}benzenesulfonamide,
4-cyano-N-(4-methylphenyl)-N-{2-oxo-2-[(2E)-2-(2-oxo-1,2-dihydro-3H-indol-3-ylidene)hydrazino]ethyl}benzenesulfonamide,
4-ethoxy-N-{2-[(2Z)-2-(2-fluorobenzylidene)hydrazino]-2-oxoethyl}-N-(4-methylphenyl)benzenesulfonamide,
(3E)-3-[({[(4-ethoxyphenyl)sulfonyl]-4-methylanilino}acetyl)hydrazono]-2-oxo-2,3-dihydro-1H-indole-5-sulfonic acid,
N-(4-methylphenyl)-N-{2-oxo-2-[(2E)-2-(2-oxo-1,2-dihydro-3H-indol-3-ylidene)hydrazino]ethyl}[1,1'-biphenyl]-4-sulfonamide,
N-(4-methylphenyl)-N-{2-oxo-2-[(2E)-2-(2-oxo-1,2-dihydro-3H-indol-3-ylidene)hydrazino]ethyl}-4-phenoxybenzenesulfonamide,
4-ethoxy-N-{2-[(2Z)-2-(2-hydroxybenzylidene)hydrazino]-2-oxoethyl}-N-(4-methylphenyl)benzenesulfonamide,
N-(2-{(2Z)-2-[4-(diethylamino)-2-hydroxybenzylidene]hydrazino}-2-oxoethyl)-4-ethoxy-N-(4-methylphenyl)benzenesulfonamide,
4-ethoxy-N-(2-{(2Z)-2-[(2-hydroxy-1-naphthyl)methylene]hydrazino}-2-oxoethyl)-N-(4-methylphenyl)benzenesulfonamide,
4-ethoxy-N-(4-methylphenyl)-N-{2-oxo-2-[(2Z)-2-(3-oxo-2,3-dihydro-1H-inden-1-ylidene)hydrazino]ethyl}benzenesulfonamide,
4'-methoxy-N-(4-methylphenyl)-N-{2-oxo-2-[(2Z)-2-(2-oxo-1,2-dihydro-3 H-indol-3-ylidene)hydrazino]ethyl}[1,1'-biphenyl]-4-sulfonamide,
4-ethoxy-N-{2-[(2Z)-2-(1-methyl-2-oxo-1,2-dihydro-3H-indol-3-ylidene)hydrazino]-2-oxoethyl}-N-(4-methylphenyl)benzenesulfonamide,
N-(2-{(2E)-2-[1-(2,4-dihydroxyphenyl)ethylidene]hydrazino}-2-oxoethyl)-4-ethoxy-N-(4-methylphenyl)benzenesulfonamide,
3,4-dimethoxy-N-(4-methylphenyl)-N-{2-oxo-2-[(2E)-2-(2-oxo-1,2-dihydro-3H-indol-3-ylidene)hydrazino]ethyl}benzenesulfonamide,
4-ethoxy-N-(2-{(2Z)-2-[1-(2-hydroxy-1-naphthyl)ethylidene]hydrazino}-2-oxoethyl)-N-(4-methylphenyl)benzenesulfonamide,
4-ethoxy-N-(2-{(2E)-2-[1-(1-hydroxy-2-naphthyl)ethylidene]hydrazino}-2-oxoethyl)-N-(4-methylphenyl)benzenesulfonamide,
4-tert-butyl-N-(4-chlorophenyl)-N-{2-oxo-2-[(2E)-2-(2-oxo-1,2-dihydro-3H-indol-3-ylidene)hydrazino]ethyl}benzenesulfonamide,
N-(4-chlorophenyl)-3,4-dimethoxy-N-{2-oxo-2-[(2E)-2-(2-oxo-1,2-dihydro-3H-indol-3-ylidene)hydrazino]ethyl}benzenesulfonamide, 4-tert-butyl-N-(4-methylphenyl)-N-{2-oxo-2-[(2E)-2-(2-oxo-1,2-dihydro-3H-indol-3-ylidene)hydrazino]ethyl}benzenesulfonamide, N-(4-methylphenyl)-N-{2-oxo-2-[(2E)-2-(2-oxo-1,2-dihydro-3H-indol-3-ylidene)hydrazino]ethyl}-4-propyl-benzenesulfonamide, 4-butoxy-N-(4-methylphenyl)-N-{2-oxo-2-[(2E)-2-(2-oxo-1,2-dihydro-3H-indol-3-ylidene)hydrazino]ethyl}benzenesulfonamide, 4-butoxy-N-(4-chlorophenyl)-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-propoxybenzenesulfonamide, N-(4-methylphenyl)-N-{2-oxo-2-[(2Z)-2-(2-oxo-1,2-dihydro-3H-indol-3-ylidene)hydrazino]ethyl}-4-tert-pentylbenzenesulfonamide, N-(4-methylphenyl)-N-{2-oxo-2-[(2Z)-2-(2-oxo-1,2-dihydro-3H-indol-3-ylidene)hydrazino]ethyl}-4-propoxybenzenesulfonamide, N-(4-methylphenyl)-N-{2-oxo-2-[(2Z)-2-(2-oxo-1,2-dihydro-3H-indol-3-ylidene)hydrazino]ethyl}-2-thiophenesulfonamide, N-(4-chlorophenyl)-N-{2-oxo-2-[(2Z)-2-(2-oxo-1,2-dihydro-3H-indol-3-ylidene)hydrazino]ethyl}-2-thiophenesulfonamide, N-(4-chlorophenyl)-N-{2-[(2E)-2-(2-hydroxybenzylidene)hydrazino]-2-oxoethyl}-3,4-dimethoxybenzene sulfonamide, N-(4-chlorophenyl)-4-ethoxy-N-{2-[(2E)-2-(2-hydroxybenzylidene)hydrazino]-2-oxoethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-tert-pentylbenzenesulfonamide, N-(4-chlorophenyl)-4-ethoxy-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-propyl-benzenesulfonamide, 4-ethoxy-N-{1-methyl-2-oxo-2-[(2Z)-2-(2-oxo-1,2-dihydro-3H-indol-3-ylidene)hydrazino]ethyl}-N-(4-methylphenyl)benzenesulfonamide, 4-ethoxy-N-{1-(hydroxymethyl)-2-oxo-2-[(2Z)-2-(2-oxo-1,2-dihydro-3H-indol-3-ylidene)hydrazino]ethyl}-N-(4-methylphenyl)benzenesulfonamide, N-(4-chlorophenyl)-4-ethoxy-N-{2-[(2E)-2-(1H-imidazol-2-ylmethylene)hydrazino]-2-oxoethyl}benzenesulfonamide, N-(4-chlorophenyl)-4-ethoxy-N-{2-oxo-2-[(2E)-2-(2-pyridinylmethylene)hydrazino]ethyl}benzenesulfonamide, 4-fluoro-N-(4-methylphenyl)-N-{2-oxo-2-[(2Z)-2-(2-oxo-1,2-dihydro-3H-indol-3-ylidene)hydrazino]ethyl}benzenesulfonamide, 4-fluoro-N-{2-[(2E)-2-(2-hydroxybenzylidene)hydrazino]-2-oxoethyl}-N-(4-methylphenyl)benzenesulfonamide, 4-ethoxy-N-[2-((2E)-2-{2-[hydroxy(oxido)amino]benzylidene}hydrazino)-2-oxoethyl]-N-(4-methylphenyl)benzenesulfonamide, N-{2-[(2E)-2-(2-aminobenzylidene)hydrazino]-2-oxoethyl}-4-ethoxy-N-(4-methylphenyl)benzenesulfonamide, N-(2-{(E)-[2-(2-{[(4-ethoxyphenyl)sulfonyl]-4-methylanilino}acetyl)hydrazono]methyl}phenyl)acetamide, N-(4-chlorophenyl)-4-[2-(4-morpholinyl)ethoxy]-N-{2-oxo-2-[2-(2-oxo-1,2-dihydro-3H-indol-3-ylidene)hydrazino]ethyl}benzenesulfonamide, N-(4-methylphenyl)-4-[2-(4-morpholinyl)ethoxy]-N-{2-oxo-2-[(2Z)-2-(2-oxo-1,2-dihydro-3H-indol-3-ylidene)hydrazino]ethyl}benzenesulfonamide, N-(4-chlorophenyl)-4-[2-(dimethylamino)ethoxy]-N-{2-oxo-2-[(2Z)-2-(2-oxo-1,2-dihydro-3H-indol-3-ylidene)hydrazino]ethyl}benzenesulfonamide, 4-[2-(dimethylamino)ethoxy]-N-(4-methylphenyl)-N-{2-oxo-2-[(2Z)-2-(2-oxo-1,2-dihydro-3H-indol-3-ylidene)hydrazino]ethyl}benzenesulfonamide, 4-[3-(dimethylamino)propoxy]-N-(4-methylphenyl)-N-{2-oxo-2-[(2Z)-2-(2-oxo-1,2-dihydro-3H-indol-3-ylidene)hydrazino]ethyl}benzenesulfonamide, N-(4-chlorophenyl)-4-[3-(dimethylamino)propoxy]-N-{2-oxo-2-[(2Z)-2-(2-oxo-1,2-dihydro-3H-indol-3-ylidene)hydrazino]ethyl}benzenesulfonamide, N-(4-chlorophenyl)-4-ethoxy-N-{2-oxo-2-[(2Z)-2-(2-oxo-1,2-dihydro-3H-pyrrolo[3,2-c]pyridin-3-ylidene)hydrazino]ethyl}benzenesulfonamide, N-(4-chlorophenyl)-4-{[2-(4-morpholinyl)ethyl]amino}-N-{2-oxo-2-[(2Z)-2-(2-oxo-1,2-dihydro-3H-indol-3-ylidene)hydrazino]ethyl}benzenesulfonamide, 3-{4-[(4-methyl{2-oxo-2-[(2Z)-2-(2-oxo-1,2-dihydro-3H-indol-3-ylidene)hydrazino]ethyl}anilino)sulfonyl]phenyl}propanamide, N-(4-chlorophenyl)-N-{2-oxo-2-[(2Z)-2-(2-oxo-1,2-dihydro-3H-indol-3-ylidene)hydrazino]ethyl}-4-(2-thienylmethoxy)benzenesulfonamide, N-(4-chlorophenyl)-4-[2-(2-methoxyethoxy)ethoxy]-N-{2-oxo-2-[(2Z)-2-(2-oxo-1,2-dihydro-3H-indol-3-ylidene)hydrazino]ethyl}benzenesulfonamide, N-(4-chlorophenyl)-4-(2-methoxyethoxy)-N-{2-oxo-2-[(2Z)-2-(2-oxo-1,2-dihydro-3H-indol-3-ylidene)hydrazino]ethyl}benzenesulfonamide, N-(4-chlorophenyl)-N-{2-oxo-2-[(2Z)-2-(2-oxo-1,2-dihydro-3H-indol-3-ylidene)hydrazino]ethyl}-4-[3-(3-pyridinyl)propoxy]benzenesulfonamide, N-(4-chlorophenyl)-N-{2-oxo-2-[(2Z)-2-(2-oxo-1,2-dihydro-3H-indol-3-ylidene)hydrazino]ethyl}-4-[3-(2-pyridinyl)propoxy]benzenesulfonamide, 4-(2-methoxyethoxy)-N-(4-methylphenyl)-N-{2-oxo-2-[(2Z)-2-(2-oxo-1,2-dihydro-3H-indol-3-ylidene)hydrazino]ethyl}benzenesulfonamide, 4-ethoxy-N-{2-[(2E)-2-(1H-indol-3-ylmethylene)hydrazino]-2-oxoethyl}-N-(4-methylphenyl)benzenesulfonamide, 4-ethoxy-N-(2-{(2E)-2-[(2-methyl-1H-indol-3-yl)methylene]hydrazino}-2-oxoethyl)-N-(4-methylphenyl)benzenesulfonamide, N-(4-chlorophenyl)-4-[3-(dimethylamino)propoxy]-N-{2-oxo-2-[(2Z)-2-(2-oxo-1,2-dihydro-3H-pyrrolo[3,2-c]pyridin-3-ylidene)hydrazino]ethyl}benzenesulfonamide, (3Z)-3-({[4-chloro({4-[3-dimethylamino)propoxy]phenyl}sulfonyl)anilino]acetyl}hydrazono)-2-oxo-2,3-dihydro-1H-indole-7-carboxylic acid, methyl (3Z)-3-({[4-chloro({4-[3-(dimethylamino)propoxy]phenyl}sulfonyl)anilino]acetyl}hydrazono)-2-oxo-2,3-dihydro-1H-indole-7-carboxylate, 4-ethoxy-N-{2-oxo-2-[(2Z)-2-(2-oxo-1,2-dihydro-3H-indol-3-ylidene)hydrazino]ethyl}-N-(2-pyrimidinyl)benzenesulfonamide, 3-{4-[(4-chloro{2-oxo-2-[(2Z)-2-(2-oxo-1,2-dihydro-3H-indol-3-ylidene)hydrazino]ethyl}anilino)sulfonyl]phenyl}-N-[3-(dimethylamino)propyl]propanamide, N-(4-chlorophenyl)-4-[3-(4-methyl-1-piperazinyl)-3-oxopropyl]-N-{2-oxo-2-[(2Z)-2-(2-oxo-1,2-dihydro-3H-indol-3-ylidene)hydrazino]ethyl}benzenesulfonamide, 3-(benzyloxy)-2-({[4-chloro[(3,4-dimethoxyphenyl)sulfonyl]anilino}acetyl)amino]propanamide, 3-(benzyloxy)-2-({[4-chloro(phenylsulfonyl)anilino]acetyl}amino)propanamide, 2-[({[(4-ethoxyphenyl)sulfonyl]-4-methylanilino}acetyl)amino]-2-phenylacetamide, 3-(3,4-dichlorophenyl)-2-[({[(4-fluorophenyl)sulfonyl]-4-methoxyanilino}acetyl)amino]propanamide, 2-[2-({[(4-ethoxyphenyl)sulfonyl]-4-methoxyanilino}acetyl)-1,2,3,4-tetrahydro-3-isoquinolinyl]acetamide, 2-({[(4-ethoxyphenyl)sulfonyl]-4-methoxyanilino}acetyl)-1-isoindolinecarboxamide, 2-[2-({[(3,4-dimethoxyphenyl)sulfonyl]-4-methoxyanilino}acetyl)-1,2,3,4-tetrahydro-3-isoquinolinyl]acetamide, N-({4-chloro[(4-ethoxyphenyl)sulfonyl]anilino}acetyl)valine, 2-[({[(4-ethoxyphenyl)sulfonyl]-4-fluoroanilino}acetyl)amino]-3-(1H-indol-3-yl)propanamide, 2-[({[(4-ethoxyphenyl)sulfonyl]-4-fluoroanilino}acetyl)amino]-2-phenylacetamide, N-({[(3,4-dimethoxyphenyl)sulfonyl]-4-fluoroanilino}acetyl)valine, 1-({[(4-ethoxyphenyl)sulfonyl]-4-methylanilino}acetyl)-5-phenyl-2-pyrrolidinecarboxamide, 2-[2-({[(4-ethoxyphenyl)sulfonyl]anilino}acetyl)-1,2,3,4-tetrahydro-3-isoquinolinyl]acetamide, 2-[2-({[(4-ethoxyphenyl)sulfonyl]-4-methylanilino}acetyl)-1,2,3,4-tetrahydro-3-isoquinolinyl]acetamide, 2-[({[(4-ethoxyphenyl)sulfonyl]-4-methoxyanilino}acetyl)amino]-4-phenylbutanamide, 2-({[(4-ethoxyphenyl)sulfonyl]-4-methoxyanilino}acetyl)-1,2,3,4-tetrahydro-3-isoquinolinecarboxamide, 2-[({[(4-ethoxyphenyl)sulfonyl]-4-methoxyanilino}acetyl)amino]-3-(1H-indol-3-yl)propanamide, 1-({[(4-ethoxyphenyl)sulfonyl]-4-fluoroanilino}acetyl)-5-phenyl-2-pyrrolidinecarboxamide, and 3-(3,4-dichlorophenyl)-2-({[4-fluoro(phenylsulfonyl)anilino]acetyl}amino)propanamide.

29. A method comprising
administering the sulfanilide of claim 9 to a mammal in need thereof.

30. The method of claim 29, wherein the mammal is in need of treatment for preterm labor, premature birth, dysmenorrheal, inappropriate secretion of vasopressin, congestive heart failure, arterial hypertension, liver cirrhosis, nephritic syndrome or ocular hypertension.

31. The method of claim 29, wherein the mammal is a human.

32. The method according to claim 29, wherein the sulfanilide is administered in an amount effective for treating at least one of preterm labor, premature birth, dysmenorrheal, inappropriate secretion of vasopressin, congestive heart failure, arterial hypertension, liver cirrhosis, nephritic syndrome or ocular hypertension.

33. A method comprising
administering the sulfanilide of claim 12 to a mammal in need thereof.

34. The method of claim 33, wherein the mammal is in need of treatment for at least one of preterm labor, premature birth, dysmenorrheal, inappropriate secretion of vasopressin, congestive heart failure, arterial hypertension, liver cirrhosis, nephritic syndrome and ocular hypertension.

35. The method of claim 33, wherein the mammal is a human.

36. The method according to claim 33, wherein the sulfanilide is administered in an amount effective for treating at least one of preterm labor, premature birth, dysmenorrhea, inappropriate secretion of vasopressin, congestive heart failure, arterial hypertension, liver cirrhosis, nephritic syndrome or ocular hypertension.

37. The method of claim 29, wherein the mammal is in need of treatment of preterm labor, premature birth, or dysmenorrhea.

38. The method of claim 33, wherein the mammal is in need of treatment of preterm labor, premature birth, or dysmenorrhea.

39. The method of claim 29, wherein the sulfanilide is administered in an amount effective for modulating an oxytocin and/or a vasopressin receptor.

40. The method of claim 33, wherein the sulfanilide is administered in an amount effective for modulating an oxytocin and/or a vasopressin receptor.

41. The method of claim 39, wherein modulating includes blocking the oxytocin or vasopressin receptor or antagonizing the binding of oxytocin and/or vasopressin to the receptor.

42. The method of claim 40, wherein modulating includes blocking the oxytocin or vasopressin receptor or antagonizing the binding of oxytocin and/or vasopressin to the receptor.

43. A pharmaceutical composition containing at least one sulfanilide according to claim 12 and a pharmaceutically acceptable carrier, diluent or excipient.

* * * * *

UNITED STATES PATENT AND TRADEMARK OFFICE
CERTIFICATE OF CORRECTION

PATENT NO. : 7,312,358 B2  
APPLICATION NO. : 10/399040  
DATED : December 25, 2007  
INVENTOR(S) : Anna Quattropani et al.

It is certified that error appears in the above-identified patent and that said Letters Patent is hereby corrected as shown below:

Title Page, (75) Inventors:, "Catherine Joran-Lebrun,"
     should read -- Catherine Jorand-Lebrun, --.

Column 1, line 27, "specific G protein-coupled receptors currently classifid into"
     should read -- specific G protein-coupled receptors currently classified into --.

Column 3, line 3, "prevent disorders mediated by the oxytocin receptor, like"
     should read -- preventing disorders mediated by the oxytocin receptor, like --.

Column 6, line 26, "$R^4$ and RW are independently selected from the group"
     should read -- $R^4$ and $R^5$ are independently selected from the group --.

Column 7, line 39, "substituted aryl and mor particularly preferred are"
     should read -- substituted aryl and more particularly preferred are --.

Column 16, line 43, " 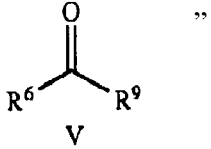 "

should read -- 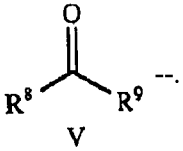 --.

Column 16, line 56, "conditions described in the litterature as shown in"
     should read -- conditions described in the literature as shown in --.

Column 17, line 32, "$R^1$ and $R^3$ are as above defined, can be prepared from the"
     should read -- $R^2$ and $R^3$ are as above defined, can be prepared from the --.

Column 18, line 8, "halides and sulfonates, DX, using a base and an"
     should read -- halides and sulfonates, IX, using a base and an --.

UNITED STATES PATENT AND TRADEMARK OFFICE
CERTIFICATE OF CORRECTION

| | |
|---|---|
| PATENT NO. | : 7,312,358 B2 |
| APPLICATION NO. | : 10/399040 |
| DATED | : December 25, 2007 |
| INVENTOR(S) | : Anna Quattropani et al. |

It is certified that error appears in the above-identified patent and that said Letters Patent is hereby corrected as shown below:

Column 19, line 18, "As a further alternative, compounds of general Formula m"
    should read -- As a further alternative, compounds of general Formula III --.

Column 20, line 27, "usual reaction conditions described in the litterature as"
    should read -- usual reaction conditions described in the literature as --.

Column 22, line 56, "XVI, are subjectd to the reaction conditions outlined"
    should read -- XVI, are subjected to the reaction conditions outlined --.

Column 23, line 50, "in the C(O)—OR moiety of the compounds In, VI,"
    should read -- in the C(O)—OR moiety of the compounds III, VI, --.

Column 27, line 36, "XXV, such as, e.g., Rink resin, using standard"
    should read -- XXIV, such as, e.g., Rink resin, using standard --.

Column 30, line 35, "the compounds according to Formula I and Formula H for"
    should read -- the compounds according to Formula I and Formula II for --.

Column 31, line 64, "which is incorporated herein be reference."
    should read -- which is incorporated herein by reference. --.

Column 33, line 25, "zono]-2-oxo-2,3-dihydro-H-indole-5-sulfonic Acid"
    should read -- zono]-2-oxo-2,3-dihydro-1H-indole-5-sulfonic Acid --.

Column 34, line 4, "was added to a suspention of NaH (13.6 mmol, 0.593 mg of"
    should read -- was added to a suspension of NaH (13.6 mmol, 0.593 mg of --;
    line 45, "niethylanilino}acetyl)hydrazono]-2-oxo-2,3-dihydro-1H-"
    should read -- methylanilino}acetyl)hydrazono]-2-oxo-2,3-dihydro-1H- --.

Column 35, line 28, "recristallized from MeOH. A bright yellow solid (74 mg,"
    should read -- recrystallized from MeOH. A bright yellow solid (74 mg, --;
    line 38, "11.27 (s, 1H, NH), 12.50 (br s, 1H, CONBN, minor isomer"
    should read -- 11.27 (s, 1H, NH), 12.50 (br s, 1H, CONHN, minor isomer --.

Column 36, line 1, "and recristallized in THF/H$_2$O. A yellow powder (48 mg,"
    should read -- and recrystallized in THF/H$_2$O. A yellow powder (48 mg, --;
    line 52, "and recristallized in EtOH. A yellow solid (65 mg, 47%) was"
    should read -- and recrystallized in EtOH. A yellow solid (65 mg, 47%) was --.

UNITED STATES PATENT AND TRADEMARK OFFICE
CERTIFICATE OF CORRECTION

PATENT NO.       : 7,312,358 B2
APPLICATION NO.  : 10/399040
DATED            : December 25, 2007
INVENTOR(S)      : Anna Quattropani et al.

It is certified that error appears in the above-identified patent and that said Letters Patent is hereby corrected as shown below:

Column 37, line 28, "recristallized in MeOH. A bright yellow solid (197 mg, 58%)"
should read -- recrystallized in MeOH. A bright yellow solid (197 mg, 58%) --;
line 40, "$M^+(ESI^+)$: 493; $M^-(ESI^-)$: 491. Analysis calculated for"
should read -- $M^+(ES^+)$: 493; $M^-(ES^-)$: 491. Analysis calculated for --.

Column 38, line 66, "CONHN, minor isomer (35%)), (br s, 1H, CONBN,"
should read -- CONHN, minor isomer (35%)), (br s, 1H, CONHN, --.

Column 52, line 44, "N-(4-methylphenyl)-N-{2-oxo-2-[(2E)-2-(2-oxo-12-"
should read -- N-(4-methylphenyl)-N-{2-oxo-2-[(2E)-2-(2-oxo-1,2- --.

Column 53, line 61, "4.95 (br s, 2H, NCH2CO, minor isomer (35%)), 6.95 (n,"
should read -- 4.95 (br s, 2H, NCH2CO, minor isomer (35%)), 6.95 (m, --.

Column 56, line 65, "was obtained in 58.4% purity by IPLC (MaxPlot detection"
should read -- was obtained in 58.4% purity by HPLC (MaxPlot detection --.

Column 58, line 5, "M.p. 188-189° C. IR (neat) σ 2962, 1673, 1507, 1488,"
should read -- M.p. 188-189° C. IR (neat) ν 2962, 1673, 1507, 1488, --.

Column 58, line 58, "IR (neat) σ 2988, 1632, 1488, 1351, 1262, 1155, 1084"
should read -- IR (neat) ν 2988, 1632, 1488, 1351, 1262, 1155, 1084 --.

Column 59, line 67, "4.10 (q, 2H, 3=6.78 Hz), 4.52 (s, 2H, NCH2CO, major"
should read -- 4.10 (q, 2H, J=6.78 Hz), 4.52 (s, 2H, NCH2CO, major --.

Column 60, line 38, "7.33-7.47 (m, 3H), 7.49-7.78 (m, 6H), 11.28 (s, 1H, 1H),"
should read -- 7.33-7.47 (m, 3H), 7.49-7.78 (m, 6H), 11.28 (s, 1H, NH), --.

Column 70, line 39, "M.p. 255° C. IR (neat) σ 2971, 1682, 1506, 1492, 1350,"
should read -- M.p. 255° C. IR (neat) ν 2971, 1682, 1506, 1492, 1350, --.

Column 73, line 34, "CH3), 2.68 (s, 6H, $N(CH3)_2$), 2.94 (m, 2H, minor isomer"
should read -- CH3), 2.68 (s, 6H, N(CH3)2), 2.94 (m, 2H, minor isomer --.

Column 78, line 8, "was obtained as a colorless oil, in 97% purity by BPLC"
should read -- was obtained as a colorless oil, in 97% purity by HPLC --.

UNITED STATES PATENT AND TRADEMARK OFFICE
CERTIFICATE OF CORRECTION

PATENT NO. : 7,312,358 B2
APPLICATION NO. : 10/399040
DATED : December 25, 2007
INVENTOR(S) : Anna Quattropani et al.

It is certified that error appears in the above-identified patent and that said Letters Patent is hereby corrected as shown below:

Column 79, line 1, "1H, NH), 12.46 (br s, 1H, CONBN, minor isomer (35%)),"
    should read -- 1H, NH), 12.46 (br s, 1H, CONHN, minor isomer (35%)), --;
      line 47, "Methyl Ester Building Block, 1H into III* by Heck Reaction"
    should read -- Methyl Ester Building Block, III into III* by Heck Reaction --;
      line 48, "Followed by Hydrogenation (Scheme 2); e.g., Methyl"
    should read -- followed by Hydrogenation (Scheme 2); e.g., Methyl --;
      line 54, "in DMW (3.5 mL) was added, followed by"
    should read -- in DMF (3.5 mL) was added, followed by --;
      line 55, "acrylamide (78 mg, 1.11 mmol), triphenylphosphine"
    should read -- acrylamide (78 mg, 1.1 mmol), triphenylphosphine --;
      line 56, "mg, 0.11 mmol, 10 mol %) and palladium diacetate"
    shouuld read -- mg, 0.1 mmol, 10 mol %) and palladium diacetate --.

Column 80, line 66, "minor isomer (35%)), 13.64 (br s, 1H, CONBN, major"
    should read -- minor isomer (35%)), 13.64 (br s, 1H, CONHN, major --.

Column 82, line 2, "azodicarboxylate (19.97 n2L, 128.44 mmol) was added"
    should read -- azodicarboxylate (19.97 mL, 128.44 mmol) was added --;
      line 6, "and th resulting crude oil was dissolved in ethyl acetate"
    should read -- and the resulting crude oil was dissolved in ethyl acetate --.

Column 83, line 20, "M.p. 232° C.; IR (neat) σ 3060, 1694, 1596, 1467, 1353,"
    should read -- M.p. 232° C.; IR (neat) $v$ 3060, 1694, 1596, 1467, 1353, --;
      line 30, "$C_{27}H_{29}Cl_2N_5O_5S.0.5H_2O$: C, 52.69; H, 4.91; N, 11.38; Cl,"
    should read -- $C_{27}H_{29}Cl_2N_5O_5S=0.5\ H_2O$: C, 52.69; H, 4.91; N, 11.38; Cl, --.

Column 84, line 7, "IR (neat) σ 1718, 1674, 1651, 1487, 1195, 1123 cm$^{-1}$."
    should read -- IR (neat) $v$ 1718, 1674, 1651, 1487, 1195, 1123 cm$^{-1}$. --;
      line 8, "$^1$HNMR (DMSO-$d_6$, 300 MHz) 2.11 (m, 2H), 2.82"
    should read -- $^1$H NMR (DMSO-$d_6$, 300 MHz) δ 2.11 (m, 2H), 2.82 --.

Column 85, line 59, "$^1$H NMR (D)MSO-d, 300 MHz) δ 1.85 (m, 2H), 2.13"
    should read -- $^1$H NMR (DMSO-$d_6$, 300 MHz) δ 1.85 (m, 2H), 2.13 --.

UNITED STATES PATENT AND TRADEMARK OFFICE
CERTIFICATE OF CORRECTION

PATENT NO. : 7,312,358 B2
APPLICATION NO. : 10/399040
DATED : December 25, 2007
INVENTOR(S) : Anna Quattropani et al.

It is certified that error appears in the above-identified patent and that said Letters Patent is hereby corrected as shown below:

Column 87, line 54, "product, eg. 3-(4-{[4-chloro(2-hydrazino-2-oxo ethyl)"
 should read -- product, e.g. 3-(4-{[4-chloro(2-hydrazino-2-oxoethyl) --;
 line 55, "amino]sulfonylphenyl)-N-[3-(dimethylamino)propyl]-pro-"
 should read -- anilino]sulfonyl}phenyl)-N-[3-(dimethylamino)propyl]-pro- --;
 line 56, "(1170.2 mg, 49% yield) was obtained as a"
 should read -- (170.2 mg, 49% yield) was obtained as a --.

Column 89, line 3, "1H, CONHN, major isomer (60%)); $M^+(ESI^-)$: 623.12;"
 should read -- 1H, CONHN, major isomer (60%)); $M^+(ESI^+)$: 623.12; --.

Column 120, line 42, "significant binding to the Via receptor."
 should read -- significant binding to the $V_{1a}$ receptor. --.

Column 122, Table 2, line 36, "hydrazinocarbonylmethyl)-N-p-totyl-"
 should read -- hydrazinocarbonylmethyl)-N-p-tolyl- --.

Column 125, line 35, "Labelling with fluo-4: 50 kg fluo-4 (fluorescent marker)"
 should read -- Labelling with fluo-4: 50 $\mu$g fluo-4 (fluorescent marker) --.

Column 137, line 11, "formula (1)."
 should read -- formula (I). --.

Column 146, line 41, "a tertiary amino group, a quartemary ammonium moiety,"
 should read -- a tertiary amino group, a quartenary ammonium moiety, --.

Column 147, line 40, "tertiary amino group, a quartemary ammonium moiety,"
 should read -- tertiary amino group, a quarternary ammonium moiety, --.

UNITED STATES PATENT AND TRADEMARK OFFICE
CERTIFICATE OF CORRECTION

PATENT NO.         : 7,312,358 B2
APPLICATION NO.  : 10/399040
DATED              : December 25, 2007
INVENTOR(S)       : Anna Quattropani et al.

It is certified that error appears in the above-identified patent and that said Letters Patent is hereby corrected as shown below:

Column 148, lines 31-33, "The sulfanilide according to claim 9, wherein R and $R^7$ form together an tetrahydroisoquinoline or an oxindole ring."
should read -- The sulfanilide according to claim 9, wherein $R^6$ and $R^7$ form together an tetrahydroisoquinoline or an oxindole ring. --.

Signed and Sealed this

Sixteenth Day of December, 2008

JON W. DUDAS
*Director of the United States Patent and Trademark Office*